(12) United States Patent
Shipman

(10) Patent No.: US 11,713,339 B2
(45) Date of Patent: Aug. 1, 2023

(54) MACROCYCLIZATION OF PEPTIDOMIMETICS

(71) Applicant: UNIVERSITY OF WARWICK, Coventry (GB)

(72) Inventor: Michael Shipman, Coventry (GB)

(73) Assignee: UNIVERSITY OF WARWICK, Coventry (GB)

( * ) Notice: Subject to any disclaimer, the term of this patent is extended or adjusted under 35 U.S.C. 154(b) by 0 days.

(21) Appl. No.: 17/042,489

(22) PCT Filed: Mar. 28, 2019

(86) PCT No.: PCT/GB2019/050896
§ 371 (c)(1),
(2) Date: Sep. 28, 2020

(87) PCT Pub. No.: WO2019/186174
PCT Pub. Date: Oct. 3, 2019

(65) Prior Publication Data
US 2021/0024579 A1    Jan. 28, 2021

(30) Foreign Application Priority Data

Mar. 28, 2018 (GB) .................................. 1805088

(51) Int. Cl.
*A61K 38/00* (2006.01)
*C07K 7/02* (2006.01)
*C07K 7/54* (2006.01)
*G01N 33/68* (2006.01)

(52) U.S. Cl.
CPC ........... *C07K 7/54* (2013.01); *G01N 33/6803* (2013.01); *A61K 38/00* (2013.01)

(58) Field of Classification Search
CPC ............. A61K 38/00; C07K 7/02; C07K 7/54
See application file for complete search history.

(56) References Cited

U.S. PATENT DOCUMENTS 7,589,170 B1 * 9/2009 Smythe .................... C07K 7/64
530/300

OTHER PUBLICATIONS

International Search Report and Written Opinion issued for Application No. PCT/GB2019/050896, dated Jul. 3, 2019, 16 pages.
International Report on Patentability issued for Application No. PCT/GB2019/050896, dated Sep. 29, 2020.
Powell, Nicola H., et al. "Synthesis and structure of oxetane containing tripeptide motifs." Chemical Communications 50.63 (2014): 8797-8800.
McLaughlin, Martin, et al. "Oxetanyl peptides: novel peptidomimetic modules for medicinal chemistry." Organic letters 16.16 (2014): 4070-4073.
Beadle, Jonathan D., et al. "Solid-phase synthesis of oxetane modified peptides." Organic letters 19.12 (2017): 3303-3306.
Möller, Guido P., et al. "Oxetanyl amino acids for peptidomimetics." Organic Letters 19.10 (2017): 2510-2513.
Bull, James A., et al. "Oxetanes: recent advances in synthesis, reactivity, and medicinal chemistry." Chemical reviews 116.19 (2016): 12150-12233.
Beadle, J. et al. "Synthesis of oxetane-and azetidine-containing spirocycles related to the 2, 5-diketopiperazine framework." Synlett 27.1 (2015): 169-172.
Marti-Centelles, Vicente, et al. "Macrocyclization reactions: the importance of conformational, configurational, and template-induced preorganization." Chemical Reviews 115.16(2015): 8736-8834.
Arap, Wadih, Renata Pasqualini, and Erkki Ruoslahti. "Cancer treatment by targeted drug delivery to tumor vasculature in a mouse model." Science 279.5349 (1998): 377-380.
Avan, Ilker, C. Dennis Hall, and Alan R. Katritzky. "Peptidomimetics via modifications of amino acids and peptide bonds." Chemical Society Reviews 43.10 (2014): 3575-3594.
Bockus, Andrew T., Cayla M. McEwen, and R. Scott Lokey. "Form and function in cyclic peptide natural products: a pharmacokinetic perspective." Current topics in medicinal chemistry 13.7 (2013): 821-836.
Boutureira, Omar, et al. "Site-Selective Modification of Proteins with Oxetanes." Chemistry (Weinheim an der Bergstrasse, Germany) 23.27 (2017): 6483.
Cardote, Teresa AF, and Alessio Ciulli. "Cyclic and macrocyclic peptides as chemical tools to recognise protein surfaces and probe protein-protein interactions." ChemMedChem 11.8 (2016): 787-794.

(Continued)

*Primary Examiner* — Julie Ha
(74) *Attorney, Agent, or Firm* — Meunier Carlin & Curfman LLC

(57) ABSTRACT

A method of macrocyclization of peptidomimetics is described which comprises substitution of one or more of the backbone amide C=O bonds with a turn-inducing motif. The method is general with enhancements seen across a range of ring sizes (e.g. tri-, tetra-, penta- and hexapeptides). Specifically, a peptidomimetic macrocycle is described comprising a carbonyl bioisosteric turn-inducing element having the structure:

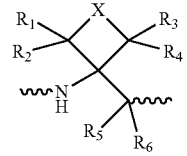

wherein X is a heteroatom; and wherein $R_1$ to $R_6$ are each independently selected from alkyl, aryl, heteroaryl and H.

8 Claims, 10 Drawing Sheets

Specification includes a Sequence Listing.

(56) References Cited

OTHER PUBLICATIONS

Dougherty, Patrick G., Ziqing Qian, and Dehua Pei. "Macrocycles as protein-protein interaction inhibitors." Biochemical Journal 474.7 (2017): 1109-1125.

Fairweather, Kelly A., et al. "Synthesis of all-L cyclic tetrapeptides using pseudoprolines as removable turn inducers." Organic letters 12.14 (2010): 3136-3139.

Frost, John R., Conor CG Scully, and Andrei K. Yudin. "Oxadiazole grafts in peptide macrocycles." Nature chemistry 8.12 (2016): 1105.

Graziadio, Alessandra, et al. "NGR tumor-homing peptides: structural requirements for effective Apn (CD13) targeting." Bioconjugate Chemistry 27.5 (2016): 1332-1340.

Hubert, Jonathan G., et al. "Synthetic fermentation of β-peptide macrocycles by thiadiazole-forming ring-closing reactions." Chemical science 9.8 (2018): 2159-2167.

Johnson, Amber M., and Eric V. Anslyn. "Reversible macrocyclization of peptides with a conjugate acceptor." Organic letters 19.7 (2017): 1654-1657.

Le, Diane N., et al. "Cyclizing pentapeptides: Mechanism and application of dehydrophenylalanine as a traceless turn-inducer." Organic letters 19.1 (2017): 114-117.

Malins, Lara R., et al. "Peptide macrocyclization inspired by non-ribosomal imine natural products." Journal of the American Chemical Society 139.14 (2017): 5233-5241.

Martínez-Sáez, Nuria, et al. "Oxetane Grafts Installed Site-Selectively on Native Disulfides to Enhance Protein Stability and Activity In Vivo." Angewandte Chemie International Edition 56.47 (2017): 14963-14967.

McCarver, Stefan J., et al. "Decarboxylative peptide macrocyclization through photoredox catalysis." Angewandte Chemie 129.3 (2017): 746-750.

Nielsen, Daniel S., et al. "Orally absorbed cyclic peptides." Chemical reviews 117.12 (2017): 8094-8128.

Passioura, Toby, and Hiroaki Suga. "A RaPID way to discover nonstandard macrocyclic peptide modulators of drug targets." Chemical Communications 53.12 (2017): 1931-1940.

Puentes, Alfredo R., et al. "Peptide macrocyclization assisted by traceless turn inducers derived from Ugi peptide ligation with cleavable and resin-linked amines." Organic letters 19.15 (2017): 4022-4025.

Rodriguez, Luis M. De Leon, Andreas J. Weidkamp, and Margaret A. Brimble. "An update on new methods to synthesize cyclotetrapeptides." Organic & biomolecular chemistry 13.25 (2015): 6906-6921.

Roesner, Stefan, et al. "Macrocyclisation of small peptides enabled by oxetane incorporation." Chemical science 10.8 (2019): 2465-2472.

Rojas, Anthony J., et al. "Divergent unprotected peptide macrocyclisation by palladium-mediated cysteine arylation." Chemical science 8.6 (2017): 4257-4263.

Skropeta, Danielle, Katrina A. Jolliffe, and Peter Turner. "Pseudoprolines as removable turn inducers: tools for the cyclization of small peptides." The Journal of organic chemistry 69.25 (2004): 8804-8809.

Stephens, Thomas C., et al. "Synthesis of cyclic peptide mimetics via the successive ring expansion of lactams." Chemistry: A European Journal (2017): 13314-13318.

Tang, Jian, et al. "Synthesis of bioactive and stabilized cyclic peptides by macrocyclization using C (sp 3)-H activation." Chemical science 8.6 (2017): 4565-4570.

Tang, Yan-chun, et al. "Synthesis of cyclopentapeptides and cycloheptapeptides by DEPBT and the influence of some factors on cyclization." The journal of peptide research 60.2 (2002): 95-103.

White, Christopher J., and Andrei K. Yudin. "Contemporary strategies for peptide macrocyclization." Nature chemistry 3.7 (2011): 509.

Wong, Michelle SY, Deni Taleski, and Katrina A. Jolliffe. "Synthesis of dichotomin A: Use of a penicillamine-derived pseudoproline to furnish native valine residues." Australian Journal of Chemistry 68.4 (2015): 627-634.

Wuitschik, Georg, et al. "Oxetanes in drug discovery: structural and synthetic insights." Journal of medicinal chemistry 53.8 (2010): 3227-3246.

Yudin, Andrei K. "Macrocycles: lessons from the distant past, recent developments, and future directions." Chemical science 6.1 (2015): 30-49.

Zorzi, Alessandro, Kaycie Deyle, and Christian Heinis. "Cyclic peptide therapeutics: past, present and future." Current opinion in chemical biology 38 (2017): 24-29.

Jolliffe; "The Pseudoproline Approach to Peptide Cyclization"; Aust. J. Chem. 2018, 71, 723-730; dated Aug. 13, 2018; 8 pages.

Office Action issued in CN Application No. 2019800334253; dated Nov. 2, 2022; 15 pages.

* cited by examiner

Figure 1. Extracted ion chromatograms of peptide macrocyclizations for 1 to 3 (top) and 2 to 4 (bottom).
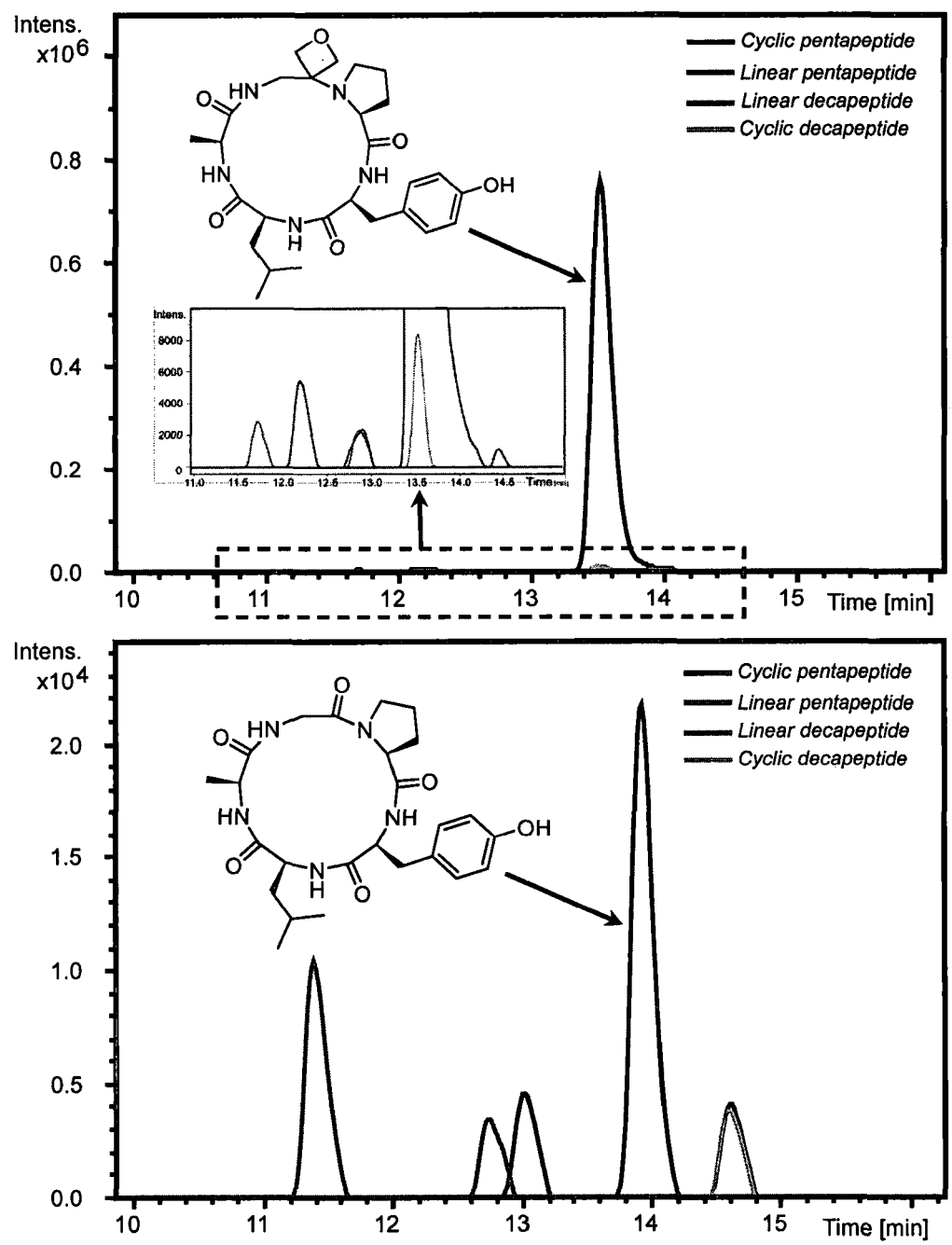

Figure 2. Spectra of Cyclo(Trp-Leu-Gly-Gly) (33)
¹H NMR (500 MHz, CD₃OD)
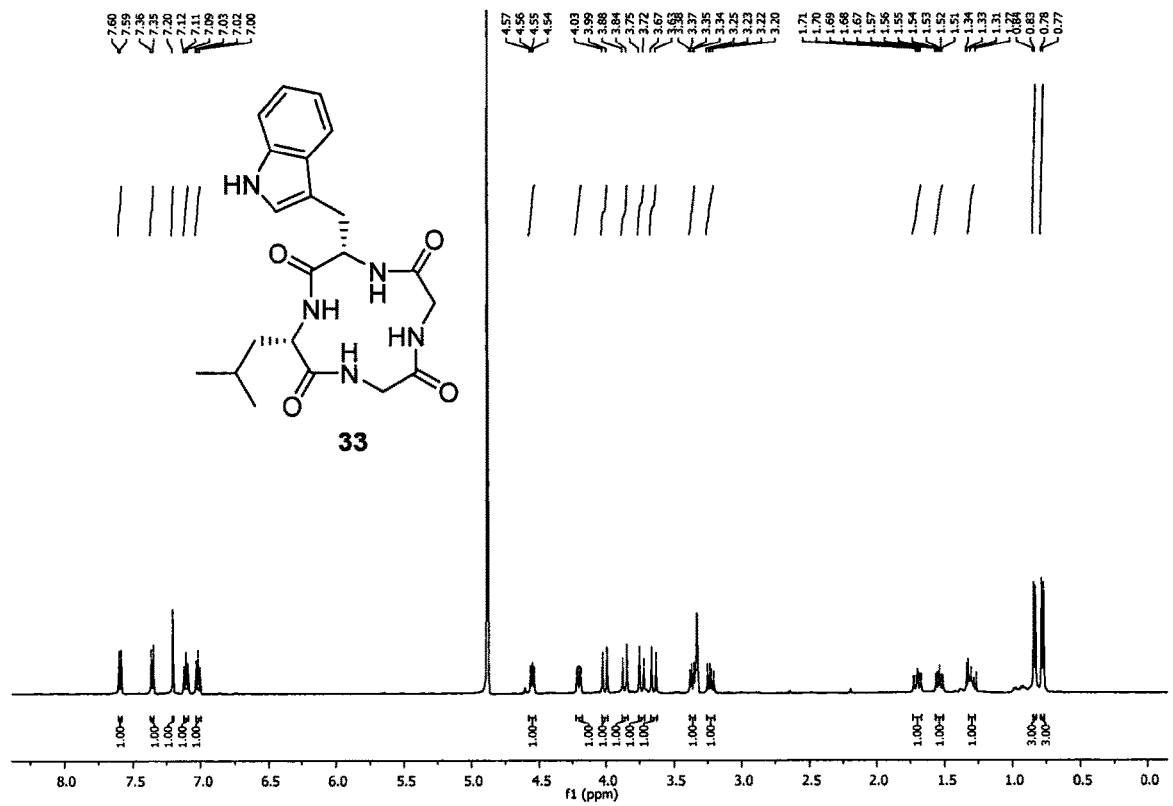
¹³C NMR (126 MHz, CD₃OD)
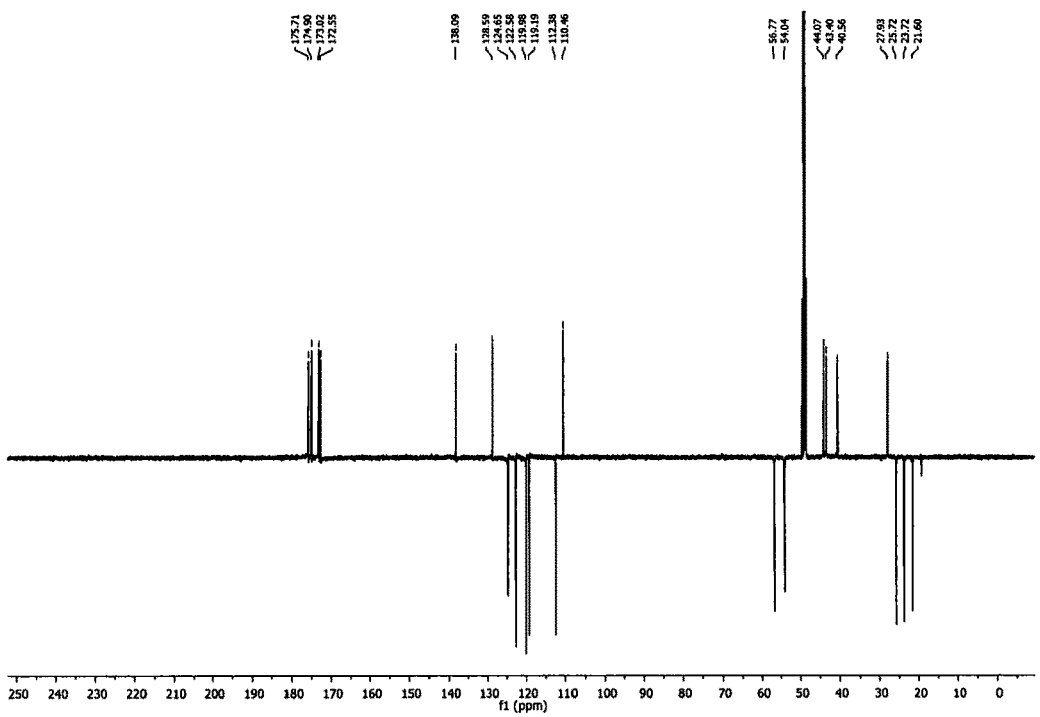

Figure 3: Spectra of Cyclo(Trp-Leu-GOx-Gly) (5)
¹H NMR (500 MHz, DMSO-*d6*)
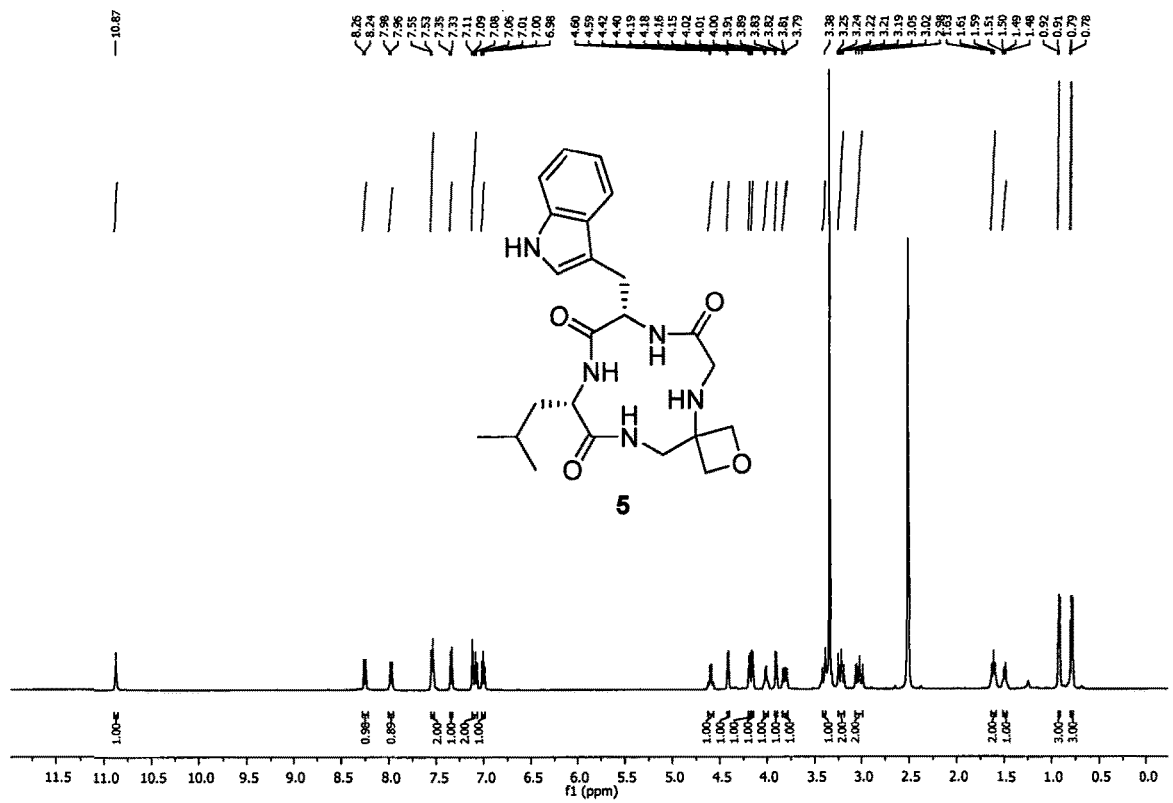
¹³C NMR (126 MHz, DMSO-*d6*)
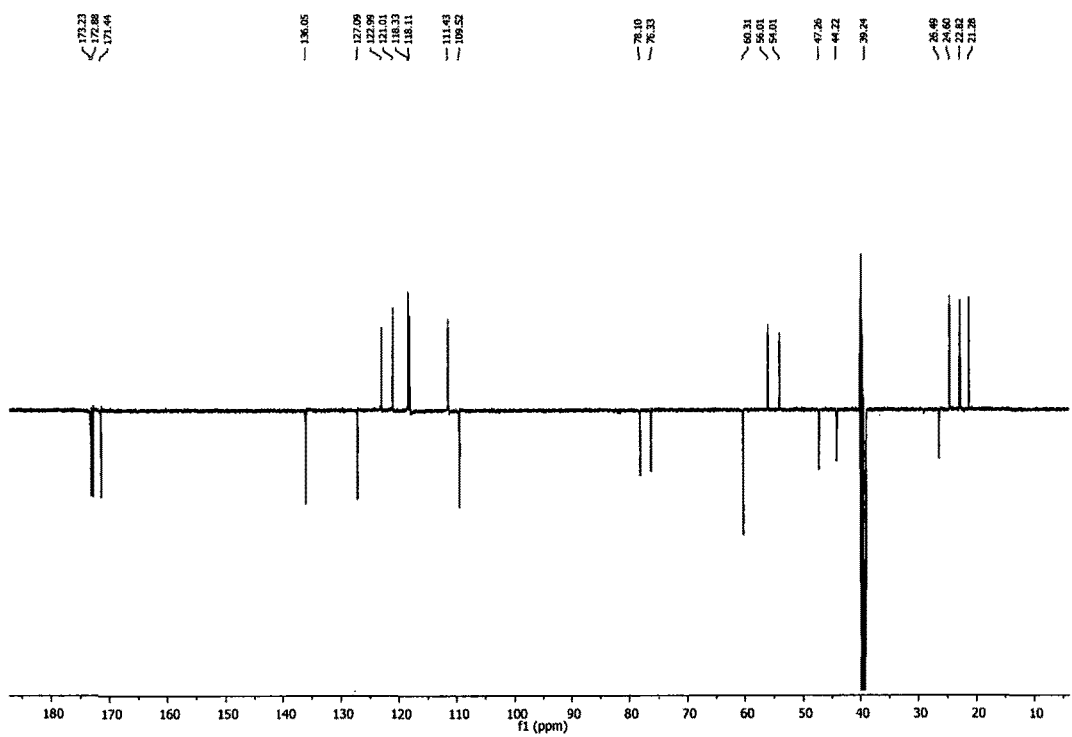

Figure 4. Spectra for Cyclo(Ala-GOx-Ala-Tyr-Leu) (8)
¹H NMR (400 MHz, CD₃OD)
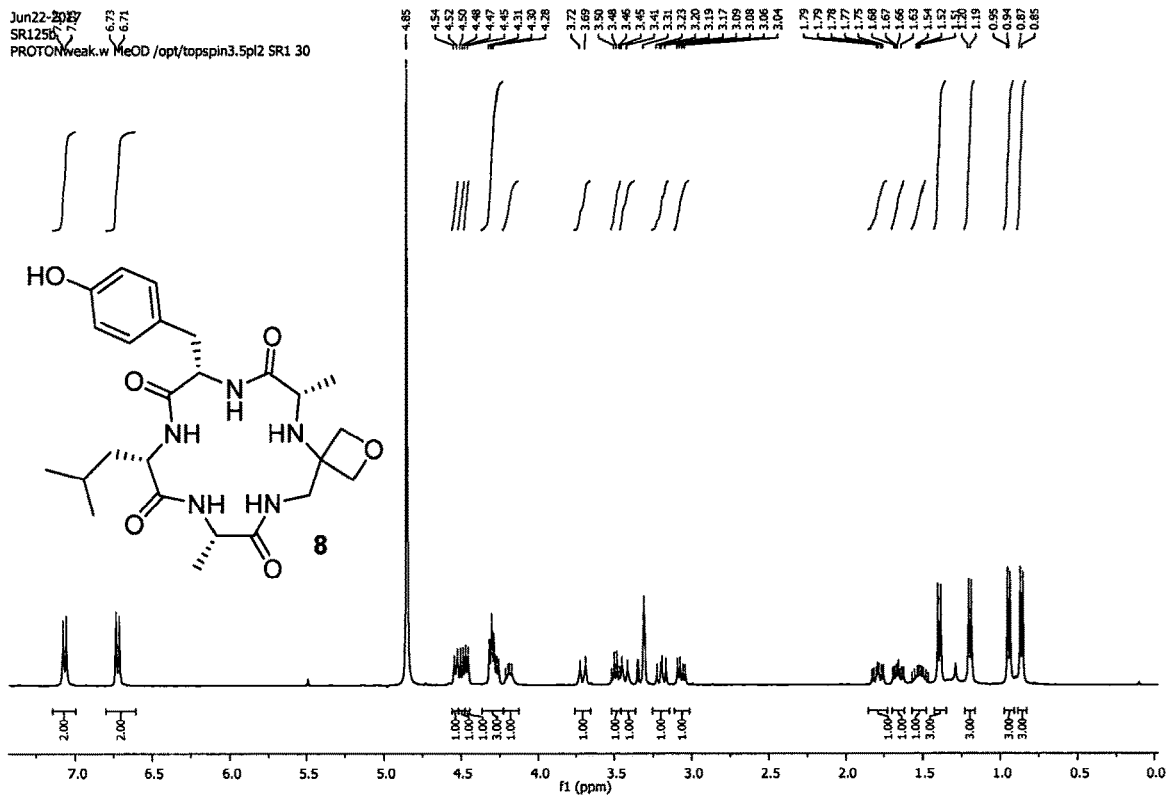
¹³C NMR (126 MHz, CD₃OD)
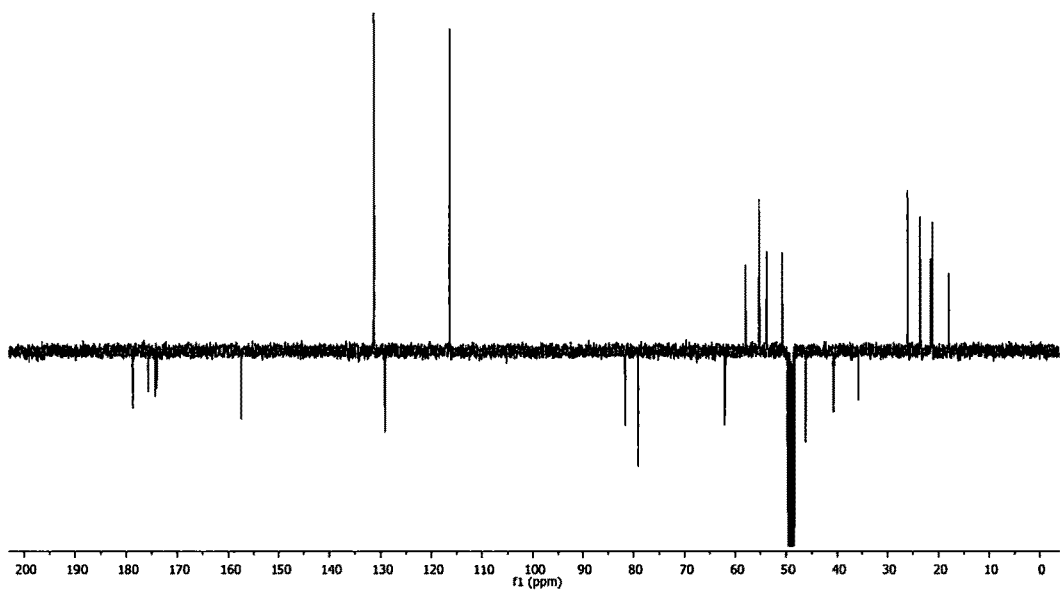

Figure 5. Spectra for Cyclo(Ala-Gly-Ala-Tyr-Leu) (10)
¹H NMR (400 MHz, CD₃OD)
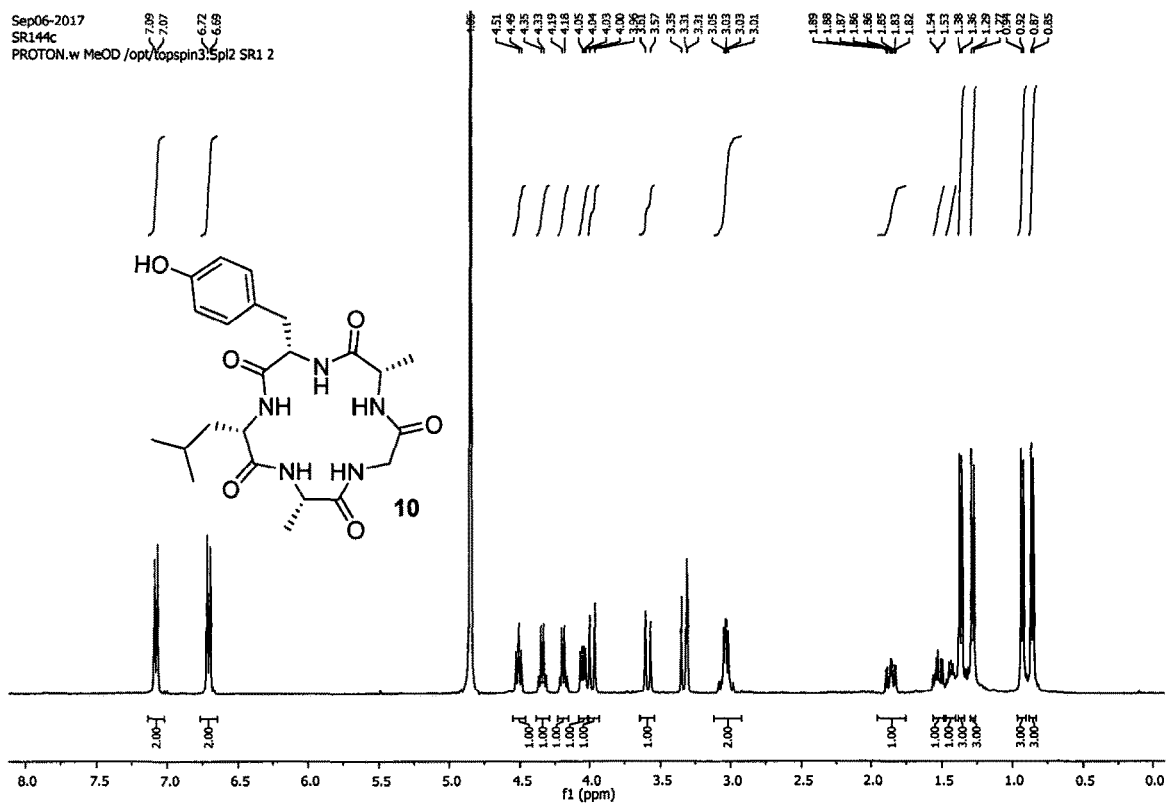
¹³C NMR (101 MHz, CD₃OD)
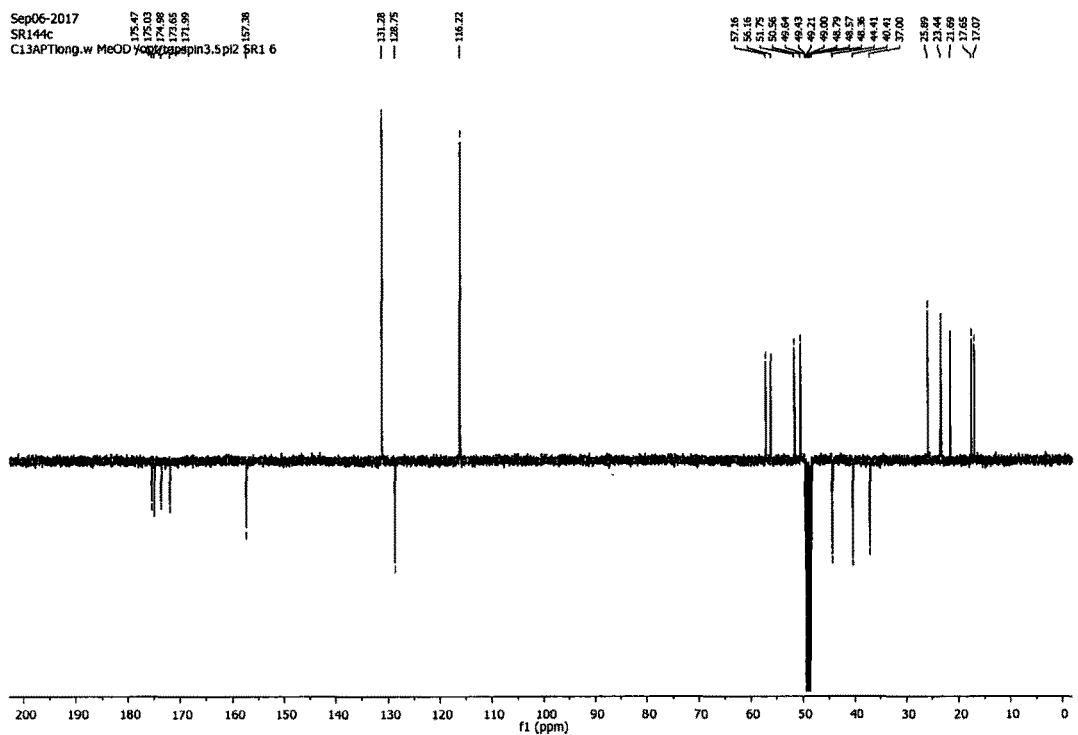

Figure 6. Spectra of Cyclo(H-Cys-Asn-GOx-Arg-Cys-OH (12)
¹H NMR (500 MHz, D₂O @ 323 K)
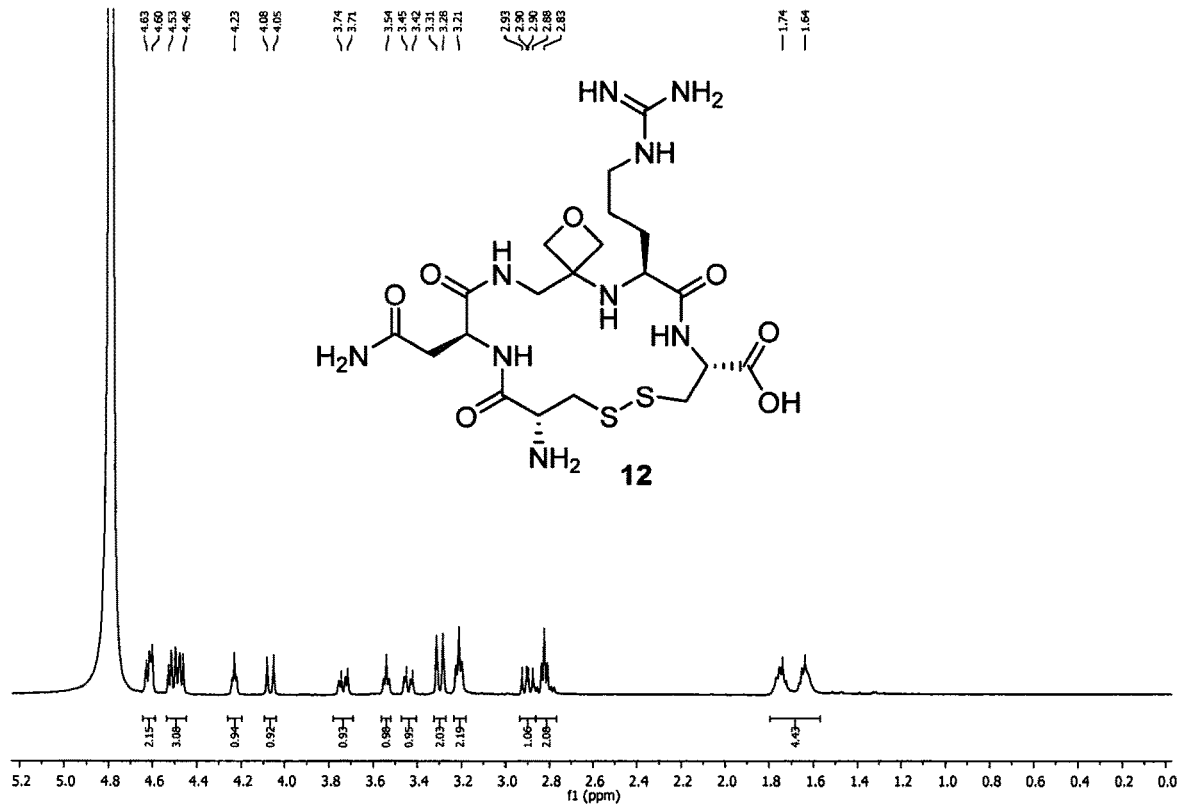
¹³C NMR (126 MHz, D₂O @ 323 K)
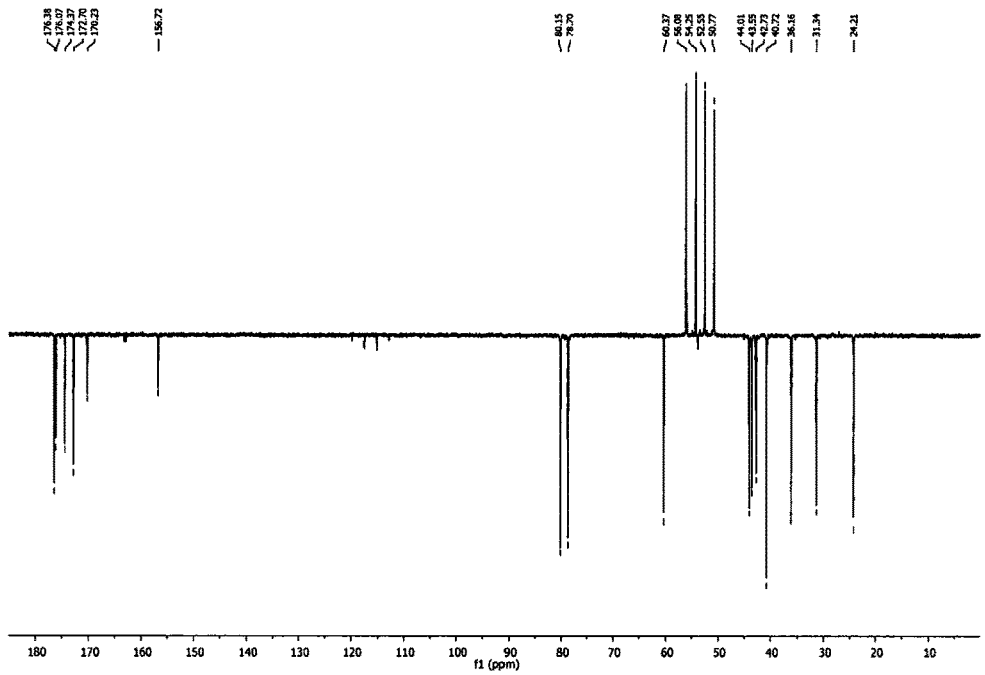

Figure 7. Spectra of Cyclo(Boc-Cys-GOx-Cys-OtBu) (13)
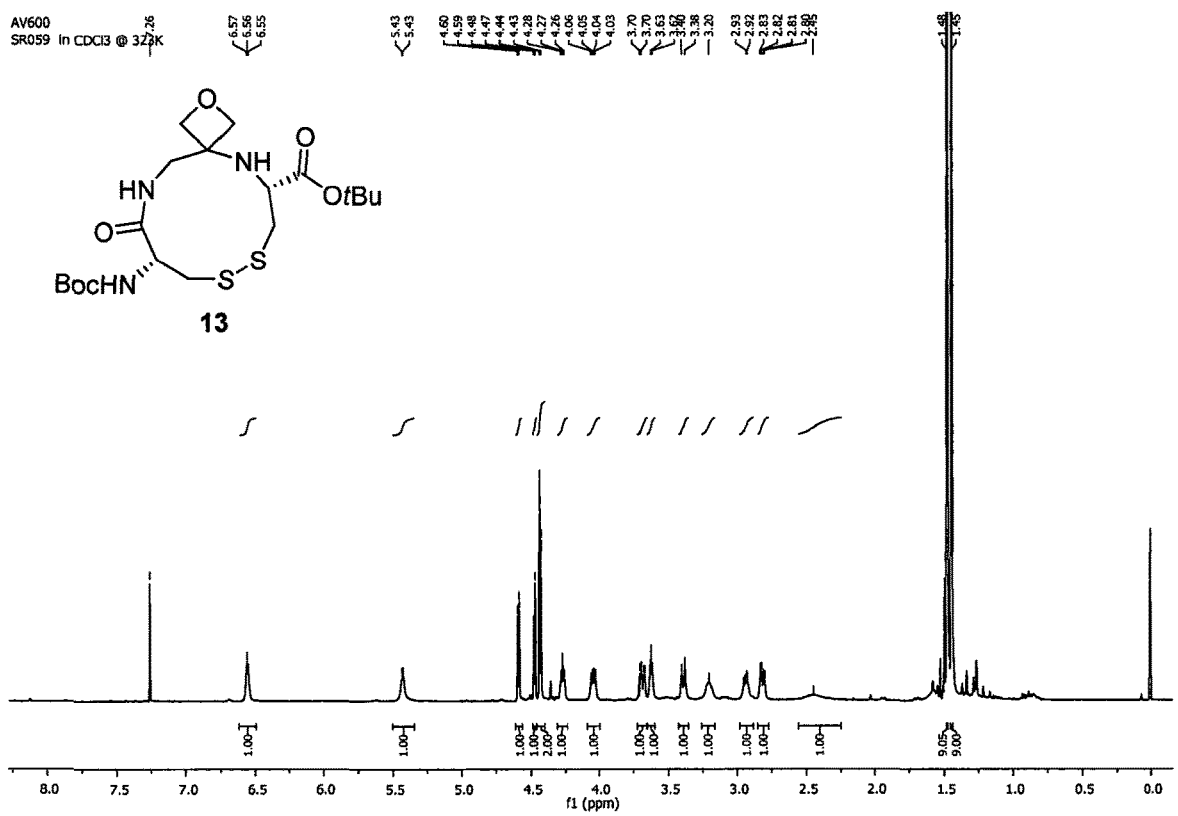

Figure 8a. Inhibition of APN by oxetane modified peptide 12. The shown data are the average of two independent experiments performed in duplicate. Error bars are displaying standard deviations.

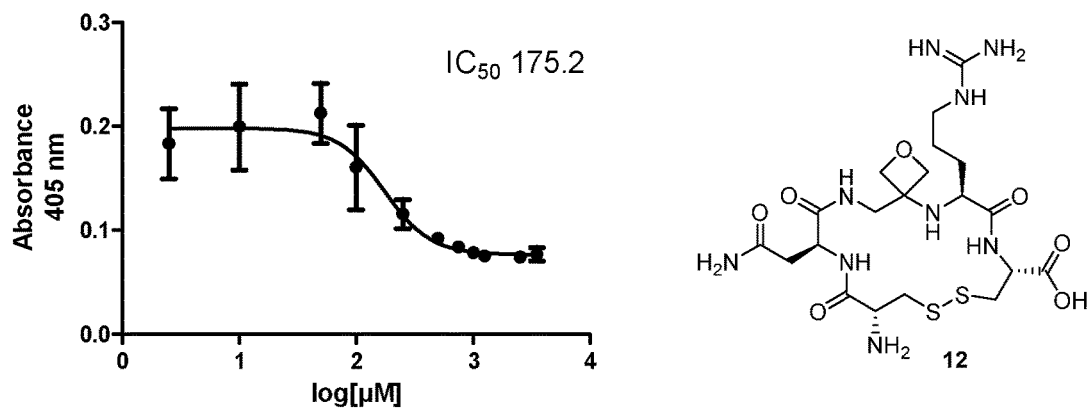

Figure 8b. Inhibition of APN by parent peptide 15. The shown data are the average of two independent experiments performed in duplicate and triplicate, respectively. Error bars are displaying standard deviations.

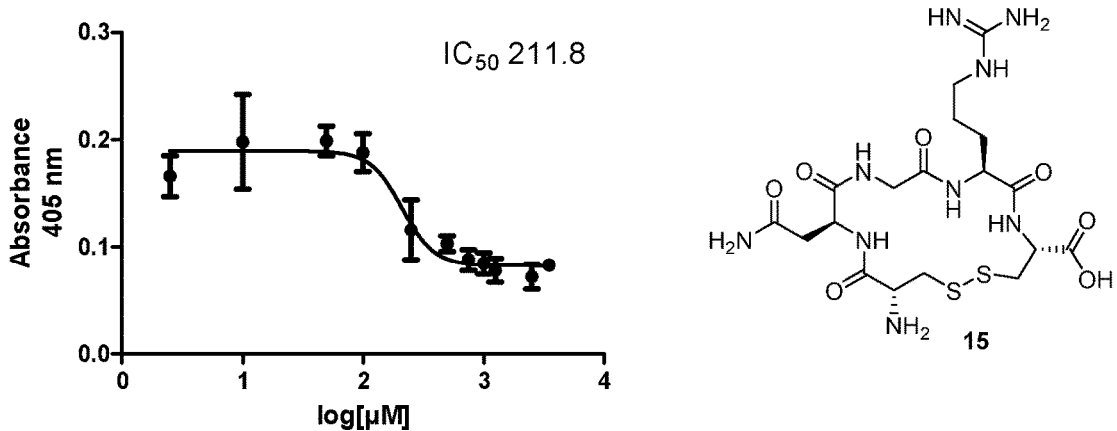

Figure 9. Conversion of linear peptides 6 & 7 to cyclic peptides 8 & 9 and dimer 42 over 74 hours
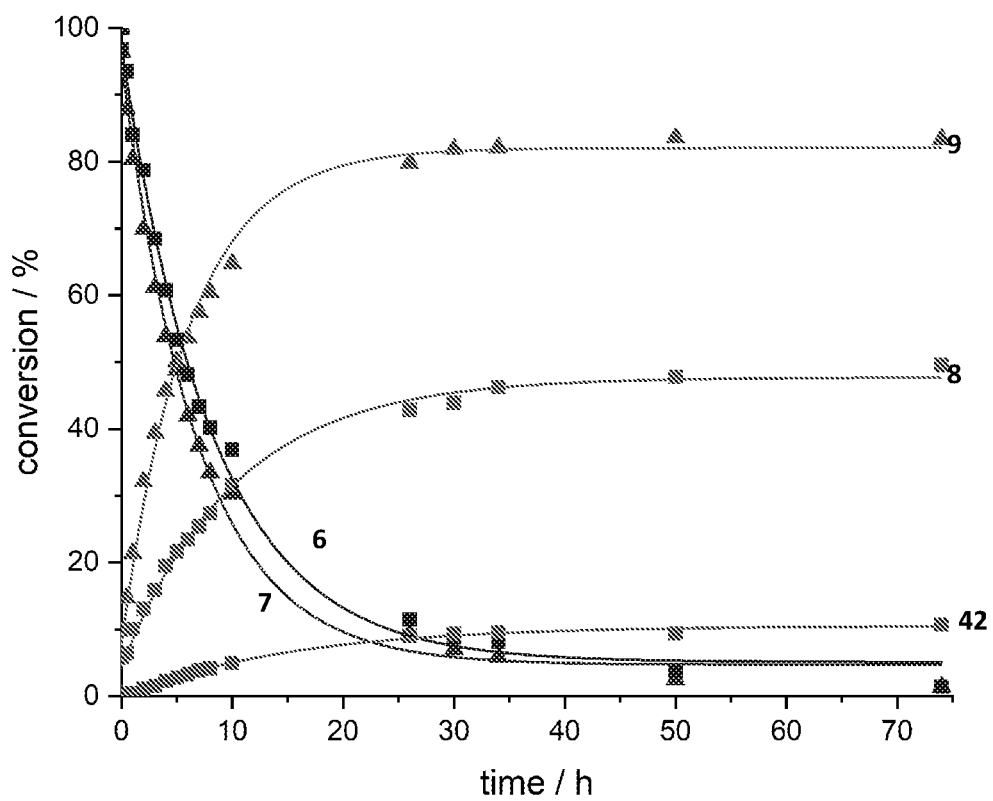

Figure 10. LCMS traces for oxetane and azetidine-containing cyclic peptides in TFA after 24 hours
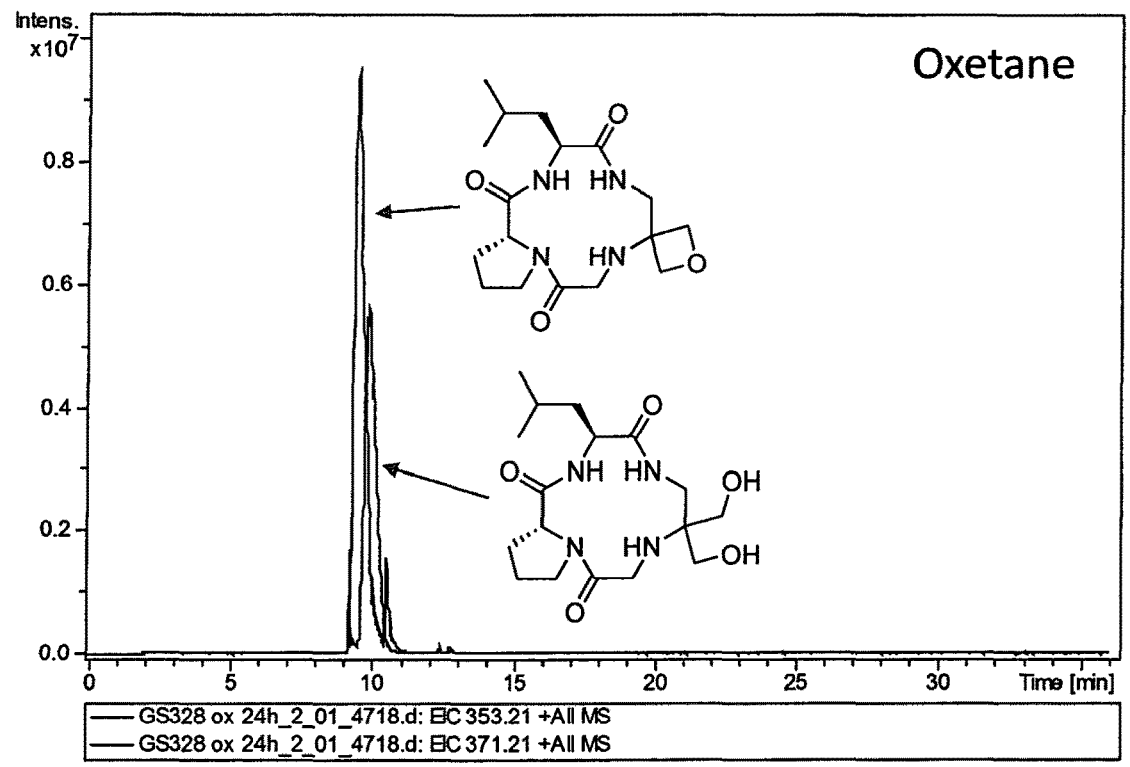
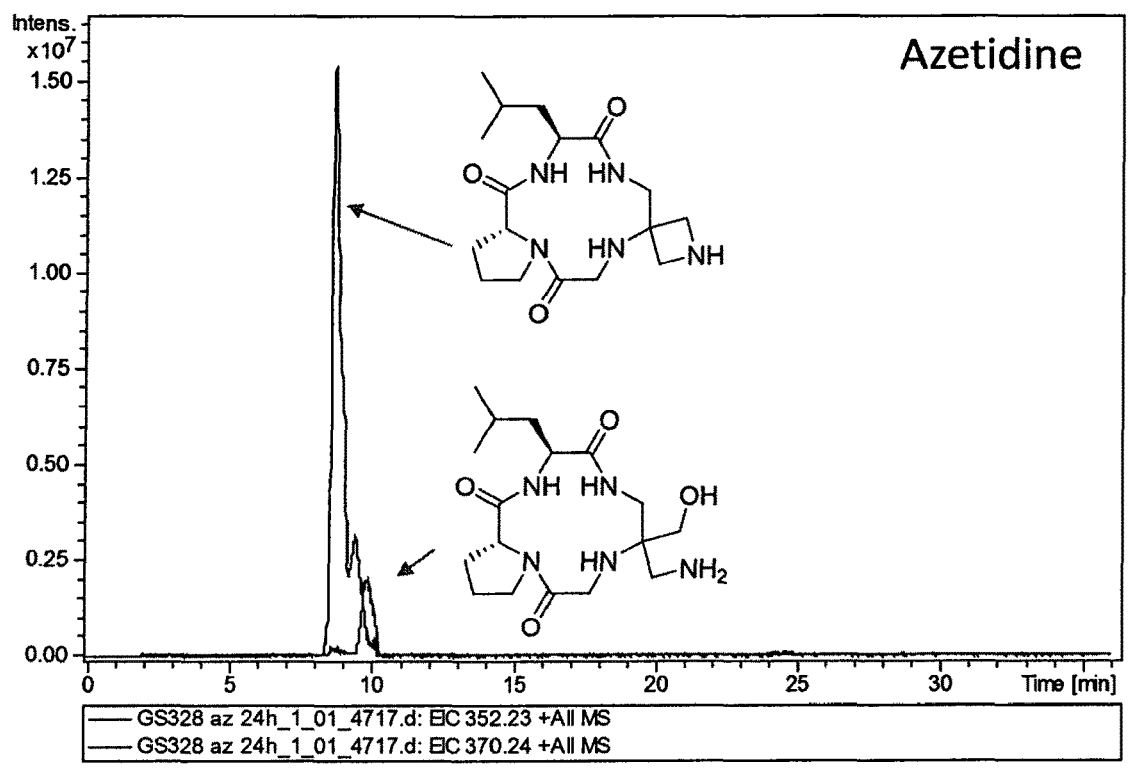

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Short chain linear peptide

<400> SEQUENCE: 1

Leu Ala Gly Pro Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Short chain cyclic peptide

<400> SEQUENCE: 2

Leu Ala Gly Pro Tyr
1               5

<210> SEQ ID NO 3
<211> LENGTH: 4
<212> TYPE: PRT
<213> ORGANISM: Artificial Sequence
<220> FEATURE:
<223> OTHER INFORMATION: Short chain linear peptide

<400> SEQUENCE: 3

Trp Leu Gly Gly
1

<210> SEQ ID NO 4
<211> LENGTH: 4
<212> TYPE: PRT
<213> ORGANISM: Artificial Sequence
<220> FEATURE:
<223> OTHER INFORMATION: Short chain cyclic peptide

<400> SEQUENCE: 4

Trp Leu Gly Gly
1

<210> SEQ ID NO 5
<211> LENGTH: 4
<212> TYPE: PRT
<213> ORGANISM: Artificial Sequence
<220> FEATURE:
<223> OTHER INFORMATION: Short chain linear peptide

<400> SEQUENCE: 5

Pro Leu Gly Gly
1

<210> SEQ ID NO 6
<211> LENGTH: 4
<212> TYPE: PRT
<213> ORGANISM: Artificial Sequence
```

```
<220> FEATURE:
<223> OTHER INFORMATION: Short chain cyclic peptide

<400> SEQUENCE: 6

Pro Leu Gly Gly
1

<210> SEQ ID NO 7
<211> LENGTH: 5
<212> TYPE: PRT
<213> ORGANISM: Artificial Sequence
<220> FEATURE:
<223> OTHER INFORMATION: Short chain linear peptide

<400> SEQUENCE: 7

Ala Gly Ala Tyr Leu
1               5

<210> SEQ ID NO 8
<211> LENGTH: 5
<212> TYPE: PRT
<213> ORGANISM: Artificial Sequence
<220> FEATURE:
<223> OTHER INFORMATION: Short chain cyclic peptide

<400> SEQUENCE: 8

Ala Gly Ala Tyr Leu
1               5

<210> SEQ ID NO 9
<211> LENGTH: 6
<212> TYPE: PRT
<213> ORGANISM: Artificial Sequence
<220> FEATURE:
<223> OTHER INFORMATION: Short chain linear peptide

<400> SEQUENCE: 9

His Leu Ala Gly Ala Tyr
1               5

<210> SEQ ID NO 10
<211> LENGTH: 4
<212> TYPE: PRT
<213> ORGANISM: Artificial Sequence
<220> FEATURE:
<223> OTHER INFORMATION: Short chain cyclic peptide

<400> SEQUENCE: 10

Leu Gly Gly Trp
1

<210> SEQ ID NO 11
<211> LENGTH: 5
<212> TYPE: PRT
<213> ORGANISM: Artificial Sequence
<220> FEATURE:
<223> OTHER INFORMATION: Short chain linear peptide
<220> FEATURE:
<221> NAME/KEY: MOD_RES
<222> LOCATION: (3)..(3)
<223> OTHER INFORMATION: bAla

<400> SEQUENCE: 11

Leu Ala Xaa Ala Tyr
1               5

<210> SEQ ID NO 12
```

```
<211> LENGTH: 5
<212> TYPE: PRT
<213> ORGANISM: Artificial Sequence
<220> FEATURE:
<223> OTHER INFORMATION: Short chain cyclic peptide
<220> FEATURE:
<221> NAME/KEY: MOD_RES
<222> LOCATION: (3)..(3)
<223> OTHER INFORMATION: bAla

<400> SEQUENCE: 12

Leu Ala Xaa Ala Tyr
1               5

<210> SEQ ID NO 13
<211> LENGTH: 4
<212> TYPE: PRT
<213> ORGANISM: Artificial Sequence
<220> FEATURE:
<223> OTHER INFORMATION: Short chain linear peptide

<400> SEQUENCE: 13

Pro Leu Gly Gly
1

<210> SEQ ID NO 14
<211> LENGTH: 4
<212> TYPE: PRT
<213> ORGANISM: Artificial Sequence
<220> FEATURE:
<223> OTHER INFORMATION: Short chain cyclic peptide

<400> SEQUENCE: 14

Pro Leu Gly Gly
1

<210> SEQ ID NO 15
<211> LENGTH: 5
<212> TYPE: PRT
<213> ORGANISM: Artificial Sequence
<220> FEATURE:
<223> OTHER INFORMATION: Short chain cyclic peptide

<400> SEQUENCE: 15

Cys Asp Gly Arg Cys
1               5
```

MACROCYCLIZATION OF PEPTIDOMIMETICS

FIELD OF THE INVENTION

The present invention relates to the composition, method of incorporation, and use of a carbonyl mimetic modification onto a peptide chain to enable cyclisation of linear peptidomimetics.

More specifically, the invention relates to novel methods for making peptidomimetic macrocycles in which a carbonyl group is replaced by a bioisoteric turn-inducing motif. Such methods enable the reliable and efficient synthesis of cyclic peptides which may find use, for example, in drug discovery programmes.

The invention further relates to novel peptidomimetic macrocycles which include the bioisoteric turn-inducing motif and which may be used as medicaments in therapy.

Bioisoteric forms of cyclic peptide drugs which are in clinical use or under clinical evaluation in which a carbonyl group is replaced by the turn-inducing motif can be synthesised more efficiently using the methods of the present invention. The invention also relates to such modified cyclic peptide drugs, to methods for their synthesis and their use in therapy.

BACKGROUND TO THE INVENTION

Currently more than 40 cyclic peptide drugs are in clinical use with the vast majority derived from natural products (e.g. cyclosporine, vancomycin).[1] Compared to their linear counterparts, cyclic peptides benefit from enhanced cell permeability, increased target affinity, and resistance to proteolytic degradation.[2] Moreover, they are capable of acting as inhibitors against some of the most challenging targets, including protein-protein interactions (PPIs).[3] One major obstacle to the discovery and development of new cyclic peptide drugs relates to the difficulties associated with their synthesis.[4] The head-to-tail cyclization of short peptides containing seven or less amino acids is especially challenging. Common problems encountered during cyclization are C-terminal epimerization, cyclooligomerization and the appearance of side products arising from polymerization (Scheme 1). Consequently, there is a pressing need to discover new macrocyclization strategies that can provide easy access to a variety of small cyclic peptide scaffolds.[5]

A macrocyclic ring is defined within this document to mean a single continuous loop of 11 atoms or more. It is preferable that the ring consists of no more than 10 amino acids which can be native, non-native, or amino acid analogues.

Macrocyclic rings can be formed through cyclisation reactions of linear peptides or peptidomimetics through a number of ring closure strategies[4e]. These include:
- head-to-tail cyclizations (e.g. the amide, N-terminus, reacts with the carboxylic acid, C-terminus, to form an amide bond),
- head-to-side-chain cyclizations (e.g. the amide, N-terminus, reacts with a side-chain R group such as the carboxyl on an aspartic acid, or glutamic acid to form an amide bond),
- side-chain-to-tail (e.g. the carboxyl, C-terminus, reacts with a side-chain R group such as an hydroxyl on a serine, or threonine to form an ester bond, or with a thiol group on a cysteine to form a thioester bond),
- and side-chain-to-side-chain cyclizations (e.g. the side chains of two cysteine residues reacting to form a disulfide bond).

However, the efficiency of these reactions for short peptide chains is low and synthesis of macrocycles with fewer than 8 amino acids being particularly limited and challenging[6].

The incorporation of turn-inducing elements such as a pseudoproline, a N-alkylated, or a D-amino acid into a linear peptide has been reported to enhance the efficiency of peptide macrocyclizations.[4c,6] However, macrocyclization using these turn-inducing elements is restricted by a combination of factors including peptide length, the need for multiple turn-inducing elements to be incorporated, and peptide sequence requirements (e.g. cyclizing a tripeptide using pseudoproline and two other prolines[4e], and a further example, to cyclize a tetrapeptide at a high yield two alternating residues must be able to be converted to pseudoproline, limiting these residues to either Ser, Thr, or Cys[4e]). Additionally the location of these turn-inducing elements within the linear peptide chain plays a crucial, and sometimes detrimental, role in macrocycle yield[6b]. Recent studies in our laboratory on tripeptides in which the C=O of the central amide bond had been replaced by an oxetane ring, which is a carbonyl bioisostere, revealed that this element is turn-inducing.[7] Consequently, introduction of carbonyl bioisosteres into the backbone of a linear peptide offers a new way to improve macrocyclization efficiency by bringing the C- and N-termini into close proximity (Scheme 1):

Scheme 1: Difficulties associated with making small cyclic peptides and improvements arising from oxetane introduction. m, n = 0, 1, 2, ... and R = amino acid side chains.

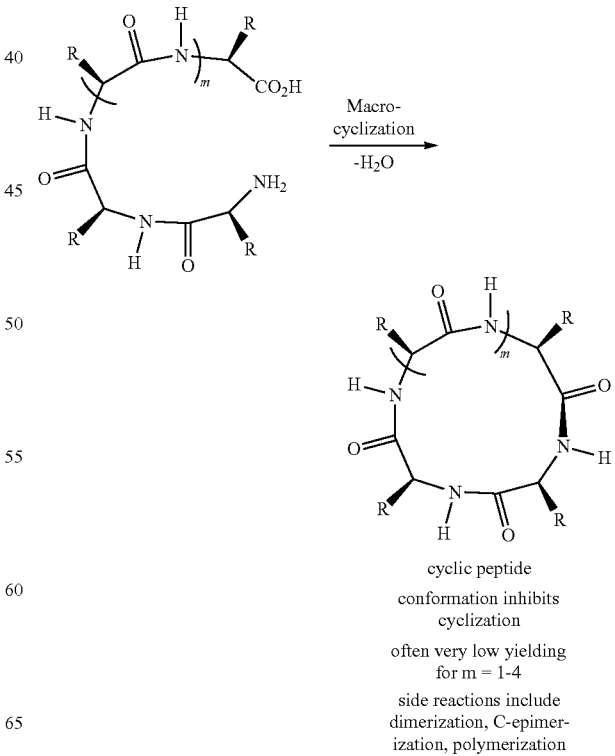

cyclic peptide conformation inhibits cyclization often very low yielding for m = 1-4 side reactions include dimerization, C-epimerization, polymerization

-continued

This study:

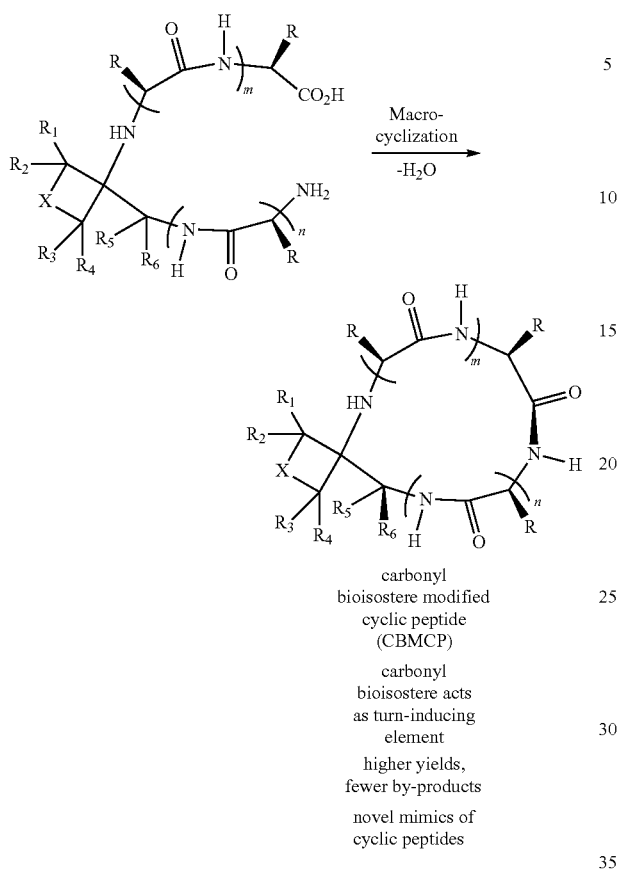

carbonyl
bioisostere modified
cyclic peptide
(CBMCP)

carbonyl
bioisostere acts
as turn-inducing
element higher yields,
fewer by-products novel mimics of
cyclic peptides In addition to being good steric mimics, carbonyl bioisosteres are turn-inducing elements which can increase product yields (in some cases 3-fold) and decrease the amount of byproducts, such as dimeric peptide cyclizations, formed. This means that cyclizations can be conducted on a larger scale under less dilute conditions to yield a purer product. Furthermore carbonyl bioisosteric turn-inducing elements are efficient for peptide cyclization when incorporated at any point in the peptide chain, and for multiple types of cyclisation.

Importantly, the use of oxetanes as bioisosteres in small-molecule drug discovery is well established,[8] with applications in peptide science beginning to emerge.[9,10] For example, the grafting of oxetanes onto the cysteine side chains of proteins and antibodies can significantly improve their stability and activity.[9] Separately, the serum half-life and in vivo analgesic properties of linear peptides such as Leu-enkephalin can be improved by oxetane incorporation.[10] However, there are no examples of oxetanes or analogous bioisosteric motifs being employed as turn-inducing elements for the purpose of synthesizing peptidomimetic macrocycles.

The present invention demonstrates that a number of challenging peptide macrocyclizations are shown to be significantly improved by the incorporation of carbonyl bioisosteric turn-inducing elements, and that carbonyl bioisostere modified cyclic peptides (CBMCPs) can be effective mimics of conventional cyclic peptides, as demonstrated in biological activity assays. On this basis, one can propose that CBMCPs are a valuable new class of peptidomimetic for use in biomedical applications, including drug discovery.

SUMMARY OF THE INVENTION

The invention provides, as a first aspect:
1. A peptidomimetic macrocycle comprising a carbonyl bioisosteric turn-inducing element, where the turn-inducing element is:

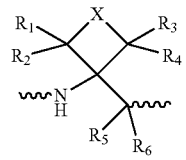

a. Whereby X is a heteroatom
   b. Where $R_{1-6}$ are alkyl, aryl, heteroaryl or H
2. A structure according to 1 where X is NH, O, or S
3. A structure according to 1 where X is a sulfide, sulfone, or sulfoxide
4. A structure according to 1 where X is a secondary or tertiary amine
5. A structure according to 1 where the turn-inducing element is:

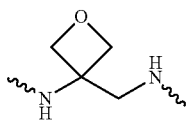

6. A structure according to 1 where the turn-inducing element is:

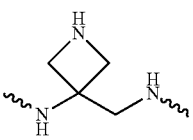

The invention provides, as a second aspect:
7. A method of synthesizing a peptidomimetic macrocycle, comprising the steps:
   a. Synthesizing a linear peptidomimetic comprising the turn-inducing element
   b. Performing a cyclisation reaction of the linear peptidomimetic
8. A method according to 7 where the turn-inducing element is:

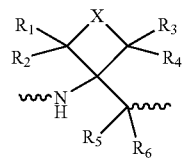

a. Whereby X is a heteroatom
   b. Where $R_{1-6}$ are alkyl, aryl, heteroaryl or H
9. A method according to 7 with the turn-inducing element according to 8 where X is NH, O, or S
10. A method according to 7 with the turn-inducing element according to 8 where X is a sulfide, sulfone, or sulfoxide 11. A method according to 7 with the turn-inducing element according to 8 where X is a secondary or tertiary amine
12. A method according to 7 where the turn-inducing element is:

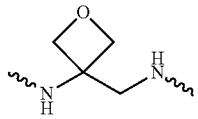

13. A method according to 7 where the turn-inducing element is:

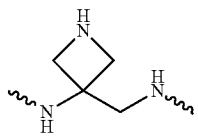

14. A method according to 7 where the cyclisation is a head-to-tail reaction
15. A method according to 7 where the cyclisation is a sidechain-to-sidechain reaction
16. A method according to 7 where the cyclisation is a head-to-sidechain reaction
17. A method according to 7 where the cyclisation is a sidechain-to-tail reaction
18. A method according to 7 whereby sidechain-to-sidechain cyclisation is achieved by an amide, ester, thioester, or disulfide bond formation
19. A method according to 7 using solution-phase peptide synthesis
20. A method according to 7 using solid-phase peptide synthesis The invention provides, as a third aspect:
21. The use of the following reagent to introduce a carbonyl bioisosteric turn-inducing element for the synthesis of a peptidomimetic macrocycle:

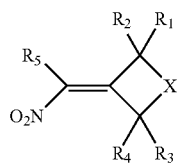

a. Whereby X is a heteroatom
b. Whereby $R_{1-5}$ are alkyl, aryl, heteroaryl or H
22. The use of a reagent according to 21 where X is NH, O, or S
23. The use of a reagent according to 21 where X is a sulfide, sulfone, or sulfoxide
24. The use of a reagent according to 21 where X is a secondary or tertiary amine
25. The use of a reagent according to 21 where the reagent is:

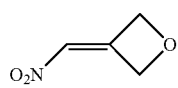

26. The use of a reagent according to 21 where the reagent is:

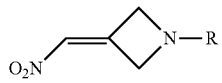

a. Whereby R is H, alkyl, aryl, heteroaryl, or a removable protecting group such as Boc, or Cbz or others known to one skilled in the art The invention provides, as a fourth aspect:
27. A macrocyclic peptide comprising the turn-inducing feature in 1 for use in the manufacture of medicaments.

DETAILED DESCRIPTION OF THE INVENTION

The terms "macrocycle" and "macrocyclic ring" are used interchangeably herein to refer to a molecule having a chemical structure including a continuous ring formed by at least 11 covalently bonded atoms.

The term "peptidomimetic macrocycle" as used herein refers to a compound comprising a plurality of amino acid residues and/or amino acid analogue residues linked by a plurality of peptide bonds. The peptidomimetic macrocycles herein disclosed may optionally include one or more non-peptide bonds between one or more amino acid residues and/or amino acid analogue residues.

As used herein, the term "amino acid" refers to a molecule containing both an amino group and a carboxyl group bound to a carbon which is designated the α-carbon. Suitable amino acids include both the D- and L-isomers of the naturally-occurring amino acids (herein also referred to as "native" amino acids), as well as any non-naturally occurring amino acids (herein also referred to as "non-native" amino acids) which may be prepared by organic synthesis or other metabolic routes. Unless otherwise indicated, the term "amino acid" is intended to include amino acid analogues.

As would be understood, the term "residue" when used in the context of an "amino acid residue" or an "amino acid analogue residue" refers to the moiety formed when the amino acid or amino acid analogue has taken part in a reaction to covalently link it to at least one other amino acid or amino acid analogue in the formation of a linear or cyclic peptide. Covalent linkage of an amino acid or amino acid analogue may result from reaction of a terminal group (e.g. —OH or —NH$_2$) or, where the amino acid or amino acid analogue includes a side-chain having a functional group, from reaction of that functional group.

The terms "naturally occurring amino acid", "natural amino acid", and "native amino acid" are used interchangeably herein to refer to any one of the amino acids commonly found in peptides synthesised in nature, and known by the one letter abbreviations A, R, N, C, D, Q, E, G, H, I, L, K, M, F, P, S, T, W, Y, U and V.

The terms "non-naturally occurring amino acid", "non-natural amino acid", and "non-native amino acid" are used interchangeably herein to refer to an amino acid which is not commonly found in peptides synthesised in nature and which may, for example, be prepared by organic synthesis or other metabolic routes. Non-naturally occurring amino acids are structurally similar to a natural amino acid and can be substituted for an amino acid in the formation of a peptidomimetic macrocycle as herein described. They include, for example, D-isomers of the naturally occurring amino acids, amino acids having a non-natural side-chain, amino acids having two substituents on the α-carbon, and dehydroamino acids. Other, non-limiting, examples include compounds which are structurally identical to a natural amino acid as defined herein, except for the inclusion of one or more additional methylene groups between the amino and carboxyl group (e.g. α-amino β-carboxy acids), or for the substitution of the amino or carboxy group by a similarly reactive group (e.g. substitution of the primary amine with a secondary or tertiary amine, or substitution of the carboxy group with an ester). N-methylated amino acids are one, non-limiting, example of a non-naturally occurring amino acid.

As used herein, the term "amino acid analogue" refers to a molecule which mimics the properties of an amino acid and which can be substituted for an amino acid in the formation of a peptidomimetic macrocycle as herein described. Amino acid analogues include, for example, compounds made by manipulation of one or more components of the backbone of an amino acid.

As used herein, the term "amino acid side-chain" refers to a moiety attached to the α-carbon in an amino acid. For example, the amino acid side-chain for alanine is methyl, etc. Other non-naturally occurring amino acid side-chains are contemplated herein and include those that occur in nature (e.g. an amino acid metabolite) and those which can be made synthetically (e.g. an α,α di-substituted amino acid).

The term "α,α di-substituted amino acid" refers to a molecule containing both an amino group and a carboxyl group bound to a carbon which is designated the α-carbon, and which is attached to two natural or non-natural amino acid side-chains.

As used herein, the terms "carbonyl bioisosteric" or "carbonyl bioisotere" refer to a moiety which has chemical substituents or groups with similar physical and/or chemical properties to a carbonyl group and which thus produces broadly similar biological properties to a carbonyl group.

As used herein, the term "alkyl" refers to a monovalent saturated, linear or branched, hydrocarbon chain. Examples of alkyl groups include, but are not limited to, methyl, ethyl, n-propyl, iso-propyl, n-butyl, iso-butyl, sec-butyl, tert-butyl, n-pentyl, iso-pentyl, neo-pentyl, n-hexyl, etc. An alkyl group preferably contains from 1-6 carbon atoms, e.g. 1-4 carbon atoms. Unless stated otherwise, any "alkyl" group may be substituted by one or more substituents, which may be identical or different.

As used herein, the term "haloalkyl" refers to an alkyl group as defined herein having one or more halo substituents. Examples of such groups include —$CH_2F$, —$CHF_2$, —$CF_3$, —$CCl_3$, —$CHCl_2$, —$CH_2CF_3$, etc.

As used herein, the term "alkoxy" refers to an —O-alkyl group, wherein alkyl is as defined herein. Examples of alkoxy groups include, but are not limited to, methoxy, ethoxy, propyloxy, etc.

As used herein, the term "aryl" is intended to cover aromatic, carbocyclic ring systems. Such ring systems may be monocyclic or polycyclic (e.g. bicyclic) and contain at least one unsaturated aromatic ring. Where these contain polycyclic rings, these may be fused or bridged. Preferably such systems contain from 6-20 carbon atoms, preferably from 6 to 14 carbon atoms, e.g. either 6 or 10 carbon atoms. Examples of such groups include phenyl, 1-napthyl and 2-napthyl. Unless stated otherwise, any "aryl" group may be substituted by one or more substituents, which may be identical or different.

As used herein, the term "heteroaryl" is intended to cover heterocyclic aromatic groups. Such groups may be monocyclic or bicyclic and contain at least one unsaturated heteroaromatic ring system. Where these are monocyclic, these comprise 5- or 6-membered rings containing at least one heteroatom selected from nitrogen, oxygen and sulphur and contain sufficient conjugated bonds to form an aromatic system. Where these are bicyclic, these may be fused with a carbocyclic or heterocyclic ring and may contain from 9-11 ring atoms. Examples of heteroaryl groups include thiophene, thienyl, pyridyl, thiazolyl, furyl, pyrrolyl, triazolyl, imidazolyl, oxadiazolyl, oxazolyl, pyrazolyl, imidazolonyl, oxazolonyl, thiazolonyl, tetrazolyl, thiadiazolyl, benzimidazolyl, benzooxazolyl, benzofuryl, indolyl, isoindolyl, pyridonyl, pyridazinyl, pyrimidinyl, imidazopyridyl, oxazopyridyl, thiazolopyridyl, imidazopyridazinyl, oxazolopyridazinyl, thiazolopyridazinyl and purinyl. Unless stated otherwise, any "heteroaryl" may be substituted by one or more substituents, which may be identical or different.

As used herein, the term "heteroatom" refers to any atom that is other than carbon or hydrogen. Preferably, it refers to nitrogen, oxygen or sulphur.

Unless otherwise specified, any of the groups defined herein may be substituted in one or more positions with a suitable substituent. Where more than one substituent group is present, these may be the same or different. Suitable substituents include $C_{1-6}$ alkyl (e.g. $C_{1-3}$ alkyl, preferably —$CH_3$), $C_{1-6}$ haloalkyl (e.g. $C_{1-3}$ haloalkyl), hydroxy, $C_{1-6}$ alkoxy (e.g. $C_{1-3}$ alkoxy, preferably —$OCH_3$), amino, cyano, nitro, and halogen atoms (e.g. F, Cl, Br or I).

The peptidomimetic macrocycles herein described may contain one or more chiral centres and may therefore exist in different stereoisomeric forms. The term "stereoisomer" refers to compounds which have identical chemical constitution but which differ in respect of the spatial arrangement of the atoms or groups. Examples of stereoisomers are enantiomers and diastereomers. The term "enantiomers" refers to two stereoisomers of a compound, which are non-superimposable mirror images of one another. The term "diastereoisomers" refers to stereoisomers with two or more chiral centres, which are not mirror images of one another. The invention is considered to extend to diastereomers and enantiomers, as well as racemic mixtures, of any of the compounds herein described.

The compounds herein described may be synthesised enantioselectively or diastereoselectively or may be resolved into their enantiomers and/or diastereomers. For example, where these contain only one chiral centre, these may be provided in the form of a racemate or racemic mixture (a 50:50 mixture of enantiomers) or any mixture of diastereomers or enantiomers in non-racemic form, or these may be provided as pure enantiomers. Any of the compounds which occur as racemates may be separated into their enantiomers by methods known in the art, such as column separation on chiral phases or by recrystallisation from an optically active solvent. Those compounds with at least two asymmetric carbon atoms may be resolved into their diastereomers on the basis of their physical-chemical differences using methods known per se, e.g. by chromatography, kinetic resolution by means of bio-catalysis, and/or fractional crystallisation, and where these compounds are obtained in racemic form, they may subsequently be resolved into their enantiomers (either partially to obtain enantiomerically/diastereomerically enriched mixtures or in full to obtain substantially pure compounds).

The term "pharmaceutically acceptable salt" as used herein refers to any pharmaceutically acceptable organic or inorganic salt of any of the compounds herein described.

The term "pharmaceutically acceptable" means that the compound or composition complies with the standards set in national or international legislation for medicinal products, e.g. the so-called Pharmacopeia (Ph. Eur., BP, USP, etc.), and is compliant with the regulations defined in national or international documentations defining the framework for medicinal products for human and veterinary use. Any such compounds or compositions, either alone or when combined with other components of a formulation, must in principle be chemically and/or toxicologically compatible with any route of administration of the medicinal product to the subject (e.g. human or non-human) to be treated.

By "a pharmaceutical composition" is meant a composition in any form suitable to be used for a medical purpose.

As used herein, "treatment" or "therapy" includes any therapeutic application that can benefit a human or non-human animal (e.g. a non-human mammal). Treatment may be in respect of an existing disease or condition or it may be prophylactic.

As used herein, a "pharmaceutically effective amount" relates to an amount that will lead to the desired pharmacological and/or therapeutic effect, i.e. an amount of the agent which is effective to achieve its intended purpose.

As used herein, a "protecting group" relates to a chemical group which can be introduced into a molecule by chemical modification of a functional group to obtain chemoselectivity in a subsequent chemical reaction. Protecting groups may be introduced onto a specific functional group in a polyfunctional molecule to block its reactivity under reaction conditions needed to make modifications elsewhere in the molecule. Suitable protecting groups should be readily, but selectively, introduced into the desired functional group, be stable to the reagents employed in the subsequent reaction steps and, ideally, be capable of being removed under mild conditions when no longer required. Non-limiting examples of suitable protecting groups include Boc, Fmoc, Cbz (benzyloxycarbonyl), Alloc (allyloxycarbonyl), tBu group, trityl, 2,4-dimethyoxybenzyl, 9-fluorenylmethyl, benzyl, TBDMS, allyl, o-nitrobenzyl, Bn, p-methylbenzyl, acetamidomethyl, Pbf (2,2,4,6,7-pentamethyl-2,3-dihydrobenzofuran-5-sulfonyl), 9-xanthenyl, tosyl, benzyloxylmethyl and formyl. Suitable protecting groups are well known to a person skilled in the art.

In one aspect the invention provides a peptidomimetic macrocycle comprising a carbonyl bioisosteric turn-inducing element as defined herein.

The peptidomimetic macrocycle may contain one or more turn-inducing elements, for example one or two of such turn-inducing elements. In one embodiment, the macrocycle contains one carbonyl bioisosteric turn-inducing element as defined herein.

The turn-inducing element may, for example, be represented by the following structure:

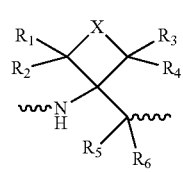

(I)

wherein:

X is a heteroatom, for example oxygen, nitrogen or sulphur; and $R_1$ to $R_6$ are each independently selected from alkyl, aryl, heteroaryl and H.

Where X is oxygen in formula (I), a moiety containing an oxetane ring is provided as the turn-inducing element.

Where X is nitrogen in formula (I), a moiety containing an azetidine ring is provided as the turn-inducing element. As will be understood, in the case where X is nitrogen, it is intended that the nitrogen atom with be covalently linked to another atom or group to complete its valency. Where the nitrogen atom is linked to hydrogen, it will be understood that X is a secondary amine. Where the nitrogen atom is linked to a moiety which is other than hydrogen, it will be understood that X is a tertiary amine. In one embodiment, X is $NR^b$ where $R^b$ is H or $C_{1-6}$ alkyl, preferably $C_{1-3}$ alkyl, e.g. methyl. In an embodiment, X is NH.

Where X is sulphur in formula (I), it will be understood that formula (I) may contain a moiety including sulphur. For example, X may be sulphide (—S—), sulfone (—SO$_2$—), or sulfoxide (—SO—).

In one embodiment, each of $R_1$ to $R_6$ is independently selected from alkyl (e.g. $C_{1-6}$ alkyl) and H. In one embodiment, each of $R_1$ to $R_6$ is H.

In one embodiment, X is either oxygen or nitrogen, and each of $R_1$ to $R_6$ is independently selected from alkyl (e.g. $C_{1-6}$ alkyl) and H.

In one embodiment, X is oxygen or nitrogen, and each of $R_1$ to $R_6$ is H, resulting in a peptidomimetic macrocycle according to the invention which incorporates one or more (e.g. one) of the following structures:

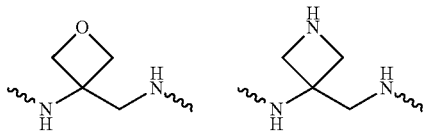

As will be understood from the description of the invention, and the examples presented herein, the peptidomimetic macrocycles according to the invention are a bioisoteric form of a peptide-containing macrocycle in which one or more (e.g. one) of the backbone carbonyl groups of the macrocycle is replaced with an optionally substituted heteroatom-containing ring, e.g. an optionally substituted oxetane or azetidine ring. Viewed in this way, the turn-inducing element as herein described may, alternatively, be represented by the following structure which replaces the C=O group of an amino acid residue or amino acid analogue residue in the macrocyclic ring:

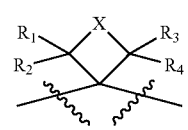

(II)

wherein X, and $R_1$ to $R_4$ are as herein defined.

In one embodiment of formula (II), X is O or $NR^b$, where $R^b$ is selected from H and $C_{1-6}$ alkyl (e.g. methyl).

In one embodiment of formula (II), each of $R_1$ to $R_4$ is independently selected from H and $C_{1-6}$ alkyl (e.g. methyl). In one embodiment, $R_1$ to $R_4$ are all hydrogen.

Examples of structures for the moiety of formula (II) are as follows:

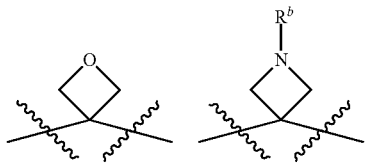

where $R^b$ is H or $C_{1-6}$ alkyl, preferably $C_{1-3}$ alkyl, e.g. methyl. Preferably, $R^b$ is H.

In addition to the turn-inducing element(s) as herein defined, the peptidomimetic macrocycles according to the invention comprise a plurality of amino acid residues and/or amino acid analogue residues linked by a plurality of peptide bonds. The macrocycles may also contain a linker or "linking group" which serves to form the macrocycle, for example by linking of two amino acid residues and/or amino acid analogue residues within the molecule. The peptidomimetic macrocycles may also include one or more non-peptide bonds between one or more amino acid residues and/or amino acid analogue residues.

The macrocyclic ring may comprise a single continuous loop of at least 11 atoms which are covalently bonded to one another to form the "backbone" of the macrocycle. The "backbone" of the macrocycle will be understood to be the continuous chain of atoms which are covalently linked to one another to form the ring. The backbone of the macrocyclic ring may, for example, comprise up to 50 atoms, for example from 11 to 30 atoms, preferably from 12 to 25 atoms, e.g. from 12 to 21 atoms, which are covalently linked to one another. In one embodiment, the backbone of the macrocycle will comprise 12, 15, 18 or 21 covalently bonded atoms.

In addition to the turn-inducing element(s) herein described, the macrocyclic ring will generally comprise up to 10 amino acid or amino acid analogue residues, preferably 2 to 10, for example 2 to 8. In some embodiments, it may contain 2 to 6 amino acid or amino acid analogue residues, for example 2 to 5. In addition to the turn-inducing element (s), the macrocyclic ring may for example comprise 2, 3, 4, 5 or 6 amino acid residues or amino acid analogue residues.

As herein described, the amino acid residues present in the macrocyclic ring may be derived from any natural (i.e. native) or non-natural (i.e. non-native) amino acid, or they may be derived from any amino acid analogue as herein defined. Suitable amino acid residues may readily be determined by those skilled in the art.

In one embodiment, the peptidomimetic macrocycle includes one or more residues of natural (or "native") amino acids which are independently selected from the following:

| Amino acid | Code | Side-chain |
|---|---|---|
| Glycine | G | H |
| Alanine | A | Me |
| Valine | V | |
| Isoleucine | I | |
| Leucine | L | |
| Methionine | M | S |
| Cysteine | C | SH |
| Selenocysteine | U | SeH |
| Phenylalanine | F | |
| Tyrosine | Y | OH |
| Proline | P | |
| Tryptophan | W | NH |
| Arginine | R | NH, $NH_2$ |
| Histidine | H | N, NH |
| Lysine | K | $NH_2$ |
| Aspartic Acid | D | COOH |

| Amino acid | Code | Side-chain |
|---|---|---|
| Glutamic Acid | E | —CH₂CH₂COOH |
| Serine | S | —CH₂OH |
| Threonine | T | —CH(OH)CH₃ |
| Asparagine | N | —CH₂C(O)NH₂ |
| Glutamine | Q | —CH₂CH₂C(O)NH₂ |

In the case where an amino acid residue is derived from proline, the "side-chain" may be considered to comprise the saturated 5-membered ring which is formed together with the adjacent —NH— group of the amino acid. Any amino acid residue present in the macrocyclic ring which is derived from proline may thus be represented by the following structure:

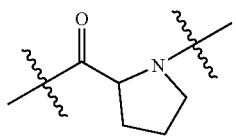

The macrocyclic rings herein described will generally be formed through a cyclisation reaction of the corresponding linear peptides (i.e. also referred to herein as a linear peptide "precursor"). As will be understood, the nature of the bonding between the amino acid residues in the macrocycle will be determined by the specific method used to produce the macrocycle and, in particular, the ring closure strategy. This, in turn, will influence the nature of the atoms which make up the backbone of the macrocyclic ring.

In the case where the macrocycle is formed as a result of a "head-to-tail" cyclisation (i.e. the N-terminus of a first amino acid residue reacts with the C-terminus of a second amino acid residue to form an amide bond), the atoms in the backbone of the macrocycle will generally include C and N, for example they may consist only of C and N.

Where the macrocycle is formed as a result of a "head-to-side-chain" cyclisation (i.e. the N terminus of a first amino acid reacts with a side-chain of a second amino acid residue, e.g. a carboxylic acid present in an aspartic acid or glutamic acid residue, to form an amide bond), the atoms in the backbone of the macrocycle will generally include C and N, but may also include other atoms such as S and O.

Where the macrocycle is formed as a result of a "side-chain-to-tail" cyclisation (i.e. the C-terminus of a first amino acid residue reacts with a side-chain of a second amino acid residue, e.g. hydroxyl on a serine or threonine residue to form an ester bond, or a thiol group on a cysteine to form a thioester bond), the atoms in the backbone of the macrocycle will generally include C and N, but may also include additional atoms such as S and O.

In the case where the macrocycle is formed as a result of a "side-chain-to-side-chain" cyclisation (i.e. a side-chain of a first amino acid reacts with a side-chain of a second amino acid, e.g. a carboxylic acid of an aspartic acid residue reacts with an amine of a lysine residue to form an amide bond, or two cysteine side-chains react to form a disulfide bond), the atoms in the backbone of the macrocycle will generally comprise C and N, but may also include additional atoms such as S and O.

In one embodiment, the peptidomimetic macrocycles herein described are formed through a "head-to-tail" cyclisation of a linear peptide precursor. Such compounds may be represented by formula (a), and also include the stereoisomers and pharmaceutically acceptable salts thereof:

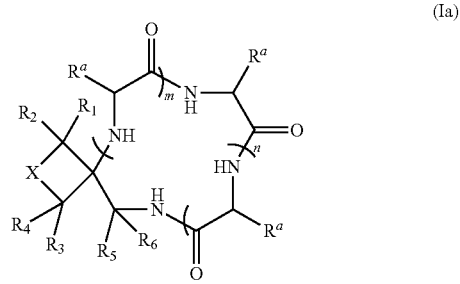

(Ia)

wherein
X is a heteroatom, preferably O or NR, where $R^b$ is selected from H and $C_{1-6}$ alkyl;
$R_1$ to $R_6$ are each independently selected from alkyl (e.g. $C_{1-6}$ alkyl), aryl, heteroaryl and hydrogen;
each $R^a$ is independently selected from an amino acid side-chain (e.g. a side-chain of a naturally occurring or "native" amino acid, or a side-chain of a non-naturally occurring or "non-native" amino acid), or together with the adjacent —NH— group, $R^a$ may form a saturated 5-membered ring;
n is an integer from 0 to 5, preferably 1, 2 or 3; and
m is an integer from 0 to 5, preferably 1, 2 or 3;
with the proviso that m+n≥2.

In one embodiment, the invention provides macrocyclic compounds of formula (Ia) in which $R_1$ to $R_4$ and $R_6$ are each H. Such compounds may be represented by formula (Ia'), and also include the stereoisomers and pharmaceutically acceptable salts thereof:

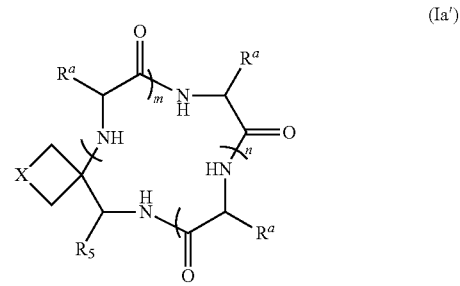

(Ia')

wherein

X is a heteroatom, preferably O or $NR^b$, where $R^b$ is selected from H and $C_{1-6}$ alkyl;

$R_5$ is alkyl (e.g. $C_{1-6}$ alkyl), aryl, heteroaryl or hydrogen, preferably hydrogen;

each $R^a$ is independently selected from an amino acid side-chain (e.g. a side-chain of a naturally occurring or "native" amino acid, or a side-chain of a non-naturally occurring or "non-native" amino acid), or together with the adjacent —NH— group, $R^a$ may form a saturated 5-membered ring;

n is an integer from 0 to 5, preferably 1, 2 or 3; and m is an integer from 0 to 5, preferably 1, 2 or 3;

with the proviso that m+n≥2.

In one embodiment of formula (Ia) or (Ia'), $R_5$ is hydrogen or $C_{1-6}$ alkyl, preferably hydrogen or methyl.

In one embodiment of formula (Ia) or (Ia'), the sum of n+m is 2, 3, 4, 5, or 6.

In another embodiment, the peptidomimetic macrocycles herein described are formed through "side-chain-to-side-chain" cyclisation of a linear peptide precursor, for example by reaction of thiol groups on two, non-adjacent, cysteine residues. Such compounds may be represented by formula (Ib), and also include the stereoisomers and pharmaceutically acceptable salts thereof:

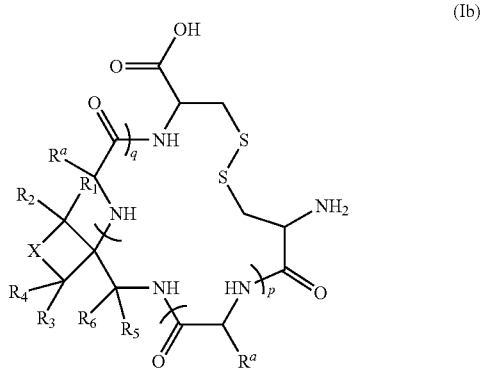

(Ib)

wherein

X is a heteroatom, preferably O or $NR^b$, where $R^b$ is selected from H and $C_{1-6}$ alkyl;

$R_1$ to $R_6$ are each independently selected from alkyl (e.g. $C_{1-6}$ alkyl), aryl, heteroaryl and hydrogen;

each $R^a$ is independently selected from an amino acid side-chain (e.g. a side-chain of a naturally occurring or "native" amino acid, or a side-chain of a non-naturally occurring or "non-native" amino acid), or together with the adjacent —NH— group, $R^a$ may form a saturated 5-membered ring;

p is an integer from 0 to 5, preferably 0, 1 or 2; and q is an integer from 0 to 5, preferably 0, 1 or 2;

with the proviso that p+q≥1.

In one embodiment, the invention provides macrocyclic compounds of formula (Ib) in which $R_1$ to $R_4$ and $R_6$ are each H. Such compounds may be represented by formula (Ib'), and also include the stereoisomers and pharmaceutically acceptable salts thereof:

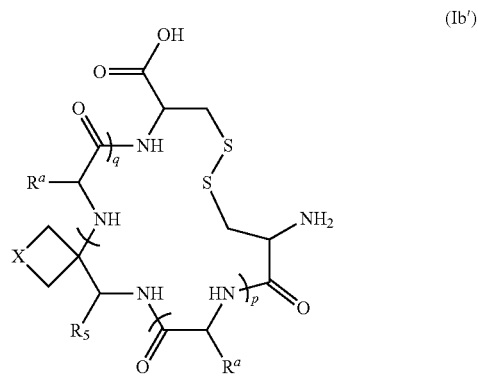

(Ib')

wherein

X is a heteroatom, preferably O or NR, where $R^b$ is selected from H and $C_{1-6}$ alkyl;

$R_5$ is alkyl (e.g. $C_{1-6}$ alkyl), aryl, heteroaryl or hydrogen, preferably hydrogen;

each $R^a$ is independently selected from an amino acid side-chain (e.g. a side-chain of a naturally occurring or "native" amino acid, or a side-chain of a non-naturally occurring or "non-native" amino acid), or together with the adjacent —NH— group, $R^a$ may form a saturated 5-membered ring;

p is an integer from 0 to 5, preferably 0, 1 or 2; and q is an integer from 0 to 5, preferably 0, 1 or 2;

with the proviso that p+q≥1.

In one embodiment of formula (Ib) or (Ib'), $R_5$ is hydrogen or $C_{1-6}$ alkyl, preferably hydrogen or methyl.

In one embodiment of formula (Ib) or (Ib'), the sum of p+q is 1, 2 or 3. In certain embodiments of formula (Ib) or (Ib'), p=q, or p+1=q, or q+1=p.

In another aspect the invention provides a protected derivative of any of the peptidomimetic macrocycles herein described, for example a protected derivative of a compound of formula (Ia), (Ia'), (Ib) or (Ib'), in which one or more functional groups are replaced by one or more protecting groups. Examples of suitable protecting groups include Boc, Fmoc, Cbz (benzyloxycarbonyl), Alloc (allyloxycarbonyl), tBu group, trityl, 2,4-dimethyoxybenzyl, 9-fluorenylmethyl, benzyl, TBDMS, allyl, o-nitrobenzyl, Bn, p-methylbenzyl, acetamidomethyl, Pbf (2,2,4,6,7-pentamethyl-2,3-dihydrobenzofuran-5-sulfonyl), 9-xanthenyl, tosyl, benzyloxylmethyl and formyl. In one embodiment, the protecting groups may be selected from Boc, Fmoc, Cbz, tBu, trityl, benzyl and TBDMS. For example, one or more of the NH moieties of the amino acid residues may be protected by a protecting group, including without limitation Fmoc and Boc. When more than one protecting group is present, these may be the same or different.

In one embodiment, X in each of formulae (Ia), (Ia'), (Ib) and (Ib') is $NR^b$, where $R^b$ is selected from H and $C_{1-6}$ alkyl.

In any of the compounds of formulae (Ia), (Ia'), (Ib) and (Ib') herein described, $R^a$ may preferably be selected from any of the side-chains present in glycine, cysteine, alanine, leucine, tyrosine, tryptophan, valine, isoleucine, or lysine, or $R^a$ together with the adjacent —NH— group may form a saturated 5-membered ring.

Examples of macrocyclic peptidomimetic compounds according to the invention include the following, their stereoisomers, and pharmaceutically acceptable salts thereof:

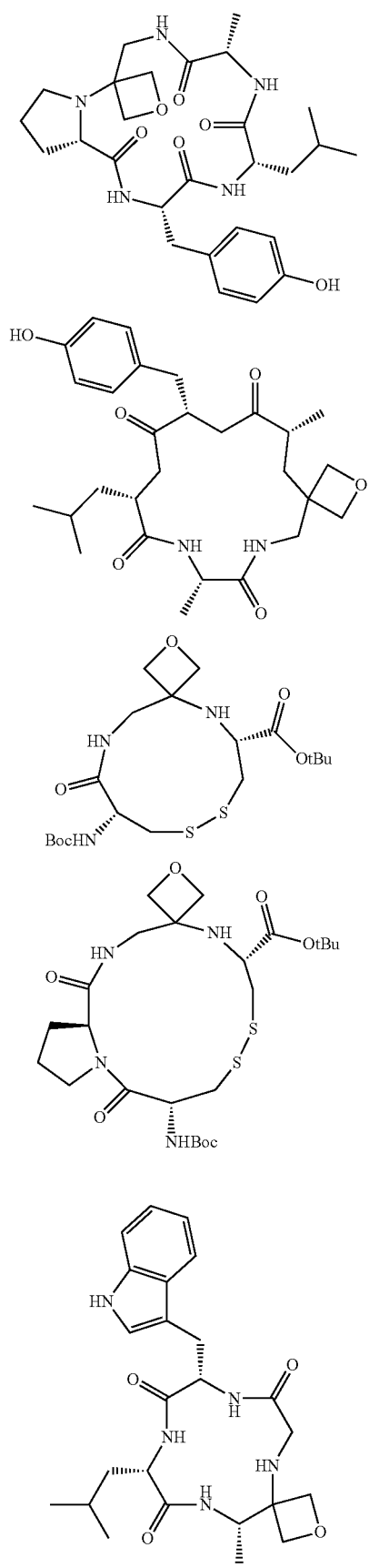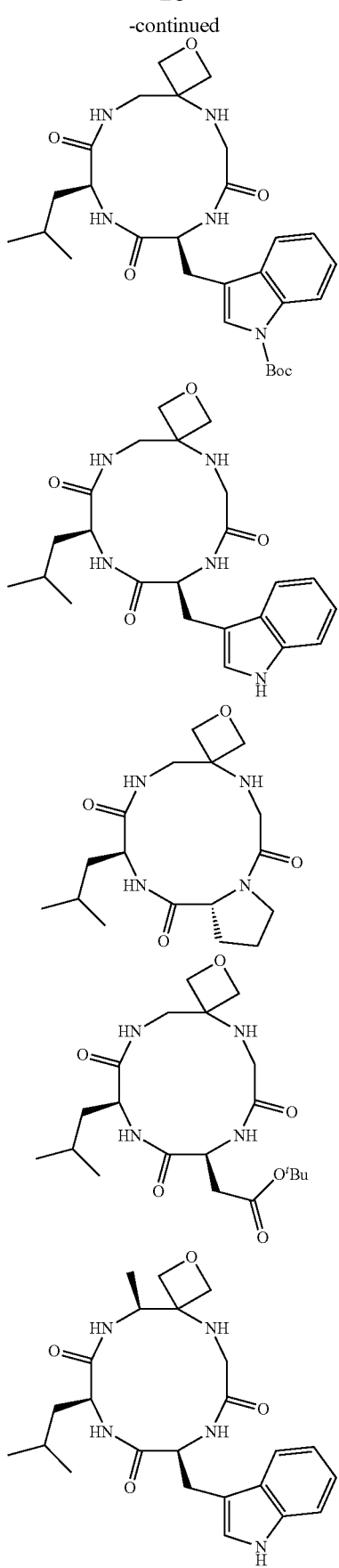

-continued
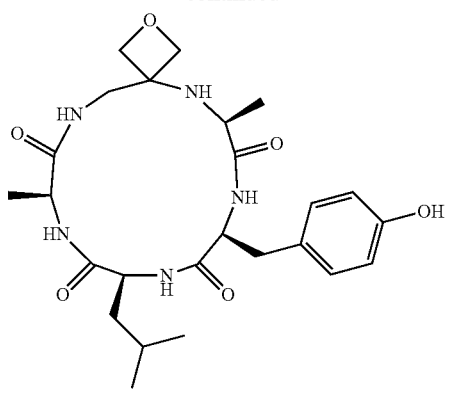
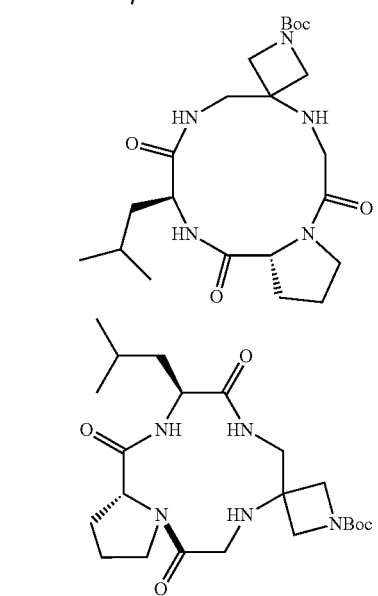
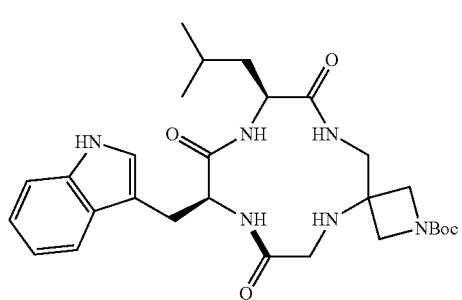
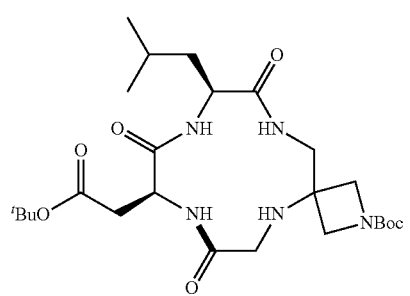
-continued
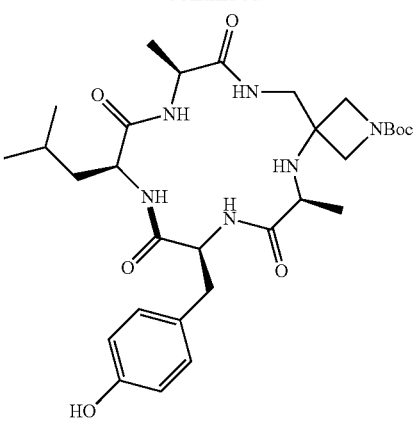
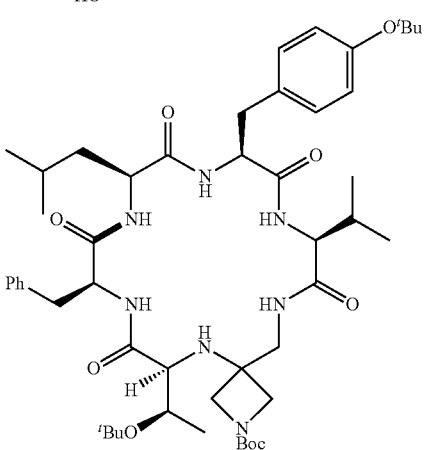
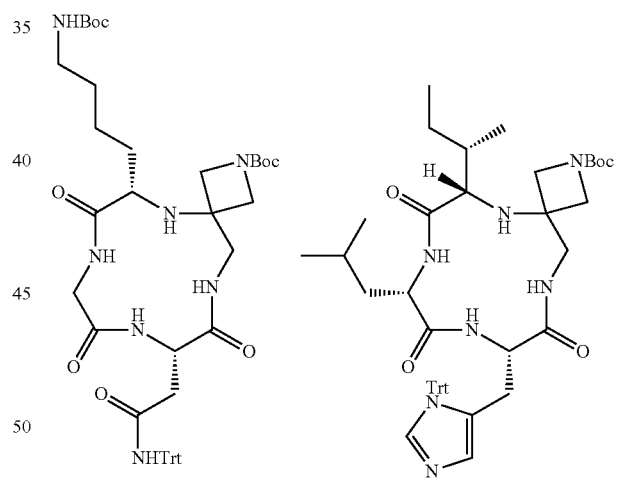
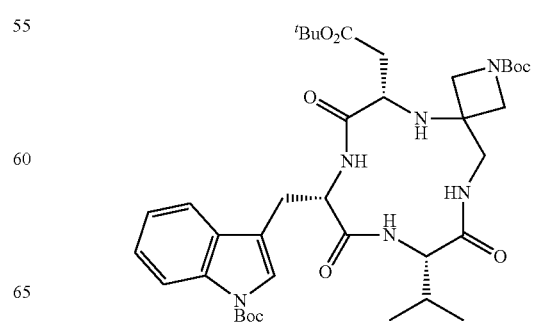

21
-continued
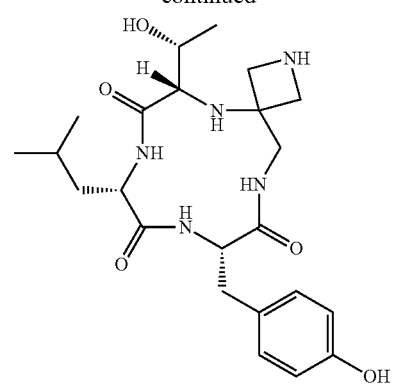
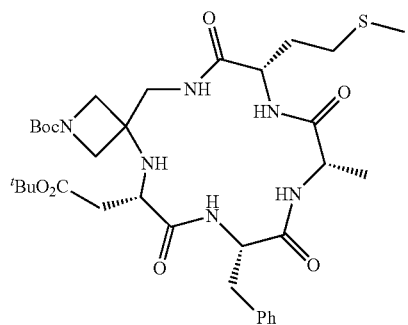
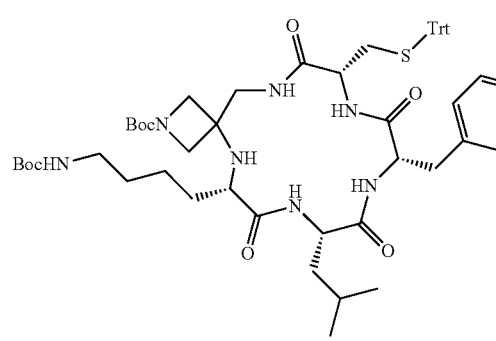
22
-continued
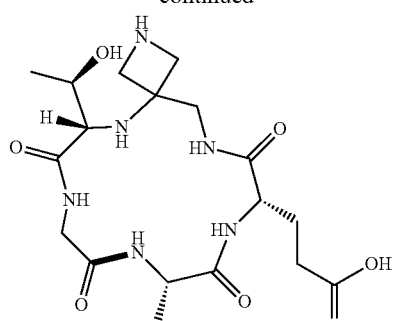
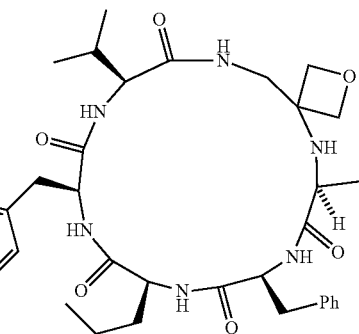
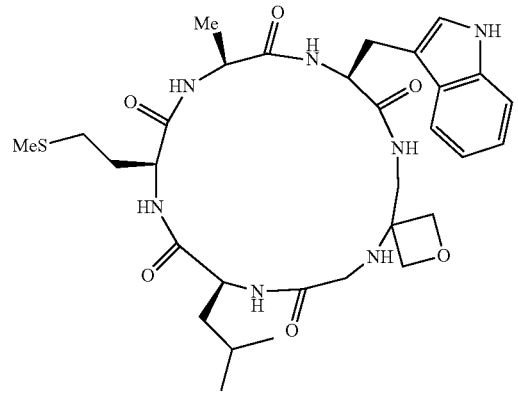
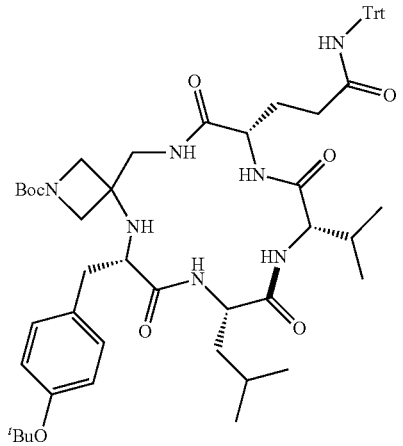
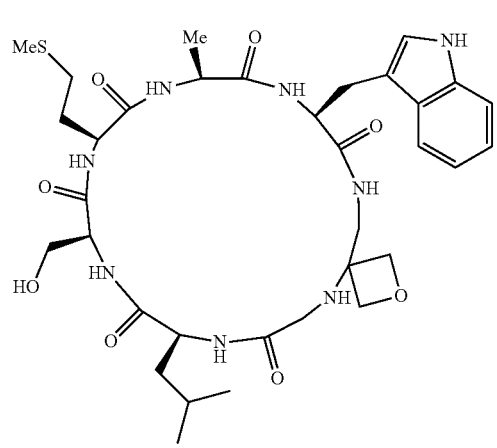

-continued

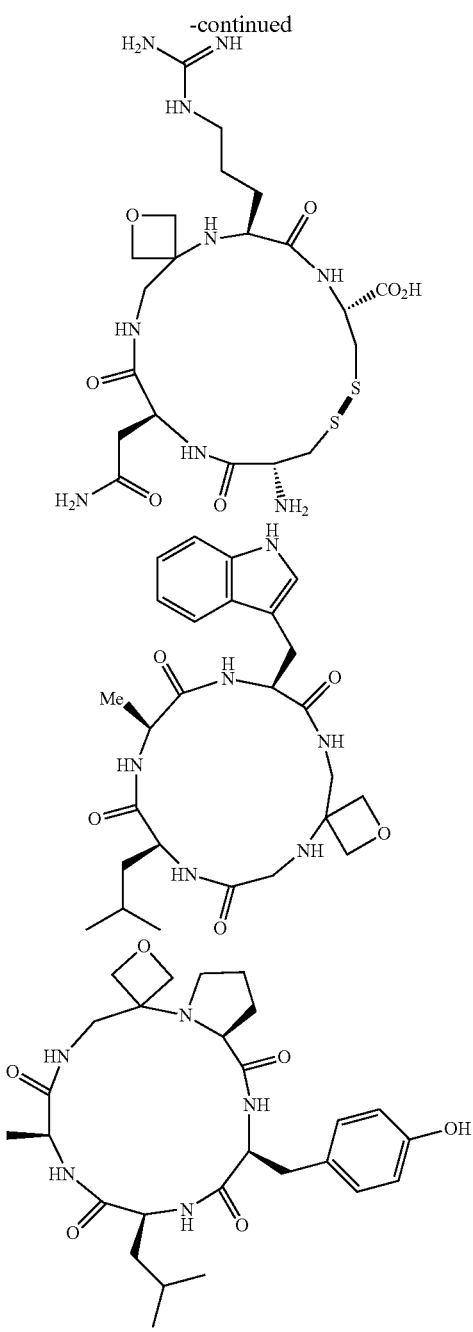

The peptidomimetic macrocycles herein described are synthesised from the corresponding linear peptide (or linear peptide "precursor") which includes the defined turn-inducing element. This is then subjected to a macrocyclisation reaction to form the desired macrocycle.

In another aspect, the invention thus provides a method of synthesising a peptidomimetic macrocycle comprising a turn-inducing element as herein defined, said method comprising the following steps:
 a. synthesising a linear peptidomimetic comprising the turn-inducing element (herein also referred to as the "linear peptide precursor"); and
 b. performing a cyclisation reaction of the linear peptidomimetic.

Methods for the synthesis of linear peptides are well known in the art and include both solution phase and solid phase peptide synthesis (SPPS) methods. Any such methods may be used in preparation of the linear peptide precursor herein described. Starting materials for any of the methods herein described, such as amino acids and amino acid analogues are either known from the literature, commercially available, or may be made by methods known in the literature.

SPPS is generally preferred for use in the preparation of the macrocyclic compounds of the invention. The general principle of this type of synthesis is as follows:

(a) A first N-protected amino acid (the protecting group is commonly t-butoxycarbonyl, abbreviated to Boc) is attached to a solid support (commonly a cross-linked polystyrene resin) at its C-terminal end via an acid labile bond with a linking group (commonly a benzyl ester).

(b) The N-protecting group of the first amino acid is removed (without detachment of the amino acid from the solid support), and a second N-protected amino acid is coupled to the first amino acid (commonly by use of a carbodiimide coupling agent).

(c) This sequence is repeated with the required number of N-protected amino acids until the desired linear peptide has been formed, still attached at its carboxyl end to the solid support.

(d) The N-protecting group of the final amino acid is removed and the resulting linear peptide is separated from the solid support by cleavage of the linking group (for example, using trifluoroethanol, TFE).

In an alternative embodiment, a SPPS method can be carried out by using a C-protected amino acid in which the amino acid is attached to the solid support at its N-terminus via a suitable linking group. The same principles as described for the above N-protected amino acid apply, except that the C-protecting group is removed, a second C-protected amino acid is coupled to the first, and the sequence is repeated as required. The final C-protecting group is then removed and the peptide is separated from the solid support by cleavage of the linking group.

The linear peptide precursor can alternatively be synthesised using conventional solution phase peptide synthesis in which successive amino acids are successively coupled in solution until the desired peptide is formed.

Peptides and amino acids from which peptides are synthesized tend to have reactive side groups as well as reactive terminal ends. When synthesizing a peptide, it is important that the amino group on one peptide reacts with the carboxyl group on another peptide. Undesired reactions at side groups or at the wrong terminal end of an amino acid produce undesirable by-products, sometimes in significant quantities. These can seriously impair yield. To minimize side-reactions, it is conventional practice to appropriately mask reactive side groups and terminal ends of reactants using protecting groups. To avoid side reactions involving an amine group of an amino acid (or peptide), such amine groups can be masked with a protecting group during the coupling reaction. Two well-known amine protecting groups are the Boc group and the Fmoc groups. Many others have also been described in the literature, for example Cbz (benzyloxycarbonyl) and Alloc (allyloxycarbonyl). To avoid side reactions involving a carboxylic acid group of an amino acid (or peptide), such carboxylic acid groups can be masked with a protecting group during the coupling reaction. A well-known carboxylic acid protecting group is the tBu group. Many others have also been described in the literature, for example trityl, 2,4-dimethyoxybenzyl, 9-fluorenylmethyl and benzyl.

To avoid side reactions involving reactive groups on the side-chains of the amino acids (or peptide), additional protecting groups can be used. For example, if the side-chain contains a hydroxyl group, suitable protecting groups such as TBDMS, allyl, o-nitrobenzyl, Bn and tBu can be used. If the side-chain contains a thiol group, protecting groups such as p-methylbenzyl, acetamidomethyl and trityl can be used. If the side-chain contains a guanidino group, protecting groups such as Pbf (2,2,4,6,7-pentamethyl-2,3,-dihydrobenzofuran-5-sulfonyl) and Boc can be used. If the side-chain contains an amide group, protecting groups such as 9-xanthenyl and trityl can be used. If the side-chain contains an imidazole, protecting groups such as tosyl, benzyloxylmethyl, Boc or trityl can be used. If the side-chain contains an indole group, protecting groups such as formyl and Boc can be used. Suitable protecting groups are well known in the art and may readily be selected by those skilled in the art.

The linear peptide precursor containing the turn-inducing element can be made using two distinct methods which are described in more detail herein.

In one method, introduction of the turn-inducing motif (e.g. oxetane or azetidine) can be achieved by (i) conjugate addition of the N-terminus of the growing peptide to 3-(nitromethylene) oxetane or 3-(nitromethylene) azetidine, and (ii) nitro group reduction and in situ coupling of the resulting amine to the next protected amino acid, preactivated as its succinyl ester. This is demonstrated in the scheme below:

In one embodiment, a compound of formula (III) can be employed in synthesising the linear precursor containing the turn inducing element:

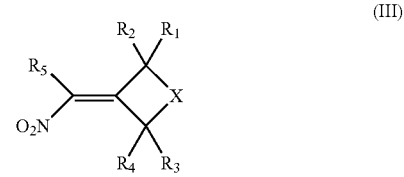

wherein X and $R_1$ to $R_5$ are as herein defined.

In one embodiment of formula (III), X is either O or $NR^b$ where $R^b$ is as herein defined. In another embodiment, each of $R_1$ to $R_5$ is hydrogen.

Examples of the compound of formula (III) include the following:

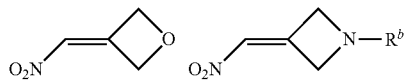

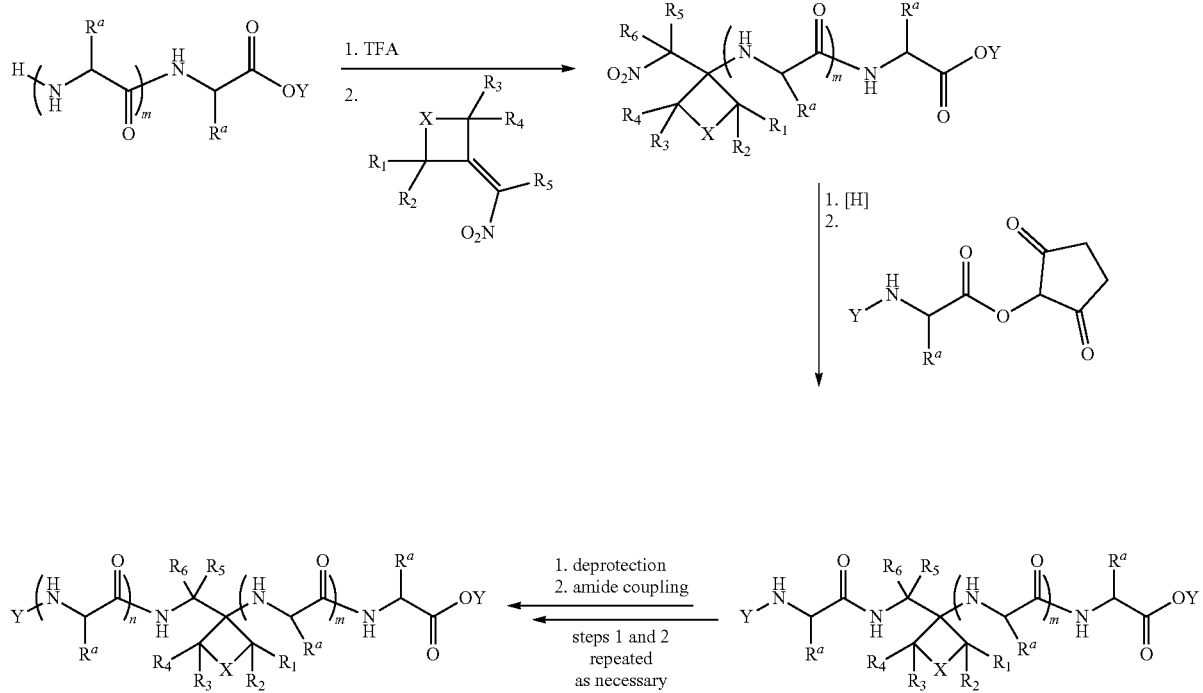

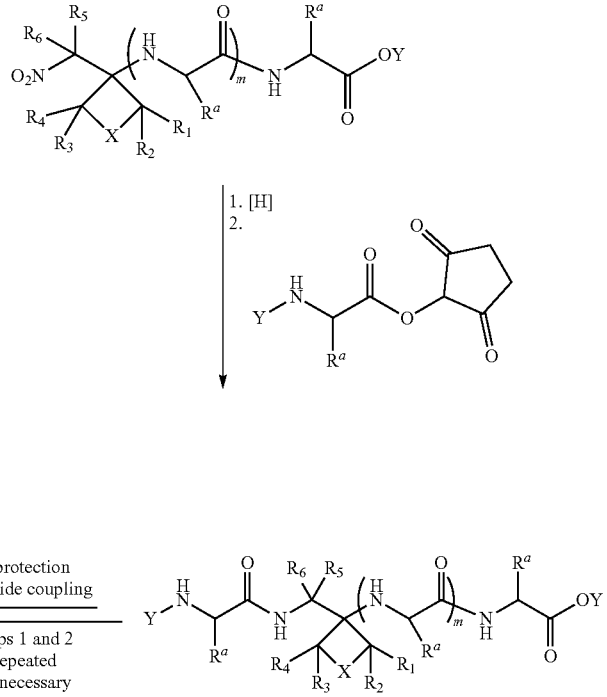

wherein m, n, $R^a$, $R_1$, $R_2$, $R_3$, $R_4$, $R_5$ and X are as defined herein;

$R_6$ is hydrogen; and

Y is any conventional protecting group, such as Boc, Fmoc Cbz (benzyloxycarbonyl), Alloc (allyloxycarbonyl), tBu group, trityl, 2,4-dimethyoxybenzyl, 9-fluorenylmethyl, or benzyl.

wherein $R^b$ is H, alkyl, aryl, heteroaryl, or a removable protecting group such as Boc, Fmoc, or Cbz.

In a further aspect, the invention also provides the use of a reagent of formula (III) to introduce a carbonyl bioisosteric turn-inducing element in the preparation of a peptidomimetic macrocycle as herein defined.

In another method, pre-formed protected dipeptide building blocks containing the turn-inducing element (e.g. oxetane or azetidine) are incorporated into the growing peptide chain. This is demonstrated in the scheme below:

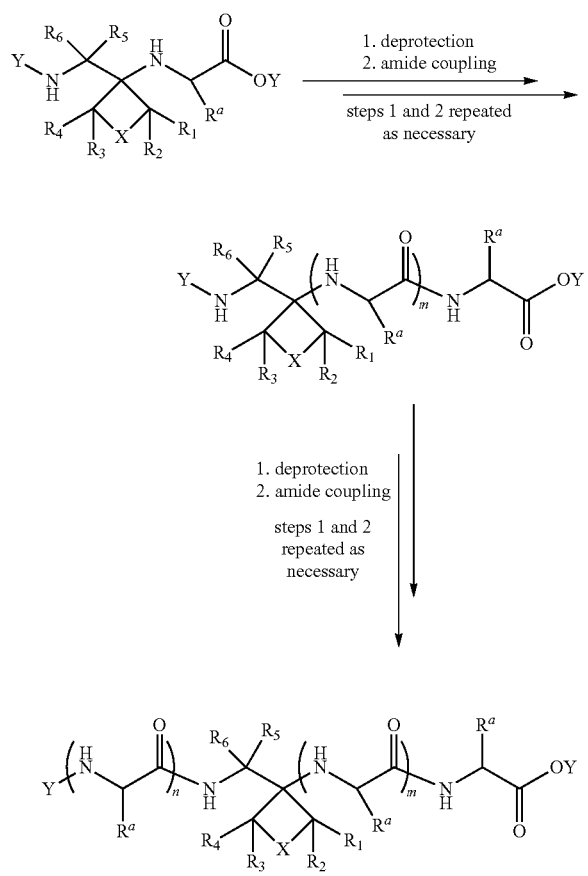

wherein m, n, $R^a$, $R_1$, $R_2$, $R_3$, $R_4$, $R_5$, $R_6$ and X are as defined herein; and Y is any conventional protecting group, such as Boc, Fmoc Cbz (benzyloxycarbonyl), Alloc (allyloxycarbonyl), tBu group, trityl, 2,4-dimethyoxybenzyl, 9-fluorenylmethyl, or benzyl.

Macrocyclisation of the linear peptide precursor which incorporates the turn-inducing element provides the desired peptidomimetic macrocycle. The step of cyclisation may involve any of the following: a head-to-tail reaction; a sidechain-to-sidechain reaction (e.g. one achieved by an amide, ester, thioester, or disulfide bond formation; a head-to-sidechain reaction; or a sidechain-to-tail reaction. Head-to-tail and sidechain-to-sidechain reactions are generally preferred and may be illustrated by way of the following reaction schemes:

Head-to-Tail Reaction:

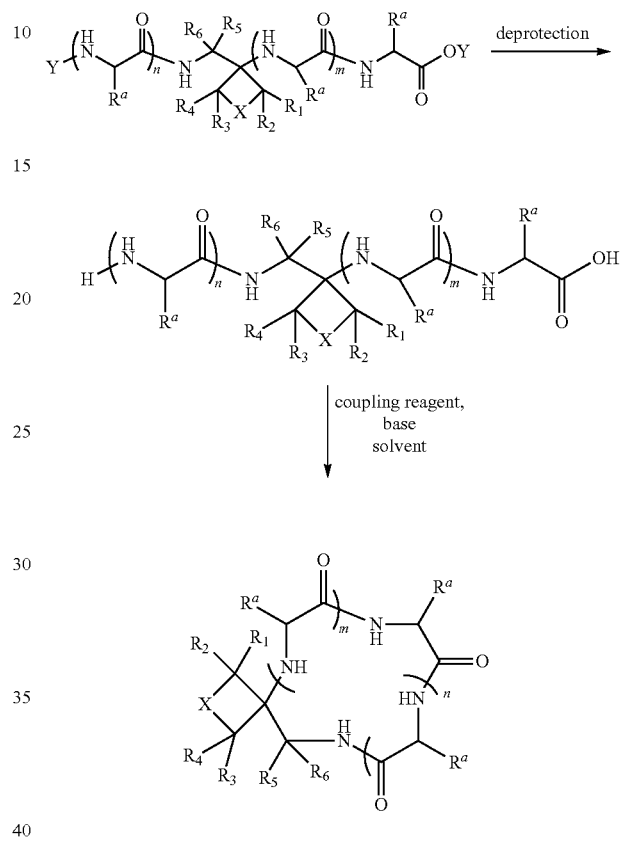

wherein m, n, $R^a$, $R_1$, $R_2$, $R_3$, $R_4$, $R_5$, $R_6$ and X are as herein defined; and Y is any conventional protecting group, such as Boc, Fmoc Cbz (benzyloxycarbonyl), Alloc (allyloxycarbonyl), tBu group, trityl, 2,4-dimethyoxybenzyl, 9-fluorenylmethyl, or benzyl.

Side-Chain-to-Side-Chain Reaction:

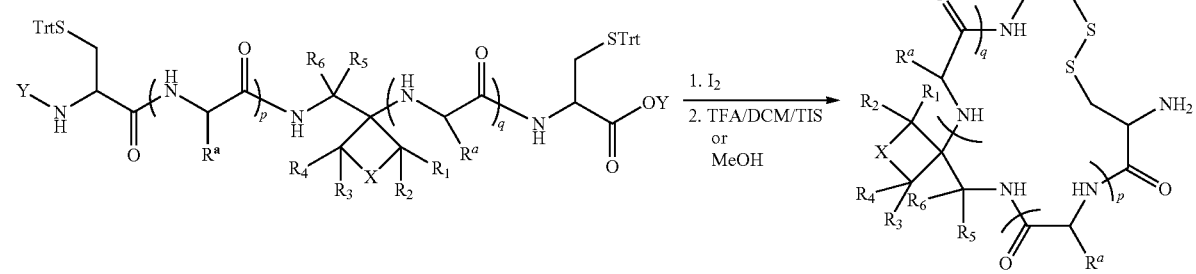

wherein m, n, $R^a$, $R_1$, $R_2$, $R_3$, $R_4$, $R_5$, $R_6$ and X are as defined herein; and Y is any conventional protecting group, such as Boc, Fmoc Cbz (benzyloxycarbonyl), Alloc (allyloxycarbonyl), tBu group, trityl, 2,4-dimethyoxybenzyl, 9-fluorenylmethyl, or benzyl.

In carrying out the macrocyclisation methods herein described, suitable concentrations for the linear peptidomimetic may, for example, range from 0.0001 to 1M, e.g. 0.001 to 1M. It has been found that the presence of the turn-inducing element as herein described may enable the macrocyclisation reaction to be performed at higher concentrations without adversely affecting the yield of the desired macrocycle.

Any of the peptidomimetic macrocycles obtained or obtainable by any of the synthetic methods herein described form a further aspect of the invention.

As discussed herein, a major obstacle to the discovery and development of new cyclic peptide drugs is the current difficulties in their synthesis. The improved methods described herein enable rapid, reliable and efficient synthesis of bioisoteres of known cyclic peptides as well as new cyclic peptide moieties. One application of the technology described herein is in drug discovery in which libraries containing large numbers of cyclic peptides can readily be produced and analysed using known screening methods to determine new drug candidates.

In a further aspect, the invention thus provides a library of compounds for use in drug screening, wherein said library comprises a plurality of peptidomimetic macrocyclic compounds as herein described. Methods of screening carried out in respect of any such library also form part of the invention.

The pharmacological properties of any of the compounds of the invention can be analysed using standard assays for functional activity. Many of the peptidomimetic macrocyclic compounds herein described will have valuable pharmacological properties.

In a further aspect, the invention thus provides a peptidomimetic macrocyclic compound as herein described, or an isomer or pharmaceutically acceptable salt thereof, for use in therapy or for use as a medicament. Unless otherwise specified, the term "therapy" as used herein is intended to include both treatment and prevention.

In another aspect, the invention provides the use of a peptidomimetic macrocyclic compound as herein described, or an isomer or pharmaceutically acceptable salt thereof, in the manufacture of a medicament for use in therapy.

In another aspect, the invention provides a method of medical treatment of a human or non-human animal body to treat or prevent a condition, disease or disorder, said method comprising the step of administering to said body a pharmaceutically effective amount of a peptidomimetic macrocyclic compound as herein described, or an isomer or pharmaceutically acceptable salt thereof.

For use in therapy, any of the compounds herein described may be provided in the form of a pharmaceutically acceptable salt. The term "pharmaceutically acceptable salt" as used herein refers to any pharmaceutically acceptable organic or inorganic salt of any of the compounds herein described. A pharmaceutically acceptable salt may include one or more additional molecules such as counter-ions. The counter-ions may be any organic or inorganic group which stabilises the charge on the parent compound.

If the compound according to the invention is a base, a suitable pharmaceutically acceptable salt may be prepared by reaction of the free base with an organic or inorganic acid. Non-limiting examples of acids which may be used for this purpose include hydrochloric acid, hydrobromic acid, sulfuric acid, sulfonic acid, methanesulfonic acid, phosphoric acid, fumaric acid, succinic acid, lactic acid, citric acid, tartaric acid, maleic acid, acetic acid, trifluoroacetic acid and ascorbic acid. If the compound according to the invention is an acid, a suitable pharmaceutically acceptable salt may be prepared by reaction of the free acid with an organic or inorganic base. Non-limiting examples of bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

When used in therapy, the compounds herein described will typically be administered in the form of a pharmaceutical composition. In a further aspect there is provided a pharmaceutical formulation comprising a peptidomimetic macrocyclic compound as herein described, or an isomer or pharmaceutically acceptable salt thereof, together with one or more pharmaceutically acceptable carriers or excipients.

Pharmaceutical compositions may be formulated in conventional manner using readily available ingredients. Thus, the compounds of the invention may be incorporated with one or more conventional carriers, diluents and/or excipients, to produce a pharmaceutical composition such as conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, etc. Suitable excipients, carriers or diluents are well known to those skilled in the art.

The nature of the therapy will be dependent on the properties of the cyclic peptides herein described, but they may, for example, be used in the treatment or prevention of any of the following: bacterial infections, fungal infections, and cancers.

The precise dosage of the active compound to be administered and the length of the course of treatment will be dependent on a number of factors including for example, the age and weight of the subject, the specific condition requiring treatment and its severity, and the route of administration. Suitable dosages can readily be determined by those of skill in the art.

Results presented herein in respect of the impact of oxetane modification on the bioactivity of the derived macrocyclic peptides indicate that the oxetane motif is an excellent bioisotere of the amide bond that it replaces. This finding is expected to extend to all turn-inducing elements herein described and opens up the possibility for new methods to prepare cyclic peptide drugs in clinical use or which are under clinical evaluation without impacting on their biological activity.

In a broader aspect, the invention thus provides a method for the preparation of a cyclic peptide drug comprising the step of cyclisation of a linear peptide precursor which incorporates one or more turn-inducing elements as herein described. The method may further include the step of preparation of the linear peptide precursor, for example according to any of the methods herein described.

Any bioisotere of a cyclic peptide drug made by such a method also forms part of the invention. In another aspect, the invention thus provides a bioisotere of a cyclic peptide drug which incorporates one or more turn-inducing elements as herein described. As will be understood, as a result of incorporation of a turn-inducing element as described herein, the bioisoteric cyclic peptide drug will be identical to the original drug molecule in all respects except for the replacement of one or more (e.g. one) of the original carbonyl groups by a 4-membered heterocyclic ring which forms part of the turn-inducing element which is described herein, e.g. an optionally substituted oxetane or azetidine ring.

When viewed in this way, the invention can be considered to provide a cyclic peptide drug which comprises at least one moiety having the formula:

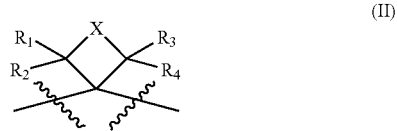

(II)

wherein X, and $R_1$ to $R_4$ are as herein defined.

In one embodiment of formula (II), X is O or $NR^b$, where $R^b$ is selected from H and $C_{1-6}$ alkyl (e.g. methyl).

In one embodiment of formula (II), each of $R_1$ to $R_4$ is independently selected from H and $C_{1-6}$ alkyl (e.g. methyl). In one embodiment, $R_1$ to $R_4$ are all hydrogen.

Any stereoisomer and/or pharmaceutically acceptable salt of a bioisotere of a cyclic peptide drug as herein described also forms part of the invention.

Any cyclic peptide drug in clinical use or in clinical evaluation may be modified as herein described. Such drugs include those listed in the following reviews: Zorzi et al., Current Opinion in Chemical Biology 38: 24-29, 2017 and Nielsen et al., Chem. Rev. 117: 8094-8128, 2017, the entire contents of which are incorporated herein by reference.

Non-limiting examples of cyclic peptide drugs which have been approved by the FDA and EMA and which may be modified as herein described include the following:

Anidulafungin (Vicuron/Pfizer),

Lanreotide (Ipsen),

Telavancin (Theravance),

Romidepsin (Gloucester Pharmaceuticals/Celgene),

Peginesatide (Affymax/Takeda),

Linaclotide (Forest Labs/Ironwood Pharmaceuticals),

Pasireotide (Novartis),

Dalbavancin (Durata Therapeutics/Teva),

Oritavancin (The Medicines Company),

Daptomycin; and

Vancomycin.

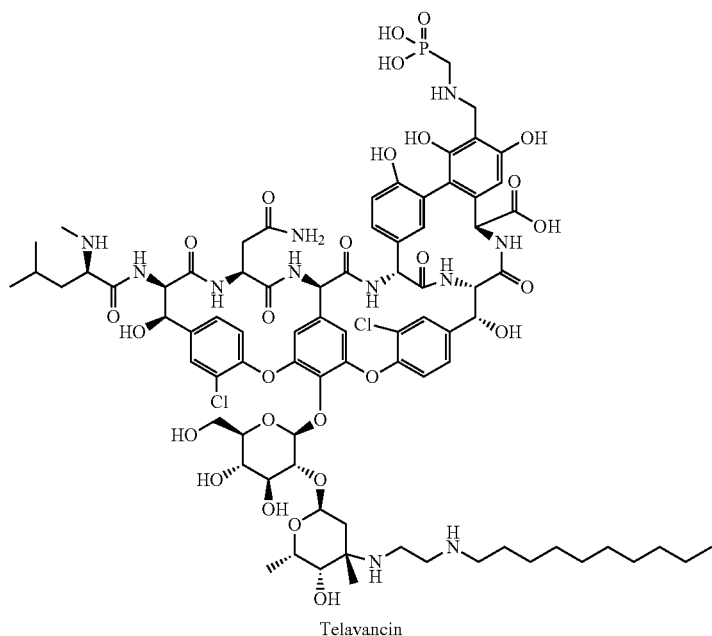

Telavancin

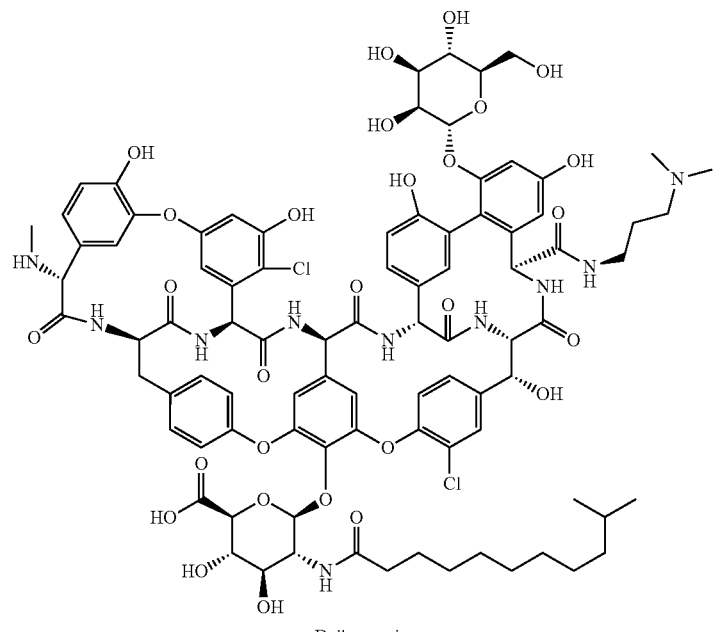
Dalbavancin
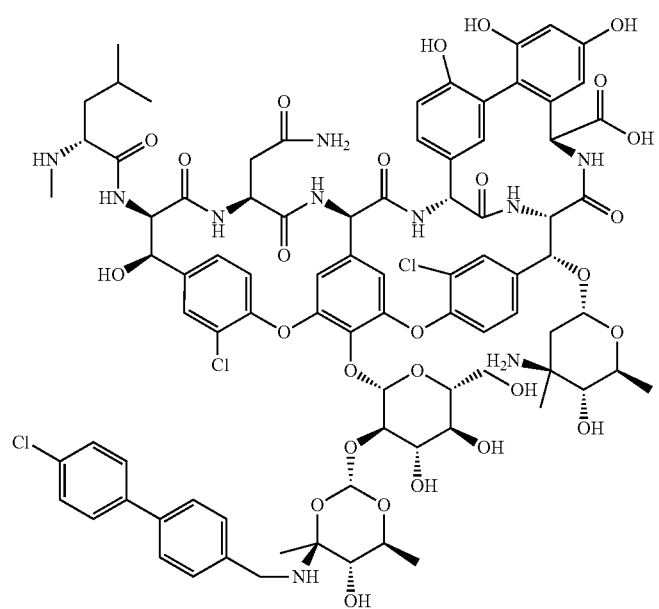
Oritavancin

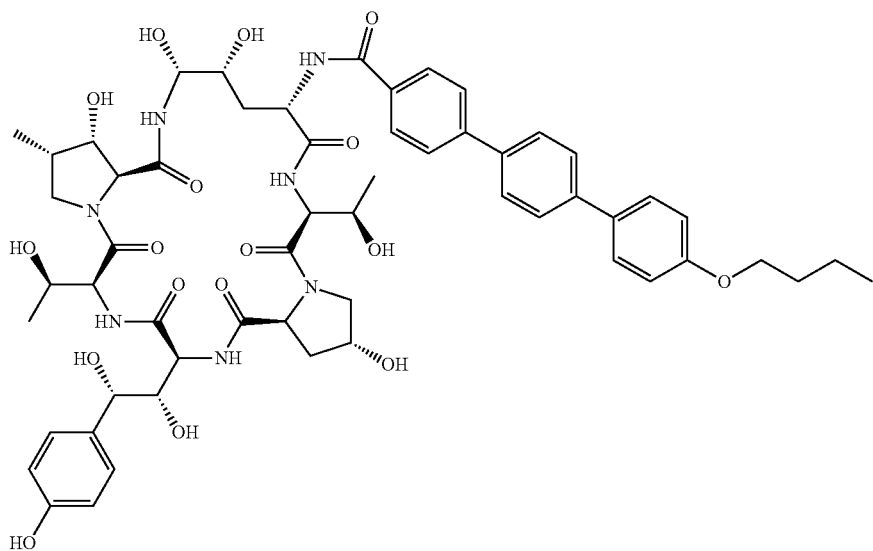
Anidulafungin
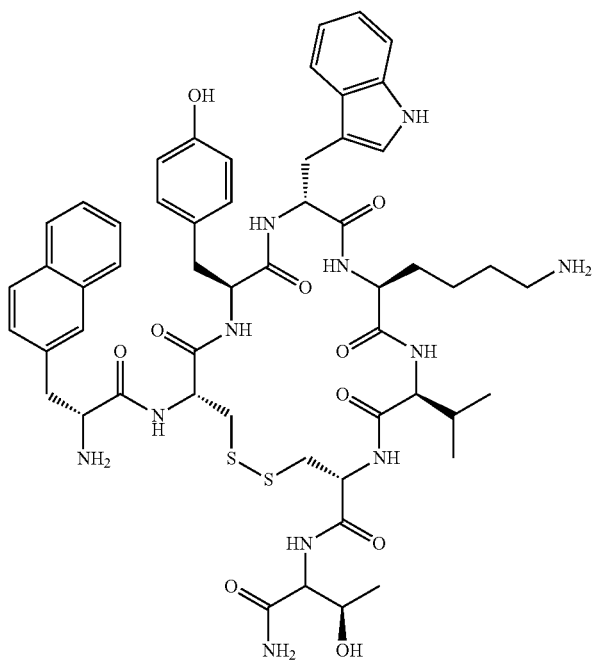
Lanreotide

-continued
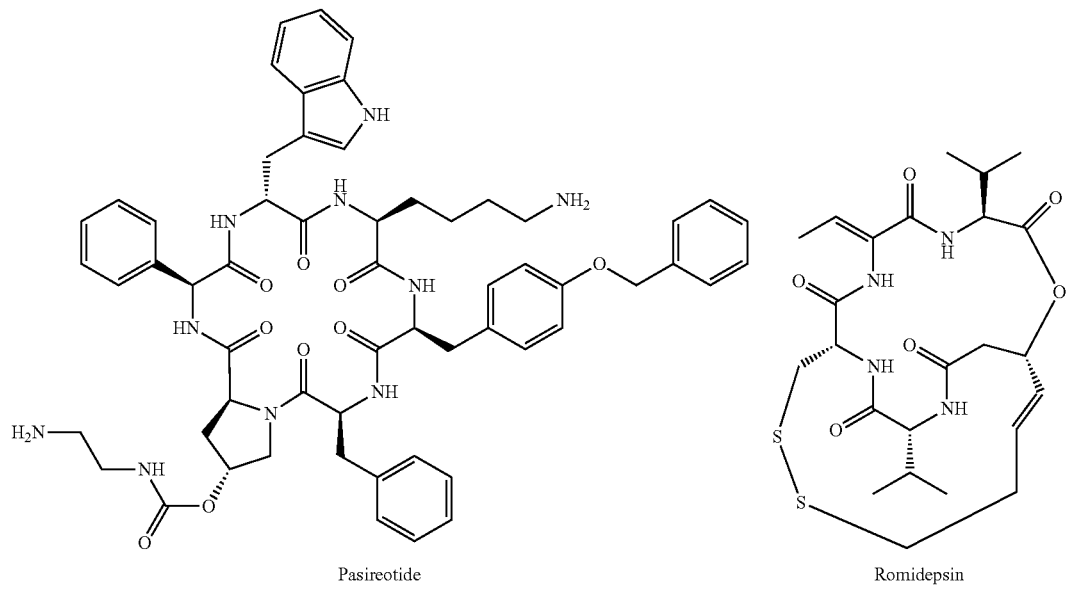
Pasireotide
Romidepsin
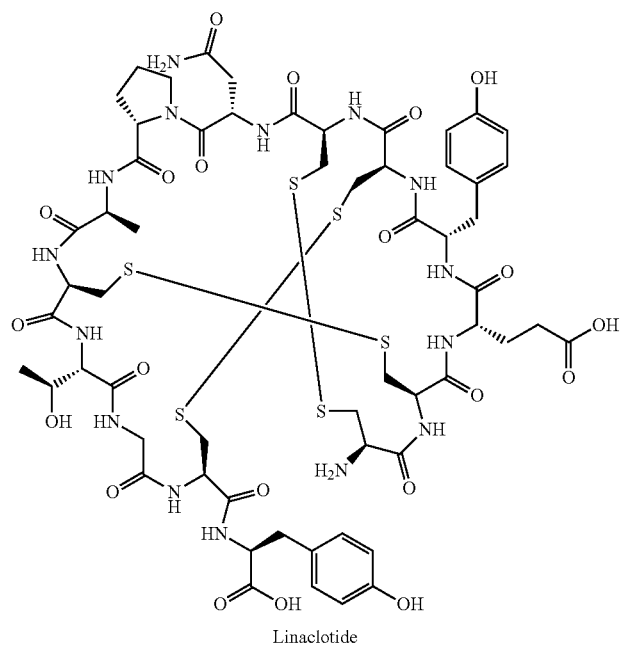
Linaclotide

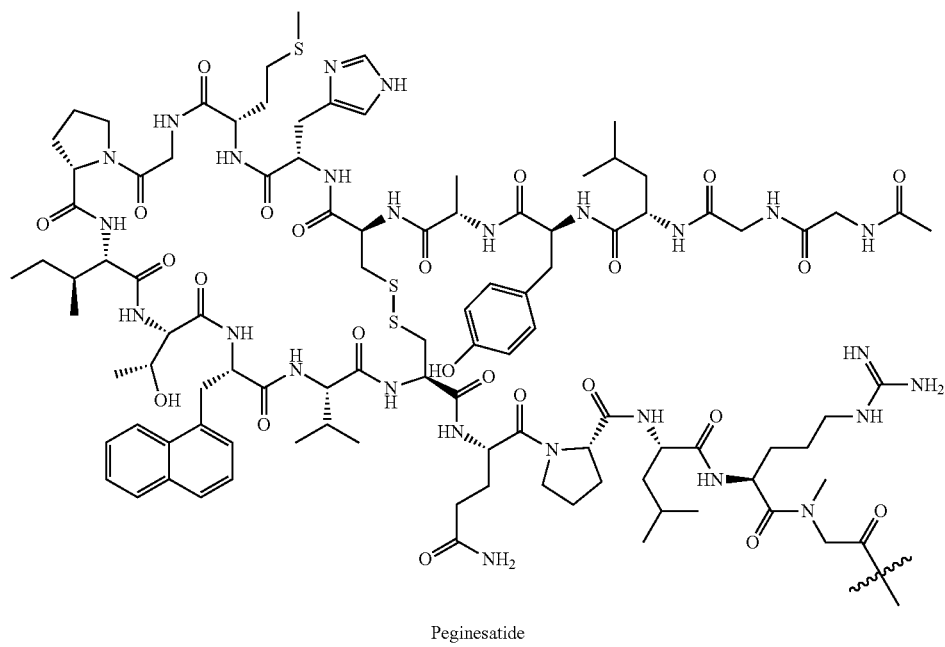

Peginesatide

Other non-limiting examples of cyclic peptide drugs which may be modified as herein described include:

Cyclic tetrapeptides (such as CJ-15208, Apicidin, Chlamydocin, Beauveriolides (e.g. Beauveriolide I and III) and HIV fusion inhibitors);

Cyclic pentapeptides (such as DMP-728, cyclochlorotine and Astin C, BL3020-1, Romidepsin, Largazole, Complement C5aR Antagonists (e.g. 3D53/PMX53), Actinomycin D, Leucine cyclic peptides (e.g. cyclo[(L-Leu)$_5$], cyclo[(L-Leu)$_6$] and cyclo-[(L-Leu)$_5$(D-Leu)]))

Cyclic hexapeptides (such as Desmopressinm Melanotan II, Oxytocin, Anidulafungin, Caspofungin, Micafungin, Somatostatin (e.g. Somatostatin-14), Octreotide, Beauvericine, Enniatins, Nepadutant, Bouvardin, Pristinamycin (e.g. Pristinamycin IA and IIA, NXL103), 1-NMe3, Cyclo-[Arg-Arg-Arg-Arg-NapthylAla-Phe]);

Cyclic heptapeptides (such as Sanguinamide A and Danamides, Rhizonin A, Microcystin LR, YM254890, CHEC-7, Polymyxin B and B$_2$, Bacitracin A);

Cyclic octapeptides (such as PF1022A, Emodepside, WH1Fungin, Griselimycin, Dihydromycoplanecin, Mycoplanecin);

Cyclic nona- and deca-peptides (such as CHEC-9, AFPep, Antamanide, Cyclolinopeptide, Cyclopeptolide 1, Permetin A, Surotomycin);

Cyclic undecapeptides (such as Cyclosporin A, NIM811, THR-123;

Cyclic dodeca- and tridecapeptides (such as cerulide, L-phenylalanine-dipicolinate macrocycle); and Cyclic tetradecapeptides and beyond (such as conotoxins, Duramycin, and Kalata B$_1$).

A particular example of a cyclic peptide drug which may be modified according to the invention is Cyclosporin A:

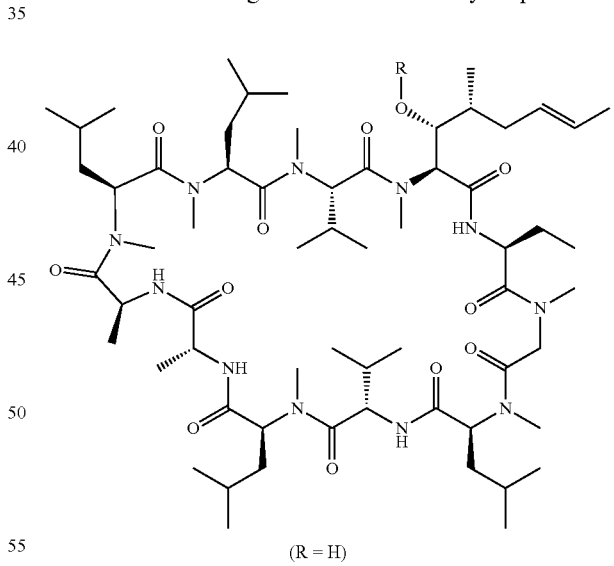

(R = H)

The invention will now be described in more detail by way of the following non-limiting Examples and with reference to the accompanying figures, in which:

FIG. 1—Extracted ion chromatograms of peptide macrocyclizations for 1 to 3 (top) and 2 to 4 (bottom);

FIG. 2—Spectra of Cyclo(Trp-Leu-Gly-Gly) (33);

FIG. 3—Spectra of Cyclo(Trp-Leu-GOx-Gly) (5);

FIG. 4—Spectra for Cyclo(Ala-GOx-Ala-Tyr-Leu) (8);

FIG. 5—Spectra for Cyclo(Ala-Gly-Ala-Tyr-Leu) (10);

FIG. 6—Spectra of Cyclo(H-Cys-Asn-GOx-Arg-Cys-OH (12);

FIG. 7—Spectra of Cyclo(Boc-Cys-GOx-Cys-OtBu) (13);

FIG. 8—a. Inhibition of APN by oxetane modified peptide 12. The shown data are the average of two independent experiments performed in duplicate. Error bars are displaying standard deviations. b. Inhibition of APN by parent peptide 15. The shown data are the average of two independent experiments performed in duplicate and triplicate, respectively. Error bars are displaying standard deviations;

FIG. 9—Conversion of linear peptides 6 & 7 to cyclic peptides 8 & 9 and dimer 42 over 74 hours;

FIG. 10—LCMS traces for oxetane and azetidine-containing cyclic peptides in TFA after 24 hours.

EXAMPLES

General Experimental Information

Reaction mixtures were stirred magnetically. All chemicals were purchased from Acros Organics, Alfa Aesar, Fluorochem or Sigma-Aldrich and used as received unless otherwise mentioned. Preloaded 2-chlorotrityl resins were purchased from Merck, the polymer matrix is copoly (styrene-1% DVB), 200-400 mesh. TNBS test kit picrylsulfonic acid (ca. 1% in DMF) 10 mL/N,N-diisopropylethylamine (ca. 10% in DMF) 10 mL for detection of primary amines was purchased from TC Chemicals. Anhydrous solvents were purchased from Sigma-Aldrich or Acros Organics in Sure-Seal™ bottles. All other solvents were reagent grade and used as received. Petroleum ether refers to the fraction that boils in the range of 40-60° C. $^1$H Nuclear Magnetic Resonance (NMR) spectra were recorded in $CDC_3$, $CD_3OD$ or DMSO-$d_6$, using a Bruker HD400 (400 MHz), AV500 (500 MHz) or AV600 (600 MHz) Fourier transform spectrometer. Chemical shifts (δH) are quoted in parts per million (ppm) and referred to the residual protic solvent signals of CDCl3 (7.26 ppm), $CD_3OD$ (3.31 ppm) or DMSO-$d_6$ (2.50 ppm). 1H NMR coupling constants are reported in hertz and refer to apparent multiplicities. Data are reported as follows: chemical shift, multiplicity (s=singlet, br. s=broad singlet, d=doublet, t=triplet, q=quartet, quint=quintet, sext=sextet, sept=septet, m=multiplet, dd=doublet of doublet, etc.), coupling constant, integration, and assignment. $^{13}$C NMR spectra were recorded at 101, 126 or 151 MHz. Chemical shifts (SC) are quoted in ppm referenced to CHCl$_3$ (77.16 ppm), $CD_3OD$ (49.00 ppm) or DMSO-d6 (39.52 ppm). NMR assignments were deduced using 2D experiments (COSY, HSQC and HMBC). NH and OH are not visible in protic solvents (CD$_3$OD). In most cases, Azetidinyl amine NH (in the $^1$H) and the quaternary azetidine carbon (in the $^{13}$C) is missing, and other selected missing peaks are noted on a compound by compound basis. Low-resolution mass spectra were recorded on an Agilent 6130B single Quad (ESI) instrument. High resolution mass spectra were recorded using a Bruker MaXis Impact. All infrared spectra were recorded on the neat compounds using a Bruker ALPHA-Platinum FTIR spectrometer, irradiating between 4000 cm$^{-1}$ and 600 cm$^{-1}$. Only strong and selected absorbances ($v_{max}$) are reported. Analytical TLC was performed on aluminium backed silica plates (Merck, Silica Gel 60 F254, 0.25 mm). Compounds were visualised by fluorescence quenching or by staining the plates with 10% solution of phosphomolybdic S3 acid (H$_3$PMo$_{12}$O$_{40}$) in EtOH or 1% solution of potassium permanganate (KMnO$_4$) in water followed by heating. Flash column chromatography was performed on silica gel (Aldrich or Fluorochem, Silica Gel 60, 40-63 μm). All mixed solvent eluents are reported as v/v solutions. Optical rotations were obtained using an AA1000 polarimeter at 589 nm (Na D-line) in a cell with a path length of 2 dm. Specific rotation values are given in (deg mL)/(g dm). Melting points were measured with a Gallenkamp melting point apparatus.

Example 1—Synthesis of Head-to-Tail Cyclisations

Initially, a general route for the synthesis of linear peptides containing the carbonyl bioisoteric turn-inducing element in the backbone was developed as illustrated below for pentapeptide 1:

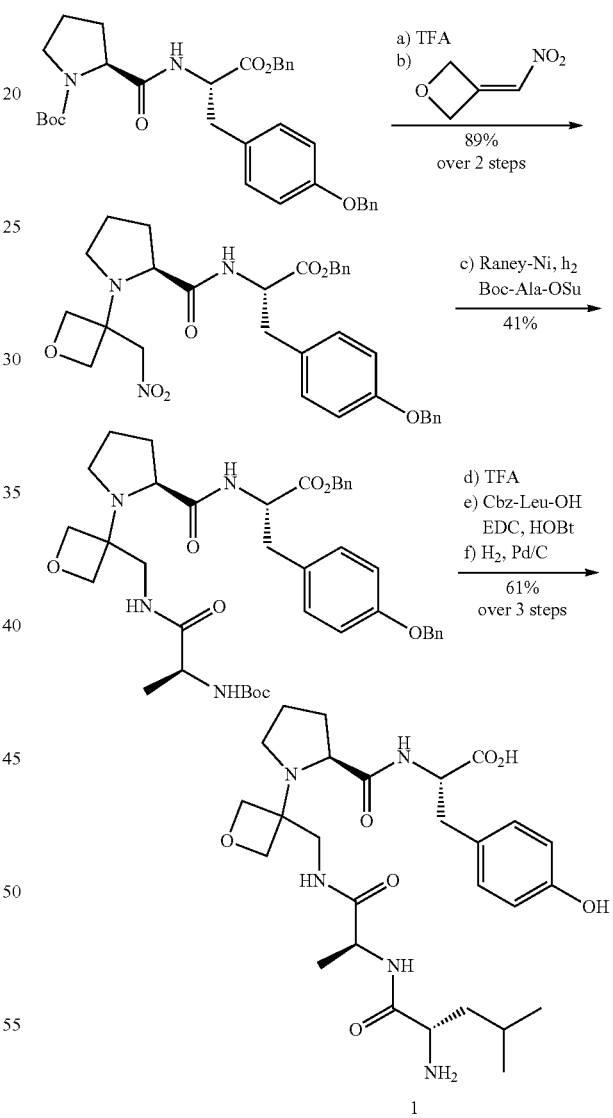

Turn-inducing element introduction was achieved by: (i) conjugate addition of the N-terminus of the growing peptide to the appropriately substituted nitroalkene (e.g. 3-(nitromethylene)oxetane); (ii) nitro group reduction and in situ coupling of the resulting amine to the next protected amino acid, preactivated as its succinyl ester.[7,11] Conventional peptides (e.g. 2) were made for comparison purposes. For all head-to-tail cyclizations, Bn ester/Z-protection of the C- and N-termini was used to allow synthesis of salt-free precursors by use of a final hydrogenolysis step. This enabled reliable comparisons in product yields to be made across different substrates.

The impact of the introduction of this turn-inducing element on macrocyclization, ring closure of 1 to 3 was studied under a variety of conditions (see Table 1, entries 1-5). This substrate was chosen because the cyclization of the corresponding unmodified pentapeptide 2 to 4 is very low yielding even under high dilution (Table 1, entries 6-8).[12] Upon introduction of the turn-inducing modification, a 3-fold yield improvement was observed. Best results were obtained using PyBOP (Table 1, entry 3), although DEPBT and HATU are also effective. Of practical importance, the reaction can be conducted on a larger scale (0.5 mmol) under less dilute conditions (0.005 M) without loss of yield (Table 1, entry 1).

TABLE 1

Impact of oxetane modification on the cyclization efficiency of a pentapeptide.

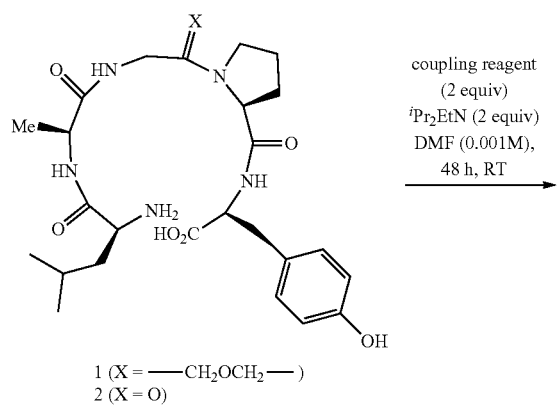

1 (X = —CH$_2$OCH$_2$—)
2 (X = O)

3 (X = —CH$_2$OCH$_2$—)
4 (X = O)

| entry | substrate[a] | coupling reagent[b] | product | yield (%)[c] |
|---|---|---|---|---|
| 1 | 1 | DEPBT | 3 | 48 (50)[d] |
| 2 | 1 | DEPBT[e] | 3 | 33 |
| 3 | 1 | PyBOP | 3 | 60 |
| 4 | 1 | HATU | 3 | 53 |
| 5 | 1 | T3P | 3 | 28 |
| 6 | 2 | DEPBT | 4 | 13[f] |
| 7 | 2 | PyBOP | 4 | 23 |
| 8 | 2 | HATU | 4 | 15 |

[b]3-(Diethoxy-phosphoryloxy)-1,2,3,-benzotriazin-4(3H)-one (DEPBT); O-(7-azabenzotriazol-1-yl)-N,N,N',N'-tetramethyluronium hexafluorophosphate (HATU); benzotriazol-1-yloxytri(pyrrolidino) phosphonium hexafluorophosphate (PyBOP); 1-propylphosphonic anhydride (T3P).
[c]Isolated yield after column chromatography.
[d]Yield in parenthesis relates to larger scale reaction (0.5 mmol) run at higher concentration (0.005M).
[e]$^i$Pr$_2$EtN omitted.
[f]Taken from ref 12.

Insights into the impact of the turn-inducing element introduction on the efficiency of this macrocydization were revealed by LC-MS analysis (see FIG. 1). In the formation of 4, there are significant quantities of unreacted linear pentapeptide 2 even after 48 h. In contrast, for turn-inducing element containing 1, essentially complete consumption of starting material is seen on this timescale. The reaction is also much cleaner with fewer by-products. In the cyclization to 4, linear and cyclic decapeptides arising from substrate dimerization alongside a second cyclic pentapeptide are evident (FIG. 1, bottom). In contrast, these by-products are seen in only trace quantities in the formation of 3 (FIG. 1, top). Thus, significant improvements in this difficult macrocydization can be realized through introduction of the turn-inducing element.

To determine the scope of this chemistry, other head-to-tail macrocyclizations were studied:

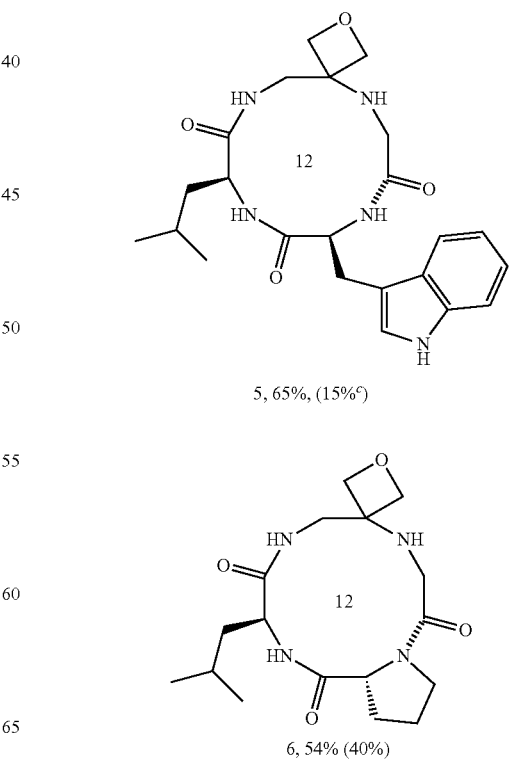

5, 65%, (15%[c])

6, 54% (40%)

-continued

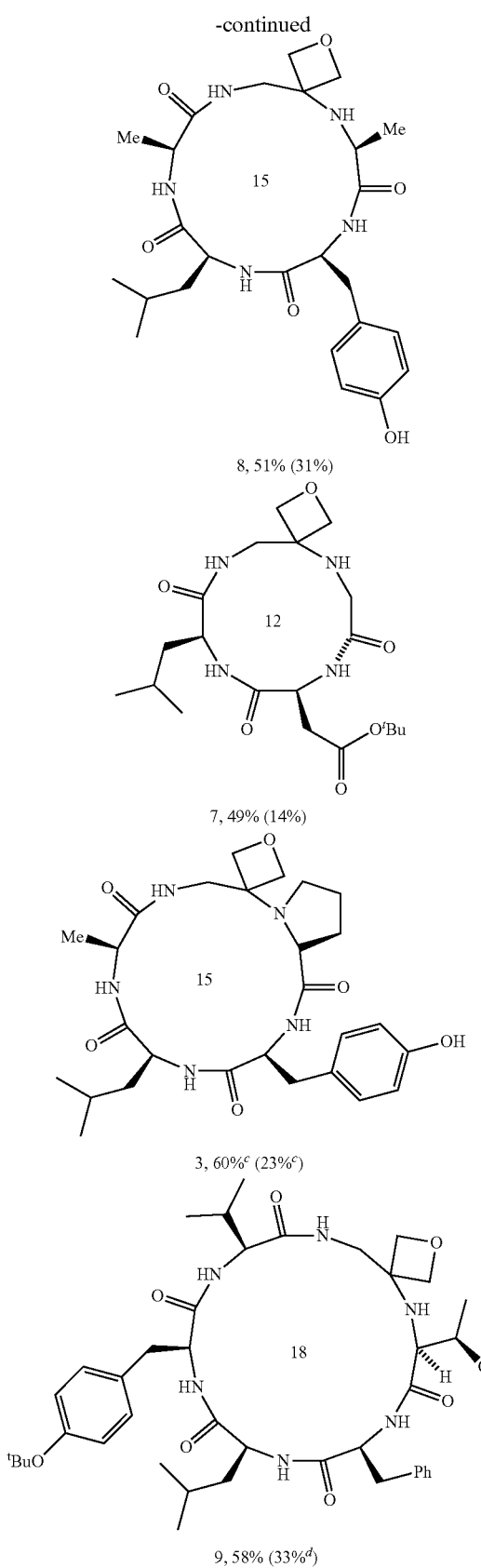

8, 51% (31%)

7, 49% (14%)

3, 60%[c] (23%[c])

9, 58% (33%[d])

Oxetane modified cyclic peptides by head-to-tail macrocyclization. [b] Bond formed in macrocyclization indicated in bold in the ring; yield in parenthesis for the cyclization of linear peptide with C=O rather than oxetane in backbone. [c] PyBOP as activator. [d] DMTMM tetrafluoroborate as activator.

Data taken from ref 13.

Tetrapeptides 5-7, pentapeptide 8 and hexapeptide 9 all cyclize in higher yields than the corresponding unmodified peptides.

Example 1a—Detailed Example for Previous Cyclization Methods without the Carbonyl Bioisosteric Turn-Inducing Element Preparation of Cyclic Tetrapeptides 33, 36, and 39:

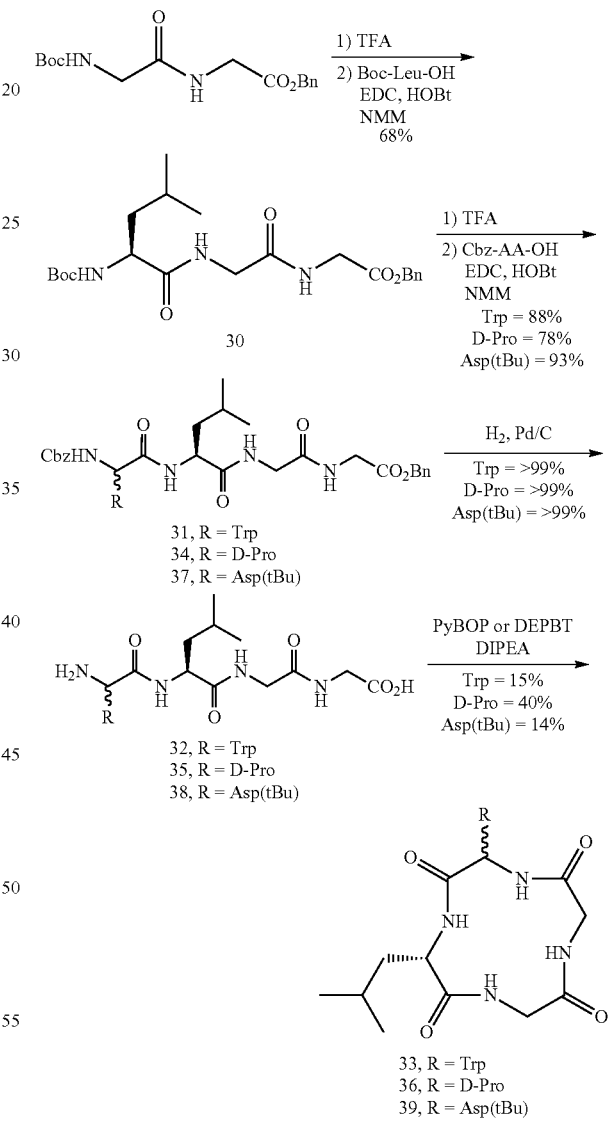

Boc-Leu-Gly-Gly-OBn (30): To a solution of dipeptide TsOH·H-Gly-Gly-OBn[3] (3.94 g, 10.0 mmol, 1.0 equiv) in $CH_2Cl_2$ (100 mL) was added Boc-Leu-OH (2.43 g, 10.5 mmol, 1.05 equiv), EDC·HCl (2.01 g, 10.5 mmol, 1.05 equiv), HOBt·$H_2O$ (1.42 g, 10.5 mmol, 1.05 equiv) and NMM (4.40 mL, 40.0 mmol, 4.0 equiv), and the mixture was stirred at room temperature for 24 h. The mixture was diluted with EtOAc (100 mL) and washed with brine (3×100 mL), dried over $Na_2SO_4$, filtered and concentrated in vacuo. The residue was purified by column chromatography ($SiO_2$, $CH_2Cl_2$/EtOAc 1:1→EtOAc) to give Boc-Leu-Gly-Gly-OBn (30) (2.98 g, 6.84 mmol, 68%) as a white solid.

Cbz-Trp-Leu-Gly-Gly-OBn (31): To a solution of Boc-Leu-Gly-Gly-OBn (30) (0.93 g, 2.15 mmol, 1.0 equiv) in $CH_2Cl_2$ (2.5 mL) was added TFA (2.5 mL) and the mixture was stirred at room temperature for 1 h (Gas evolution!). The mixture was concentrated under reduced pressure and the resulting residue repeatedly dissolved in $CH_2Cl_2$ (3×25 mL) and concentrated in vacuo to give the crude amine. The residue was dissolved in $CH_2Cl_2$ (22 mL), Cbz-Trp-OH (0.73 g, 2.15 mmol, 1.0 equiv), EDC·HCl (0.41 g, 2.15 mmol, 1.0 equiv), HOBt·$H_2O$ (0.29 g, 2.15 mmol, 1.0 equiv) and NMM (0.95 mL, 8.60 mmol, 4.0 equiv) were added, and the mixture was stirred at room temperature for 24 h. The mixture was diluted with EtOAc (25 mL) and washed with brine (3×25 mL), dried over $Na_2SO_4$, filtered and concentrated in vacuo. The residue was purified by column chromatography ($SiO_2$, $CH_2Cl_2$/MeOH 40:1) to give Cbz-Trp-Leu-Gly-Gly-OBn (31) (1.21 g, 1.89 mmol, 88%) as a white solid.

H-Trp-Leu-Gly-Gly-OH (32): To a solution of tetrapeptide Cbz-Trp-Leu-Gly-Gly-OBn (31) (900 mg, 1.37 mmol, 1.0 equiv) in MeOH (15 mL) was added 10 wt % Pd/C (90 mg, 10 wt %) and the reaction flask was evacuated, filled with nitrogen, evacuated, and placed under an atmosphere of hydrogen (balloon). The reaction mixture was stirred at room temperature for 16 h, placed under nitrogen and filtered through a plug of Celite, which was washed with MeOH (3×). The filtrate was concentrated in vacuo to give H-Trp-Leu-Gly-Gly-OH (32) as a white solid (590 mg, 1.37 mmol, quant. yield), which required no further purification.

Cyclo(Trp-Leu-Gly-Gly) (33): To a solution of H-Trp-Leu-Gly-Gly-OH (32) (86 mg, 0.20 mmol, 1.0 equiv) in anhydrous DMF (200 mL, 0.001 M) under an atmosphere of nitrogen was added PyBOP (208 mg, 0.40 mmol, 2.0 equiv) and DIPEA (70 µL, 0.40 mmol, 2.0 equiv) and the mixture was stirred for 48 h at room temperature. The solvent was removed under reduced pressure, and the residue was purified twice by column chromatography ($SiO_2$, DCM/MeOH 92.5:7.5→4:1) to give cyclic tetrapeptide 33 as a yellow solid (13 mg, 31 µmol, 15%). $R_f$ ($CH_2Cl_2$/MeOH 9:1) 0.20; mp 216-219° C.; $^1$H NMR (500 MHz, $CD_3OD$) $\delta_H$ 7.59 (d, J=7.9 Hz, 1H, ArH), 7.36 (d, J=8.1 Hz, 1H, ArH), 7.20 (s, 1H, ArH), 7.11 (t, J=7.5 Hz, 1H, ArH), 7.02 (t, J=7.5 Hz, 1H, ArH), 4.55 (dd, J=8.2, 5.2 Hz, 1H, CHα-Trp), 4.20 (dd, J=10.6, 4.4 Hz, 1H, CHα-Leu), 4.01 (d, J=16.8 Hz, 1H, CHHGly), 3.86 (d, J=16.1 Hz, 1H, CHHGly), 3.74 (d, J=16.1 Hz, 1H, CHHGly), 3.65 (d, J=16.8 Hz, 1H, CHHGly), 3.39-3.34 (m, 1H, CHHβ-Trp), 3.23 (dd, J=14.9, 8.3 Hz, 1H, CHHβ-Trp), 1.73-1.65 (m, 1H, CHHβ-Leu), 1.54 (ddd, J=13.9, 9.6, 4.5 Hz, 1H, CHHβ-Leu), 1.36-1.26 (m, 1H, CHγ-Leu), 0.84 (d, J=6.6 Hz, 3H, $CH_3$δ-Leu), 0.78 (d, J=6.6 Hz, 3H, $CH_3$δ-Leu); $^{13}$C NMR (126 MHz, $CD_3OD$) δc 175.7 (C=O), 174.9 (C=O), 173.0 (C=O), 172.6 (C=O), 138.1 (C), 128.6 (C), 124.7 (CH), 122.6 (CH), 120.0 (CH), 119.2 (CH), 112.4 (CH), 110.5 (C), 56.8 (CH, α-Trp), 54.0 (CH, α-Leu), 44.1 ($CH_2$, Gly), 43.4 ($CH_2$, Gly), 40.6 ($CH_2$, β-Leu), 27.9 ($CH_2$, β-Trp), 25.7 (CH, γ-Leu), 23.7 ($CH_3$, δ-Leu), 21.6 ($CH_3$, δ-Leu); $v_{max}$ (neat)=3298, 2869, 1645, 1522, 1234, 742 cm$^{-1}$; MS (ESI$^+$) m/z 849 [2M+Na]$^+$; HRMS (ESI$^+$) calcd. for $C_{42}H_{54}N_{10}NaO_8$ [2M+Na]$^+$ 849.4018. found 849.4020. $[α]_D^{27}$ −16.6 (c 0.04, MeOH). Spectra in FIG. 2.

Example 1b—Detailed Example of a Head-to-Tail Cyclisation for a Tetrapeptide

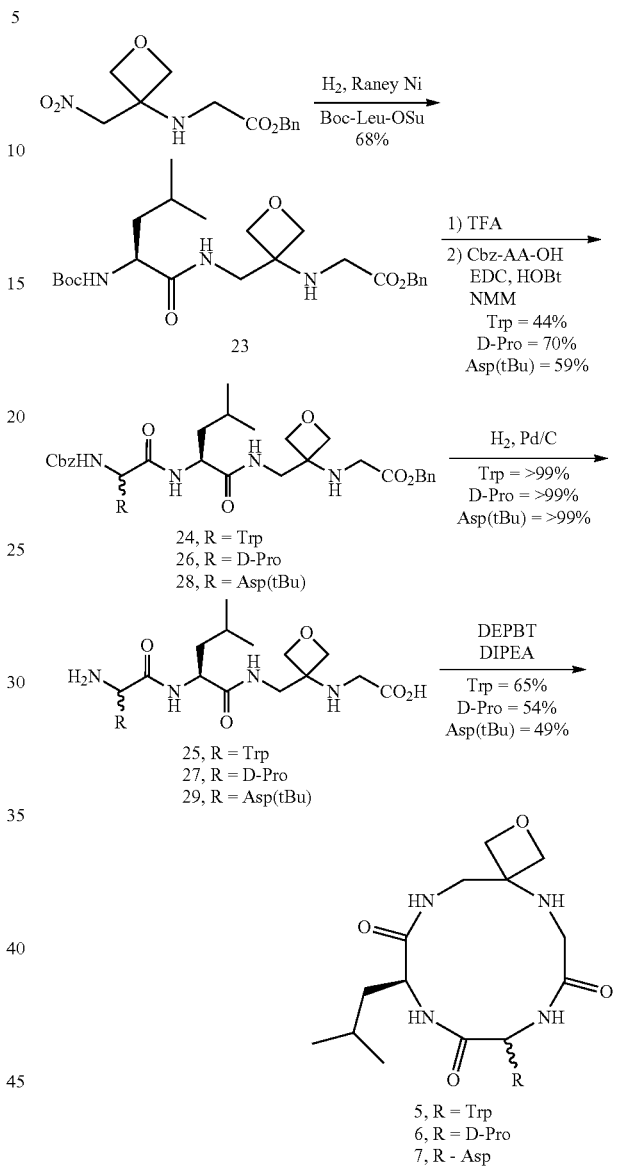

Boc-Leu-GOx-Gly-OBn (23): To a solution of $NO_2$-GOx-Gly-OBn[2] (1.70 g, 6.06 mmol, 1.0 equiv) in THF (60 mL) was added Boc-Leu-OSu (2.98 g, 9.09 mmol, 1.5 equiv) and Raney Ni (slurry in $H_2O$, 6.0 mL). The solution was placed under an atmosphere of nitrogen, evacuated and filled with hydrogen (balloon). The reaction mixture was stirred vigorously for 4.0 h at room temperature. Then, the mixture was filtered through a plug of Celite eluting with EtOAc, concentrated under reduced pressure, the filtrate was suspended in EtOAc (50 mL), washed with saturated $Na_2CO_3$ (3×50 mL), dried over $Na_2SO_4$ and concentrated in vacuo. Boc-Leu-GOx-Gly-OBn (23) was afforded after purification by column chromatography ($SiO_2$, EtOAc/PE 3:2) as a colourless viscous oil (1.91 g, 4.13 mmol, 68%).

Cbz-Trp-Leu-GOx-Gly-OBn (24): To a solution of tripeptide Boc-Leu-GOx-Gly-OBn 23 (1.29 g, 2.79 mmol, 1.0 equiv) in $CH_2Cl_2$ (3.0 mL) was added TFA (3.0 mL) and the mixture was stirred at room temperature for 1 h (Caution—gas evolution!). The reaction mixture was concentrated under reduced pressure and the resulting residue repeatedly dissolved in CH$_2$Cl$_2$ (3×25 mL) and concentrated under reduced pressure to give the crude amine. The residue was dissolved in a mixture of CH$_2$Cl$_2$ (30 mL), Cbz-Trp-OH (0.94 g, 2.79 mmol, 1.0 equiv), EDC·HCl (0.53 g, 2.79 mmol, 1.0 equiv), HOBt·H$_2$O (0.38 g, 2.79 mmol, 1.0 equiv) and NMM (1.23 mL, 11.2 mmol, 4.0 equiv) were added subsequently, and the reaction mixture was stirred at room temperature for 24 h. The reaction mixture was diluted with EtOAc (30 mL) and washed with brine (30 mL), dried over Na$_2$SO$_4$, filtered and concentrated under reduced pressure. The residue was purified by column chromatography (SiO$_2$, 49:1 CH$_2$Cl$_2$/MeOH) to give tetrapeptide Cbz-Trp-Leu-GOx-Gly-OBn (24) (834 mg, 1.22 mmol, 44%) as a colourless viscous oil.

H-Trp-Leu-GOx-Gly-OH (25): To a solution of tetrapeptide Cbz-Trp-Leu-GOx-Gly-OBn (24) (683 mg, 1.00 mmol, 1.0 equiv) in MeOH (10 mL) was added 10 wt % Pd/C (68 mg, 10 wt %) and the reaction flask was evacuated, filled with nitrogen, evacuated, and placed under an atmosphere of hydrogen (balloon). The reaction mixture was stirred at room temperature for 16 h, placed under nitrogen and filtered through a plug of Celite, which was washed with MeOH (3×). The filtrate was concentrated in vacuo to give tetrapeptide H-Trp-Leu-GOx-Gly-OH (25) as a yellow solid (458 mg, 1.00 mmol) in quantitative yield.

Cyclo(Trp-Leu-GOx-Gly) (5): To a solution of tetrapeptide H-Trp-Leu-GOx-Gly-OH (25) (46 mg, 0.10 mmol, 1.0 equiv) in anhydrous DMF (100 mL, 0.001 M) under an atmosphere of nitrogen was added DEPBT (60 mg, 0.10 mmol, 2.0 equiv) and DIPEA (35 μL, 0.10 mmol, 2.0 equiv) and the reaction mixture was stirred for 48 h at room temperature. The solvent was removed under reduced pressure at 60° C. over 30 min, and the residue was dried in vacuo. The residue was analysed by LCMS and purified twice by column chromatography (SiO$_2$, CH$_2$Cl$_2$/MeOH 19:1→9:1) to give cyclic tetrapeptide (5) as a yellow solid (29 mg, 65 μmol, 65%). R$_f$ (CH$_2$Cl$_2$/MeOH 9:1) 0.41; mp 200-203° C.; $^1$H NMR (500 MHz, DMSO-d6) δ$_H$ 10.87 (s, 1H, NH), 8.25 (d, J=10.4 Hz, 1H, NH), 7.97 (d, J=9.1 Hz, 1H, NH), 7.56-7.50 (m, 2H, NH, ArH), 7.34 (d, J=8.0 Hz, 1H, ArH), 7.11 (s, 1H, ArH), 7.08 (t, J=7.5 Hz, 1H, ArH), 7.00 (t, J=7.4 Hz, 1H, ArH), 4.59 (q, J=9.3 Hz, 1H, CHα-Trp), 4.41 (d, J=6.3 Hz, 1H, OCHH-Ox), 4.18 (d, J=6.9 Hz, 1H, OCHH-Ox), 4.15 (d, J=6.3 Hz, 1H, OCHH-Ox), 4.04-3.97 (m, 1H, CHα-Leu), 3.90 (d, J=6.9 Hz, 1H, OCHH-Ox), 3.81 (dd, J=13.3, 7.7 Hz, 1H, CHHGly or CHHGOx), 3.43-3.37 (m, 1H, CHHGly or CHHGOx), 3.26-3.18 (m, 2H, CHHGly or CHHGOx, CHHβ-Trp), 3.07-2.97 (m, 2H, CHHGly or CHHGOx, CHHβ-Trp), 1.65-1.57 (m, 2H, CHHβ-Leu, CHγ-Leu), 1.53-1.45 (m, 1H, CHHβ-Leu), 0.92 (d, J=6.1 Hz, 3H, CH$_3$δ-Leu), 0.79 (d, J=6.1 Hz, 3H, CH$_3$δ-Leu). N.B. Secondary amine NH not observed; $^{13}$C NMR (126 MHz, DMSO-d6) δ$_C$ 173.2 (C=O), 172.9 (C=O), 171.4 (C=O), 136.1 (C), 127.1 (C), 123.0 (CH), 121.0 (CH), 118.3 (CH), 118.1 (CH), 111.4 (CH), 109.5 (C), 78.1 (OCH$_2$), 76.3 (OCH$_2$), 60.3 (C, Ox), 56.0 (CH, α-Trp), 54.0 (CH, α-Leu), 47.3 (CH$_2$, GOx or CH$_2$, Gly), 44.2 (CH$_2$, GOx or CH$_2$, Gly), 39.2 (CH$_2$, β-Leu), 26.5 (CH$_2$, β-Trp), 24.6 (CH, γ-Leu), 22.8 (CH$_3$, δ-Leu), 21.3 (CH$_3$, δ-Leu); ν$_{max}$ (neat)=3278, 2954, 1660, 1516, 740 cm$^{-1}$; MS (ESI$^+$) m/z 464 [M+Na]$^+$; HRMS (ESI$^+$) calcd. for C$_{23}$H$_{31}$N$_5$NaO$_4$ [M+Na]$^+$ 464.2268. found 464.2270. [α]$_D^{26}$ −60.3 (c 0.01, MeOH). See FIG. 3.

Example 2—the Effect of the Location of the Turn-Inducing Motif on Macrocyclic Yield Macrocyclization to pentapeptide 8 (from pentapeptides 44, 49, 54, and 61) by formation of all four possible amide bonds was examined to see whether the location of the turn-inducing element relative to the amide bond being formed is important:

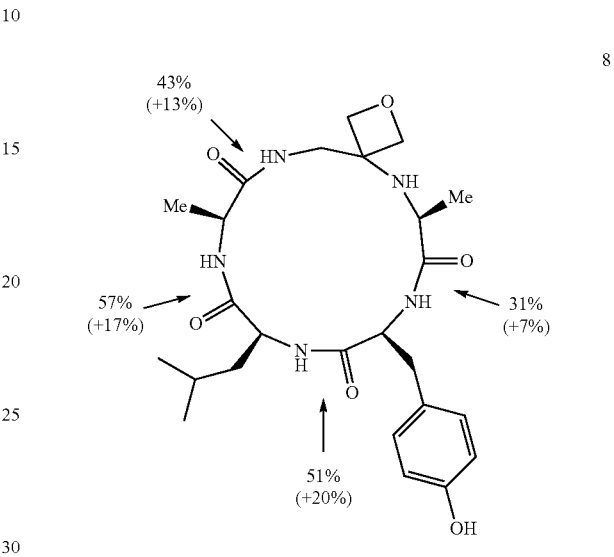

8

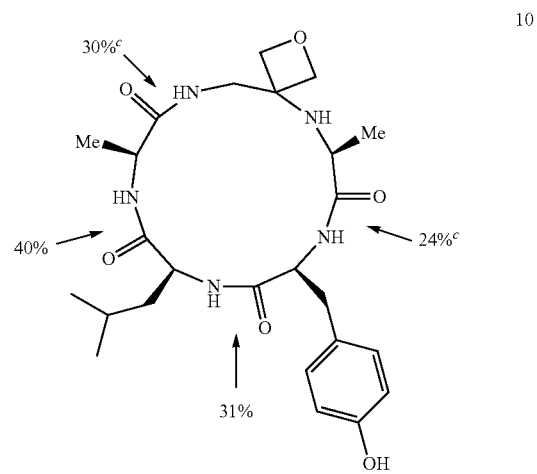

10

Macrocyclization efficiency as a function of location of oxetane relative to forming amide bond.[b] Average of two runs. [c] Taken from ref 12

The yields were compared with those obtained making pentapeptide 10 by the same disconnections. This approach removes inherent differences in cyclization efficiency associated with amide bond formation between different amino acid residues. For all four pairs of cyclization studied, the turn-inducing-modified system outperformed the C=O system leading to higher product yields. However, it appears that larger improvements are seen when the modification is more centrally located along the precursor backbone.

Details of Macrocyclisation to Pentapeptide 8
Preparation of Pentapeptide 44:

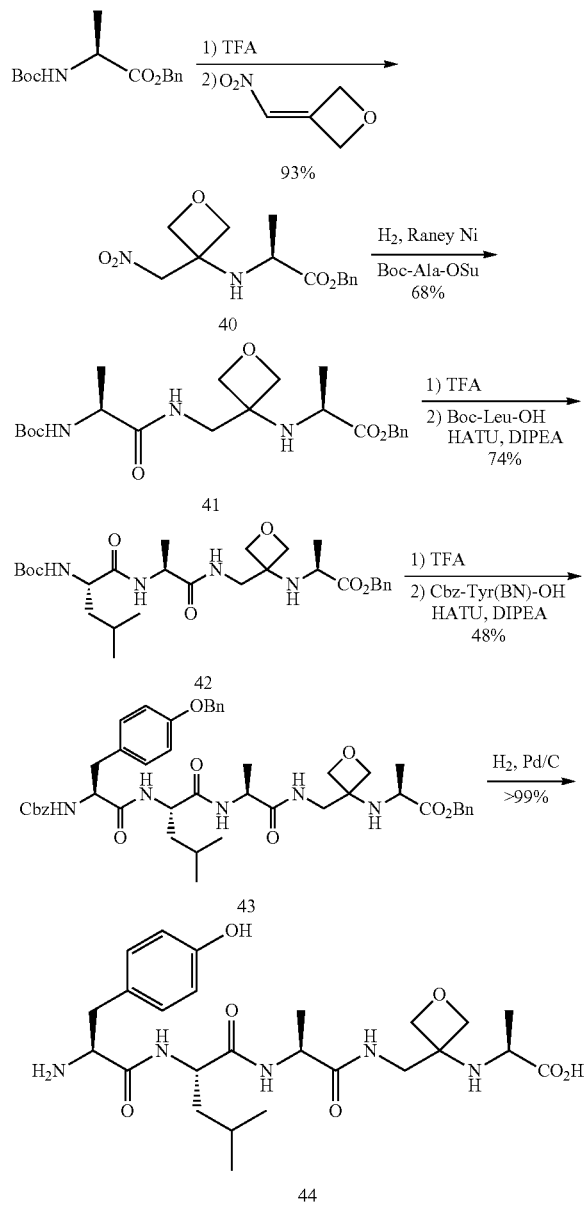

NO$_2$-GOx-Ala-OBn (40): To a solution of Boc-Ala-OBn (3.36 g, 12.0 mmol, 1.0 equiv) in CH$_2$Cl$_2$ (12 mL) was added TFA (12 mL) and the mixture was stirred at room temperature for 1 h. The mixture was concentrated under reduced pressure and the resulting residue repeatedly dissolved in CH$_2$Cl$_2$ (3×20 mL) and concentrated in vacuo to give the crude amine. In a second reaction vessel, oxetane-3-one (1.54 mL, 24.0 mmol, 2.0 equiv), nitromethane (1.82 mL, 33.6 mmol, 2.8 equiv) and triethylamine (670 µL, 4.80 mmol, 0.4 equiv) were combined at 0° C. and stirred for 1 h at room temperature. The mixture was dissolved in anhydrous CH$_2$Cl$_2$ (40 mL), cooled to −78° C., and triethylamine (6.70 mL, 48.0 mmol, 4.0 equiv) was added followed by dropwise addition of a solution of methanesulfonyl chloride (1.86 mL, 24.0 mmol, 2.0 equiv) in anhydrous CH$_2$Cl$_2$ (12 mL). The reaction mixture was stirred at −78° C. for 1.5 h and a solution of the crude amine and triethylamine (2.52 mL, 18.0 mmol, 1.5 equiv) in anhydrous CH$_2$Cl$_2$ (40 mL) was added slowly via syringe. The reaction mixture was allowed to warm to room temperature and stirred for 16 h. A saturated solution of NH$_4$Cl (50 mL) was added and stirred for 10 min. The layers were separated and the aqueous one extracted with CH$_2$Cl$_2$ (2×30 mL) and EtOAc (2×30 mL). The combined organic phases were washed with sat. NaHCO$_3$ solution (50 mL), brine (50 mL), dried over MgSO$_4$, filtered and concentrated in vacuo. The residue was purified by column chromatography (SiO$_2$, PE/EtOAc 2:1→1:1) to give 40 (3.28 g, 11.1 mmol, 93%) as an orange oil.

Boc-Ala-GOx-Ala-OBn (41): To a solution of NO$_2$-GOx-Ala-OBn (40) (3.18 g, 10.8 mmol, 1.0 equiv) in THF (108 mL) was added Boc-Ala-OSu (6.18 g, 21.6 mmol, 2.0 equiv), NaHCO$_3$ (3.63 g, 43.2 mmol, 4.0 equiv) and Raney Ni (slurry in H$_2$O, 22 mL). The solution was placed under an atmosphere of nitrogen, evacuated and filled with hydrogen (balloon). The reaction mixture was stirred vigorously for 4.0 h at room temperature. Then, the mixture was filtered through a plug of Celite eluting with EtOAc, the filtrate was washed with saturated Na$_2$CO$_3$ (3×50 mL) and concentrated in vacuo. Boc-Ala-GOx-Ala-OBn (41) was afforded after purification by column chromatography (SiO$_2$, PE/EtOAc 1:1→EtOAc) as a pale-yellow oil (3.20 g, 7.34 mmol, 68%).

Boc-Leu-Ala-GOx-Ala-OBn (42): To a solution of Boc-Ala-GOx-Ala-OBn (41) (915 mg, 2.10 mmol, 1.0 equiv) in CH$_2$Cl$_2$ (2.5 mL) was added TFA (2.5 mL) and the mixture was stirred at room temperature for 1 h. The reaction mixture was concentrated under reduced pressure and the resulting residue repeatedly dissolved in CH$_2$Cl$_2$ (3×10 mL) and concentrated under reduced pressure to give the crude amine. The residue was dissolved in CH$_2$Cl$_2$ (21 mL), Boc-Leu-OH (583 mg, 2.50 mmol, 1.2 equiv), HATU (958 mg, 2.50 mmol, 1.2 equiv) and DIPEA (1.46 mL, 8.40 mmol, 4.0 equiv) were added subsequently, and the reaction mixture was stirred at room temperature for 16 h. The reaction mixture was diluted with CH$_2$Cl$_2$ (30 mL) and washed with 10% citric acid solution (2×50 mL) and saturated NaHCO$_3$ solution (2×50 mL), dried over MgSO$_4$, filtered and concentrated under reduced pressure. The residue was purified by flash column chromatography (SiO$_2$, EtOAc) to give tetrapeptide 42 (855 mg, 1.56 mmol, 74%) as an off-white solid.

Cbz-Tyr(Bn)-Leu-Ala-GOx-Ala-OBn (43): To a solution of Boc-Leu-Ala-GOx-Ala-OBn (42) (637 mg, 1.16 mmol, 1.0 equiv) in CH$_2$Cl$_2$ (2.0 mL) was added TFA (2.0 mL) and the mixture was stirred at room temperature for 1 h. The mixture was concentrated under reduced pressure and the resulting residue repeatedly dissolved in CH$_2$Cl$_2$ (3×10 mL) and concentrated under reduced pressure to give the crude amine. The residue was dissolved in CH$_2$Cl$_2$ (12 mL), Cbz-Tyr(Bn)-OH (565 mg, 1.39 mmol, 1.2 equiv), HATU (565 mg, 1.39 mmol, 1.2 equiv) and DIPEA (808 µL, 4.64 mmol, 4.0 equiv) were added, and the reaction mixture was stirred at room temperature for 16 h. The reaction mixture was diluted with CH$_2$Cl$_2$ (20 mL) and washed with 10% citric acid solution (2×30 mL) and saturated NaHCO$_3$ solution (2×30 mL), dried over MgSO$_4$, filtered and concentrated under reduced pressure. The residue was purified by flash column chromatography (SiO$_2$, CH$_2$Cl$_2$/MeOH 19:1→9:1) to give pentapeptide 43 (463 mg, 0.55 mmol, 48%) as an off-white solid.

H-Tyr-Leu-Ala-GOx-Ala-OH (44): To a solution of pentapeptide 43 (348 mg, 0.42 mmol) in anhydrous MeOH (4.0 mL) was added 10 wt % Pd/C (35 mg, 10 wt %) and the reaction flask was evacuated, filled with nitrogen, evacuated, and placed under an atmosphere of hydrogen (balloon). The reaction mixture was stirred at room temperature for 16 h, placed under nitrogen and filtered through a plug of Celite, which was washed with MeOH (3×). The filtrate was concentrated in vacuo to give 44 as an off-white solid (273 mg, >99%), which required no further purification.

Preparation of Pentapeptide 49:

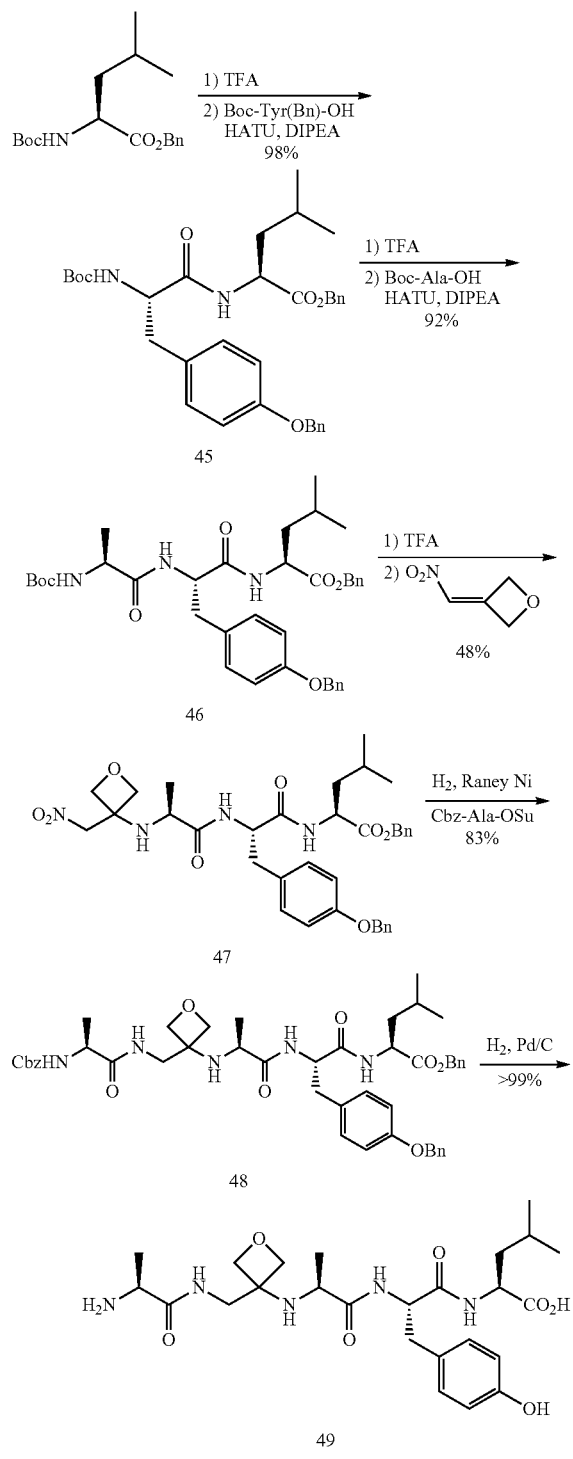

Boc-Tyr(Bn)-Leu-OBn (45): To a solution of Boc-Leu-OBn (8.04 g, 25.0 mmol, 1.0 equiv) in $CH_2Cl_2$ (25 mL) was added TFA (25 mL) and the mixture was stirred at room temperature for 1 h. The reaction mixture was concentrated under reduced pressure and the resulting residue repeatedly dissolved in $CH_2Cl_2$ (3×20 mL) and concentrated under reduced pressure to give the crude amine. The residue was dissolved in $CH_2Cl_2$ (250 mL), Boc-Tyr(Bn)-OH (11.1 g, 30.0 mmol, 1.2 equiv), HATU (11.4 g, 30.0 mmol, 1.2 equiv) and DIPEA (17.4 mL, 100 mmol, 4.0 equiv) were added subsequently, and the reaction mixture was stirred at room temperature for 16 h. The reaction mixture was washed with 10% citric acid solution (2×100 mL) and saturated $NaHCO_3$ solution (2×100 mL), dried over $MgSO_4$, filtered and concentrated under reduced pressure. The residue was purified by column chromatography ($SiO_2$, PE/EtOAc 2:1→1:1) to give dipeptide 45 (14.1 g, 24.5 mmol, 98%) as a white solid.

Boc-Ala-Tyr(Bn)-Leu-OBn (46): To a solution of Boc-Tyr(Bn)-Leu-OBn (45) (12.9 g, 22.5 mmol, 1.0 equiv) in $CH_2Cl_2$ (22.5 mL) was added TFA (22.5 mL) and the mixture was stirred at room temperature for 1 h. The reaction mixture was concentrated under reduced pressure and the resulting residue repeatedly dissolved in $CH_2Cl_2$ (3×20 mL) and concentrated in vacuo to give the crude amine. The residue was dissolved in $CH_2Cl_2$ (225 mL), Boc-Ala-OH (5.11 g, 27.0 mmol, 1.2 equiv), HATU (10.3 g, 27.0 mmol, 1.2 equiv) and DIPEA (15.7 mL, 90.0 mmol, 4.0 equiv) were added, and the mixture was stirred at room temperature for 16 h. The reaction mixture was washed with 10% citric acid solution (2×100 mL) and saturated $NaHCO_3$ solution (2×100 mL), dried over $MgSO_4$, filtered and concentrated under reduced pressure. The residue was purified by column chromatography ($SiO_2$, PE/EtOAc 1:1) to give tripeptide 46 (13.4 g, 20.7 mmol, 92%) as a white foam.

$NO_2$-GOx-Ala-Tyr(Bn)-Leu-OBn (47): To a solution of Boc-Ala-Tyr(Bn)-Leu-OBn (46) (3.87 g, 6.00 mmol, 1.0 equiv) in $CH_2Cl_2$ (6.0 mL) was added TFA (6.0 mL) and the mixture was stirred at room temperature for 1 h. The reaction mixture was concentrated under reduced pressure and the resulting residue repeatedly dissolved in $CH_2Cl_2$ (3×10 mL) and concentrated under reduced pressure to give the crude amine. In a second reaction vessel, oxetane-3-one (770 µL, 12.0 mmol, 2.0 equiv), nitromethane (910 µL, 16.8 mmol, 2.8 equiv) and triethylamine (335 µL, 2.40 mmol, 0.4 equiv) were combined at 0° C. and stirred for 1 h at room temperature. The mixture was dissolved in anhydrous $CH_2Cl_2$ (20 mL), cooled to −78° C., and triethylamine (3.35 mL, 24.0 mmol, 4.0 equiv) was added followed by dropwise addition of a solution of methanesulfonyl chloride (930 µL, 12.0 mmol, 2.0 equiv) in anhydrous $CH_2Cl_2$ (6.0 mL). The reaction mixture was stirred at −78° C. for 1.5 h and a solution of the crude amine and triethylamine (1.26 mL, 9.0 mmol, 1.5 equiv) in anhydrous $CH_2Cl_2$ (20 mL) was added slowly via syringe. The reaction mixture was allowed to warm to room temperature and stirred for 16 h. A saturated solution of $NH_4Cl$ (30 mL) was added and stirred for 10 min. The layers were separated and the aqueous one extracted with $CH_2Cl_2$ (2×20 mL) and EtOAc (2×20 mL). The combined organic phases were washed with saturated aqueous $NaHCO_3$ solution (30 mL), brine (30 mL), dried over $MgSO_4$, filtered and concentrated under reduced pressure. The residue was purified by column chromatography ($SiO_2$, PE/EtOAc 1:1→EtOAc) to give 47 (1.90 g, 2.88 mmol, 48%) as an off-white solid.

Cbz-Ala-GOx-Ala-Tyr(Bn)-Leu-OBn (48): To a solution of $NO_2$-GOx-Ala-Tyr(Bn)-Leu-OBn (47) (1.26 g, 1.90 mmol, 1.0 equiv) in THF (20 mL) was added Cbz-Ala-OSu (1.22 g, 3.80 mmol, 2.0 equiv), NaHCO$_3$ (638 mg, 7.60 mmol, 4.0 equiv) and Raney Ni (slurry in H$_2$O, 4.0 mL). The solution was placed under an atmosphere of nitrogen, evacuated and filled with hydrogen (balloon). The mixture was stirred for 2.5 h at room temperature, filtered through a plug of Celite eluting with EtOAc, and the filtrate was concentrated in vacuo. Pentapeptide 48 was afforded after purification by column chromatography (SiO$_2$, EtOAc-CH$_2$Cl$_2$/MeOH 9:1) as an off-white foam (989 mg, 1.18 mmol, 83%).

H-Ala-GOx-Ala-Tyr-Leu-OH (49): To a solution of pentapeptide 48 (1.75 g, 2.09 mmol) in anhydrous MeOH (21 mL) was added 10 wt % Pd/C (175 mg, 10 wt %) and the reaction flask was evacuated, filled with nitrogen, evacuated, and placed under an atmosphere of hydrogen (balloon). The reaction mixture was stirred at room temperature for 16 h, placed under nitrogen and filtered through a plug of Celite, which was washed with MeOH (3×). The filtrate was concentrated in vacuo to give 49 as a white solid (1.14 g, >99%), which required no further purification.

Preparation of Pentapeptide 54:

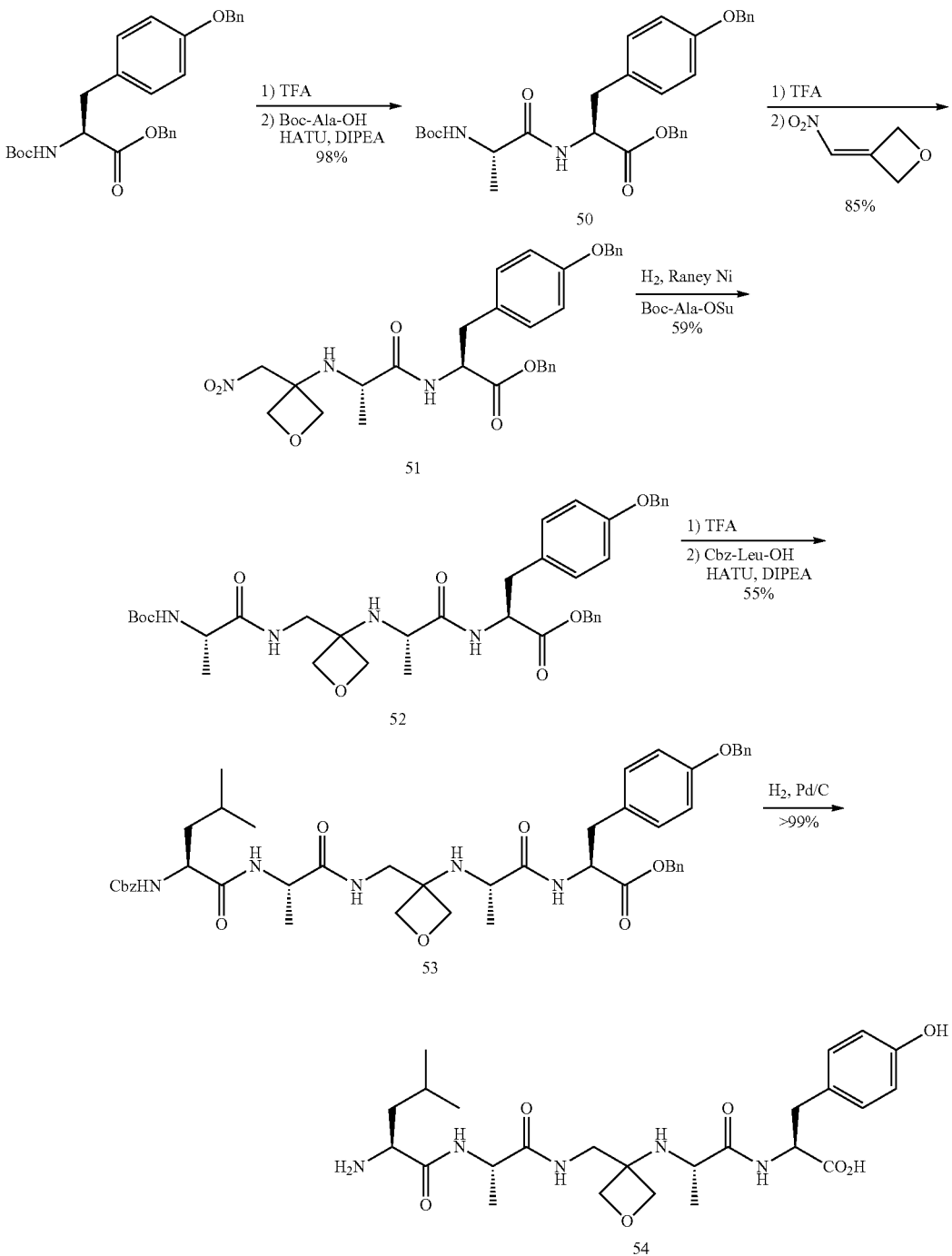

Boc-Ala-Tyr(Bn)-OBn (50): To a solution of Boc-Tyr (Bn)-OBn (11.3 g, 25.0 mmol, 1.0 equiv) in CH$_2$Cl$_2$ (25 mL) was added TFA (25 mL) and the mixture was stirred at room temperature for 30 min (Caution—gas evolution!). The reaction mixture was concentrated under reduced pressure and the resulting residue repeatedly dissolved in CH$_2$Cl$_2$ (3×20 mL) and concentrated under reduced pressure to give the crude amine. The residue was dissolved in CH$_2$Cl$_2$ (250 mL), Boc-Ala-OH (5.68 g, 30.0 mmol, 1.2 equiv), HATU (11.4 g, 30.0 mmol, 1.2 equiv) and DIPEA (17.4 mL, 100 mmol, 4.0 equiv) were added subsequently, and the reaction mixture was stirred at room temperature for 16 h. The reaction mixture was washed with 10% citric acid solution (2×100 mL) and saturated NaHCO$_3$ solution (2×100 mL), dried over MgSO$_4$, filtered and concentrated under reduced pressure. The residue was purified by column chromatography (SiO$_2$, PE/EtOAc 2:1→1:1) to give dipeptide 50 (13.1 g, 24.5 mmol, 98%) as a white solid.

O$_2$N-GOx-Ala-Tyr(Bn)-OBn (51): To a solution of Boc-Ala-Tyr(Bn)-OBn (50) (3.20 g, 6.00 mmol, 1.0 equiv) in CH$_2$Cl$_2$ (6.0 mL) was added TFA (6.0 mL) and the mixture was stirred at room temperature for 1 h. The reaction mixture was concentrated under reduced pressure and the resulting residue repeatedly dissolved in CH$_2$Cl$_2$ (3×10 mL) and concentrated under reduced pressure to give the crude amine. In a second reaction vessel, oxetane-3-one (770 µL, 22.0 mmol, 2.0 equiv), nitromethane (910 µL, 16.8 mmol, 2.8 equiv) and triethylamine (335 µL, 2.40 mmol, 0.4 equiv) were combined at 0° C. and stirred for 1 h at room temperature. The mixture was dissolved in anhydrous CH$_2$Cl$_2$ (40 mL), cooled to −78° C., and triethylamine (3.35 mL, 24.0 mmol, 4.0 equiv) was added followed by dropwise addition of a solution of methanesulfonyl chloride (930 µL, 12.0 mmol, 2.0 equiv) in anhydrous CH$_2$Cl$_2$ (12 mL). The reaction mixture was stirred at −78° C. for 1.5 h and a solution of the crude amine and triethylamine (1.26 mL, 9.00 mmol, 1.5 equiv) in anhydrous CH$_2$Cl$_2$ (20 mL) was added slowly via syringe. The reaction mixture was allowed to warm to room temperature and stirred for 16 h. A saturated solution of NH$_4$Cl (50 mL) was added and stirred for 10 min. The layers were separated and the aqueous one extracted with CH$_2$Cl$_2$ (2×30 mL) and EtOAc (2×30 mL). The combined organic phases were washed with saturated aqueous NaHCO$_3$ solution (50 mL), brine (50 mL), dried over MgSO$_4$, filtered and concentrated under reduced pressure. The residue was purified by column chromatography (SiO$_2$, PE/EtOAc 1:1→EtOAc) to give 51 (2.79 g, 5.09 mmol, 85%) as an orange wax-like solid.

Boc-Ala-GOx-Ala-Tyr(Bn)-OBn (52): To a solution of NO$_2$-GOx-Ala-Tyr(Bn)-OBn (51) (2.66 g, 4.86 mmol, 1.0 equiv) in THF (48 mL) was added Boc-Ala-OSu (2.78 g, 9.71 mmol, 2.0 equiv), NaHCO$_3$ (1.63 g, 19.4 mmol, 4.0 equiv) and Raney Ni (slurry in H$_2$O, 10 mL). The solution was placed under an atmosphere of nitrogen, evacuated and filled with hydrogen (balloon). The reaction mixture was stirred vigorously for 4.0 h at room temperature. Then, the mixture was filtered through a plug of Celite eluting with EtOAc, the filtrate was washed with saturated Na$_2$CO$_3$ (3×50 mL) and concentrated under reduced pressure. Boc-Ala-GOx-Ala-Tyr(Bn)-OBn (52) was afforded after purification by column chromatography (SiO$_2$, EtOAc) as an off-white foam (1.96 g, 2.85 mmol, 59%).

Cbz-Leu-Ala-GOx-Ala-Tyr(Bn)-OBn (53): To a solution of Boc-Ala-GOx-Ala-Tyr(Bn)-OBn (52) (1.81 g, 2.63 mmol, 1.0 equiv) in CH$_2$Cl$_2$ (3.0 mL) was added TFA (3.0 mL) and the mixture was stirred at room temperature for 10 min. The reaction mixture was concentrated under reduced pressure and the resulting residue repeatedly dissolved in CH$_2$Cl$_2$ (3×10 mL) and concentrated in vacuo to give the crude amine. The residue was dissolved in a mixture of CH$_2$Cl$_2$ (26 mL) and DMF (5.0 mL), Cbz-Leu-OH (837 mg, 3.15 mmol, 1.2 equiv), HATU (1.20 g, 3.15 mmol, 1.2 equiv) and DIPEA (1.83 mL, 10.5 mmol, 4.0 equiv) were added subsequently, and the reaction mixture was stirred at room temperature for 16 h. The mixture was diluted with CH$_2$Cl$_2$ (30 mL) and washed with 10% citric acid solution (2×50 mL) and saturated NaHCO$_3$ solution (2×50 mL), dried over MgSO$_4$, filtered and concentrated under reduced pressure. The residue was purified by flash column chromatography (SiO$_2$, CH$_2$Cl$_2$/MeOH 98:2→97:3→96:4) to give pentapeptide 53 (1.21 g, 1.45 mmol, 55%) as a white foam.

H-Leu-Ala-GOx-Ala-Tyr-OH (54): To a solution of pentapeptide 53 (1.14 g, 1.36 mmol) in anhydrous MeOH (14 mL) was added 10 wt % Pd/C (114 mg, 10 wt %) and the reaction flask was evacuated, filled with nitrogen, evacuated, and placed under an atmosphere of H$_2$ (balloon). The reaction mixture was stirred at room temperature for 16 h, placed under N$_2$ and filtered through a plug of Celite, which was washed with MeOH (3×). The filtrate was concentrated in vacuo to give 54 as an off-white solid (742 mg) in quantitative yield.

Preparation of Pentapeptide 61:

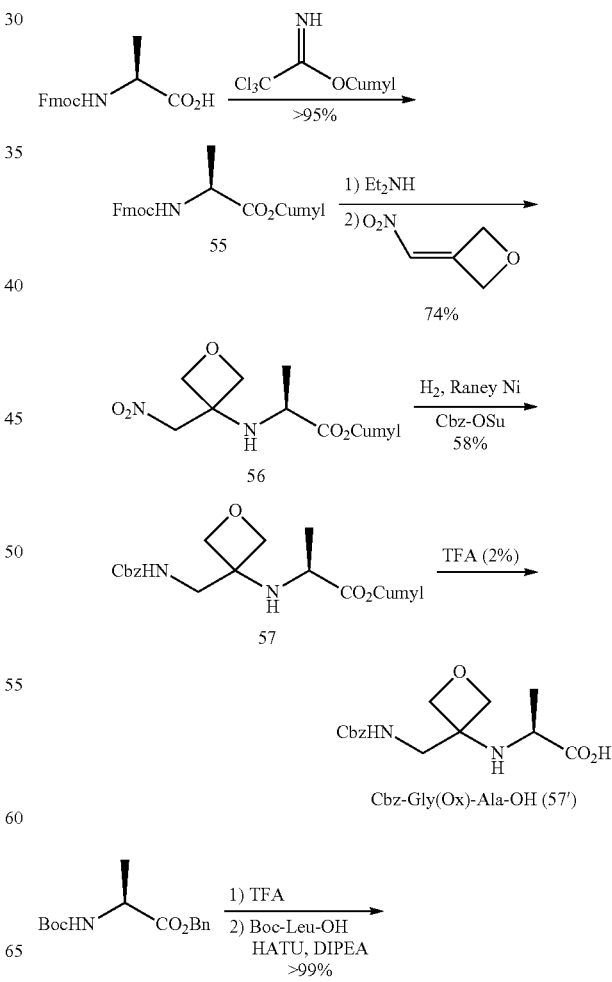

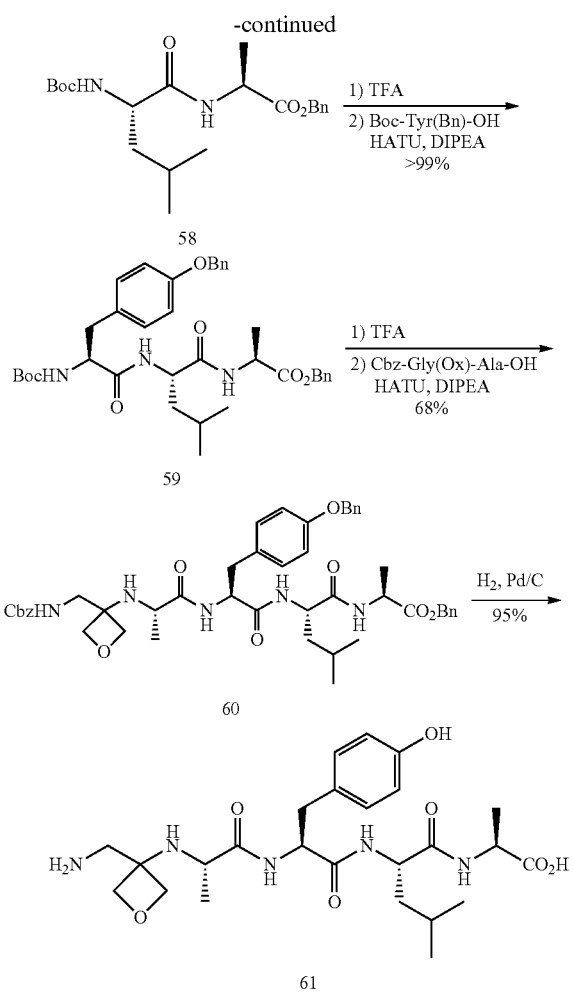

concentrated under reduced pressure and the resulting residue repeatedly dissolved in $CH_2Cl_2$ (3×15 mL) and concentrated under reduced pressure to give the crude amine. In a second reaction vessel, oxetane-3-one (1.10 mL, 17.2 mmol, 2.0 equiv), nitromethane (1.30 mL, 24.1 mmol, 2.8 equiv) and triethylamine (480 μL, 3.44 mmol, 0.4 equiv) were combined at 0° C. and stirred for 1 h at room temperature. The mixture was dissolved in anhydrous $CH_2Cl_2$ (60 mL), cooled to −78° C., and triethylamine (4.80 mL, 34.4 mmol, 4.0 equiv) was added followed by dropwise addition of a solution of methanesulfonyl chloride (1.33 mL, 17.2 mmol, 2.0 equiv) in anhydrous $CH_2Cl_2$ (18 mL). The reaction mixture was stirred at −78° C. for 1.5 h and the solution of the crude amine in anhydrous $CH_2Cl_2$ (30 mL) was added slowly via syringe. The reaction mixture was allowed to warm to room temperature and stirred for 16 h. A saturated solution of $NH_4Cl$ (50 mL) was added and stirred for 10 min. The layers were separated and the aqueous one extracted with $CH_2Cl_2$ (2×30 mL) and EtOAc (2×30 mL). The combined organic phases were washed with saturated aqueous $NaHCO_3$ solution (50 mL), brine (50 mL), dried over $MgSO_4$, filtered, and concentrated in vacuo. The residue was purified by column chromatography ($SiO_2$, PE/EtOAc 2:1→1:1) to give 56 (2.04 g, 6.33 mmol, 74%) as a pale-yellow oil.

Cbz-GOx-Ala-OCumyl (57): To a solution of $NO_2$-GOx-Ala-OCumyl (56) (2.04 g, 6.32 mmol, 1.0 equiv) in THF (65 mL) was added N-(benzyloxycarbonyloxy) succinimide (3.15 g, 12.6 mmol, 2.0 equiv), $NaHCO_3$ (2.12 g, 25.2 mmol, 4.0 equiv) and Raney Ni (slurry in $H_2O$, 6.3 mL). The mixture was placed under an atmosphere of nitrogen, evacuated and filled with hydrogen (balloon). The reaction mixture was stirred vigorously for 2.5 h at room temperature. Then, the mixture was filtered through a plug of Celite eluting with EtOAc, the filtrate was washed with sat. $Na_2CO_3$ (3×50 mL) and concentrated under reduced pressure. Cbz-GOx-Ala-OCumyl (57) was afforded after purification by column chromato-graphy ($SiO_2$, PE/EtOAc 2:1→1:1-EtOAc) as a pale yellow oil (1.55 g, 3.63 mmol, 58%).

Boc-Leu-Ala-OBn (58): To a solution of Boc-Ala-OBn (4.56 g, 16.3 mmol, 1.0 equiv) in $CH_2Cl_2$ (16 mL) was added TFA (16 mL) and the mixture was stirred at room temperature for 1 h. The reaction mixture was concentrated under reduced pressure and the resulting residue repeatedly dissolved in $CH_2Cl_2$ (3×20 mL) and concentrated under reduced pressure to give the crude amine. The residue was dissolved in $CH_2Cl_2$ (160 mL), Boc-Leu-OH (4.53 g, 19.6 mmol, 1.2 equiv), HATU (7.45 g, 19.6 mmol, 1.2 equiv) and DIPEA (11.4 mL, 65.2 mmol, 4.0 equiv) were added subsequently, and the reaction mixture was stirred at room temperature for 16 h. The reaction mixture was diluted with $CH_2Cl_2$ (50 mL) and washed with 10% citric acid solution (2×100 mL) and sat. $NaHCO_3$ solution (2×100 mL), dried over $MgSO_4$, filtered and concentrated under reduced pressure. The residue was purified by flash column chromatography ($SiO_2$, PE/EtOAc 2:1→1:1) to give dipeptide 58 (6.40 g, 16.3 mmol, >99%) as a colourless viscous oil.

Boc-Tyr(Bn)-Leu-Ala-OBn (59): To a solution of Boc-Leu-Ala-OBn (58) (5.85 g, 14.9 mmol, 1.0 equiv) in $CH_2Cl_2$ (15 mL) was added TFA (15 mL) and the mixture was stirred at room temperature for 1 h. The reaction mixture was concentrated under reduced pressure and the resulting residue repeatedly dissolved in $CH_2Cl_2$ (3×20 mL) and concentrated under reduced pressure to give the crude amine. The residue was dissolved in $CH_2Cl_2$ (150 mL), Boc-Tyr(Bn)-OH (6.40 g, 17.2 mmol, 1.2 equiv), HATU (6.54 g, 17.2

Fmoc-Ala-OCumyl (55): To sodium hydride (60% dispersion in mineral oil, 280 mg, 7.00 mmol, 0.5 equiv) in anhydrous diethyl ether (28 mL) was added freshly distilled 2-phenyl-2-propanol (4.20 g, 30.8 mmol, 2.2 equiv) at 0° C. and the mixture was stirred for 1 h at room temperature. The reaction mixture was cooled to 0° C., 2,2,2-trichloroacetonitrile (2.80 mL, 28.0 mmol, 2.0 equiv) were added slowly and stirring was continued for 3 h at ambient temperature. The solvent was removed under reduced pressure and the residue re-dissolved in PE (7.0 mL), anhydrous MeOH (283 μL, 7.00 mmol, 0.5 equiv) was added and the solution was stirred for 10 min at room temperature. The mixture was filtered through a plug of Celite eluting with PE and the filtrate was concentrated in vacuo to give the crude imidate. To a suspension of Fmoc-Ala-OH (4.36 g, 14.0 mmol, 1.0 equiv) in $CH_2Cl_2$ (80 mL) was added a solution of the imidate in $CH_2Cl_2$ (15 mL) and the mixture was stirred for 16 h at room temperature. The reaction mixture was filtered through a plug of Celite eluting with $CH_2Cl_2$, the solvent was removed in vacuo, and the residue was purified by column chromatograph ($SiO_2$, PE/EtOAc 4:1) to give Fmoc-Ala-OCumyl (55) (6.00 g, 14.0 mmol, quant. yield) contaminated with small amounts of 2-phenyl-2-propanol (85: 15 by $^1$H NMR) as a pale-yellow oil.

$O_2N$-GOx-Ala-OCumyl (56): To a solution of Fmoc-Ala-OCumyl (55) (3.70 g, 8.60 mmol, 1.0 equiv) in $CH_2Cl_2$ (9.0 mL) was added diethylamine (9.0 mL) and the mixture was stirred at room temperature for 1 h. The reaction mixture was mmol, 1.2 equiv) and DIPEA (10.4 mL, 59.6 mmol, 4.0 equiv) were added subsequently, and the reaction mixture was stirred at room temperature for 16 h. The mixture was diluted with $CH_2Cl_2$ (50 mL) and washed with 10% citric acid solution (2×100 mL) and saturated $NaHCO_3$ solution (2×100 mL), dried over $MgSO_4$, filtered and concentrated under reduced pressure. The residue was purified by flash column chromatography ($SiO_2$, PE/EtOAc 2:1→1:1) to give tripeptide 59 (9.60 g, 14.9 mmol, >99%) as a white solid.

Cbz-GOx-Ala-Tyr(Bn)-Leu-Ala-OBn (60): Cbz-GOx-Ala-OCumyl (57) (853 mg, 2.00 mmol, 1.0 equiv) was stirred in 2% $TFA/CH_2Cl_2$ (40 mL) at room temperature for 90 min. The reaction mixture was concentrated under reduced pressure and the resulting residue repeatedly dissolved in $CH_2Cl_2$ (3×20 mL) and concentrated under reduced pressure to give the crude acid. In a separate reaction flask Boc-Tyr(Bn)-Leu-Ala-OBn (59) (1.29 g, 2.00 mmol, 1.0 equiv) was dissolved in $CH_2Cl_2$ (2.0 mL), TFA (2.0 mL) was added and the mixture was stirred at room temperature for 1 h. The reaction mixture was concentrated under reduced pressure and the resulting residue repeatedly dissolved in $CH_2Cl_2$ (3×20 mL) and concentrated under reduced pressure to give the crude amine. The residue was dissolved in a mixture of $CH_2Cl_2$ (20 mL) and DMF (1.0 mL) and added to the crude acid. HATU (760 mg, 2.00 mmol, 1.0 equiv) and DIPEA (1.39 mL, 8.00 mmol, 4.0 equiv) were added subsequently, and the reaction mixture was stirred at room temperature for 16 h. The reaction mixture was diluted with EtOAc (50 mL), washed with brine (2×50 mL), 1.0 M HCl (3×50 mL), saturated $NaHCO_3$ solution (3×50 mL), brine (50 mL), dried over $MgSO_4$, filtered and concentrated under reduced pressure. The residue was purified by flash column chromatography ($SiO_2$, EtOAc) to give pentapeptide 60 (1.15 g, 1.37 mmol, 68%) as a white foam.

H-GOx-Ala-Tyr-Leu-Ala-OH (61): To a solution of pentapeptide 60 (316 mg, 0.38 mmol) in anhydrous MeOH (4.0 mL) was added 10 wt % Pd/C (32 mg, 10 wt %) and the reaction flask was evacuated, filled with nitrogen, evacuated, and placed under an atmosphere of hydrogen (balloon). The reaction mixture was stirred at room temperature for 5 h, placed under nitrogen and filtered through a plug of Celite, which was washed with MeOH (3×). The filtrate was concentrated in vacuo to give 61 as an off-white solid (189 mg, 0.36 mmol, 95%), which required no further purification.

Representative example for cyclisation: Cyclo(Ala-GOx-Ala-Tyr-Leu) (8): To a solution of H-Ala-GOx-Ala-Tyr-Leu-OH (49) (52 mg, 0.10 mmol, 1.0 equiv) in anhydrous DMF (100 mL, 0.001 M) under an atmosphere of nitrogen was added DEPBT (60 mg, 0.20 mmol, 2.0 equiv) and DIPEA (35 μL, 0.20 mmol, 2.0 equiv) and the reaction mixture was stirred for 24 h at room temperature. The solvent was removed under reduced pressure, and the residue was purified twice by column chromatography ($SiO_2$, $CH_2Cl_2$/MeOH 9:1→4:1) to give the cyclic pentapeptide (8) as a white solid (27 mg, 54 μmol, 54%). $R_f$($CH_2Cl_2$/MeOH 4:1) 0.57; mp 213-217° C.; $^1$H NMR (400 MHz, $CD_3OD$) $\delta_H$ ppm 7.06 (d, J=8.3 Hz, 2H, ArH), 6.72 (d, J=8.3 Hz, 2H, ArH), 4.53 (d, J=7.8 Hz, 1H, OCHH-Ox), 4.49 (q, J=7.1 Hz, 1H, CHα-Ala), 4.46 (d, J=6.2 Hz, 1H, OCHH-Ox), 4.32-4.25 (m, 3H, 2×OCHH-Ox, CHα-Leu), 4.19 (dd, J=9.9, 6.1 Hz, 1H, CHα-Tyr), 3.70 (d, J=14.0 Hz, 1H, CHHGOx), 3.49 (q, J=6.9 Hz, 1H, CHα-Ala), 3.43 (d, J=14.0 Hz, 1H, CHHGOx), 3.20 (dd, J=13.4, 10.4 Hz, 1H, CHHβ-Tyr), 3.07 (dd, J=13.4, 6.1 Hz, 1H, CHHβ-Tyr), 1.79 (ddd, J=13.9, 11.2, 4.7 Hz, 1H, CHHβ-Leu), 1.70-1.62 (m, 1H, CHHβ-Leu), 1.57-1.48 (m, 1H, CHγ-Leu), 1.38 (d, J=7.1 Hz, 3H, $CH_3$β-Ala), 1.20 (d, J=6.9 Hz, 3H, $CH_3$β-Ala), 0.94 (d, J=6.6 Hz, 3H, $CH_3$δ-Leu), 0.86 (d, J=6.5 Hz, 3H, $CH_3$δ-Leu); $^{13}$C NMR (101 MHz, $CD_3OD$) $\delta_C$ ppm 178.7 (C=O), 175.6 (C=O), 174.3 (C=O), 173.9 (C=O), 157.4 (C), 131.3 (CH), 129.1 (C), 116.3 (CH), 81.6 ($OCH_2$), 79.0 ($OCH_2$), 62.0 (C, Ox), 57.9 (CH, α-Tyr), 55.2 (CH, α-Leu), 53.7 (CH, α-Ala), 50.7 (CH, α-Ala), 46.2 ($CH_2$, GOx), 40.7 ($CH_2$, β-Leu), 35.7 ($CH_2$, β-Tyr), 25.9 (CH, γ-Leu), 23.5 ($CH_3$, δ-Leu), 21.5 ($CH_3$, β-Ala), 21.2 ($CH_3$, δ-Leu), 17.9 ($CH_3$, β-Ala); $v_{max}$ (neat)=3260, 2958, 1647, 1513, 1232, 965, 828 cm$^{-1}$; MS (ESI$^+$) m/z 504 [M+H]$^+$, 526 [M+Na]$^+$; HRMS (ESI$^+$) calcd. for $C_{25}H_{38}N_5O_6$ [M+H]$^+$ 504.2817. found 504.2818. $[\alpha]_D^{28}$ −69.7 (c 0.06, MeOH). See FIG. 4 for spectra.

Details of Macrocyclisation of Pentapeptide 10
Preparation of Pentapeptide 64:

Boc-Gly-Ala-Tyr(Bn)-Leu-OBn (62): To a solution of Boc-Ala-Tyr(Bn)-Leu-OBn (46) 1.00 g, 1.55 mmol, 1.0 equiv) in $CH_2Cl_2$ (10 mL) was added TFA (2.0 mL) and the mixture was stirred at room temperature for 1 h. The mixture was concentrated under reduced pressure and the resulting residue repeatedly dissolved in $CH_2Cl_2$ (3×10 mL) and concentrated under reduced pressure to give the crude amine. The residue was dissolved in $CH_2Cl_2$ (16 mL), Boc-Gly-OH (326 mg, 1.86 mmol, 1.2 equiv), HATU (707 mg, 1.86 mmol, 1.2 equiv) and DIPEA (1.08 mL, 6.20 mmol, 4.0 equiv) were added subsequently, and the mixture was stirred at room temperature for 16 h. The reaction mixture was diluted with $CH_2Cl_2$ (20 mL) and washed with 10% citric acid solution (2×20 mL) and saturated $NaHCO_3$ solution (2×20 mL), dried over $MgSO_4$, filtered and concentrated under reduced pressure. The residue was purified by column chromatography ($SiO_2$, PE/EtOAc 1:1→EtOAc) to give tetrapeptide 62 (912 mg, 1.30 mmol, 84%) as a white solid.

Cbz-Ala-Gly-Ala-Tyr(Bn)-Leu-OBn (63): To a solution of Boc-Gly-Ala-Tyr(Bn)-Leu-OBn (62) (861 mg, 1.23 mmol, 1.0 equiv) in $CH_2Cl_2$ (10 mL) was added TFA (1.5 mL) and the mixture was stirred at room temperature for 1 h. The reaction mixture was concentrated under reduced pressure and the resulting residue repeatedly dissolved in $CH_2Cl_2$ (3×10 mL) and concentrated under reduced pressure to give the crude amine. The residue was dissolved in $CH_2Cl_2$ (13 mL), Cbz-Ala-OH (328 mg, 1.47 mmol, 1.2 equiv), HATU (559 mg, 1.47 mmol, 1.2 equiv) and DIPEA (853 µL, 4.90 mmol, 4.0 equiv) were added subsequently, and the mixture was stirred at room temperature for 16 h. The reaction mixture was diluted with $CH_2Cl_2$ (20 mL) and washed with 10% citric acid solution (2×20 mL) and saturated $NaHCO_3$ solution (2×20 mL), dried over $MgSO_4$, filtered and concentrated under reduced pressure. The residue was purified by column chromatography ($SiO_2$, $CH_2Cl_2$/MeOH 19:1→9:1) to give pentapeptide 63 (928 mg, 1.15 mmol, 93%) as a white solid.

H-Ala-Gly-Ala-Tyr-Leu-OH (64): To a solution of pentapeptide 63 (820 mg, 1.01 mmol) in anhydrous DMF (20 mL) was added 10 wt % Pd/C (82 mg, 10 wt %) and the reaction flask was evacuated, filled with nitrogen, evacuated, and placed under an atmosphere of hydrogen (balloon). The reaction mixture was stirred at room temperature for 24 h, placed under nitrogen and filtered through a plug of Celite, which was washed with MeOH (3×). The filtrate was concentrated in vacuo to give 64 as a tan-coloured solid (418 mg, 65%), which required no further purification. N.B. The product was isolated as a complex with 2.0 equiv of DMF. Preparation of Pentapeptide 68:

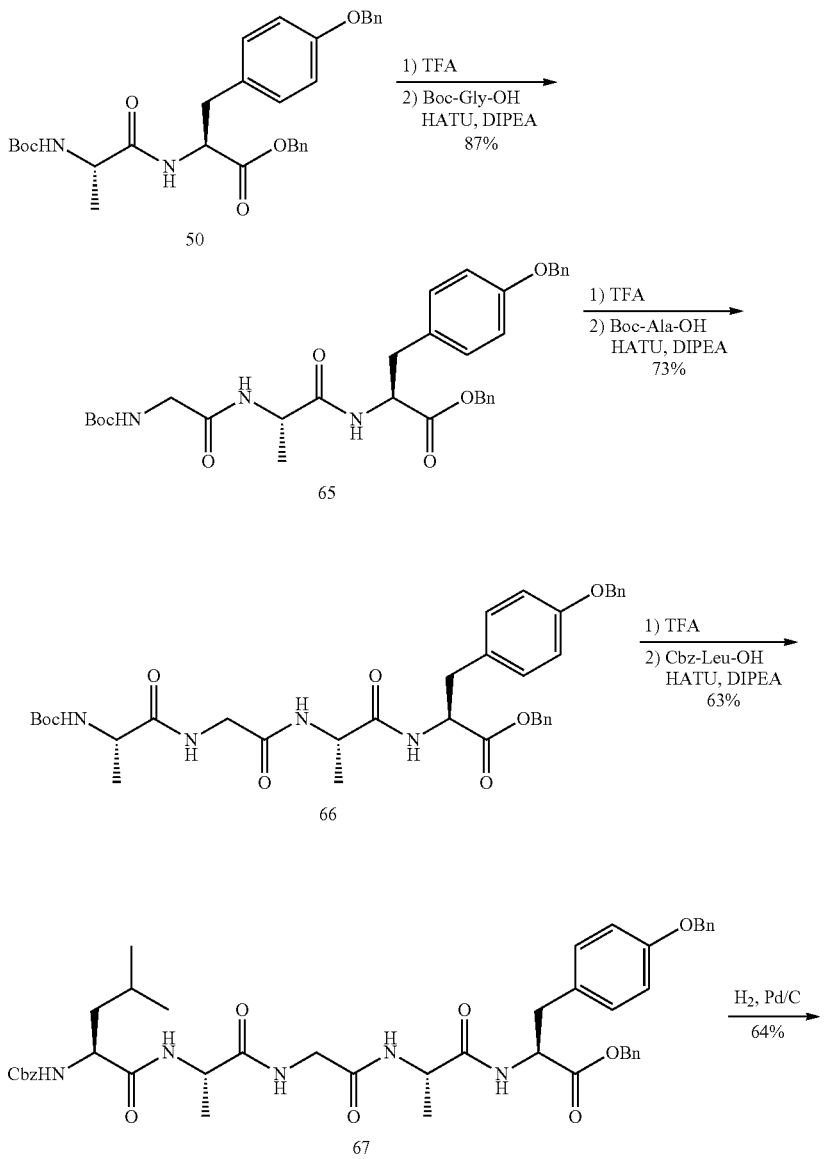

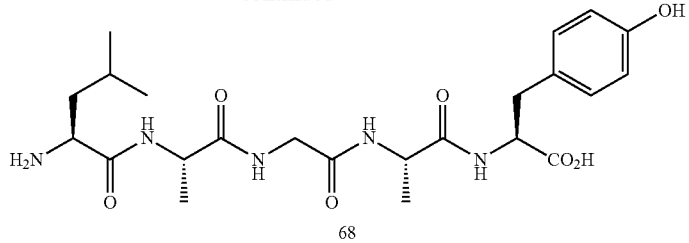

68

Boc-Gly-Ala-Tyr(Bn)-OBn (65): To a solution of Boc-Ala-Tyr(Bn)-OBn (50) (2.66 g, 5.00 mmol, 1.0 equiv) in $CH_2Cl_2$ (5.0 mL) was added TFA (5.0 mL) and the mixture was stirred at room temperature for 30 min (Caution—gas evolution!). The reaction mixture was concentrated under reduced pressure and the resulting residue repeatedly dissolved in $CH_2Cl_2$ (3×10 mL) and concentrated under reduced pressure to give the crude amine. The residue was dissolved in a mixture of $CH_2Cl_2$ (50 mL) and DMF (10 mL), Boc-Gly-OH (1.05 g, 6.00 mmol, 1.2 equiv), HATU (2.28 g, 6.00 mmol, 1.2 equiv) and DIPEA (3.48 mL, 20.0 mmol, 4.0 equiv) were added subsequently, and the mixture was stirred at room temperature for 16 h. The reaction mixture was washed with 10% citric acid solution (2×50 mL) and saturated $NaHCO_3$ solution (2×50 mL), dried over $MgSO_4$, filtered and concentrated under reduced pressure. The residue was purified by column chromatography ($SiO_2$, PE/EtOAc 1:1→EtOAc) to give tripeptide Boc-Gly-Ala-Tyr(Bn)-OBn (65) (2.57 g, 4.36 mmol, 87%) as a white foam.

Boc-Ala-Gly-Ala-Tyr(Bn)-OBn (66): To a solution of Boc-Gly-Ala-Tyr(Bn)-OBn (65) (887 mg, 1.50 mmol, 1.0 equiv) in $CH_2Cl_2$ (2.0 mL) was added TFA (2.0 mL) and the mixture was stirred at room temperature for 30 min (Caution—gas evolution!). The reaction mixture was concentrated under reduced pressure and the resulting residue repeatedly dissolved in $CH_2Cl_2$ (3×10 mL) and concentrated under reduced pressure to give the crude amine. The residue was dissolved in a mixture of $CH_2Cl_2$ (15 mL) and DMF (5.0 mL), Boc-Ala-OH (341 mg, 1.80 mmol, 1.2 equiv), HATU (684 mg, 1.80 mmol, 1.2 equiv) and DIPEA (1.05 mL, 6.00 mmol, 4.0 equiv) were added subsequently, and the mixture was stirred at room temperature for 16 h. The reaction mixture was washed with 10% citric acid solution (2×50 mL) and saturated $NaHCO_3$ solution (2×50 mL), dried over $MgSO_4$, filtered and concentrated under reduced pressure. The residue was purified by column chromatography ($SiO_2$, EtOAc) to give tetrapeptide Boc-Ala-Gly-Ala-Tyr(Bn)-OBn (66) (725 mg, 1.10 mmol, 73%) as a white solid.

Cbz-Leu-Ala-Gly-Ala-Tyr(Bn)-OBn (67): To a solution of Boc-Ala-Gly-Ala-Tyr(Bn)-OBn (66) (642 mg, 0.97 mmol, 1.0 equiv) in $CH_2Cl_2$ (2.0 mL) was added TFA (1.0 mL) and the mixture was stirred at room temperature for 30 min (Caution—gas evolution!). The reaction mixture was concentrated under reduced pressure and the resulting residue repeatedly dissolved in $CH_2Cl_2$ (3×10 mL) and concentrated under reduced pressure to give the crude amine. The residue was dissolved in a mixture of $CH_2Cl_2$ (5.0 mL) and DMF (5.0 mL), Cbz-Leu-OH (309 mg, 1.16 mmol, 1.2 equiv), HATU (441 mg, 1.16 mmol, 1.2 equiv) and DIPEA (696 µL, 3.88 mmol, 4.0 equiv) were added subsequently, and the mixture was stirred at room temperature for 16 h. The reaction mixture was washed with 10% citric acid solution (2×50 mL) and saturated $NaHCO_3$ solution (2×50 mL), dried over $MgSO_4$, filtered and concentrated under reduced pressure. The residue was purified by column chromatography ($SiO_2$, $CH_2Cl_2$/MeOH 98:2-496:4) to give pentapeptide Cbz-Leu-Ala-Gly-Ala-Tyr(Bn)-OBn (67) (496 mg, 0.61 mmol, 63%) as a white solid.

H-Leu-Ala-Gly-Ala-Tyr-OH (68): To a solution of pentapeptide 67 (402 mg, 0.50 mmol) in a mixture of anhydrous MeOH (15 mL) and DMF (5.0 mL) was added 10 wt % Pd/C (40 mg, 10 wt %) and the reaction flask was evacuated, filled with nitrogen, evacuated, and placed under an atmosphere of hydrogen (balloon). The reaction mixture was stirred at room temperature for 16 h, placed under nitrogen and filtered through a plug of Celite, which was washed with MeOH (3×). The filtrate was concentrated in vacuo to give 68 as an off-white solid (199 mg) in 64% yield. N.B. The product was obtained as a complex with 2.0 equiv of DMF.

Representative example for cyclisation: Cyclo(Ala-Gly-Ala-Tyr-Leu) (10): To a solution of H-Ala-Gly-Ala-Tyr-Leu-OH (64) (50 mg, 0.10 mmol, 1.0 equiv) in anhydrous DMF (100 mL, 0.001 M) under an atmosphere of nitrogen was added DEPBT (60 mg, 0.20 mmol, 2.0 equiv) and DIPEA (35 µL, 0.20 mmol, 2.0 equiv) and the mixture was stirred for 24 h at room temperature. The solvent was removed in vacuo and the residue was purified twice by column chromatography ($SiO_2$, $CH_2Cl_2$/MeOH 9:1→4:1) to give the cyclic pentapeptide 10 as a white solid (20 mg, 42 µmol, 42%). $R_f$ ($CH_2Cl_2$/MeOH 4:1) 0.48; mp 294-296° C. (decomposition). Lit. 284-286° C.;[4] $^1$H NMR (400 MHz, $CD_3OD$) $\delta_H$ ppm 7.08 (d, J=8.4 Hz, 2H, ArH), 6.70 (d, J=8.4 Hz, 2H, ArH), 4.51 (t, J=8.0 Hz, 1H, CHα-Tyr), 4.34 (q, J=7.0 Hz, 1H, CHα-Ala), 4.19 (q, J=7.3 Hz, 1H, CHα-Ala), 4.04 (dd, J=10.5, 5.2 Hz, 1H, CHα-Leu), 3.98 (d, J=14.7 Hz, 1H, CHH-Gly), 3.59 (d, J=14.7 Hz, 1H, CHH-Gly), 3.06 (dd, J=12.3, 6.1 Hz, 1H, CHHβ-Tyr), 3.01 (dd, J=12.3, 7.5 Hz, 1H, CHHβ-Tyr), 1.86 (ddd, J=13.5, 10.7, 4.8 Hz, 1H, CHHβ-Leu), 1.57-1.48 (m, 1H, CHHβ-Leu), 1.47-1.40 (m, 1H, CHγ-Leu), 1.37 (d, J=7.1 Hz, 3H, $CH_3$β-Ala), 1.28 (d, J=7.3 Hz, 3H, $CH_3$β-Ala), 0.93 (d, J=6.5 Hz, 3H, $CH_3$δ-Leu), 0.86 (d, J=6.4 Hz, 3H, $CH_3$δ-Leu); $^{13}$C NMR (101 MHz, $CD_3OD$) $\delta_C$ ppm 175.5 (C=O), 175.03 (C=O), 174.98 (C=O), 173.7 (C=O), 172.0 (C=O), 157.4 (C), 131.3 (CH), 128.8 (C), 116.2 (CH), 57.2 (CH, α-Tyr), 56.2 (CH, α-Leu), 51.8 (CH, α-Ala), 50.6 (CH, α-Ala), 44.4 ($CH_2$, Gly), 40.4 ($CH_2$, β-Leu), 37.0 ($CH_2$, β-Tyr), 25.9 (CH, γ-Leu), 23.4 ($CH_3$, δ-Leu), 21.7 ($CH_3$, δ-Leu), 17.7 ($CH_3$, β-Ala), 17.1 ($CH_3$, β-Ala); $v_{max}$ (neat)=3279, 1648, 1631, 1530, 1514, 1440, 1384, 1226, 1087 $cm^{-1}$; MS (ESI$^+$) m/z 498 [M+Na]$^+$; HRMS (ESI$^+$) calcd. for $C_{23}H_{33}N_5NaO_6$ [M+Na]$^+$ 498.2323. found 498.2322. $[α]_D^{26}$ −82.8 (c 0.20, MeOH). Lit. $[α]_D^{20}$ −104 (c 0.10, $C_2H_5OH$).[4] See FIG. 5 for spectra.

The preparation of cyclic pentapeptides 8 and 10 by different bond formations is summarized below:

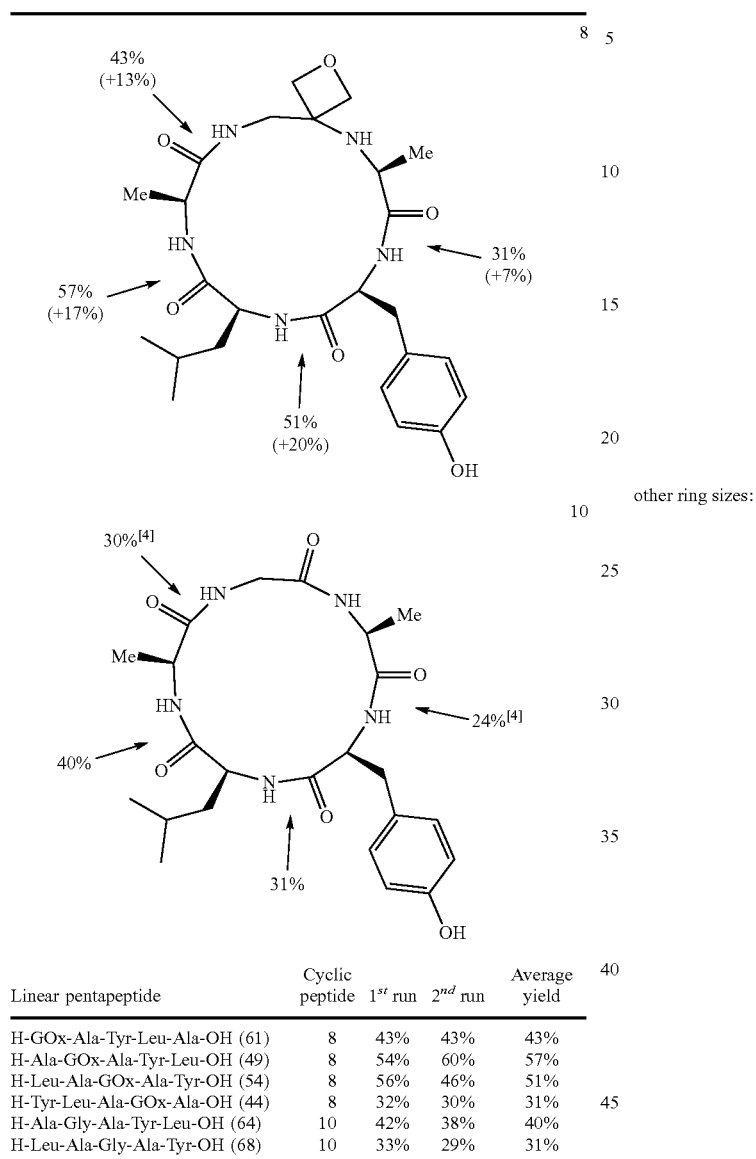

| Linear pentapeptide | Cyclic peptide | 1st run | 2nd run | Average yield |
|---|---|---|---|---|
| H-GOx-Ala-Tyr-Leu-Ala-OH (61) | 8 | 43% | 43% | 43% |
| H-Ala-GOx-Ala-Tyr-Leu-OH (49) | 8 | 54% | 60% | 57% |
| H-Leu-Ala-GOx-Ala-Tyr-OH (54) | 8 | 56% | 46% | 51% |
| H-Tyr-Leu-GOx-Ala-Ala-OH (44) | 8 | 32% | 30% | 31% |
| H-Ala-Gly-Ala-Tyr-Leu-OH (64) | 10 | 42% | 38% | 40% |
| H-Leu-Ala-Gly-Ala-Tyr-OH (68) | 10 | 33% | 29% | 31% |

Example 3—Synthesis of Sidechain-to-Sidechain Cyclisations

The methodology can be used to make disulfide containing macrocycles through oxidative cyclization of cysteine side chains:

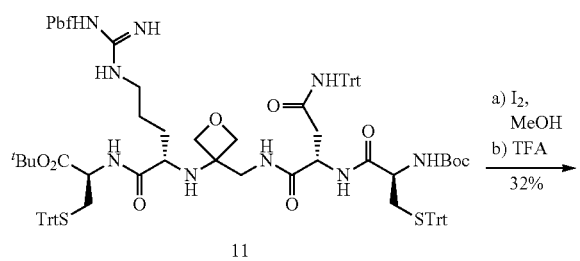

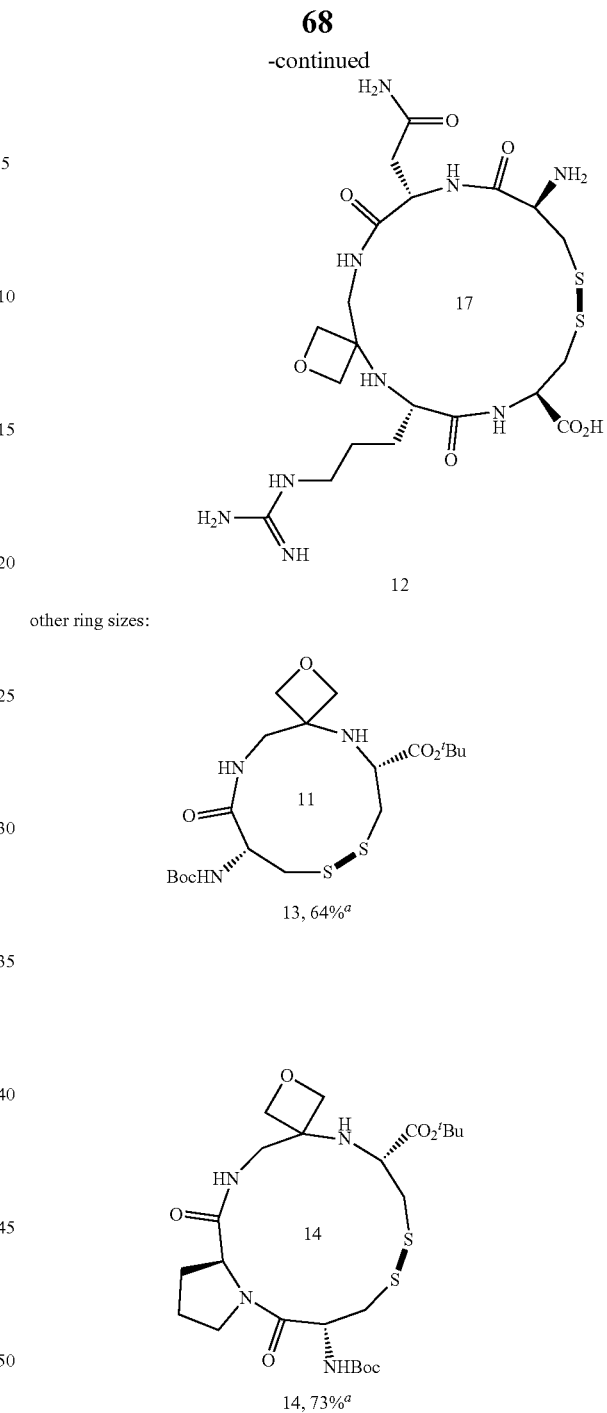

Oxetane modified cyclic peptides by disulfide bond formation

Treatment of 11 with iodine provided the 17-membered macrocycle by way of trityl deprotection and disulfide bond formation. Subsequent reaction with TFA facilitated removal of the side chain protecting groups providing 12 after reverse-phase HPLC purification. Importantly, the four-membered turn-inducing element is sufficiently stable to survive the strongly acid conditions required to globally deprotect the side-chains. Smaller 11- and 14-membered macrocycles 13 and 14 were also conveniently produced in high yields using this chemistry.

Example 3a—Detailed Example of a Sidechain-to-Sidechain Cyclisation for a Pentapeptide
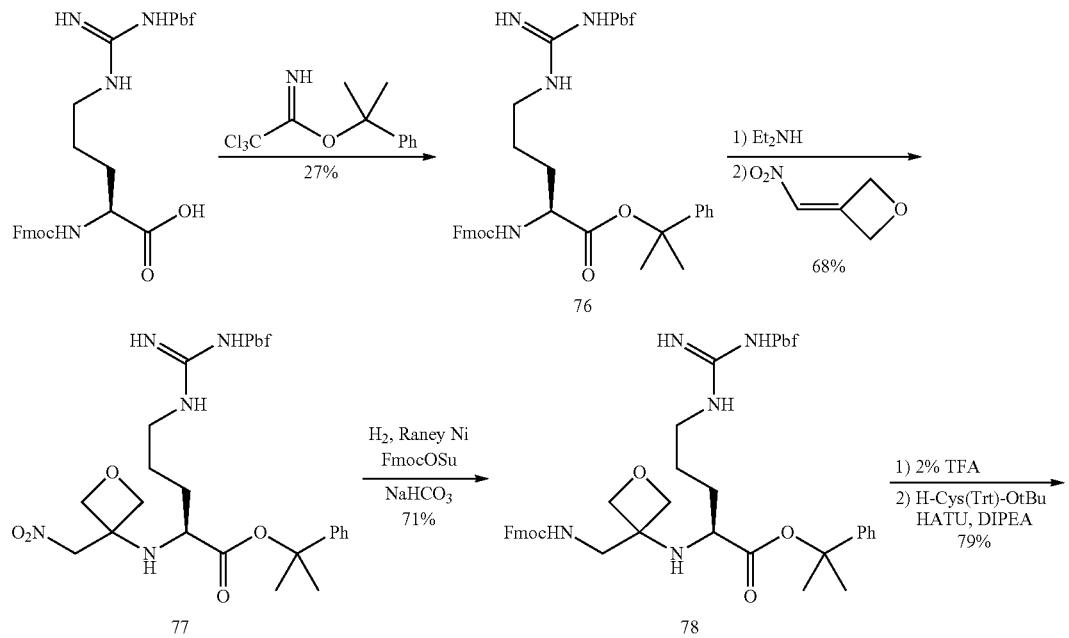
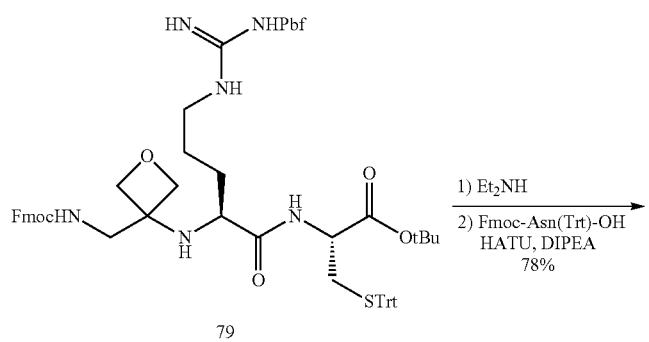
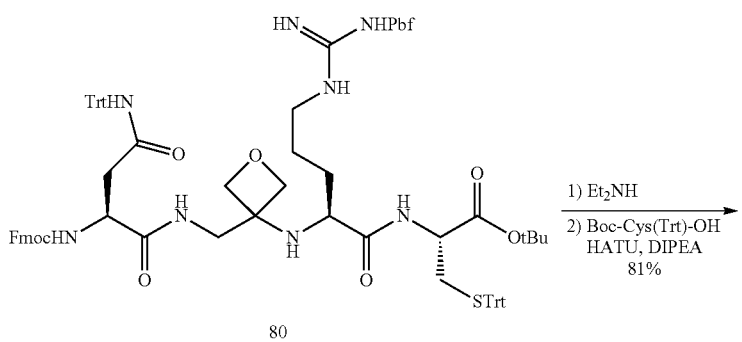

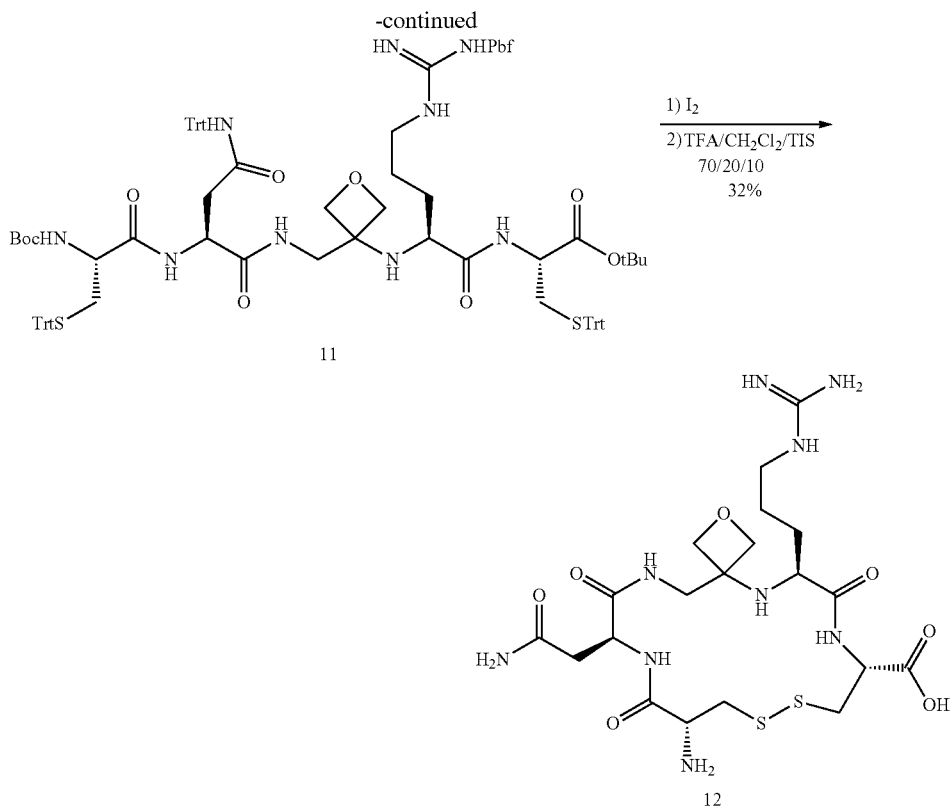

Fmoc-Arg(Pbf)-OCumyl (76): To sodium hydride (60% dispersion in mineral oil, 200 mg, 5.00 mmol, 0.5 equiv) in anhydrous diethyl ether (20 mL) was added freshly distilled 2-phenyl-2-propanol (3.00 g, 22.0 mmol, 2.2 equiv) at 0° C. and the mixture was stirred for 1 h at room temperature. The reaction mixture was cooled to 0° C., 2,2,2-trichloroacetonitrile (2.00 mL, 20.0 mmol, 2.0 equiv) were added slowly and stirring was continued for 3 h at ambient temperature. The solvent was removed under reduced pressure and the residue re-dissolved in petroleum ether (5.0 mL), anhydrous MeOH (202 µL, 5.00 mmol, 0.5 equiv) was added and the solution was stirred for 10 min at room temperature. The mixture was filtered through a plug of Celite eluting with PE and the filtrate was concentrated under reduced pressure to give the crude imidate. To a suspension of Fmoc-Arg(Pbf)-OH (6.49 g, 10.0 mmol, 1.0 equiv) in $CH_2Cl_2$ (60 mL) was added a solution of the imidate in $CH_2Cl_2$ (15 mL) and the mixture was stirred for 16 h at room temperature. The reaction mixture was filtered through a plug of Celite eluting with $CH_2Cl_2$, the solvent was removed in vacuo, and the residue was purified by column chromatography ($SiO_2$, PE/EtOAc 1:1→EtOAc) to give Fmoc-Arg(Pbf)-OCumyl (76) (2.10 g, 2.74 mmol, 27%) as a white solid.

$NO_2$-GOx-Arg(Pbf)-OCumyl (77): To a solution of Fmoc-Arg(Pbf)-OCumyl (76) (2.40 g, 3.13 mmol, 1.0 equiv) in $CH_2Cl_2$ (3.5 mL) was added diethylamine (3.5 mL) and the mixture was stirred at room temperature for 1 h. The reaction mixture was concentrated under reduced pressure and the resulting residue repeatedly dissolved in $CH_2Cl_2$ (3×10 mL) and concentrated under reduced pressure to give the crude amine. In a second reaction vessel, oxetane-3-one (410 µL, 6.26 mmol, 2.0 equiv), nitromethane (475 µL, 8.76 mmol, 2.8 equiv) and triethylamine (174 µL, 1.25 mmol, 0.4 equiv) were combined at 0° C. and stirred for 1 h at room temperature. The mixture was dissolved in anhydrous $CH_2Cl_2$ (24 mL), cooled to −78° C., and triethylamine (1.74 mL, 12.5 mmol, 4.0 equiv) was added followed by dropwise addition of a solution of methanesulfonyl chloride (485 µL, 6.26 mmol, 2.0 equiv) in anhydrous $CH_2Cl_2$ (6.0 mL). The reaction mixture was stirred at −78° C. for 1.5 h and a solution of the crude amine in anhydrous $CH_2Cl_2$ (12 mL) was added slowly via syringe. The reaction mixture was allowed to warm to room temperature and stirred for 16 h. A saturated solution of $NH_4Cl$ (30 mL) was added and stirred for 10 min. The layers were separated and the aqueous layer was extracted with $CH_2Cl_2$ (2×20 mL) and EtOAc (2×20 mL). The combined organic phases were washed with saturated aqueous $NaHCO_3$ solution (30 mL), brine (30 mL), dried over $MgSO_4$, filtered, and concentrated under reduced pressure. The residue was purified by column chromatography ($SiO_2$, PE/EtOAc 1:1→EtOAc) to give 77 (1.41 g, 2.14 mmol, 68%) as an orange foam.

Fmoc-GOx-Arg(Pbf)-OCumyl (78): To a solution of $NO_2$-GOx-Arg(Pbf)-OCumyl (77) (1.41 g, 2.14 mmol, 1.0 equiv) in THF (22 mL) was added Fmoc N-hydroxysuccinimide ester (1.44 g, 4.28 mmol, 2.0 equiv), $NaHCO_3$ (719 mg, 8.56 mmol, 4.0 equiv) and Raney Ni (slurry in $H_2O$, 2.2 mL). The reaction mixture was placed under an atmosphere of nitrogen, evacuated and filled with hydrogen (balloon). The reaction mixture was stirred vigorously for 2.5 h at room temperature, filtered through a plug of Celite eluting with EtOAc, and the filtrate was concentrated under reduced pressure. Fmoc-GOx-Arg(Pbf)-OCumyl (78) was afforded after purification by column chromatography ($SiO_2$, PE/EtOAc 1:1→EtOAc) as a white foam (1.29 g, 1.51 mmol, 71%).

Fmoc-GOx-Arg(Pbf)-Cys(Trt)-OtBu (79): Fmoc-GOx-Arg(Pbf)-OCumyl (78) (256 mg, 0.30 mmol, 1.0 equiv) was dissolved in 2% TFA/CH$_2$Cl$_2$ (0.05 M) and stirred at room temperature for 2 h following a procedure from Beadle et al.[5] The reaction mixture was concentrated under reduced pressure, and the resulting residue was repeatedly re-suspended in CH$_2$Cl$_2$ (3×15 mL) and the solvent removed under reduced pressure. Meanwhile, diethylamine (2.0 mL) was added to a solution of Fmoc-Cys(Trt)-OtBu (81) (298 mg, 0.45 mmol, 1.5 equiv) in CH$_2$Cl$_2$ (2.0 mL) and the reaction mixture was stirred at room temperature for 1 h. The mixture was concentrated under reduced pressure and the resulting residue repeatedly dissolved in CH$_2$Cl$_2$ (3×15 mL) and concentrated under reduced pressure to give the crude amine. The crude Fmoc-GOx-Arg(Pbf)-OH was dissolved in DMF (5.0 mL) and HATU (125 mg, 0.33 mmol, 1.1 equiv), diisopropylethyl-amine (204 μL, 1.20 mmol, 4.0 equiv) and the crude amine in DMF (2.0 mL) were added successively. The reaction mixture was stirred at room temperature for 48 h and the solvent removed under reduced pressure. The residue was purified by flash column chromatography (SiO$_2$, PE/EtOAc 1:1→5% MeOH in CH$_2$Cl$_2$) to give tripeptide 79 (268 mg, 0.24 mmol, 79%) as a white foam;

Fmoc-Asn(Trt)-GOx-Arg(Pbf)-Cys(Trt)-OtBu (80): Diethylamine (2.0 mL) was added to a solution of Fmoc-GOx-Arg(Pbf)-Cys(Trt)-OtBu (79) (262 mg, 0.23 mmol, 1.0 equiv) in CH$_2$Cl$_2$ (2.0 mL) and the reaction mixture was stirred at room temperature for 1 h. The mixture was concentrated in vacuo and the resulting residue repeatedly dissolved in CH$_2$Cl$_2$ (3×15 mL) and concentrated under reduced pressure to give the crude amine. HATU (132 mg, 0.35 mmol, 1.5 equiv), diisopropylethylamine (181 μL, 1.10 mmol, 3.0 equiv) and Fmoc-Asn(Trt)-OH (208 mg, 0.35 mmol, 1.5 equiv) were added to the crude amine in CH$_2$Cl$_2$ (5.0 mL). The reaction mixture was stirred at room temperature for 16 h and the solvent was removed in vacuo. The residue was purified by flash column chromatography (SiO$_2$, CH$_2$Cl$_2$→5% MeOH in CH$_2$Cl$_2$) to give tetrapeptide 80 (262 mg, 0.18 mmol, 78%) as a white foam;

Fmoc-Cys(Trt)-Asn(Trt)-GOx-Arg(Pbf)-Cys(Trt)-OtBu (11): Diethylamine (1.0 mL) was added to a solution of Fmoc-GOx-Arg(Pbf)-Cys(Trt)-OtBu (80) (200 mg, 0.14 mmol, 1.0 equiv) in CH$_2$Cl$_2$ (1.0 mL) and the reaction mixture was stirred at room temperature for 1 h. The reaction mixture was concentrated under reduced pressure and the resulting residue repeatedly dissolved in CH$_2$Cl$_2$ (3×15 mL) and concentrated under reduced pressure to give the crude amine. HATU (76 mg, 0.20 mmol, 1.4 equiv), diisopropylethylamine (105 μL, 0.60 mmol, 3.0 equiv) and Boc-Cys(Trt)-OH (94 mg, 0.20 mmol, 1.4 equiv) were added to the crude amine in CH$_2$Cl$_2$ (5.0 mL). The reaction mixture was stirred at room temperature for 16 h and the solvent removed under reduced pressure. The residue was purified by flash column chromatography (SiO$_2$, CH$_2$Cl$_2$→5% MeOH in CH$_2$Cl$_2$) to give pentapeptide 11 (191 mg, 0.11 mmol, 81%) as a white foam;

Cyclo(H-CVs-Asn-GOx-Arg-CVs-OH) (12): The fully protected pentapeptide 11 (66.5 mg, 0.04 mmol, 1.0 equiv) was dissolved in MeOH (2.0 mL) and slowly added to a solution of iodine (30 mg, 0.12 mmol, 3.0 equiv) in MeOH (2.0 mL). The mixture was stirred for 1 h at room temperature, cooled to 0° C. and saturated aqueous Na$_2$S$_2$O$_2$ was added until a nearly colourless solution was obtained. The mixture was concentrated in vacuo to a volume of ca. 0.5 mL, EtOAc (10 mL) was added, the solution was washed with 0.1 M aqueous Na$_2$S$_2$O$_2$ solution (5.0 mL), dried over Na$_2$SO$_4$ and filtered. The crude product was treated with 70% TFA/20% CH$_2$Cl$_2$/10% TIS under anhydrous conditions for 2.5 h at room temperature. The cleavage cocktail was removed under a steam of nitrogen and the crude peptide precipitated in cold diethyl ether. After centrifugation, the peptide was dissolved in water and further purified by HPLC (0-3 min 3%, 3-10 min 25%, 10-15 min 100%, R$_t$=7.32 min) to give the cyclic peptide 12 as a white solid (7.4 mg, 32% yield over two steps). mp 161-165° C. (decomposition); $^1$H NMR (500 MHz, D$_2$O @ 323 K) δ$_H$ ppm 4.70 (m, 1H, CHα-Asn) 4.56-4.51 (m, 2H, OCHH-Ox, CHα-Cys), 4.45-4.36 (m, 3H, OCH$_2$—Ox, OCHH-Ox), 4.14 (t, J=4.9 Hz, 1H, CHα-Cys), 3.98 (d, J=14.6 Hz, 1H, CHHGOx), 3.64 (dd, J=14.7, 5.5 Hz, 1H, CHHβ-Cys), 3.45 (t, J=6.2 Hz, 1H, CHα-Arg), 3.35 (dd, J=14.7, 4.5 Hz, 1H, CHHβ-Cys), 3.21 (d, J=14.6 Hz, 2H, CHHβ-Cys, CHH-GOx), 3.12 (t, J=6.6 Hz, 2H, CH$_2$δ-Arg), 2.81 (dd, J=14.6, 10.6 Hz, 1H, CHHβ-Cys), 2.78-2.68 (m, 2H, CH$_2$β-Asn), 1.70-1.61 (m, 2H, CH$_2$β-Arg), 1.59-1.49 (m, 2H, CH$_2$γ-Arg). N.B. CHα-Asn underwater peak; $^{13}$C NMR (126 MHz, D$_2$O @ 323 K) δ$_C$ ppm 176.4 (C═O), 176.1 (C═O), 174.4 (C═O), 172.7 (C═O), 170.2 (C═O), 156.7 (C═NH), 80.2 (OCH$_2$), 78.7 (OCH$_2$), 60.4 (C, Ox), 56.1 (CH, α-Arg), 54.3 (CH, α-Cys), 52.6 (CH, α-Cys), 50.8 (CH, α-Asn), 44.0 (CH$_2$ β-Cys), 43.6 (CH$_2$, GOx), 42.7 (CH$_2$ β-Cys), 40.7 (CH$_2$, δ-Arg), 36.2 (CH$_2$, β-Asn), 31.3 (CH$_2$, β-Arg), 24.2 (CH$_2$, γ-Arg); ν$_{max}$ (neat)=2943, 1660, 1409, 1285, 1170, 697, 466 cm$^{-1}$; MS (ESI$^+$) m/z 578 [M+H]$^+$, 600 [M+Na]$^+$; HRMS (ESI$^+$) calcd. for C$_2$H$_{36}$N$_9$O$_7$S$_2$ [M+H]$^+$ 578.2174. found 578.2178. [α]$_D^{28}$ −81.3 (c 0.0004, DMF). See FIG. 6.

Example 3b—Detailed Example of a Sidechain-to-Sidechain Cyclisation for a Tripeptide

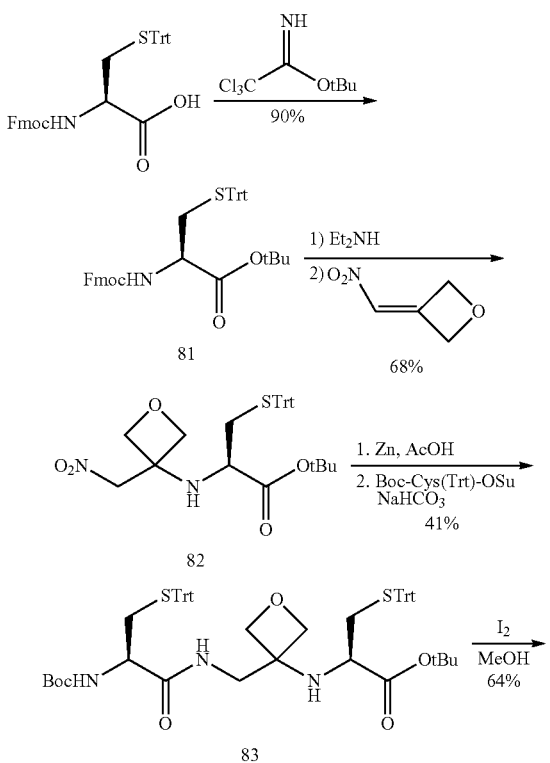

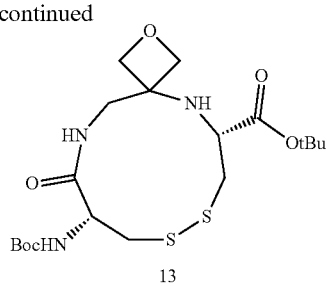

13

Fmoc-Cys(Trt)-OtBu (81): To a suspension of Fmoc-Cys (Trt)-OH (11.7 g, 20.0 mmol, 1.0 equiv) in anhydrous CH$_2$Cl$_2$ (160 mL) was added tert-butyl 2,2,2-trichloroacetimidate (8.74 g, 40.0 mmol, 2.0 equiv) and the mixture was stirred at ambient temperature for 3 d. The mixture was filtered through a pad of Celite and the solids were washed with EtOAc. The filtrate was concentrated in vacuo and the residue was purified by column chromatography (SiO$_2$, PE/EtOAc 5:1) to give 81 (11.6 g, 18.1 mmol, 90%) as a white solid.

NO$_2$-GOx-Cys(Trt)-OtBu (82): To a solution of Fmoc-Cys(Trt)-OtBu (81) (3.85 g, 6.00 mmol, 1.0 equiv) in CH$_2$Cl$_2$ (6.0 mL) was added diethylamine (6.0 mL) and the mixture was stirred at room temperature for 1 h. The reaction mixture was concentrated under reduced pressure and the resulting residue repeatedly dissolved in CH$_2$Cl$_2$ (3×20 mL) and concentrated under reduced pressure to give the crude amine. In a second reaction vessel, oxetane-3-one (770 µL, 12.0 mmol, 2.0 equiv), nitromethane (910 µL, 16.8 mmol, 2.8 equiv) and triethylamine (335 µL, 2.40 mmol, 0.4 equiv) were combined at 0° C. and stirred for 1 h at room temperature. The mixture was dissolved in anhydrous CH$_2$Cl$_2$ (40 mL), cooled to −78° C., and triethylamine (3.35 mL, 24.0 mmol, 4.0 equiv) was added followed by dropwise addition of a solution of methanesulfonyl chloride (930 µL, 12.0 mmol, 2.0 equiv) in anhydrous CH$_2$Cl$_2$ (12 mL). The reaction mixture was stirred at −78° C. for 1.5 h and a solution of the crude amine in anhydrous CH$_2$Cl$_2$ (20 mL) was added slowly via syringe. The reaction mixture was allowed to warm to room temperature and stirred for 16 h. A saturated solution of NH$_4$Cl (50 mL) was added and stirred for 10 min. The layers were separated and the aqueous one extracted with CH$_2$Cl$_2$ (2×40 mL) and EtOAc (2×40 mL). The combined organic phases were washed with saturated aqueous NaHCO$_3$ solution (30 mL), brine (30 mL), dried over MgSO$_4$, filtered, and concentrated under reduced pressure. The residue was purified by column chromatography (SiO$_2$, PE/EtOAc 4:1→2:2→1:1) to give 82 (2.18 g, 4.08 mmol, 68%) as an orange foam.

Boc-Cys(Trt)-GOx-Cys(Trt)-OtBu (83): To a solution of 82 (534 mg, 1.00 mmol, 1.0 equiv) in THF (20 mL) was added zinc powder (196 mg, 3.00 mmol, 3.0 equiv) and acetic acid (458 µL, 8.00 mmol, 8.0 equiv) and the reaction mixture was vigorously stirred with a glass-coated magnetic stir bar at room temperature for 1 h. Additional zinc powder (196 mg, 3.00 mmol, 3.0 equiv) and acetic acid (458 µL, 8.00 mmol, 8.0 equiv) were added and the mixture was stirred at ambient temperature for 1 h (repeat 3×). The mixture was cooled to 0° C. and saturated aqueous NaHCO$_3$ solution (20 mL) was added followed by Boc-Cys-OSu (841 mg, 1.50 mmol, 1.5 equiv) and the solution was stirred for 16 h at room temperature. Brine (20 mL) was added and the mixture as extracted with EtOAc (3×15 mL). The combined organic layers were washed with saturated aqueous NaHCO$_3$ solution (30 mL) and brine (30 mL), dried over MgSO$_4$, filtered and concentrated in vacuo. Purification by column chromatography (SiO$_2$, PE/EtOAc 2:1→1:1) gave tripeptide 83 (391 mg, 0.41 mmol, 41%) as a white foam.

Cyclo(Boc-Cys-GOx-Cys-OtBu) (13): To a solution of iodine (305 mg, 1.20 mmol, 3.0 equiv) in anhydrous MeOH (40 mL) was slowly added a solution of Boc-Cys(Trt)-GOx-Cys(Trt)-OtBu (83) (380 mg, 0.40 mmol, 1.0 equiv) in anhydrous MeOH (40 mL). The mixture was stirred for 1 h at room temperature, cooled to 0° C. and a saturated aqueous solution of Na$_2$S$_2$O$_2$ was added until a nearly colourless solution was obtained. The mixture was concentrated in vacuo to a volume of ca. 5 mL, EtOAc (25 mL) was added, the solution was washed with 0.1 M aqueous Na$_2$S$_2$O$_2$ solution (10 mL), dried over Na$_2$SO$_4$ and filtered. The solvent was removed in vacuo and the residue was purified by column chromatography (SiO$_2$, PE/EtOAc 1:1→EtOAc) to afford cyclic tripeptide 13 (119 mg, 0.26 mmol, 64%) as a white foam. R$_f$ (EtOAc) 0.55; mp 98-100° C.; $^1$H NMR (600 MHz, CDCl$_3$ @ 323 K) $\delta_H$ ppm 6.58-6.54 (m, 1H, NH), 5.43 (d, J=4.2 Hz, 1H, NH), 4.59 (d, J=6.5 Hz, 1H, OCHH-Ox), 4.48 (d, J=6.5 Hz, 1H, OCHH-Ox), 4.43 (d, J=6.5 Hz, 2H, 2×OCHH-Ox), 4.27 (t, J=7.2 Hz, 1H, CHα-Cys), 4.04 (dd, J=14.0, 6.8 Hz, 1H, CHHGOx), 3.69 (dd, J=14.0, 4.5 Hz, 1H, CHHGOx), 3.63 (t, J=5.8 Hz, 1H, CHα-Cys), 3.39 (d, J=13.6 Hz, 1H, CHHβ-Cys), 3.20 (br. m, 1H, CHHβ-Cys), 2.94 (dd, J=14.0, 5.1 Hz, 1H, CHHβ-Cys), 2.82 (dd, J=14.0, 5.6 Hz, 1H, CHHβ-Cys), 2.45 (br. s, 1H, NH), 1.48 (s, 9H, 3×CH$_3$, tBu), 1.45 (s, 9H, 3×CH$_3$, tBu); $^{13}$C NMR (151 MHz, CDCl$_3$ @ 323 K) $\delta_C$ ppm 172.7 (C=O), 171.5 (C=O), 155.1 (C=O, Boc), 82.8 (C, tBu), 82.3 (OCH$_2$), 80.9 (C, Boc), 79.8 (OCH$_2$), 60.0 (C, Ox), 57.1 (CH, α-Cys), 55.7 (CH, α-Cys), 46.4 (CH$_2$, GOx), 44.9 (CH$_2$, β-Cys), 28.5 (CH$_3$, tBu), 28.2 (CH$_3$, tBu). N.B. One carbon signal for CH$_2$, 3-Cys not visible; $\nu_{max}$ (neat)=3306, 2931, 1714, 1657, 1490, 1366, 1247, 1149, 971, 843, 751 cm$^{-1}$; MS (ESI$^+$) m/z 464 [M+H]$^+$, 486 [M+Na]$^+$; HRMS (ESI$^+$) calcd. for C$_{19}$H$_{33}$N$_3$NaO$_6$S$_2$ [M+Na]$^+$ 486.1703. found 486.1705; [β]$_D^{28}$ +81.4 (c 1.04, CHCl$_3$). See FIG. 7.

Example 4—the Impact of the Turn-Inducing Motif on the Properties of Cyclic Peptides Initial studies to explore the impact of the turn-inducing element modification on the properties of the derived cyclic peptides were undertaken. cCNGRC (15) is known to target Aminopeptidase N (APN), a transmembrane zinc-dependent metalloprotease involved in a variety of processes, including blood pressure regulation, cell migration, viral uptake, cell survival, and angiogenesis.[14,15] Both the modified derivative 12 and cCNGRC (15) were examined for their inhibitory activity toward porcine APN using a spectrophotometric assay (see Table 2).[15] Similar IC$_{50}$ values were observed for 12 and 15, (see FIGS. 8a and 8b) suggesting that the turn-inducing motif is an excellent bioisostere of the amide bond in this system.

TABLE 2

Relative inhibitory effects of 12 and cCNGRC (15) against porcine Aminopeptidase N (APN).

| entry | compound | IC$_{50}$ (µM) |
| --- | --- | --- |
| 1 | 12 | 175 |
| 2 | cCNGRC (15) | 212[b] |
| 3 | bestatin[c] | 4.1[b] |

[b]Values slightly lower than those reported in ref 15.
[c]Positive control.

The assay used was an in vitro inhibition assay of aminopeptidase N with oxetane modified peptide 12 and parent peptide 15. Peptide 15 was synthesised following a procedure by Piras et al.[7] using HCTU as coupling reagent and NMM as base. Oxidation was performed by on-resin cyclization as described for the biotin labelled compound. Analytical data were in accordance with the literature.

For the determination of $IC_{50}$ values of the modified peptide 12 and parent peptide 15, a protocol published by Piras et al.[7] was followed using L-leucine-p-nitroanilide as substrate and microsomal aminopeptidase from porcine kidney (pAPN, Sigma Aldrich) (18 units/mg protein). $IC_{50}$ values were calculated by following the formation of p-nitroaniline. Formation of p-nitroaniline was monitored by measurement of the UV absorption at 405 nm on a Hidex Sense plate reader. The assay was performed in a 96-well plate in PBS buffer (pH 7.2, 1.47 mM $KH_2PO_4$, 7.8 mM $Na_2HPO_4$, 137 mM NaCl, 2.7 mM KCl, 1.8 mM $CaCl_2$, 1.8 mM $MgCl_2$) at 37° C. with a total volume of 100 μL. Bestatin hydrochloride was used as positive control. Peptides were used in gradient concentrations between 2.5 μM and 3.5 mM, and bestatin in concentrations between 50 nM and 25 μM. The peptides were incubated with the enzyme (1.0 μg/mL) for 5 min. before a solution of L-leucine-p-nitroanilide was added with a final concentration of 250 μM. The plate was incubated at 37° C. for 1 hour before the p-nitroaniline was detected. $IC_{50}$ was defined as the concentration that led to 50% of maximal pAPN catalytic activity. For the calculation of the $IC_{50}$ values log of the concentration was plotted against the UV absorption in GraphPad Prism 5 using nonlinear regression (variable slope (four parameters) with interpolation) for analysis.

Example 5—Preparation of Oxetane Modified Cyclic Peptides 18-21 Via Solid Phase Peptide Synthesis (SPPS)

In an alternative method to make the linear peptides, preformed Fmoc-protected dipeptide building blocks containing the oxetane modification can be incorporated into the growing peptide chain. This method is fully compatible with standard Fmoc/tBu SPPS and avoids the need to subject the growing peptide chain to strongly reductive conditions.

Synthesis by SPPS avoids the need to purify any of the intermediates, simplifying and accelerating the process and enabling automation. This was realised through the synthesis of cyclic tetrapeptide 18 in an impressive 39% yield from commercial H-Trp(Boc)-2-ClTrt (15). Macrocycles 19-21 based on different ring sizes were readily made through further generalisation of this SPPS approach.

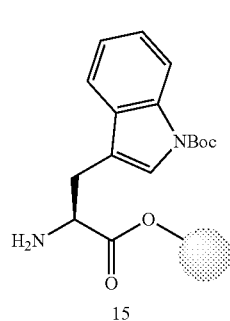

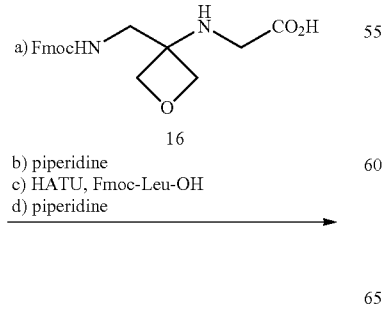

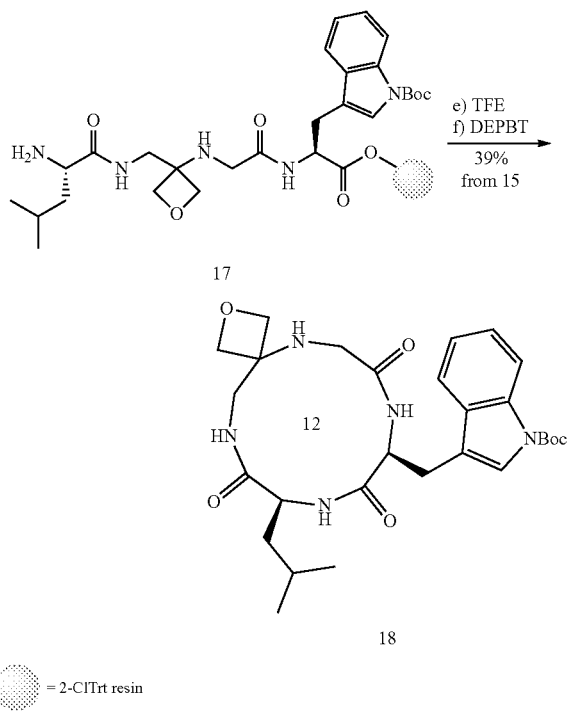

Preparation of Fmoc-GOx-Gly-OH (16):

-continued

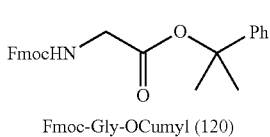

Fmoc-Gly-OCumyl (120)

To a solution of Fmoc-Gly-OH (2.00 g, 6.72 mmol, 1.0 equiv) in anhydrous CH$_2$Cl$_2$ (30 mL) were added 2-phenyl-2-propanol (3.36 g, 24.7 mmol, 3.7 equiv), DCC (1.70 g, 8.24 mmol, 1.2 equiv) and DMAP (167 mg, 1.37 mmol, 0.2 equiv) and the mixture was stirred for 24 h at room temperature. The solvent was removed in vacuo, the residue was diluted with diethyl ether (100 mL) and filtered through a plug of Celite eluting with diethyl ether. The filtrate was washed with saturated NaHCO$_3$ solution (100 mL), dried over MgSO$_4$, filtered, and concentrated under reduced pressure. The residue was purified by column chromatography (SiO$_2$, PE/EtOAc 9:1→4:1) to give Fmoc-Gly-OCumyl (120) (1.43 g, 3.44 mmol, 51%) as a white solid. R$_f$ (PE/EtOAc 2:1) 0.46; mp 109-111° C.; H NMR (500 MHz, CDCl$_3$) δ$_H$ ppm 7.78 (d, J=7.5 Hz, 2H, ArH), 7.60 (d, J=7.5 Hz, 2H, ArH), 7.43-7.26 (m, 9H, ArH), 5.31 (s, 1H, NH), 4.40 (d, J=7.2 Hz, 2H, CH$_2$—Fmoc), 4.23 (t, J=7.2 Hz, 1H, CH-Fmoc), 4.01 (d, J=5.3 Hz, 2H, CH$_2$Gly), 1.84 (s, 6H, 2×CH$_3$, cumyl); $^{13}$C NMR (126 MHz, CDCl$_3$) δ$_C$ ppm 168.7 (C=O), 156.3 (C=O, Fmoc), 145.1 (C), 143.9 (C), 141.3 (C), 128.5 (CH), 127.8 (CH), 127.4 (CH), 127.1 (CH), 125.2 (CH), 124.4 (CH), 120.1 (CH), 83.4 (C, cumyl), 67.2 (CH$_2$, Fmoc), 47.2 (CH, Fmoc), 43.5 (CH$_2$, Gly), 28.6 (CH$_3$, cumyl); ν$_{max}$ (neat)=3308, 2938, 1738, 1687, 1546, 1214, 1053, 760, 697 cm$^{-1}$; MS (ESI$^+$) m/z 438 [M+Na]$^+$, 454 [M+K]$^+$; HRMS (ESI$^+$) calcd. for C$_{26}$H$_{25}$NNaO$_4$ [M+Na]$^+$ 438.1676. found 438.1674.

O$_2$N-GOx-Gly-OCumyl (121)

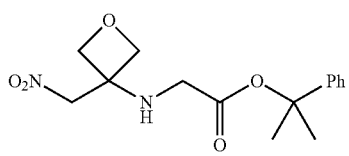

To a solution of Fmoc-Gly-OCumyl (120) (1.29 g, 3.10 mmol, 1.0 equiv) in CH$_2$Cl$_2$ (4.0 mL) was added diethylamine (4.0 mL) and the mixture was stirred at room temperature for 2 h. The reaction mixture was concentrated under reduced pressure and the resulting residue repeatedly dissolved in CH$_2$Cl$_2$ (3×15 mL) and concentrated under reduced pressure to give the crude amine. In a second reaction vessel, oxetane-3-one (398 μL, 6.21 mmol, 2.0 equiv), nitromethane (470 μL, 8.68 mmol, 2.8 equiv) and trimethylamine (173 μL, 1.24 mmol, 0.4 equiv) were combined at 0° C. and stirred for 1 h at room temperature. The mixture was dissolved in anhydrous CH$_2$Cl$_2$ (20 mL), cooled to −78° C., and trimethylamine (1.73 mL, 12.4 mmol, 4.0 equiv) was added followed by dropwise addition of a solution of methanesulfonyl chloride (481 μL, 6.21 mmol, 2.0 equiv) in anhydrous CH$_2$Cl$_2$ (6.0 mL). The reaction mixture was stirred at −78° C. for 1.5 h and a solution of the crude amine in anhydrous CH$_2$Cl$_2$ (20 mL) was added slowly via syringe. The reaction mixture was allowed to warm to room temperature and stirred for 16 h. A saturated solution of NH$_4$Cl (20 mL) was added and stirred for 10 min. The layers were separated and the aqueous one extracted with CH$_2$Cl$_2$ (2×30 mL) and EtOAc (2×30 mL). The combined organic phases were concentrated under reduced pressure and the residue was purified by column chromatography (SiO$_2$, PE/EtOAc 4:1→2:1→1:1) to give 121 (940 mg, 3.05 mmol, 98%) as an off-white solid. R$_f$ (PE/EtOAc 2:1) 0.15; mp 71-72° C.; $^1$H NMR (400 MHz, CDCl$_3$) δ$_H$ ppm 7.39-7.27 (m, 5H, ArH), 4.77 (s, 2H, NO$_2$CH$_2$), 4.57 (d, J=7.2 Hz, 2H, OCH$_2$—Ox), 4.53 (d, J=7.2 Hz, 2H, OCH$_2$—Ox), 3.53 (s, 2H, CH$_2$Gly), 2.29 (s, 1H, NH), 1.80 (s, 6H, 2×CH$_3$, cumyl); $^{13}$C NMR (101 MHz, CDCl$_3$) δ$_C$ ppm 170.6 (C=O), 145.1 (C), 128.5 (CH), 127.5 (CH), 124.4 (CH), 83.3 (C, cumyl), 78.9 (NO$_2$CH$_2$), 78.3 (2×OCH$_2$), 59.6 (C, Ox), 45.6 (CH$_2$, Gly), 28.6 (CH$_3$, cumyl); ν$_{max}$ (neat)=3293, 2979, 1736, 1545, 1364, 1215, 1140, 1101, 978, 762, 695 cm$^{-1}$; MS (ESI$^+$) m/z 331 [M+Na]$^+$; HRMS (ESI$^+$) calcd. for C$_{15}$H$_{20}$N$_2$NaO$_5$ [M+Na]$^+$ 331.1264. found 331.1268.

Fmoc-GOx-Gly-OCumyl (122)

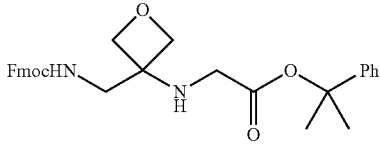

To a solution of NO$_2$-GOx-Gly-OCumyl (121) (928 mg, 3.00 mmol, 1.0 equiv) in THF (30 mL) was added Fmoc N-hydroxysuccinimide ester (2.02 g, 6.00 mmol, 2.0 equiv), NaHCO$_3$ (1.01 g, 12.0 mmol, 4.0 equiv) and Raney Ni (slurry in H$_2$, 3.0 mL). The reaction mixture was placed under an atmosphere of nitrogen, evacuated and filled with hydrogen (balloon). The mixture was stirred vigorously for 4 h at room temperature. Then, the mixture was filtered through a plug of Celite eluting with EtOAc, the filtrate was washed with saturated Na$_2$CO$_3$ (3×50 mL) and concentrated under reduced pressure. Fmoc-GOx-Gly-OCumyl (122) was afforded after purification by column chromatography (SiO$_2$, PE/EtOAc 2:1→1:1→EtOAc) as a white sticky foam (897 mg, 1.79 mmol, 60%). R$_f$ (PE/EtOAc 1:1) 0.21; $^1$H NMR (400 MHz, CDCl$_3$) δ$_H$ ppm 7.72 (d, J=7.4 Hz, 2H, ArH), 7.54 (d, J=7.4 Hz, 2H, ArH), 7.38-7.21 (m, 9H, ArH), 5.26 (s, 1H, NH), 4.48-4.24 (m, 6H, CH$_2$—Fmoc, 2×OCH$_2$—Ox), 4.16 (t, J=6.2 Hz, 1H, CH-Fmoc), 3.50 (d, J=5.1 Hz, 2H, CH$_2$GOx), 3.41 (s, 2H, CH$_2$Gly), 1.92 (br. s, 1H, NH), 1.76 (s, 6H, 2×CH$_3$, cumyl); $^{13}$C NMR (101 MHz, CDCl$_3$) δ$_C$ ppm 171.4 (C=O), 157.0 (C=O, Fmoc), 145.1 (C), 144.0 (C), 141.4 (C), 128.5 (CH), 127.8 (CH), 127.5 (CH), 127.2 (CH), 125.2 (CH), 124.4 (CH), 120.1 (CH), 83.2 (C, cumyl), 79.2 (2×OCH$_2$), 66.9 (CH$_2$, Fmoc), 59.7 (C, Ox), 47.3 (CH, Fmoc), 45.5 (CH$_2$, GOx or Gly), 45.4 (CH$_2$, GOx or Gly), 28.6 (CH$_3$, cumyl); ν$_{max}$ (neat)=3309, 2941, 1716, 1535, 1448, 1214, 1134, 974, 758, 739, 698 cm$^{-1}$; MS (ESI$^+$) m/z 501 [M+H]$^+$, 523 [M+Na]$^+$; HRMS (ESI$^+$) calcd. for C$_{30}$H$_{32}$N$_2$NaO$_5$ [M+Na]$^+$ 523.2203. found 523.2197.

Solid-Phase Peptide Synthesis of Cyclo(Leu-GOx-Gly-Trp(Boc)) (18):

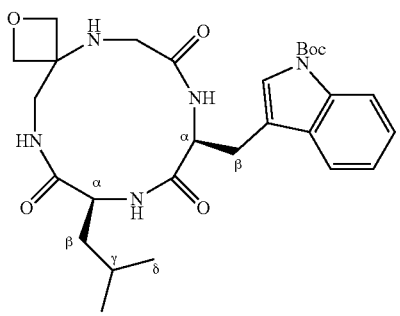

Fmoc-GOx-Gly-Cumyl (122) (200 mg, 0.40 mmol, 4.0 equiv) was stirred at room temperature in 2% TFA in CH$_2$Cl$_2$ (8.0 mL) for 2-3 h until complete deprotection of the cumyl ester was observed by TLC. The solvent was removed under reduced pressure and the resulting residue was repeatedly dissolved in CH$_2$Cl$_2$ (3×10 mL) and concentrated under reduced pressure. The crude Fmoc-GOx-Gly-OH (16) was used for coupling without further purification.

H-Trp(Boc)-2-chlorotrityl resin (15) (145 mg, 0.10 mmol, 1.0 equiv) was placed in a 10 mL reaction vessel and the resin was pre-swollen in DMF (2.0 mL) for 30 min. Fmoc-GOx-Gly-OH (16) was dissolved in DMF (4.0 mL). HATU (72 mg, 0.19 mmol, 1.9 equiv) and DIPEA (70 µL, 0.40 mmol, 4.0 equiv) were added to 2.0 mL solution of 16 and the coupling solution was added to the resin. The coupling reaction was allowed to proceed for 2 h at room temperature under slight agitation. The resin was filtered, washed with DMF (1×2.0 mL) and the coupling step was repeated before the Fmoc group was removed with 20% piperidine in DMF (2.0 mL) for 20 min at room temperature. After washing the resin with DMF (5×2.0 mL), Fmoc-Leu-OH (177 mg, 0.50 mmol, 5.0 equiv) was coupled with HATU (186 mg, 0.49 mmol, 4.9 equiv), DIPEA (174 µL, 1.00 mmol, 10 equiv) in DMF (2.0 mL) for 1 h at room temperature. In case of a positive TNBS test, the coupling step was repeated. The resin was washed with DMF (5×2.0 mL) before the Fmoc-group was removed as described before. The tetrapeptide was then cleaved from the resin with TFE in CH$_2$Cl$_2$ (1:4, 1.0 mL) for 1 h at room temperature. This was repeated twice and the combined cleavage solutions were evaporated to dryness under reduced pressure. Success of the synthesis was confirmed by mass spectrometry and NMR. The crude yield of the solid phase synthesis was approximately 70-80%.

The crude peptide was dissolved in DMF (76 mL, 1 mM) and DEPBT (45 mg, 0.15 mmol, 2.0 equiv) and DIPEA (26 µL, 0.15 mmol, 2.0 equiv) were added. The reaction mixture was stirred at room temperature for 64 h before, the solvent was removed under reduced pressure and the residue purified twice by column chromatography (5-12% MeOH in CH$_2$Cl$_2$). Cyclic tetrapeptide 18 was obtained as a sticky white/colourless solid in 39% yield (21.1 mg, 39 µmol) over the complete reaction sequence.

R$_f$ (CH$_2$Cl$_2$/MeOH 9:1) 0.55; H NMR (500 MHz, DMSO-d6) δ$_H$ 8.25 (d, J=10.3 Hz, 1H, NH), 8.03 (d, J=8.1 Hz, 1H, ArH), 7.95 (d, J=9.1 Hz, 1H, NH), 7.63 (d, J=7.7 Hz, 1H, ArH), 7.48 (s, 1H, ArH), 7.47-7.43 (m, 1H, NH), 7.34 (t, J=7.7 Hz, 1H, ArH), 7.27 (t, J=7.5 Hz, 1H, ArH), 4.61 (q, J=8.3 Hz, 1H, CHα-Trp), 4.40 (d, J=6.3 Hz, 1H, OCHH-Ox), 4.17 (d, J=6.9 Hz, 1H, OCHH-Ox), 4.15 (d, J=6.3 Hz, 1H, OCHH-Ox), 4.01 (td, J=9.8, 5.2 Hz, 1H, CHα-Leu), 3.89 (d, J=6.9 Hz, 1H, OCHH-Ox), 3.80 (dd, J=13.4, 7.8 Hz, 1H, CHHGOx), 3.44-3.35 (m, 1H, CHHGly), 3.24 (d, J=15.2 Hz, 1H, CHHGly), 3.18 (dd, J=15.0, 5.6 Hz, 1H, CHHβ-Trp), 3.07-3.03 (m, 1H, CHHβ-Trp), 3.01 (d, J=11.3 Hz, 1H, CHHGOx), 1.62 (s, 9H, 3×CH$_3$, Boc), 1.61-1.56 (m, 2H, CHH-Leu, CHγ-Leu), 1.52-1.44 (m, 1H, CHHβ-Leu), 0.91 (d, J=6.2 Hz, 3H, CH$_3$δ-Leu), 0.78 (d, J=6.2 Hz, 3H, CH$_3$δ-Leu). N.B. One NH not observed; $^{13}$C NMR (126 MHz, DMSO-d6) δ$_C$ 173.13 (C=O), 173.09 (C=O), 171.0 (C=O), 148.9 (C=O, Boc), 134.7 (C), 130.0 (C), 124.5 (CH), 123.4 (CH), 122.6 (CH), 119.1 (CH), 116.1 (C), 114.8 (CH), 83.7 (C, Boc), 78.1 (OCH$_2$), 76.3 (OCH$_2$), 60.3 (C, Ox), 55.2 (CH, α-Trp), 54.0 (CH, α-Leu), 47.2 (CH$_2$, Gly), 44.3 (CH$_2$, GOx), 39.6 (CH$_2$, β-Leu), 27.7 (CH$_3$, Boc), 25.8 (CH$_2$, β-Trp), 24.6 (CH, γ-Leu), 22.9 (CH$_3$, δ-Leu), 21.1 (CH$_3$, β-Leu); ν$_{max}$ (neat)=3266, 2925, 1672, 1532, 1225, 704 cm$^{-1}$; MS (ESI$^+$) m/z 564 [M+Na]$^+$; HRMS (ESI$^+$) calcd. for C$_{28}$H$_{39}$N$_5$NaO$_6$ [M+Na]$^+$ 564.2793. found 564.2791. [α]$_D^{27}$+10.0 (c 0.05, CHCl$_3$).

Solid-Phase Peptide Synthesis of Cyclo(Ala-Trp-GOx-Gly-Leu) (19):

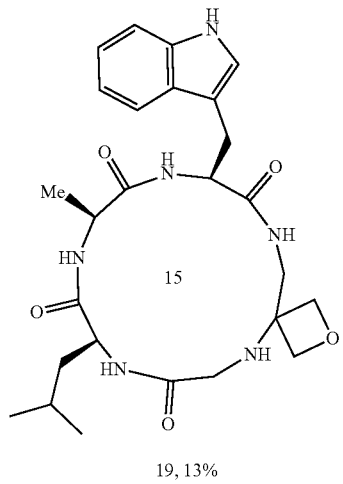 [SMILES: CC(C)C[C@@H]1NC(=O)CNC2(CNC(=O)[C@H](Cc3c[nH]c4ccccc34)NC(=O)[C@H](C)NC1=O)COC2]

19, 13%

Cyclic peptide 19 was synthesised as described above starting from H-Leu-2-chlorotrityl resin (67.5 mg, 0.05 mmol). Tryptophan was incorporated without side chain protecting group. The crude cyclic peptide was purified by preparative HPLC (solvent A: 0.1% TFA in water; solvent B: 0.1% TFA in MeCN; gradient: 0-3 min, 5% B; 3-28 min, 3-40% B; 28-32 min, 40-100% B; retention time: 28.9 min). Cyclic pentapeptide 19 was obtained after freeze-drying as TFA salt (2.4 mg, 6.5 µmol, 13%).

HRMS (ESI$^+$) calcd. for C$_{26}$H$_{37}$N$_6$O$_5$ [M+H]$^+$ 513.2820. found 513.2816.

Solid-Phase Peptide Synthesis of Cyclo(Met-Ala-Trp-GOx-Gly-Leu) (20):

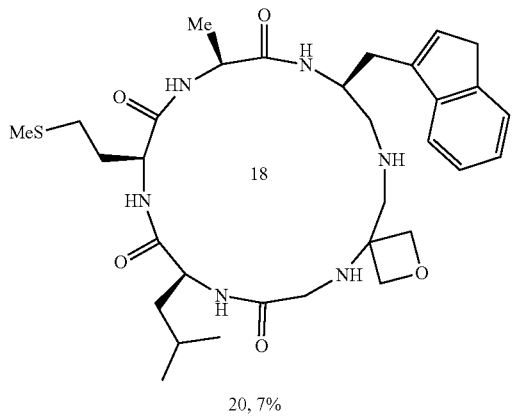 [SMILES: CSCC[C@@H]1NC(=O)[C@H](CC(C)C)NC(=O)CNC2(CNC[C@H](CC3=CCc4ccccc43)NC(=O)[C@H](C)NC1=O)COC2]

20, 7%

Cyclic peptide 20 was synthesised as described above starting from H-Leu-2-chlorotrityl resin (67.5 mg, 0.05 mmol). Tryptophan was incorporated without side chain protecting group. The crude cyclic peptide was purified by preparative HPLC (solvent A: 0.1% TFA in water; solvent B: 0.1% TFA in MeCN; gradient: 0-3 min, 5% B; 3-28 min, 3-50% B; 28-32 min, 50-100% B; retention time: 25.3 min). Cyclic hexapeptide 20 was obtained after freeze-drying as TFA salt (2.5 mg, 6.5 µmol, 7%).

HRMS (ESI$^+$) calcd. for $C_{31}H_{46}N_7O_6S^*$ [M+H]$^+$ 644.3225. found 644.3220.

Solid-Phase Peptide Synthesis of Cyclo(Ser-Met-Ala-Trp-GOx-Gly-Leu) (21):

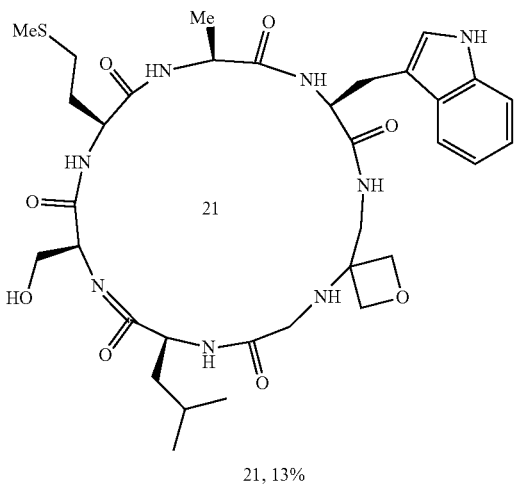

21, 13%

Cyclic peptide 21 was synthesised as described above starting from H-Leu-2-chlorotrityl resin (67.5 mg, 0.05 mmol). Tryptophan was incorporated without side chain protecting group. The crude cyclic peptide was purified by preparative HPLC (solvent A: 0.1% TFA in water; solvent B: 0.1% TFA in MeCN; gradient: 0-3 min, 5% B; 3-28 min, 3-50% B; 28-32 min, 50-100% B; retention time: 26.8 min). Cyclic heptapeptide 21 was obtained after freeze-drying as TFA salt (6.2 mg, 6.5 µmol, 13%).

HRMS (ESI$^+$) calcd. for $C_{34}H_{50}N_8NaO_8S^*$ [M+Na]$^+$ 753.3365. found 753.3358.

Example 6—Preparation of Cyclo(Trp-Leu-AOx-Gly) (12)

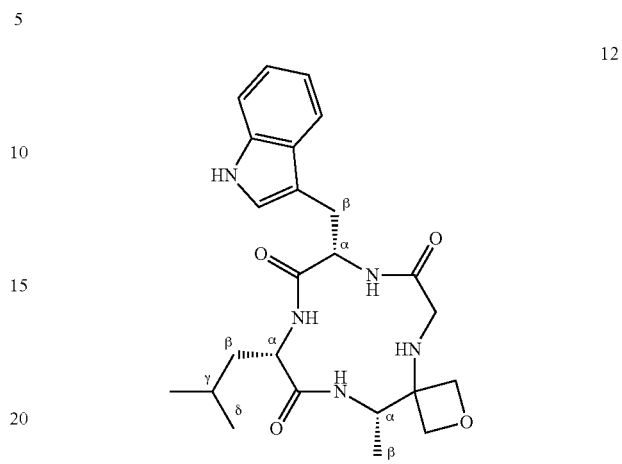

To a solution of H-Trp-Leu-AOx-Gly-OH (53) (47 mg, 0.10 mmol, 1.0 equiv) in anhydrous DMF (100 mL, 0.001 M) under an atmosphere of nitrogen was added DEPBT (60 mg, 0.20 mmol, 2.0 equiv) and DIPEA (35 µL, 0.20 mmol, 2.0 equiv) and the mixture was stirred for 48 h at room temperature. The solvent was removed under reduced pressure, and the residue was purified twice by column chromatography (SiO$_2$, CH$_2$Cl$_2$/MeOH 9:1→85:15) to give cyclic tetrapeptide 12 as a white solid (1$^{st}$ run: 22.9 mg, 50 µmol, 50%; 2$^{nd}$ run (289 µmol scale): 64.4 mg, 142 µmol, 49%). R$_f$ (CH$_2$Cl$_2$/MeOH 9:1) 0.19; mp 220-223° C.; $^1$H NMR (500 MHz, CD$_3$OD) δ$_H$ 7.62 (d, J=7.9 Hz, 1H, ArH), 7.32 (d, J=8.1 Hz, 1H, ArH), 7.12 (s, 1H, ArH), 7.10 (t, J=7.7 Hz, 1H, ArH), 7.03 (t, J=7.4 Hz, 1H, ArH), 4.93 (dd, J=10.2, 7.2 Hz, 1H, CHα-Trp), 4.57 (q, J=7.2 Hz, 1H, CHα-AOx), 4.50 (d, J=6.8 Hz, 1H, OCHH-Ox), 4.40 (d, J=6.8 Hz, 1H, OCHH-Ox), 4.38 (d, J=7.8 Hz, 1H, OCHH-Ox), 4.20 (dd, J=10.9, 4.2 Hz, 1H, CHα-Leu), 4.04 (d, J=7.8 Hz, 1H, OCHH-Ox), 3.67 (d, J=16.6 Hz, 1H, CHHGly), 3.57 (d, J=16.6 Hz, 1H, CHHGly), 3.37-3.27 (m, 1H, CHHβ-Trp), 3.21 (dd, J=15.1, 7.2 Hz, 1H, CHHβ-Trp), 1.72-1.63 (m, 1H, CHHβ-Leu), 1.59-1.48 (m, 2H, CHHβ-Leu, CHγ-Leu), 1.12 (d, J=6.9 Hz, 3H, CH$_3$β-AOx), 0.90 (d, J=6.0 Hz, 3H, CH$_3$δ-Leu), 0.73 (d, J=6.0 Hz, 3H, CH$_3$δ-Leu). N.B. CHHβ-Trp overlaps with solvent peak; $^{13}$C NMR (126 MHz, CD$_3$OD) δ$_C$ 176.4 (C=O), 175.3 (C=O), 173.7 (C=O), 138.0 (C), 128.5 (C), 123.8 (CH), 122.6 (CH), 119.9 (CH), 119.1 (CH), 112.3 (CH), 110.3 (C), 79.2 (OCH$_2$), 77.3 (OCH$_2$), 64.7 (C, Ox), 57.7 (CH, α-Trp), 55.3 (CH, α-Leu), 51.6 (CH, α-AOx), 48.8 (CH$_2$, Gly), 40.6 (CH$_2$, β-Leu), 27.6 (CH$_2$, β-Trp), 26.2 (CH, γ-Leu), 23.3 (CH$_3$, δ-Leu), 21.2 (CH$_3$, δ-Leu), 13.5 (CH$_3$, AOx). N.B. CH$_2$, Gly signal overlaps with solvent peak; ν$_{max}$ (neat)=3256, 2956, 1659, 1532, 740 cm$^{-1}$; MS (ESI$^+$) m/z 478 [M+Na]$^+$; HRMS (ESI$^+$) calcd. for C$_{24}$H$_{33}$N$_5$NaO$_4$ [M+Na]$^+$ 478.2425. found 478.2423; [α]$_D^{29}$ −108 (c 0.06, MeOH).

The successful formation of 12 containing an alanine modified residue confirms that the methodology herein described has broader applicability and is not limited to glycine substitution.

Example 7—Kinetic Measurement of the Cyclization Reaction

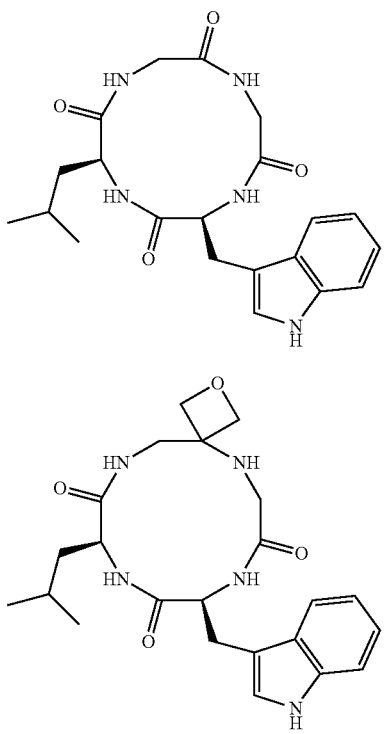

To gain a deeper understanding of reaction rates and the products formed, time-course studies of an inherently difficult to cyclise tetrapeptide WLGG (6) and corresponding oxetane modified WLGOxG (7) (where GOx=oxetane modified glycine) were undertaken. For this investigation, substrates containing a tryptophan residue were used to allow quantitative monitoring by UV spectroscopy. Both substrates were subjected to the DEPBT method and conversions monitored over 74 h. From these data, it is clear that the initial rate of formation of oxetane containing cyclic peptide 9 (see structure above) is considerably faster than 8 (see structure above), even though both linear precursors 6 and 7 are consumed at similar rates (see FIG. 9). Appreciable quantities of the unwanted dimer and cyclodimer were produced in the cyclisation of 8, explaining the lower conversion and isolated yield. In contrast, for the oxetane-modified peptide 7 clean conversion to the cyclic product 9 was observed. Taken together, these studies establish that head-to-tail ring closures to form small cyclic peptides proceed more quickly, give higher yields and produce less side products when one of the backbone carbonyl groups is replaced by an oxetane ring.

Method: HPLC measurements were conducted on an Agilent 1260 Infinity analytical HPLC system on an Agilent Eclipse Plus C18 column (5.0 μm, 4.6×150 mm) with a flow rate of 1.0 mL/min (solvent A: 0.1% TFA in water; solvent B: 0.1% TFA in MeCN; gradient: 0-3 min, 3% B; 3-14 min, 3-20% B; 14-20 min, 20% B; 20-41 min, 20-50% B; 41-43 min, 50-100% B; 43-45 min, 100% B). To separate 20 mL vials were added linear precursor 6 or 7 (10 μmol, 1.0 equiv) and anhydrous DMF (10 mL). At this time a 500 μL sample was withdrawn to determine the initial value by analytical HPLC before DEPBT (20 μmol, 2.0 equiv) and DIPEA (20 μmol, 2.0 equiv) were added to the solution. At designated time points, 500 μL of reaction mixture was taken and diluted with 200 μL distilled water. 10 μL of these samples were directly injected into the analytical HPLC. Further samples were taken after 0.5, 1, 2, 3, 4, 5, 6, 7, 8, 10, 26, 30, 34, 50 and 74 h and treated in the same manner. Signals for linear precursors 6 or 7 and cyclic peptides 8 or 9 as well as dimer 42 were integrated at 280 nm.

To check the accuracy of the integration at 280 nm, calibration curves for the linear and cyclic oxetane modified peptide 7 and 9 were measured by injecting 10 μL of stock solutions of known concentration. UV signals at 280 nm were integrated and the resulting areas plotted against the amount of injected compound in nmol. Linear fitting gave equations shown below for each compound. The obtained data show that conversions obtained from sole integration of the peaks at 280 nm are in accordance with yields obtained from the calibrations curves. The same was assumed for the parent system (compound 6 and 8). Conversions were calculated from initial integral of linear precursor determined before addition of coupling reagent and led to 49% for cyclic peptide 8, 11% for the dimer 42 and 83% for cyclic oxetane modified peptide 9. Conversion obtained for the dimer was divided by two due to two Trp-residues in the structure. Retention times of linear precursors and formed products was confirmed by LC-MS (Bruker Amazon X) under the same HPLC conditions and injection of purified compounds.

Example 8—Comparison with Other Amino Acid Modifications

To understand how significant the methodology herein disclosed is in the broader context of peptide macrocyclisation, a series of alternative modifications were made to the central G residue of LAGAY and the efficiencies of the ring closures compared. N-Methyl glycine, 2-methylalanine (Aib), ethylenediamine, dimethylethylenediamine and -alanine were all introduced in place of the glycine (see Table 3). These modifications could improve cyclisation efficiency by: (i) increasing the conformational flexibility of the peptide backbone by deletion of one of the amide bonds; (ii) enlarging the size of the macrocycle by introduction of an additional methylene group; (iii) bringing the reacting ends closer together by favouring the cis-amide conformation; or (iv) introducing a potentially beneficial Thorpe-Ingold effect. In fact, only the oxetane modification led to marked improvement in isolated yield of the derived cyclic peptides, suggesting that oxetane introduction is particularly beneficial.

TABLE 3

Synthesis of cLAGAY and impact of modifications on cyclisation.

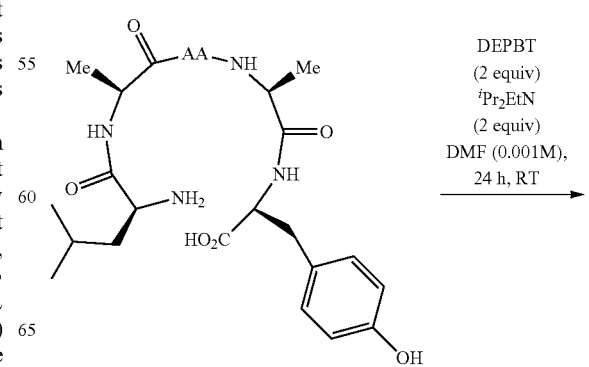

TABLE 3-continued

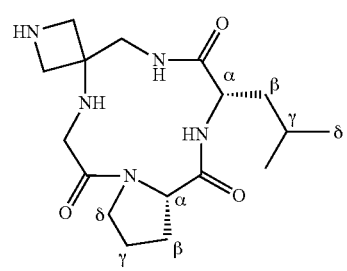 [SMILES: CC(C)C[C@@H]1NC(=O)[C@@H]2CCCN2C(=O)CNC2(CNC2)CNC1=O]

| AA | Yield | Δ% |
|---|---|---|
| | 31% | |
| | 36% | +5% |
| | 29% | −2% |
| | 28% | −3% |
| | 51% | +20% |
| | 32% | +1% |
| | 39% | +8% |

Example 9—Solution Phase Synthesis of Cyclo-((D)Pro-Leu-GAz(H)-Gly) (GAz=Azetidine Modified Glycine)

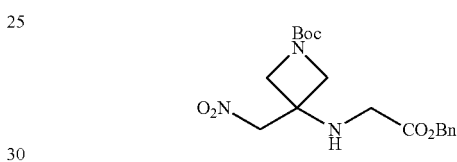

In this example the tetrapeptide was made by solution phase synthesis and deprotection of a Boc group on the azetidine ring.

Preparation of NO$_2$-GAz(Boc)-Gly-OBn:

To a solution of H-Gly-OBn·TsOH (3.49 g, 10.4 mmol, 2.0 equiv) in CH$_2$Cl$_2$ was added triethylamine (1.44 mL, 10.4 mmol, 2.0 equiv) and stirred at room temperature for 15 minutes. In a separate reaction vessel, N-Boc-3-azetidinone (0.89 g, 5.2 mmol, 1.0 equiv) in nitromethane (5.2 mL) was added triethylamine (144 μL, 1.0 mmol, 0.2 equiv) and stirred for 1 h at room temperature. The solvent was removed in vacuo and then resuspended in CH$_2$Cl$_2$ (21 mL), cooled to −78° C., and triethylamine (1.44 mL, 10.4 mmol, 2.0 equiv) was added followed by dropwise addition of methanesulfonyl chloride (0.40 mL, 5.2 mmol, 1.0 equiv). The reaction mixture was stirred at −78° C. for 1.5 h and the solution of the crude amine was added slowly via syringe. The reaction mixture was allowed to warm to room temperature and stirred for 16 h. A saturated solution of NH$_4$Cl (100 mL) was added and stirred for 10 min. The layers were separated and the aqueous one extracted with CH$_2$Cl$_2$ (2×60 mL) and EtOAc (2×60 mL). The combined organic phases were washed with saturated aqueous NaHCO$_3$ solution (100 mL), brine (100 mL), dried over Na$_2$SO$_4$, filtered and concentrated under reduced pressure. The residue was purified by column chromatography (SiO$_2$, EtOAc/PE 3:7) to yield NO$_2$-GAz(Boc)-Gly-OBn (1.66 g, 4.37 mmol, 84%) as a yellow oil. R$_f$ (EtOAc/PE 3:7) 0.34; $^1$H NMR (500 MHz, CDCl$_3$) δ 7.41-7.30 (m, 5H, ArH), 5.18 (s, 2H, CH$_2$Ph), 4.67 (s, 2H, CH$_2$NO$_2$), 4.02-3.83 (m, 4H, 2×NCH$_2$-Az), 3.51 (d, J=4.5 Hz, 2H, CH$_2$Gly), 2.33 (s, 1H, NH), 1.44 (s, 9H, 3×CH$_3$, Boc); $^{13}$C NMR (126 MHz, CDCl$_3$) δ 171.4 (C═O), 156.2 (C═O, Boc), 135.2 (C), 128.9 (CH), 128.8 (CH), 128.7 (CH), 80.6 (C, Boc), 78.7 (CH$_2$NO$_2$), 67.4 (CH$_2$, Bn), 54.3 (2×NCH$_2$), 44.9 (CH$_2$, Gly), 28.4 (CH$_3$, Boc); ν$_{max}$ (neat)=2976, 1739, 1692, 1552, 1378, 1163 cm$^{-1}$; MS (ESI$^+$) m/z 402 [M+Na]$^+$; HRMS (ESI$^+$) calcd. for C$_{18}$H$_{25}$N$_3$NaO$_6$ [M+Na]$^+$ 402.1636. found 402.1636;

Preparation of Fmoc-Leu-GAz(Boc)-Gly-OBn:

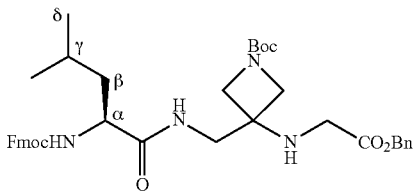

To a solution of NO$_2$-GAz(Boc)-Gly-OBn (1.66 g, 4.4 mmol, 1.0 equiv) in THF (44 mL) was added Fmoc-Leu-OSu (3.89 g, 8.6 mmol, 2.0 equiv), NaHCO$_3$ (1.47 g, 17.5 mmol, 4.0 equiv) and Raney Ni (slurry in H$_2$O, 8 mL). The solution was placed under an atmosphere of nitrogen, evacuated and filled with hydrogen (balloon). The reaction mixture was stirred vigorously for 4.0 h at room temperature. Then, the mixture was filtered through a plug of Celite eluting with EtOAc, concentrated under reduced pressure, the filtrate was suspended in EtOAc (50 mL), washed with saturated Na$_2$CO$_3$ (3×50 mL), dried over Na$_2$SO$_4$ and concentrated in vacuo. Fmoc-Leu-GAz(Boc)-Gly-OBn was afforded after purification by column chromatography (SiO$_2$, 9:1→3:2 CH$_2$Cl$_2$/EA) as a white foam (1.84 g, 2.7 mmol, 62%). R$_f$ (CH$_2$Cl$_2$/EtOAc 9:1) 0.26; mp 77-79° C.; $^1$H NMR (500 MHz, CDCl$_3$) δ 7.76 (d, J=7.5 Hz, 2H, ArH), 7.59 (d, J=7.2 Hz, 2H, ArH), 7.42-7.29 (m, 9H, ArH), 6.69 (s, 1H, NH), 5.20 (d, J=7.0 Hz, 1H, NH Fmoc), 5.11 (s, 2H, CH$_2$Ph), 4.41 (d, J=7.1 Hz, 2H, CH$_2$, Fmoc), 4.25-4.15 (m, 2H, CH, Fmoc, CHα-Leu), 3.69-3.60 (m, 4H, 2×NCH$_2$-Az), 3.52-3.35 (m, 4H, CH$_2$ Gly, CH$_2$ GAz), 1.64-1.60 (m, 3H, CHγ-Leu, CH$_2$β-Leu), 1.42 (s, 9H, 3×CH$_3$, Boc), 0.98-0.91 (m, 6H, 2×CH$_3$δ-Leu); $^{13}$C NMR (126 MHz, CDCl$_3$) δ 172.9 (C=O), 172.6 (C=O), 156.3 (C=O, Boc), 144.0 (C), 143.9 (C), 141.5 (C), 135.2 (C), 132.1 (C), 128.82 (CH), 128.77 (CH), 128.6 (CH), 127.9 (CH), 127.2 (CH), 125.2 (CH), 120.2 (CH), 80.1 (C, Boc), 67.4 (CH$_2$Ph, Bn), 67.1 (CH$_2$, Fmoc), 55.0 (2×NCH$_2$), 53.9 (CH, α-Leu), 47.3 (CH, Fmoc), 44.8 (CH$_2$, GAz), 43.5 (CH$_2$, Gly), 41.8 (CH$_2$, 3-Leu), 28.5 (CH$_3$, Boc), 24.9 (CH, γ-Leu), 23.1 (CH$_3$, δ-Leu), 22.1 (CH$_3$, δ-Leu). Note: Fmoc C=O overlaps with Boc C=O;

ν$_{max}$ (neat)=2955, 1696, 1657, 1120, 757 cm$^{-1}$; MS (ESI$^+$) m/z 685 [M+H]$^+$, 707 [M+Na]$^+$; HRMS (ESI$^+$) calcd. for C$_{39}$H$_{49}$N$_4$O$_7$ [M+H]$^+$ 685.3596. found 685.3604.

Preparation of Cbz-(D)Pro-Leu-GAz(Boc)-Gly-OBn:

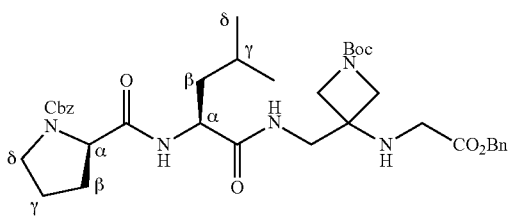 [SMILES: CC(C)C[C@H](NC(=O)[C@H]1CCCN1C(=O)OCc1ccccc1)C(=O)NCC1(NCC(=O)OCc2ccccc2)CN(C(=O)OC(C)(C)C)C1]

To a solution of tripeptide Fmoc-Leu-GAz(Boc)-Gly-OBn (752 mg, 1.1 mmol, 1.0 equiv) in CH$_2$Cl$_2$ (1 mL) was added diethylamine (1 mL) and the mixture was stirred at room temperature for 1 h. The reaction mixture was concentrated under reduced pressure and the resulting residue repeatedly dissolved in CH$_2$Cl$_2$ (3×25 mL) and concentrated under reduced pressure to give the crude amine. The residue was dissolved in CH$_2$Cl$_2$ (11 mL), Cbz-D-Pro-OH (274 mg, 1.1 mmol, 1.0 equiv), EDC·HCl (211 mg, 1.1 mmol, 1.0 equiv), HOBt-H$_2$O (149 mg, 1.1 mmol, 1.0 equiv) and NMM (484 μL, 4.4 mmol, 4.0 equiv) were added subsequently, and the reaction mixture was stirred at room temperature for 24 h. The reaction mixture was diluted with EtOAc (50 mL) and washed with brine (50 mL), dried over Na$_2$SO$_4$, filtered and concentrated in vacuo. The residue was purified by column chromatography (SiO$_2$, CH$_2$Cl$_2$/MeOH 97:3) to give tetrapeptide Cbz-D-Pro-Leu-GAz(Boc)-Gly-OBn (471 mg, 0.68 mmol, 62%) as a white foam. R$_f$ (CH$_2$Cl$_2$/MeOH 97:3) 0.18; mp 65-67° C.; $^1$H NMR (500 MHz, DMSO @ 373 K) δ 7.65 (s, 1H, NH), 7.46 (s, 1H, NH), 7.42-7.26 (m, 10H, ArH), 5.15 (s, 2H, CH$_2$Ph Bn), 5.12-5.02 (m, 2H, CH$_2$Ph Bn), 4.33-4.23 (m, 2H, CHα-Pro, CHα-Leu), 3.66-3.57 (m, 4H, 2×NCH$_2$-Az), 3.50-3.42 (m, 4H, CH$_2$ GAz, CH$_2$δ-Pro), 3.38-3.28 (m, 2H, CH$_2$ Gly), 2.17-2.09 (m, 1H, CHHγ-Pro), 1.93-1.78 (m, 3H, CHHγ-Pro, CH$_2$β-Pro), 1.64-1.47 (m, 3H, CHγ-Leu, CH$_2$β-Leu), 1.39 (s, 9H, 3×CH$_3$, Boc), 0.88 (d, J=6.4 Hz, 3H, CH$_3$δ-Leu), 0.85 (d, J=6.3 Hz, 3H, CH$_3$δ-Leu); $^{13}$C NMR (126 MHz, DMSO @ 373 K) δ 171.9 (C=O), 171.3 (C=O), 171.2 (C=O), 155.2 (C=O Cbz), 153.8 (C=O Boc), 136.4 (C), 135.5 (C), 127.7 (CH), 127.6 (CH), 127.3 (CH), 127.2 (CH), 127.0 (CH), 126.6 (CH), 77.9 (C, Boc), 65.6 (CH$_2$Ph, Bn), 65.2 (CH$_2$Ph, Bn), 59.7 (CH, α-Pro), 56.7 (2×NCH$_2$), 54.6 (C, Az), 51.1 (CH, α-Leu), 46.3 (CH$_2$, GAz), 44.1 (CH$_2$, 6-Pro), 42.7 (CH$_2$, Gly), 40.3 (CH$_2$, β-Leu), 29.7 (CH$_2$, γ-Pro), 27.6 (CH$_3$, Boc), 23.8 (CH, γ-Leu), 23.0 (CH$_2$, β-Pro), 22.2 (CH$_3$, δ-Leu), 21.1 (CH$_3$, δ-Leu); ν$_{max}$ (neat)=2955, 1740, 1667, 1407, 1120 cm$^{-1}$; MS (ESI$^+$) m/z [M+H]$^+$ 694, [M+Na]$^+$ 716; HRMS (ESI$^+$) calcd. for C$_{37}$H$_{52}$N$_5$O$_8$ 694.3810 [M+H]$^+$. found 694.3803.

Preparation of H-(D)Pro-Leu-GAz(Boc)-Gly-OH:

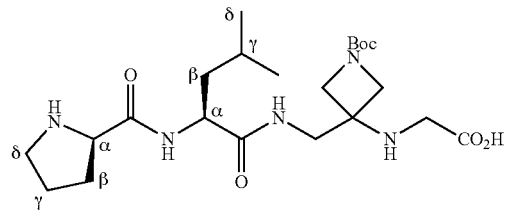 [SMILES: CC(C)C[C@H](NC(=O)[C@H]1CCCN1)C(=O)NCC1(NCC(=O)O)CN(C(=O)OC(C)(C)C)C1]

To a solution of Cbz-D-Pro-Leu-GAz(Boc)-Gly-OBn (450 mg, 0.65 mmol, 1.0 equiv) in MeOH (6.5 mL) was added 10 wt % Pd/C (45 mg, 10 wt %) and the reaction flask was evacuated, filled with nitrogen, evacuated, and placed under an atmosphere of hydrogen (balloon). The mixture was stirred at room temperature for 16 h, placed under nitrogen and filtered through a plug of Celite, which was washed with MeOH (3×). The filtrate was concentrated in vacuo to give the title compound as a white solid (304 mg, 0.647 mmol, quant. yield), which required no further purification; mp 89-91° C.; H NMR (500 MHz, MeOD) δ 4.41-4.30 (m, 2H, CHα-Leu, CHα-Pro), 3.76-3.57 (m, 5H, 2×NCH$_2$-Az, CHHGAz), 3.44-3.38 (m, 1H, CHHδ-Pro), 3.36-3.31 (m, 1H, CHHδ-Pro), 3.30-3.26 (m, 1H, CHHGAz), 3.17 (d, J=17.4 Hz, 1H, CHHGly), 3.06 (d, J=17.4 Hz, 1H, CHHGly), 2.39 (td, J=13.3, 7.8 Hz, 1H, CHHγ-Pro), 2.16-2.01 (m, 2H, CH$_2$β-Pro), 1.96 (dq, J=15.6, 7.8 Hz, 1H, CHHγ-Pro), 1.79-1.62 (m, 2H, CHγ-Leu, CHHβ-Leu), 1.61-1.54 (m, 1H, CHHβ-Leu), 1.42 (s, 9H, CH$_3$ Boc), 0.98 (d, J=6.5 Hz, 3H, CH$_3$δ-Leu), 0.92 (d, J=6.4 Hz, 3H, CH$_3$δ-Leu); $^{13}$C NMR (126 MHz, MeOD) δ 178.5

(C=O), 173.0 (C=O), 169.2 (C=O), 156.9 (C=O Boc), 79.8 (C, Boc), 60.1 (CH, α-Pro), 55.5 (2×NCH₂), 52.5 (CH, α-Leu), 46.2 (CH₂, Gly), 45.6 (CH₂, δ-Pro), 42.0 (CH₂, GAz), 39.8 (CH₂, β-Leu), 29.0 (CH₂, γ-Pro), 27.2 (CH₃, Boc), 24.8 (CH, γ-Leu), 23.8 (CH₂, β-Pro), 22.2 (CH₃, δ-Leu), 20.0 (CH₃, δ-Leu); $v_{max}$ (neat)=3262, 3052, 1651, 1556, 1387, 1118 cm$^{-1}$; MS (ESI$^+$) m/z 470 [M+H]$^+$, 492 [M+Na]$^+$; HRMS (ESI$^+$) calcd. for $C_{22}H_{40}N_5O_6$ 470.2973 [M+H]$^+$. found 470.2971;

Preparation of Cyclo-((D)Pro-Leu-GAz(Boc)-Gly):

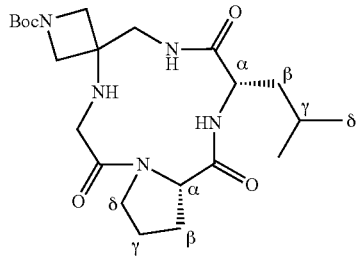 [SMILES: CC(C)C[C@@H]1NC(=O)[C@@H]2CCCN2C(=O)CNC2(CNC1=O)CN(C(=O)OC(C)(C)C)C2]

To a solution of H-D-Pro-Leu-GAz(Boc)-Gly-OH (47 mg, 0.1 mmol, 1.0 equiv) in DMF (mL, 0.001 M) was added DEPBT (60 mg, 0.2 mmol, 2.0 equiv) and DIPEA (36 µL, 0.2 mmol, 2.0 equiv) and the mixture was stirred for 48 h at room temperature. The solvent was removed in vacuo and the residue was purified by column chromatography (SiO₂, CH₂Cl₂/MeOH 40:1→19:1) to give the cyclic tetrapeptide as a glassy colourless solid (35.8 mg, 79 µmol, 79%); $R_f$ (CH₂Cl₂/MeOH 19:1) 0.40; mp 129-131° C.; $^1$H NMR (500 MHz, MeOD) δ 4.49-4.40 (m, 2H, CHα-Pro, CHα-Leu), 3.95 (s, 1H, NCHH-Az), 3.84-3.78 (m, 1H, NCHH-Az), 3.74-3.55 (m, 5H, NCHH-Az, NCHH-Az, CHHδ-Pro, CH₂Gly), 3.37-3.35 (m, 3H, CHHδ-Pro, CH₂GAz), 2.38-2.29 (m, 1H, CHHγ-Pro), 2.05-1.89 (m, 3H, CHHγ-Pro, CH₂β-Pro), 1.73-1.65 (m, 2H, CHγ-Leu, CHHβ-Leu), 1.61-1.56 (m, 1H, CHHβ-Leu), 1.45 (s, 9H, 3×CH₃Boc), 1.00 (d, J=6.1 Hz, 3H, CH₃δ-Leu), 0.95 (d, J=6.0 Hz, 3H, CH₃δ-Leu), Note: CHHδ-Pro, CH₂GAz overlaps with solvent signal; $^{13}$C NMR (126 MHz, MeOD) δ 176.3 (C=O), 175.7 (C=O), 173.0 (C=O), 158.2 (C=O, Boc), 81.2 (C, Boc), 62.1 (CH, α-Leu), 57.0 (2×NCH₂), 54.0 (CH, α-Pro), 48.4 (CH₂, GAz), 47.5 (CH₂, Gly), 38.3 (CH₂, β-Leu), 33.0 (CH₂, γ-Pro), 28.6 (CH₃, Boc), 26.1 (CH, γ-Leu), 23.5 (CH₂, β-Pro), 23.0 (CH₃, δ-Leu), 22.5 (CH₃, δ-Leu), Note: CH₂, δ-Pro overlaps with solvent signal;

$v_{max}$ (neat)=2954, 1662, 1623, 1404, 1164 cm$^{-1}$; MS (ESI$^+$) m/z 474 [M+Na]$^+$, 925 [2M+Na]$^+$; HRMS (ESI$^+$) calcd. for $C_{22}H_{37}N_5NaO_5$ [M+Na]$^+$ 474.2687. found 474.2684.

Preparation of Cyclo-((D)Pro-Leu-GAz(H)-Gly):

To a solution of Cyclo-((D)Pro-Leu-GAz(Boc)-Gly) (17.5 mg, 38.7 µmol, 1.0 equiv) in CH₂Cl₂ (1 mL) was added TFA (1 mL). The solution was stirred for 1 h at room temperature. The solvent was removed in vacuo to reveal the title compound as a pale yellow glassy solid as the TFA salt in quantitative yield, which required no further purification. $^1$H and $^{19}$F NMR using TFE as an internal standard confirmed 1 eq. TFA salt; mp 123-125° C. (decomp.); $^1$H NMR (500 MHz, MeOD) δ 4.49 (dd, J=8.1, 4.3 Hz, 1H, CHα-Pro), 4.27 (t, J=7.7 Hz, 1H, CHα-Leu), 4.01 (d, J=11.2 Hz, 1H, NCHH-Az), 3.98 (d, J=11.4 Hz, 1H, NCHH-Az), 3.81 (d, J=10.9 Hz, 1H, NCHH-Az), 3.75 (d, J=11.1 Hz, 1H, NCHH-Az), 3.70 (d, J=14.4 Hz, 1H, CHHGAz), 3.65-3.60 (m, 1H, CHHδ-Pro), 3.59-3.54 (m, 1H, CHHδ-Pro), 3.41 (d, J=8.5 Hz, 1H, CHHGly), 3.38 (d, J=8.3 Hz, 1H, CHHGly), 3.23 (d, J=14.2 Hz, 1H, CHHGAz), 2.36 (dt, J=19.7, 7.6 Hz, 1H, CHHγ-Pro), 2.04-1.88 (m, 3H, CHHγ-Pro, CH₂β-Pro), 1.71-1.60 (m, 3H, CH₂β-Leu, CHγ-Leu), 0.99 (d, J=6.4 Hz, 3H, CH₃δ-Leu), 0.94 (d, J=6.4 Hz, 3H, CH₃δ-Leu); $^{13}$C NMR (126 MHz, MeOD) δ 176.2 (C=O), 176.0 (C=O), 173.1 (C=O), 62.0 (CH, α-Pro), 59.8 (C, Az), 57.2 (NCH₂), 55.9 (CH, α-Leu), 54.2 (NCH₂), 47.5 (CH₂, GAz), 46.5 (CH₂, Gly), 39.2 (CH, 3-Leu), 33.0 (CH₂, γ-Pro), 26.1 (CH, γ-Leu), 23.7 (CH₂, β-Pro), 22.9 (CH₃, δ-Leu), 22.5 (CH₃, δ-Leu). Note: CH₂, 6-Pro overlaps with solvent signal; $v_{max}$ (neat)=2956, 1665, 1199, 1177, 1128 cm$^{-1}$; MS (ESI$^+$) m/z 352 [M+H]$^+$, 374 [M+Na]$^+$; HRMS (ESI$^+$) calcd. for $C_{17}H_{30}N_5O_3$ 352.2343 [M+H]$^+$. found 352.2338.

Example 10—Solution Phase Synthesis of Cyclo-(Leu-Tyr($^t$Bu)-Val-GAz(Boc)-Thr($^t$Bu)-Phe) (GAz=Azetidine Modified Glycine)

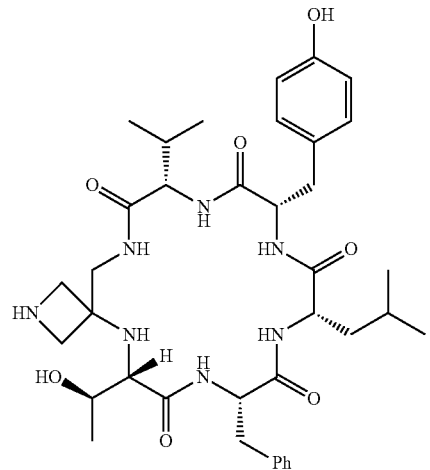 [SMILES: CC(C)C[C@@H]1NC(=O)[C@H](Cc2ccccc2)NC(=O)[C@H]([C@@H](C)O)NC2(CNC2)CNC(=O)[C@H](C(C)C)NC(=O)[C@H](Cc2ccc(O)cc2)NC1=O]

In this example the hexapeptide was made by solution phase synthesis. The example illustrates access to different ring sizes using an azetidine turn-inducing element and the tolerance of azetidine to side-chain deprotections (e.g. tyrosine, threonine).

Preparation of NO₂-GAz(Boc)-Thr($^t$Bu)-OCumyl:

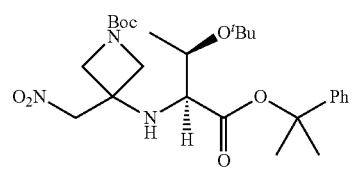 [SMILES: C[C@@H](OC(C)(C)C)[C@H](NC1(C[N+](=O)[O-])CN(C(=O)OC(C)(C)C)C1)C(=O)OC(C)(C)c1ccccc1]

To a solution of Fmoc-Thr($^t$Bu)-OCumyl (1.91 g, 3.71 mmol, 1.0 equiv) in CH₂Cl₂ (3.7 mL) was added diethylamine (3.7 mL) and the mixture was stirred at room temperature for 1 h. The reaction mixture was concentrated under reduced pressure and the resulting residue repeatedly dissolved in CH₂Cl₂ (3×15 mL) and concentrated under reduced pressure to give the crude amine. In a second reaction vessel, N-Boc-3-azetidinone (0.63 g, 3.71 mmol, 1.0 equiv), nitromethane (3.7 mL) and triethylamine (103 µL, 0.74 mmol, 0.2 equiv) were combined and stirred for 1 h at room temperature. The solvent was removed in vacuo and resuspended in CH$_2$Cl$_2$ (15 mL), cooled to −78° C., and triethylamine (1.03 mL, 7.40 mmol, 2.0 equiv) was added followed by dropwise addition of a solution of methanesulfonyl chloride (287 μL, 3.71 mmol, 1.0 equiv) in CH$_2$Cl$_2$ (3.7 mL). The reaction mixture was stirred at −78° C. for 1.5 h and the solution of the crude amine in anhydrous CH$_2$Cl$_2$ (30 mL) was added slowly via syringe. The reaction mixture was allowed to warm to room temperature and stirred for 16 h. A saturated solution of NH$_4$Cl (50 mL) was added and stirred for 10 min. The layers were separated and the aqueous one extracted with CH$_2$Cl$_2$ (2×30 mL) and EtOAc (2×30 mL). The combined organic phases were washed with saturated aqueous NaHCO$_3$ solution (50 mL), brine (50 mL), dried over MgSO$_4$, filtered, and concentrated in vacuo. The residue was purified by column chromatography (SiO$_2$, CH$_2$Cl$_2$/EtOAc 4:1) to give the title compound (1.62 g, 3.18 mmol, 86%) as a pale-yellow oil. R$_f$ (CH$_2$Cl$_2$/EtOAc 4:1) 0.30; $^1$H NMR (500 MHz, CDCl$_3$) 7.46-7.42 (m, 2H, ArH), 7.36-7.31 (m, 3H, ArH), 4.62 (d, J=13.1 Hz, 1H, CHHNO$_2$), 4.53 (d, J=13.1 Hz, 1H, CHHNO$_2$), 3.93 (d, J=9.4 Hz, 1H, NCHH-Az), 3.82-3.72 (m, 4H, NCHH-Az, NCH$_2$-Az, CHα-Thr), 3.20 (d, J=2.9 Hz, 1H, CHβ-Thr), 2.61-2.25 (m, 1H, NH), 1.83 (s, 3H, CH$_3$-Cumyl), 1.80 (s, 3H, CH$_3$-Cumyl), 1.43 (s, 9H, 3×CH$_3$ Boc), 1.20 (s, 9H, 3×CH$_3$ $^t$Bu), 1.08 (d, J=6.2 Hz, 3H, CH$_3$γ-Thr); $^{13}$C NMR (126 MHz, CDCl$_3$) δ 172.7 (C=O), 156.2 (C=O Boc), 145.2 (C), 128.4 (CH), 127.5 (CH), 124.8 (CH), 83.3 (C, Cumyl), 80.3 (C, Boc), 79.0 (CH$_2$NO$_2$), 74.2 (C, $^t$Bu), 69.2 (α-CH, Thr), 61.8 (β-CH, Thr), 54.2 (2×NCH$_2$), 28.6 (CH$_3$, $^t$Bu), 28.4 (CH$_3$, Boc), 27.9 (2×CH$_3$, Cumyl), 19.4 (CH$_3$, γ-Thr); v$_{max}$ (neat)=2975, 1700, 1555, 1377, 1194, 699 cm$^{-1}$; MS (ESI$^+$) m/z 530 [M+Na]$^+$; HRMS (ESI$^+$) calcd. for C$_{26}$H$_{41}$N$_3$NaO$_7$ 530.2837 [M+Na]$^+$. found 530.2833.

Preparation of Fmoc-Val-GAz(Boc)-Thr($^t$Bu)-OCumyl:

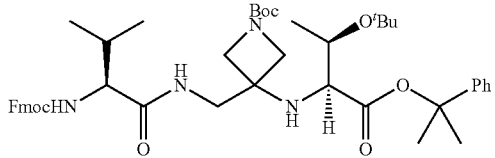

To a solution of NO$_2$-GAz(Boc)-Thr($^t$Bu)-OCumyl (1.61 g, 3.18 mmol, 1.0 equiv) in THF (32 mL) was added Fmoc-Val-OSu (2.77 g, 6.35 mmol, 2.0 equiv) and Raney Ni (slurry in H$_2$O, 6 mL). The solution was placed under an atmosphere of nitrogen, evacuated and filled with hydrogen (balloon). The reaction mixture was stirred vigorously for 4.0 h at room temperature. Then, the mixture was filtered through a plug of Celite eluting with EtOAc, concentrated in vacuo, the filtrate was diluted with EtOAc (50 mL), washed with saturated Na$_2$CO$_3$ (3×50 mL), dried over Na$_2$SO$_4$ and concentrated under reduced pressure. Fmoc-Val-GAz(Boc)-Thr($^t$Bu)-OCumyl was afforded after purification by column chromatography (SiO$_2$, CH$_2$Cl$_2$/EtOAc 19:1) as a white foam (1.53 g, 1.91 mmol, 60%); mp 73-75° C.; R$_f$ (CH$_2$Cl$_2$/EtOAc 19:1) 0.19; $^1$H NMR (500 MHz, CDCl$_3$) 7.76 (d, J=7.5 Hz, 2H, ArH), 7.59 (d, J=7.2 Hz, 2H, ArH), 7.43-7.37 (m, 4H, ArH), 7.34-7.28 (m, 4H, ArH), 7.25-7.20 (m, 1H, ArH), 6.50 (s, 1H, NH), 5.44 (d, J=8.6 Hz, 1H, NH Fmoc), 4.42 (dd, J=10.3, 7.5 Hz, 1H, CHH Fmoc), 4.34-4.28 (m, 1H, CHH Fmoc), 4.21 (t, J=7.0 Hz, 1H, CHFmoc), 4.00-3.92 (m, 1H, CHα-Thr), 3.90-3.82 (m, 1H, CHα-Val), 3.81-3.70 (m, 1H, CHHGAz), 3.62 (d, J=8.7 Hz, 1H, NCHH-Az), 3.60-3.45 (m, 3H, NCHH-Az, NCH$_2$-Az), 3.23-2.70 (m, 2H, CHHGAz, CHβ-Thr), 2.00-1.92 (m, 1H, CHβ-Val) 1.83 (s, 3H, CH$_3$-Cumyl), 1.75 (s, 3H, CH$_3$-Cumyl), 1.42 (s, 9H, 3×CH$_3$ Boc), 1.19 (s, 9H, 3×CH$_3$ $^t$Bu), 1.17 (d, J=6.1 Hz, 3H, CH$_3$γ-Thr), 0.89 (d, J=6.5 Hz, 3H, CH$_3$γ-Val), 0.85 (d, J=6.6 Hz, 1H, CH$_3$γ-Val); $^{13}$C NMR (126 MHz, CDCl$_3$) δ 174.0 (C=O), 171.6 (C=O), 156.4 (C=O, Boc, C=O Fmoc) 145.0 (C), 144.1 (C), 144.0 (2×C), 141.4 (C), 128.4 (CH), 127.8 (CH), 127.6 (CH), 127.2 (CH), 125.27 (CH), 124.7 (CH), 120.1 (CH), 83.4 (C, Cumyl), 79.8 (C, Boc), 74.2 (C, $^t$Bu), 69.2 (CHα-Thr), 67.1 (CH$_2$, Fmoc), 61.8 (CH, β-Thr), 60.4 (CHα-Val), 54.7 (2×NCH$_2$), 47.3 (CH, Fmoc), 44.0 (CH$_2$, GAz), 31.5 (CH, β-Val), 28.8 (CH$_3$, Cumyl), 28.7 (CH$_3$, Boc), 28.5 (CH$_3$, $^t$Bu), 27.3 (2×CH$_3$, Cumyl), 20.2 (CH$_3$, γ-Thr), 19.3 (CH$_3$, γ-Val), 17.8 (CH$_3$, γ-Val); v$_{max}$ (neat)=2968, 1702, 1658, 1399, 1365 cm$^{-1}$; MS (ESI$^+$) m/z 799 [M+H]$^+$, 821 [M+Na]$^+$; HRMS (ESI$^+$) calcd. for C$_{46}$H$_{62}$N$_4$NaO$_8$ 821.4460 [M+Na]$^+$. found 821.4467.

Preparation of Fmoc-Val-GAz(Boc)-Thr($^t$Bu)-Phe-OBn:

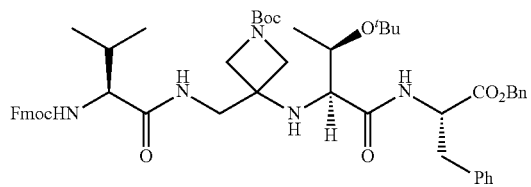

Fmoc-Val-GAz(Boc)-Thr(Bu)-OCumyl (1.47 g, 1.84 mmol, 1.0 equiv) was dissolved in 2% TFA/CH$_2$Cl$_2$ and stirred at room temperature until completion, monitored by ESI-MS. The mixture was concentrated under reduced pressure, the resulting residue was repeatedly re-dissolved in CH$_2$Cl$_2$ (20 mL) and the solvent was removed under reduced pressure. To the crude acid in CH$_2$Cl$_2$ (20 mL) was added H-Phe-OBn-HCl (0.65 g, 2.22 mmol, 1.2 equiv), NMM (1.01 mL, 9.22 mmol, 5.0 equiv), HOBt-H$_2$O (0.25 g, 1.84 mmol, 1.0 equiv) and EDC·HCl (0.35 g, 1.84 mmol, 1.0 equiv). The reaction mixture was allowed to stir for 18 h at room temperature under an atmosphere of nitrogen. The mixture was diluted with EtOAc (50 mL) and washed with brine (3×50 mL), dried (Na$_2$SO$_4$) and concentrated in vacuo to afford a yellow oil which was purified by flash column chromatography (SiO$_2$, CH$_2$C$_2$/MeOH 49:1). Fmoc-Val-GAz(Boc)-Thr($^t$Bu)-Phe-OBn was obtained as a yellow solid (1.26 g, 1.37 mmol, 74%). R$_f$ (CH$_2$Cl$_2$/MeOH 49:1) 0.44; mp 56-58° C.; $^1$H NMR (500 MHz, CDCl$_3$) δ 7.80 (d, J=8.1 Hz, 1H, NH), 7.76 (d, J=7.5 Hz, 2H, ArH), 7.63-7.57 (m, 2H, ArH), 7.42-7.27 (m, 10H, ArH), 7.22-7.18 (m, 3H, ArH), 7.08-7.02 (m, 2H, 1×NH, 1×ArH), 5.49 (d, J=8.8 Hz, 1H, NH Fmoc), 5.18 (d, J=12.1 Hz, 1H, CHHPh Bn), 5.10 (d, J=12.1 Hz, 1H. CHHPh Bn), 4.90 (dt, J=7.9, 5.9 Hz, 1H, CHα-Phe), 4.43 (dd, J=10.2, 7.5 Hz, 1H, CHHFmoc), 4.33 (dd, J=10.1, 7.5 Hz, 1H, CHHFmoc), 4.23 (t, J=7.1 Hz, 1H, CHFmoc), 4.12-4.03 (m, 1H, CHα-Val), 3.78 (d, J=8.6 Hz, 2H, NCHH-Az, CHHGAz), 3.59-3.48 (m, 4H, CHα-Thr, NCHH-Az, NCH$_2$-Az), 3.17 (dd, J=13.9, 5.5 Hz, 1H, CHHβ-Phe), 3.00 (dd, J=13.8, 7.9 Hz, 1H, CHHβ-Phe), 2.95-2.70 (m, 2H, CHα-Thr, CHHGAz), 2.40 (s, 1H, NH), 2.15-2.08 (m, 1H, CHβ-Val), 1.42 (s, 9H, 3×CH$_3$ Boc), 1.08 (s, 9H, 3×CH$_3$ $^t$Bu), 1.01-0.95 (m, 6H, CH$_3$γ-Thr, CH$_3$γ-Val), 0.93 (d, J=6.6 Hz, 3H, CH$_3$γ-Val); $^{13}$C NMR (126 MHz, CDCl$_3$) δ 173.1 (C=O), 172.1 (C=O), 156.5 (C=O Fmoc), 156.4 (C=O Boc), 144.04 (C), 143.97 (C), 141.4 (C), 136.1 (2×C), 135.1 (C), 129.3 (CH), 128.75 (CH), 128.74 (CH), 128.69 (CH), 128.66 (CH), 127.9 (CH), 127.3 (CH), 127.2 (CH), 125.3 (CH), 120.1 (CH), 79.8 (C, Boc), 74.9 (C, $^t$Bu), 67.5 (CH$_2$Ph, Bn), 67.2 (CH$_2$, Fmoc), 60.6 (CH, α-Val, CH, β-Thr), 55.6 (2×NCH$_2$), 53.3 (CH, α-Phe), 47.3 (CH, Fmoc), 38.2 (CH$_2$, β-Phe), 31.3 (CH, β-Val), 28.5 (CH$_3$, Boc or $^t$Bu), 28.4 (CH$_3$, Boc or $^t$Bu), 19.4 (CH$_3$, γ-Thr), 18.0 (2×CH$_3$, γ-Val), Note: CH$_2$, GAz, CHα-Thr missing; $v_{max}$ (neat)=2970, 1734, 1698, 1667, 1390, 1106 cm$^{-1}$; MS (ESI$^+$) m/z 918 [M+H]$^+$, 940 [M+Na]$^+$; HRMS (ESI$^+$) calcd. for C$_{53}$H$_{68}$N$_5$O$_9$ 918.5012 [M+H]$^+$. found 918.5010.

Preparation of Fmoc-Tyr($^t$Bu)-Val-GAz(Boc)-Thr($^t$Bu)-Phe-OBn:

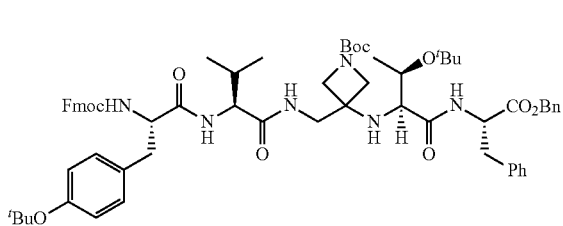

To a solution of tetrapeptide Fmoc-Val-GAz(Boc)-Thr($^t$Bu)-Phe-OBn (994 mg, 1.08 mmol, 1.0 equiv) in CH$_2$Cl$_2$ (2 mL) was added diethylamine (2 mL) and the mixture was stirred at room temperature for 1 h. The reaction mixture was concentrated under reduced pressure and the resulting residue repeatedly dissolved in CH$_2$Cl$_2$ (3×20 mL) and concentrated under reduced pressure to give the crude amine. The residue was dissolved in CH$_2$Cl$_2$ (11 mL), Fmoc-Tyr(tBu)-OH (496 mg, 1.08 mmol, 1.0 equiv), EDC·HCl (207 mg, 1.08 mmol, 1.0 equiv), HOBt·H$_2$O (146 mg, 1.08 mmol, 1.0 equiv) and NMM (475 μL, 4.32 mmol, 4.0 equiv) were added subsequently, and the mixture was stirred at room temperature for 24 h. The reaction mixture was diluted with EtOAc (50 mL) and washed with brine (3×50 mL), dried over Na$_2$SO$_4$, filtered and concentrated under reduced pressure. The residue was purified by column chromatography (SiO$_2$, CH$_2$Cl$_2$/MeOH 49:1) to give pentapeptide Fmoc-Tyr($^t$Bu)-Val-GAz(Boc)-Thr($^t$Bu)-Phe-OBn (898 mg, 0.79 mmol, 73%) as a white solid. R$_f$ (CH$_2$Cl$_2$/MeOH 97:3) 0.27; mp 103–105° C.; $^1$H NMR (500 MHz, CDCl$_3$) δ 7.82 (d, J=8.0 Hz, 1H, NH), 7.76 (d, J=7.5 Hz, 2H, ArH), 7.54 (dd, J=7.3, 2.9 Hz, 2H, ArH), 7.44–7.27 (m, 9H, ArH), 7.25–7.19 (m, 3H, ArH), 7.11–7.04 (m, 4H, ArH), 6.90 (d, J=8.1 Hz, 2H, ArH), 6.53 (d, J=6.6 Hz, 1H, NH), 5.35–5.28 (m, 1H, Fmoc NH), 5.18 (d, J=12.1 Hz, 1H, CHHPh Bn), 5.12 (d, J=12.2 Hz, 1H, CHHPh Bn), 4.91 (dd, J=13.8, 7.6 Hz, 1H, CHα-Phe), 4.55–4.36 (m, 2H, CHH Fmoc, CHα-Tyr), 4.36–4.21 (m, 2H, CHH Fmoc, CHα-Val), 4.18 (t, J=6.9 Hz, 1H, CH Fmoc), 3.86–3.41 (m, 6H, 2×NCH$_2$-Az, CHHGAz, CHα-Thr), 3.16 (dd, J=13.9, 5.7 Hz, 1H, CHHβ-Phe), 3.12–2.76 (m, 5H, CHβ-Thr, CHHGAz, CHHβ-Phe, CH$_2$-Tyr), 2.12–2.05 (m, 1H, m, 1H, CHβ-Val), 1.80 (s, 1H, NH), 1.41 (s, 9H, 3×CH$_3$ Boc), 1.31 (s, 9H, 3×CH$_3$ $^t$Bu), 1.12 (s, 9H, 3×CH$_3$ $^t$Bu), 1.02 (d, J=6.2 Hz, 3H, CH$_3$γ-Val), 0.88 (d, J=6.7 Hz, 3H, CH$_3$γ-Thr), 0.81 (d, J=6.6 Hz, 3H, CH$_3$γ-Val), Note: 1 NH missing; $^{13}$C NMR (126 MHz, CDCl$_3$) δ 173.1 (C=O), 171.8 (C=O), 171.4 (C=O), 171.1 (C=O), 156.4 (C=O Boc), 156.1 (C=O Fmoc), 154.6 (C), 143.9 (C), 143.8 (C), 141.4 (C), 136.1 (C), 135.1 (C), 131.2 (C), 129.3 (CH), 128.8 (CH), 128.74 (CH), 128.67 (CH), 128.65 (CH), 127.9 (CH), 127.3 (CH), 127.2 (CH), 125.20 (CH), 125.16 (CH), 124.5 (CH), 120.1 (CH), 79.8 (C, Boc), 78.6 (C, tBu), 74.9 (C, tBu), 67.5 (CH$_2$Ph Bn), 67.2 (CH$_2$Ph Fmoc), 58.9 (CH, α-Val), 56.3 (CH, α-Tyr), 55.6 (2×NCH$_2$), 53.4 (CH, α-Phe), 47.2 (CH, Fmoc), 38.2 (CH$_2$, β-Tyr), 37.4 (CH$_2$, β-Phe), 30.9 (CH, β-Val), 29.0 (CH$_3$, $^t$Bu), 28.5 (CH$_3$, $^t$Bu), 28.45 (CH$_3$, Boc), 19.4 (CH$_3$, γ-Val), 18.0 (CH$_3$, γ-Thr, CH$_3$, γ-Val), Note: Two aromatic quaternary C, CH$_2$ GAz, CH β-Thr and CH α-Thr missing; $v_{max}$ (neat)=2970, 1698, 1643, 1529, 1232 cm$^{-1}$; MS (ESI$^+$) m/z 1137 [M+H]$^+$, 1160 [M+Na]$^+$; HRMS (ESI$^+$) calcd. for C$_{66}$H$_{84}$N$_6$NaO$_{11}$ 1159.6090 [M+Na]$^+$. found 1159.6101.

Preparation of Cbz-Leu-Tyr($^t$Bu)-Val-GAz(Boc)-Thr($^t$Bu)-Phe-OBn:

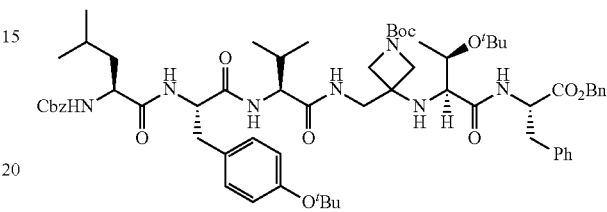

To a solution of pentapeptide Fmoc-Tyr($^t$Bu)-Val-GAz(Boc)-Thr($^t$Bu)-Phe-OBn (845 mg, 0.74 mmol, 1.0 equiv) in CH$_2$Cl$_2$ (2 mL) was added diethylamine (2 mL) and the mixture was stirred at room temperature for 1 h. The reaction mixture was concentrated under reduced pressure and the resulting residue repeatedly dissolved in CH$_2$Cl$_2$ (3×20 mL) and concentrated under reduced pressure to give the crude amine. The residue was dissolved in CH$_2$Cl$_2$ (8 mL), Cbz-Leu-OH (197 mg, 0.74 mmol, 1.0 equiv), EDC·HCl (143 mg, 0.74 mmol, 1.0 equiv), HOBt·H$_2$O (101 mg, 0.74 mmol, 1.0 equiv) and NMM (327 μL, 2.98 mmol, 4.0 equiv) were added subsequently, and the mixture was stirred at room temperature for 24 h. The reaction mixture was diluted with EtOAc (50 mL) and washed with brine (3×50 mL), dried over Na$_2$SO$_4$, filtered and concentrated under reduced pressure. The residue was purified by column chromatography (SiO$_2$, CH$_2$Cl$_2$/MeOH 97:3) to give hexapeptide Cbz-Leu-Tyr($^t$Bu)-Val-GAz(Boc)-Thr($^t$Bu)-Phe-OBn (708 mg, 0.61 mmol, 82%) as a white foam. R$_f$(CH$_2$Cl$_2$/MeOH 97:3) 0.23; mp 126–128° C.; $^1$H NMR (500 MHz, CDCl$_3$) δ 7.79 (d, J=8.1 Hz, 1H, NH), 7.43–7.15 (m, 14H, ArH, NH), 7.10–7.04 (m, 4H, ArH), 6.88 (d, J=8.1 Hz, 2H, ArH), 6.77–6.60 (m, 2H, 2×NH), 5.18–4.96 (m, 5H, 2×CH$_2$Ph, Cbz NH), 4.88 (dd, J=13.9, 7.3 Hz, 1H, CHα-Phe), 4.58–4.49 (m, 1H, CHα-Tyr), 4.34–4.25 (m, 1H, CHα-Val), 4.07–4.00 (m, 1H, CHα-Leu), 3.87–3.48 (m, 6H, CHHGAz, 2×NCH$_2$-Az, CHα-Thr), 3.21–2.80 (m, 6H, CHHGAz, CH$_2$β-Phe, CH$_2$β-Tyr, CH$_3$β-Thr), 2.57 (s, 1H, NH), 2.28–2.14 (m, 1H, CHβ-Val), 1.59–1.48 (m, 2H, CHHβ-Leu, CHγ-Leu), 1.39 (s, 10H, CHHβ-Leu, 3×CH$_3$ $^t$Bu), 1.30 (s, 9H, 3×CH$_3$ $^t$Bu), 1.11 (s, 9H, 3×CH$_3$ $^t$Bu), 1.00 (d, J=6.2 Hz, 3H, CH$_3$γ-Thr), 0.91 (d, J=6.4 Hz, 3H, CH$_3$γ-Val), 0.87–0.81 (m, 9H, CH$_3$γ-Val, 2×CH$_3$δ-Leu); $^{13}$C NMR (126 MHz, CDCl$_3$) δ 173.3 (C=O), 172.9 (C=O), 171.6 (C=O), 171.5 (C=O), 171.1 (C=O), 156.5 (C=O Boc/Cbz), 156.4 (C=O Boc/Cbz), 154.5 (C), 136.1 (C), 136.0 (C), 135.1 (C), 131.5 (C), 129.8 (CH), 129.3 (CH), 128.8 (CH), 128.73 (CH), 128.69 (CH), 128.64 (CH), 128.63 (CH), 128.4 (CH), 128.3 (CH), 127.3 (CH), 124.5 (CH), 79.7 (C, $^t$Bu), 78.5 (C, $^t$Bu), 74.9 (C, Boc), 67.40 (CH$_2$Ph Bn), 67.37 (CH$_2$Ph Bn), 61.1 (CH, α-Thr), 59.0 (CH, α-Val), 55.8 (CH, α-Tyr), 55.5 (2×NCH$_2$), 54.1 (CH, α-Leu), 53.5 (CH, α-Phe), 41.0 (CH$_2$, β-Leu), 38.2 (CH$_2$, β-Phe), 36.4 (CH$_2$, β-Tyr), 30.3 (CH, γ-Val), 29.0 (CH$_3$, $^t$Bu), 28.5 (CH$_3$, $^t$Bu), 28.4 (CH$_3$, Boc), 24.8 (CH, γ-Leu), 23.0 (CH₃, δ-Leu), 21.9 (CH₃, γ-Val), 19.5 (CH₃, δ-Leu), 17.7 (CH₃, γ-Val, CH₃, γ-Thr). Note: CH₂ GAz and CH α-Thr missing; $\nu_{max}$ (neat)=2971, 1697, 1637, 1365, 696 cm$^{-1}$; MS (ESI$^+$) m/z 1184 [M+Na]$^+$; HRMS (ESI$^+$) calcd. for $C_{65}H_{91}N_7NaO_{12}$ 1184.6618 [M+Na]$^+$. found 1184.6623.

Preparation of H-Leu-Tyr($^t$Bu)-Val-GAz(Boc)-Thr($^t$Bu)-Phe-OH:

Preparation of Cyclo-(Leu-Tyr($^t$Bu)-Val-GAz(Boc)-Thr($^t$Bu)-Phe):

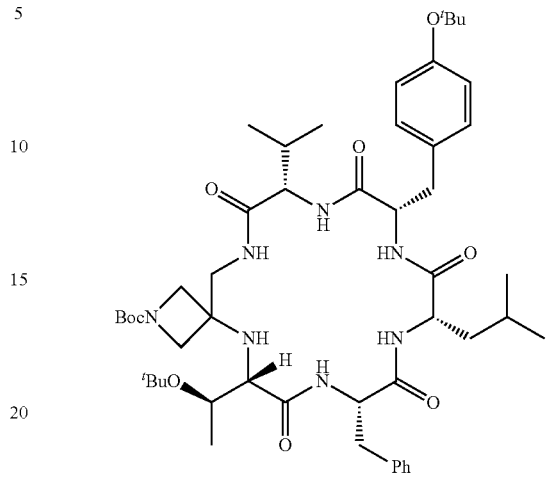

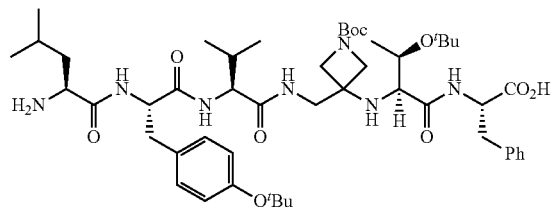 [SMILES: CC(C)C[C@H](N)C(=O)N[C@@H](Cc1ccc(OC(C)(C)C)cc1)C(=O)N[C@H](C(=O)NCC1(N[C@H](C(=O)N[C@@H](Cc2ccccc2)C(=O)O)[C@@H](C)OC(C)(C)C)CN(C(=O)OC(C)(C)C)C1)C(C)C]

To a solution of Cbz-Leu-Tyr(Bu)-Val-GAz(Boc)-Thr(Bu)-Phe-OBn (590 mg, 0.518 mmol, 1.0 equiv) in MeOH (5 mL) was added 10 wt % Pd/C (59 mg, 10 wt %) and the reaction flask was evacuated, filled with nitrogen, evacuated, and placed under an atmosphere of hydrogen (balloon). The reaction mixture was stirred at room temperature for 16 h, placed under nitrogen and filtered through a plug of Celite, which was washed with MeOH (3×). The filtrate was concentrated in vacuo to give the title compound as a white solid (491 mg, 0.517 mmol, quant. yield). mp 126-128° C.; $^1$H NMR (500 MHz, MeOD) δ 7.31-7.21 (m, 7H, ArH), 6.91 (d, J=8.3 Hz, 2H, ArH), 4.76-4.70 (m, 2H, CHα-Tyr, CHα-Phe), 4.21 (d, J=6.9 Hz, 1H, CHα-Val), 3.87-3.81 (m, 1H, CHα-Leu), 3.71-3.44 (m, 6H, CHHGAz, 2×NCH₂-Az, CHα-Thr), 3.26-3.21 (m, 2H, CHHβ-Phe, CHHβ-Tyr), 3.07-2.82 (m, 5H, CHHGAz, CHHβ-Phe, CHHβ-Tyr, CHβ-Thr), 2.10 (td, J=13.5, 6.8 Hz, 1H, CHβ-Val), 1.72-1.62 (m, 3H, CH₂β-Leu, CHγ-Leu), 1.42 (s, 9H, CH₃ Boc), 1.32 (s, 9H, CH₃ $^t$Bu), 1.14 (s, 9H, CH₃ $^t$Bu), 1.06 (d, J=5.8 Hz, 3H, CH₃γ-Thr), 0.97 (d, J=3.2 Hz, 3H, CH₃δ-Leu), 0.96 (d, J=3.0 Hz, 3H, CH₃δ-Leu), 0.94 (d, J=3.3 Hz, 3H, CH₃γ-Val), 0.93 (d, J=3.2 Hz, 3H, CH₃γ-Val); $^{13}$C NMR (126 MHz, MeOD) δ 175.4 (C=O), 174.9 (C=O), 173.8 (C=O), 173.4 (C=O), 170.8 (C=O), 158.1 (C=O Boc), 155.4 (C), 138.4 (C), 133.4 (C), 130.8 (CH), 130.4 (CH), 129.7 (CH), 128.0 (CH), 125.3 (CH), 81.2 (C, $^t$Bu), 79.5 (C, $^t$Bu), 75.6 (C, Boc), 70.7 (CH, α-Thr), 63.7 (CH, β-Thr), 60.5 (CH, α-Val), 57.1 (2×NCH₂), 56.6 (CH, α-Tyr/Phe), 54.9 (CH, α-Tyr/Phe), 52.8 (CH, α-Leu), 44.9 (CH₂, GAz), 41.8 (CH, β-Leu), 38.7 (CH₂, β-Tyr/Phe), 37.7 (CH₂, β-Tyr/Phe), 32.0 (CH, β-Val), 29.2 (CH₃, $^t$Bu), 28.9 (CH₃, $^t$Bu), 28.6 (CH₃, Boc), 25.3 (CH, γ-Leu), 23.3 (CH₃, δ-Leu), 21.8 (CH₃, δ-Leu), 20.3 (CH₃, γ-Thr), 19.9 (CH₃, γ-Val), 18.6 (CH₃, γ-Val). $\nu_{max}$ (neat)=3287, 2967, 1641, 1608, 1506, 1160 cm$^{-1}$; MS (ESI$^+$) m/z 938 [M+H]$^+$, 960 [M+Na]$^+$; HRMS (ESI$^+$) calcd. for $C_{50}H_{80}N_7NaO_{10}$ 938.5961 [M+H]$^+$. found 938.5966.

To a solution of H-Leu-Tyr($^t$Bu)-Val-GAz(Boc)-Thr($^t$Bu)-Phe-OH (94 mg, 0.1 mmol, 1.0 equiv) in DMF (20 mL, 0.005 M) was added DEPBT (60 mg, 0.2 mmol, 2.0 equiv) and DIPEA (36 μL, 0.2 mmol, 2.0 equiv) and the reaction mixture was stirred for 48 h at room temperature. The solvent was removed under reduced pressure at 60° C. over 30 min, and the residue was dried in vacuo. The residue was analysed by LCMS and purified by column chromatography (SiO₂, CH₂Cl₂/MeOH 49:1→19:1) to give the cyclic hexapeptide as a white glassy solid (52.1 mg, 57 μmol, 57%). $R_f$ (CH₂Cl₂/MeOH 19:1) 0.35; mp 156-158° C.; $^1$H NMR (500 MHz, MeOD) δ 7.38-7.31 (m, 2H, ArH), 7.29-7.24 (m, 3H, ArH), 7.15 (d, J=8.3 Hz, 2H, ArH), 6.93 (d, J=8.3 Hz, 2H, ArH), 4.62 (dd, J=9.9, 5.6 Hz, 1H, CHα-Phe), 4.36 (d, J=9.0 Hz, 1H, CHα-Val), 4.08 (dd, J=11.5, 3.3 Hz, 1H, NCHH GAz), 3.98-3.83 (m, 2H, NCHH GAz, CHH GAz), 3.81-3.71 (m, 2H, NCHH GAz, CHα-Leu), 3.66-3.49 (m, 3H, NCHH GAz, CHα-Tyr, CHHβ-Tyr), 3.37 (m, 2H, CHHβ-Tyr, CHα-Thr), 3.02-2.94 (m, 1H, CHH GAz), 2.90-2.82 (m, 1H, CHβ-Thr), 2.74 (dd, J=13.4, 10.8 Hz, 1H, CHHβ-Phe), 2.18-1.88 (m, 1H, CHβ-Val), 1.58-1.51 (m, 1H, CHHβ-Leu), 1.42 (s, 9H, CH₃ Boc), 1.35-1.30 (m, 10H, CHHβ-Leu, CH₃ $^t$Bu), 1.26-1.22 (m, 1H, CHγ-Leu), 1.09-0.97 (m, 18H, CH₃ $^t$Bu, 2×CH₃γ-Val, CH₃γ-Thr), 0.81 (d, J=6.5 Hz, 3H, CH₃δ-Leu), 0.77 (d, J=6.4 Hz, 3H, CH₃δ-Leu). Note: CHHβ-Phe overlaps with solvent signal; $^{13}$C NMR (126 MHz, MeOD) δ 176.2 (C=O), 174.9 (C=O), 174.7 (C=O), 174.5 (C=O), 172.8 (C=O), 158.2 (C=O Boc), 155.3 (C), 137.7 (C), 134.9 (C), 130.6 (CH), 130.2 (CH), 130.0 (CH), 128.3 (CH), 125.3 (CH), 81.3 (C, $^t$Bu), 79.4 (C, $^t$Bu), 75.5 (C, Boc), 69.5 (CH, α-Thr), 65.1 (CH, β-Thr), 62.6 (CH, α-Val), 59.5 (CH, α-Tyr), 57.7 (2×NCH₂), 55.8 (CH, α-Leu), 54.7 (CH, α-Phe), 40.3 (CH₂, β-Leu), 39.3 (CH₂, β-Phe), 35.1 (CH₂, β-Tyr), 33.6 (CH₂, β-Val), 29.2 (CH₃, $^t$Bu), 28.9 (CH₃, $^t$Bu), 28.6 (CH₃, Boc), 25.2 (CH, γ-Leu), 23.1 (CH₃, δ-Leu), 22.3 (CH₃, δ-Leu), 21.8 (CH₃, γ-Thr), 19.9 (CH₃, γ-Val), 19.5 (CH₃, γ-Val). Note: GAz CH₂ missing; $\nu_{max}$ (neat)=2973, 1642, 1505, 1161 cm$^{-1}$; MS (ESI$^+$) m/z 920 [M+H]$^+$, 942 [M+Na]$^+$; HRMS (ESI$^+$) calcd. for $C_2H_{76}N_7O_9$ 942.5699 [M+H]$^+$. found 942.5692.

Preparation of Cyclo-(Leu-Tyr-Val-GAz-Thr-Phe):

To a solution of Cyclo-(Leu-Tyr(tBu)-Val-GAz(Boc)-Thr(tBu)-Phe) (15.9 mg, 16.3 µmol, 1.0 equiv) in CH$_2$Cl$_2$ (1 mL) was added TFA (1 mL). The solution was stirred for 1.5 h at room temperature. The solvent was removed in vacuo to reveal the title compound as a white glassy solid as the TFA salt in quantitative yield, which required no further purification. 1H and $^{19}$F NMR using TFE as an internal standard confirmed 1 eq. TFA salt; mp 186-187° C. (decomp.); $^1$H NMR (500 MHz, MeOD) δ 7.37-7.25 (m, 5H, ArH), 7.05 (d, J=7.8 Hz, 2H, ArH), 6.73 (d, J=7.6 Hz, 2H, ArH), 4.64 (dd, J=9.8, 4.9 Hz, 1H, CHα-Phe), 4.33 (d, J=9.2 Hz, 1H, CHα-Val), 4.18 (d, J=11.0 Hz, 1H, NCHH GAz), 4.10 (dd, J=11.3, 3.5 Hz, 1H, CHα-Tyr), 4.05-3.98 (m, 2H, CHH GAz, NCHH GAz), 3.98-3.88 (m, 2H, NCH$_2$ GAz), 3.75 (t, J=7.2 Hz, 1H, CHα-Leu), 3.46 (m, 1H, CHHβ-Tyr), 3.03 (d, J=16.2 Hz, 1H, CHH GAz), 2.88-2.76 (m, 2H, CHHβ-Phe, CHβ-Thr), 2.05-1.92 (m, 1H, CHβ-Val), 1.54-1.47 (m, 1H, CHHβ-Leu), 1.43-1.32 (m, 2H, CHHβ-Leu, CHγ-Leu), 1.06 (d, J=6.5 Hz, 3H, CH$_3$γ-Thr), 1.03 (d, J=6.9 Hz, 3H, CH$_3$γ-Val), 1.00 (d, J=5.8 Hz, 3H, CH$_3$γ-Val), 0.82 (d, J=6.0 Hz, 3H, CH$_3$δ-Leu), 0.79 (d, J=6.1 Hz, 3H, CH$_3$δ-Leu) Note: CHH-Tyr, CHα-Thr and CHHβ-Phe overlaps with solvent signal; $^{13}$C NMR (126 MHz, MeOD) δ 175.4 (C=O), 174.9 (C=O), 174.7 (C=O), 174.6 (C=O), 173.0 (C=O), 157.3 (C), 137.6 (C), 131.0 (CH), 130.2 (C), 130.1 (CH), 129.8 (CH), 128.2 (CH), 116.3 (CH), 69.2 (CH, α-Thr), 66.0 (CH, β-Thr), 62.8 (CH, α-Val), 60.6 (C, GAz), 59.4 (CH, α-Tyr), 55.9 (2×NCH$_2$), 55.8 (CH, α-Leu), 54.8 (CH, α-Phe), 44.2 (CH$_2$, GAz), 40.3 (CH$_2$, β-Leu), 38.9 (CH$_2$, β-Phe), 35.1 (CH$_2$, β-Tyr), 33.4 (CH, β-Val), 25.1 (CH, γ-Leu), 22.8 (CH$_3$, β-Leu), 22.6 (CH$_3$, δ-Leu), 20.8 (CH$_3$, γ-Thr), 19.9 (CH$_3$, γ-Val), 19.5 (CH$_3$, γ-Val). ν$_{max}$ (neat)=3302, 3029, 1639, 1515, 1436, 1198, 1132 cm$^{-1}$; MS (ESI$^+$) m/z 708 [M+H]$^+$, 730 [M+Na]$^+$; HRMS (ESI$^+$) calcd. for C$_{37}$H$_{54}$N$_7$O$_7$ 708.4079 [M+Na]$^+$. found 708.4082.

Example 12—Solid Phase Synthesis of Cyclo-(Phe-Glu-GAz-Thr-Gly) (GAz=Azetidine Modified Glycine)

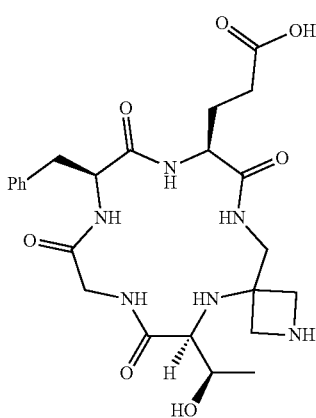 [SMILES: C[C@@H](O)[C@@H]1NC2(CNC2)CNC(=O)[C@H](CCC(=O)O)NC(=O)[C@H](Cc2ccccc2)NC(=O)CNC1=O]

In this example the pentapeptide is made by solid phase peptide synthesis with side-chain and Boc deprotection exemplified.

Preparation of Fmoc-GAz(Boc)-Thr(tBu)-OCumyl:

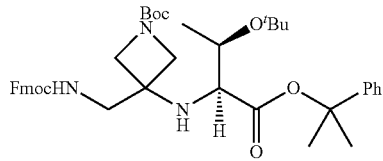

To a solution of NO$_2$-GAz(Boc)-Thr(tBu)-OCumyl (2.00 g, 3.94 mmol, 1.0 equiv) in THF (40 mL) was added Fmoc-OSu (2.67 g, 7.88 mmol, 2.0 equiv), NaHCO$_3$ (1.32 g, 15.76 mmol, 4.0 equiv) and Raney Ni (slurry in H$_2$O, 8 mL). The solution was placed under an atmosphere of nitrogen, evacuated and filled with hydrogen (balloon). The reaction mixture was stirred vigorously for 4.0 h at room temperature. Then, the mixture was filtered through a plug of Celite eluting with EtOAc, concentrated in vacuo, the filtrate was diluted with EtOAc (50 mL), washed with saturated Na$_2$CO$_3$ (3×50 mL), dried over Na$_2$SO$_4$ and concentrated under reduced pressure. Fmoc-GAz(Boc)-Thr(tBu)-OCumyl was afforded after purification by column chromatography (SiO$_2$, CH$_2$Cl$_2$/EtOAc 19:1) as a white foam (1.43 g, 2.04 mmol, 52%); R$_f$ (CH$_2$Cl$_2$/EtOAc 19:1) 0.23; mp 67-69° C.; $^1$H NMR (500 MHz, CDCl$_3$) δ 7.76 (d, J=7.5 Hz, 2H, ArH), 7.59 (d, J=4.5 Hz, 1H, ArH), 7.58 (d, J=4.4 Hz, 1H, ArH), 7.45-7.38 (m, 4H, ArH), 7.37-7.29 (m, 4H, ArH), 7.28-7.20 (m, 1H, ArH), 5.42 (t, J=5.0 Hz, 1H, Fmoc NH), 4.48-4.29 (m, 2H, CH$_2$ Fmoc), 4.19 (t, J=7.0 Hz, 1H, CH Fmoc), 3.82-3.73 (m, 1H, CHα-Thr), 3.68-3.51 (m, 2H, 2×NCH$_2$-Az, CHHGAz), 3.31-2.98 (m, 2H, CHβ-Thr, CHHGAz), 2.08 (s, 1H, NH), 1.84 (s, 3H, CH$_3$-Cumyl), 1.80 (s, 3H, CH$_3$-Cumyl), 1.43 (s, 9H, CH$_3$ Boc), 1.20 (s, 9H, CH$_3$ tBu), 1.16 (d, J=6.1 Hz, 3H, CH$_3$γ-Thr); $^{13}$C NMR (126 MHz, CDCl$_3$) δ 173.6 (C=O), 156.8 (C=O, Boc), 156.3 (C=O, Fmoc), 144.8 (C), 144.0 (C), 141.3 (C), 128.3 (CH), 127.7 (CH), 127.4 (CH), 127.0 (CH), 125.2 (CH), 124.7 (CH), 120.0 (CH), 83.2 (C, Cumyl), 79.6 (C, Boc), 74.3 (C, tBu), 69.1 (CH, α-Thr), 66.8 (CH$_2$, Fmoc) 61.8 (CH, β-Thr), 54.6 (2×NCH$_2$), 47.3 (CH Fmoc), 45.5 (CH$_2$, GAz), 28.6 (CH$_3$, Boc), 28.4 (CH$_3$, tBu), 27.5 (CH$_3$, Cumyl), 20.0 (CH$_3$, γ-Thr). Note: One CH$_3$, Cumyl overlapping; ν$_{max}$ (neat)=2974, 1699, 1364, 1100, 758 cm$^{-1}$; MS (ESI$^+$) m/z 700 [M+H]$^+$, 722 [M+Na]$^+$; HRMS (ESI$^+$) calcd. for C$_{41}$H$_{53}$N$_3$NaO$_7$ 722.3776 [M+Na]$^+$. found 722.3782.

Preparation of H-Phe-Glu(tBu)-GAz(Boc)-Thr(tBu)-Gly-OH:

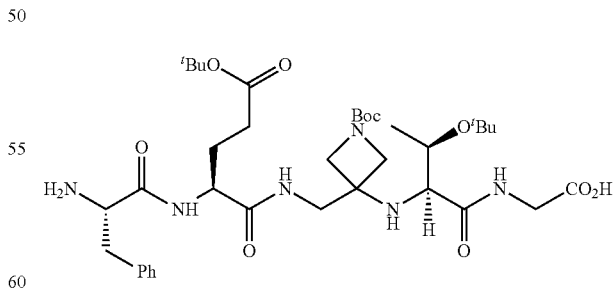

Fmoc-GAz(Boc)-Thr(tBu)-OCumyl (420 mg, 0.60 mmol, 4.0 equiv) was stirred at room temperature in 2% TFA in CH$_2$Cl$_2$ (12 mL) until complete deprotection of the cumyl ester was observed by ESI-MS. The solvent was removed under reduced pressure and the resulting residue was repeatedly dissolved in CH$_2$Cl$_2$ (3×20 mL) and concentrated under reduced pressure. The crude Fmoc-GAz(Boc)-Thr(tBu)-OH was used for coupling without further purification. H-Gly-2-chlorotrityl resin (resin loading 0.52 mmol/g, 288 mg, 0.15 mmol, 1.0 equiv) was placed in a 10 mL reaction vessel and the resin was pre-swollen in DMF (2.0 mL) for 30 min. Fmoc-GAz(Boc)-Thr(tBu)-OH was dissolved in DMF (3.0 mL). HATU (228 mg, 0.6 mmol, 4.0 equiv) and DIPEA (209 µL, 1.2 mmol, 8.0 equiv) were added and this solution was added directly to the resin. The coupling reaction was allowed to proceed for 2 h at room temperature under agitation. The resin was filtered, washed with DMF (5×2.0 mL) and in case of a positive TNBS test, the coupling step was repeated. The Fmoc group was removed with 20% piperidine in DMF (4.0 mL) for 20 min at room temperature. After washing the resin with DMF (5×2.0 mL), Fmoc-Glu (tBu)-OH (319 mg, 0.75 mmol, 5.0 equiv) was coupled with HATU (285 mg, 0.75 mmol, 5.0 equiv), DIPEA (261 µL, 1.50 mmol, 10 equiv) in DMF (3.0 mL) for 1 h at room temperature. The resin was washed with DMF (5×2.0 mL) before the Fmoc group was removed and coupled with Fmoc-Phe-OH (290 mg, 0.75 mmol, 5.0 equiv.) followed by Fmoc deprotection as described before. The pentapeptide was then cleaved from the resin with TFE in $CH_2Cl_2$ (1:4, 3.0 mL) for 1 h at room temperature. This was repeated twice and the combined cleavage solutions were evaporated to dryness under reduced pressure to reveal the title compound as a glassy white solid (74.3 mg, 0.10 mmol, 68%) which required no further purification; mp 118-120° C.; $^1$H NMR (500 MHz, MeOD) δ 7.42-7.26 (m, 5H, ArH), 4.31 (dd, J=8.6, 5.5 Hz, 1H, CHα-Glu), 4.19 (t, J=7.4 Hz, 1H, CHα-Phe), 3.98-3.57 (m, 8H, CHα-Thr, 2×NCH$_2$ GAz, CH$_2$ Gly, CHH GAz), 3.20 (dd, J=13.6, 7.4 Hz, 1H, CHHβ-Phe), 3.12-2.96 (m, 3H, CHHβ-Phe, CHH GAz, CHβ-Thr), 2.34-2.15 (m, 2H, CH$_2$γ-Glu), 2.11-2.04 (m, 1H, CHHβ-Glu), 1.99-1.87 (m, 1H, CHHβ-Glu), 1.48-1.43 (m, 18H, CH$_3$ Boc, CH$_3$ CO$_2$ tBu), 1.25-1.17 (m, 12H, CH$_3$ tBu, CH$_3$γ-Thr); $^{13}$C NMR (126 MHz, MeOD) δ 175.9 (C=O), 175.9 (C=O), 174.0 (C=O), 173.7 (C=O), 170.1 (C=O), 158.3 (C=O Boc), 136.0 (C), 130.6 (CH), 130.1 (CH), 128.7 (CH), 81.7 (C, tBu), 81.2 (C, tBu), 75.4 (C, Boc), 69.9 (CH, α-Thr), 64.3 (CH, β-Thr), 57.4 (2×NCH$_2$), 56.0 (CH, α-Phe), 55.0 (CH, α-Glu), 45.7 (CH$_2$, Gly), 44.1 (CH$_2$, GAz), 38.7 (CH$_2$, β-Phe), 32.6 (CH$_2$, γ-Glu), 29.0 (CH$_3$, CO$_2$ tBu), 28.6 (CH$_3$, Boc), 28.4 (CH$_3$, tBu), 28.1 (CH$_2$, β-Glu), 21.4 (CH$_3$, γ-Thr); $v_{max}$ (neat)=2971, 1653, 1391, 1151 cm$^{-1}$; MS (ESI$^+$) m/z 749 [M+H]$^+$, 771 [M+Na]$^+$; HRMS (ESI$^+$) calcd. for $C_{37}H_{61}N_6O_{10}$ 749.4444 [M+Na]$^+$. found 749.4438.

Preparation of Cyclo-(Phe-Glu(tBu)-GAz(Boc)-Thr(tBu)-Gly):

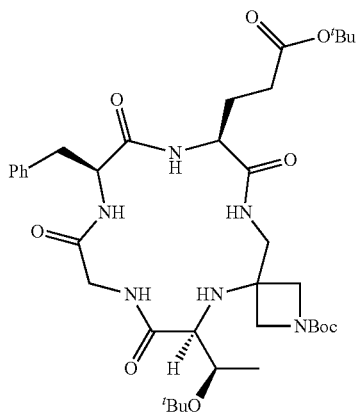 [SMILES: C[C@@H](OC(C)(C)C)[C@@H]1NC2(CNC(=O)[C@H](CCC(=O)OC(C)(C)C)NC(=O)[C@H](Cc3ccccc3)NC(=O)CNC1=O)CN(C(=O)OC(C)(C)C)C2]

To a solution of H-Phe-Glu(tBu)-GAz(Boc)-Thr(tBu)-Gly-OH (60.6 mg, 81 µmol, 1.0 equiv) in DMF (16.2 mL, 0.005 M) was added DEPBT (48.4 mg, 0.16 mmol, 2.0 equiv) and DIPEA (28 µL, 0.16 mmol, 2.0 equiv) and the reaction mixture was stirred for 68 h at room temperature. The solvent was removed under reduced pressure at 60° C. over 30 min, and the residue was dried in vacuo. The residue was purified by column chromatography (SiO$_2$, CH$_2$Cl$_2$/MeOH 49:1→19:1) to give the cyclic hexapeptide as a white glassy solid (43.2 mg, 59 µmol, 73%). R$_f$ (CH$_2$Cl$_2$/MeOH 19:1) 0.29; mp 125-127° C.; $^1$H NMR (500 MHz, MeOD) δ 7.36-7.20 (m, 5H, ArH), 4.49 (dd, J=8.9, 5.2 Hz, 1H, CHα-Glu), 4.45 (dd, J=10.0, 3.9 Hz, 1H, CHα-Phe), 4.00-3.90 (m, 2H, CHHGly, NCHH GAz), 3.83-3.74 (m, 3H, NCHH GAz, CHH GAz, CHα-Thr), 3.66 (d, J=8.3 Hz, 1H, NCHHGAz), 3.60 (d, J=8.9 Hz, 1H, NCHH GAz), 3.52 (d, J=14.6 Hz, 1H, CHHGly), 3.29 (dd, J=14.4, 4.1 Hz, 1H, CHHβ-Phe), 3.15 (d, J=4.3 Hz, 1H, CHβ-Thr), 3.02-2.94 (m, 2H, CHH GAz, CHHβ-Phe), 2.34 (t, J=7.5 Hz, 2H, CH$_2$γ-Glu), 2.25-2.14 (m, 1H, CHHβ-Glu), 2.00-1.91 (m, 1H, CHHβ-Glu), 1.51-1.44 (m, 18H, CH$_3$ Boc, CH$_3$ CO$_2$ tBu), 1.23 (s, 9H, CH$_3$ tBu), 1.10 (d, J=6.2 Hz, 3H, CH$_3$γ-Thr); $^{13}$C NMR (126 MHz, MeOD) δ 177.0 (C=O), 174.1 (C=O), 173.82 (C=O), 173.79 (C=O), 158.3 (C=O Boc), 138.4 (C), 130.0 (CH), 129.7 (CH), 128.0 (CH), 81.8 (C, tBu), 81.1 (C, tBu), 75.4 (C, Boc), 71.2 (CH, α-Thr), 62.5 (CH, β-Thr), 58.5 (2×NCH$_2$), 57.1 (CH, α-Phe), 54.0 (CH, α-Glu), 46.3 (CH$_2$ GAz), 44.8 (CH$_2$ Gly), 37.7 (CH$_2$, β-Phe), 32.8 (CH$_2$, γ-Glu), 28.64 (CH$_3$, CO$_2$ tBu), 28.58 (CH$_3$, Boc), 28.4 (CH$_3$, tBu), 28.2 (CH$_2$, β-Glu), 19.1 (CH$_3$, γ-Thr). Note: One C=O overlapping; $v_{max}$ (neat)=2974, 1649, 1532, 1366, 1152 cm$^{-1}$; MS (ESI$^+$) m/z 731 [M+H]$^+$, 753 [M+Na]$^+$; HRMS (ESI$^+$) calcd. for $C_{37}H_{58}N_6NaO_9$ 753.4157 [M+Na]$^+$. found 753.4162.

Preparation of Cyclo-(Phe-Glu-GAz-Thr-Gly):

To a solution of Cyclo-(Phe-Glu(tBu)-GAz(Boc)-Thr (tBu)-Gly) (29 mg, 40 µmol, 1.0 equiv) in CH$_2$Cl$_2$ (1 mL) was added TFA (1 mL). The solution was stirred for 1 h at room temperature. The solvent was removed in vacuo to reveal the title compound as a white glassy solid as the TFA salt in quantitative yield, which required no further purification. $^1$H and $^{19}$F NMR using TFE as an internal standard confirmed 1 eq. TFA salt; mp 81-83° C.; $^1$H NMR (500 MHz, MeOD) δ 7.37-7.29 (m, 5H, ArH), 4.50 (dd, J=9.7, 4.3 Hz, 1H, CHα-Glu), 4.39 (dd, J=10.0, 4.4 Hz, 1H, CHα-Phe), 4.26 (d, J=10.9 Hz, 1H, NCHH GAz), 4.03 (d, J=14.9 Hz, 1H, CHH Gly), 3.91 (d, J=11.0 Hz, 1H, NCHH GAz), 3.78 (d, J=10.3 Hz, 1H, NCHH GAz), 3.74-3.63 (m, 3H, CHH GAz, NCHH GAz, CHα-Thr), 3.54 (d, J=14.9 Hz, 1H, CHH Gly), 3.25 (dd, J=14.4, 4.4 Hz, 1H, CHHβ-Phe), 3.10-2.98 (m, 3H, CHH GAz, CHHβ-Phe, CHβ-Thr), 2.43-2.26 (m, 3H, CH$_2$γ-Glu, CHHβ-Glu), 2.05-1.92 (m, 1H, CHHβ-Glu), 1.20 (d, J=6.3 Hz, 3H, CH$_3$γ-Thr); $^{13}$C NMR (126 MHz, MeOD) δ 176.5 (C=O), 176.4 (C=O), 175.1 (C=O), 174.4 (C=O), 173.9 (C=O), 138.1 (C), 130.0 (CH), 129.7 (CH), 128.1 (CH), 70.4 (CH, α-Thr), 63.3 (CH, β-Thr), 60.3 (C, Az), 60.0 (NCH$_2$), 59.1 (CH, α-Phe), 53.5 (NCH$_2$), 53.5 (CH, α-Glu), 45.9 (CH$_2$ GAz), 44.4 (CH$_2$ Gly), 37.4 (CH$_2$, β-Phe), 31.3 (CH$_2$, γ-Glu), 27.8 (CH$_2$, β-Glu), 19.2 (CH$_3$, γ-Thr); $v_{max}$ (neat)=3273, 3033, 2922, 1649, 1538, 1177 cm$^{-1}$; MS (ESI$^+$) m/z 519 [M+H]$^+$, 541 [M+Na]$^+$; HRMS (ESI$^+$) calcd. for $C_{24}H_{35}N_6O_7$ 519.2562 [M+H]$^+$. found 519.2555.

Example 13—Solution Phase Synthesis of Other Azetidine-Containing Peptide Macrocycles The following protected cyclic peptides were prepared by solution phase peptide synthesis using methods analogous to those in Examples 10 and 11 (the figures below the structures give the yield). Deprotection using 50% TFA/DCM for 1 hour provided the corresponding deprotected analogues.

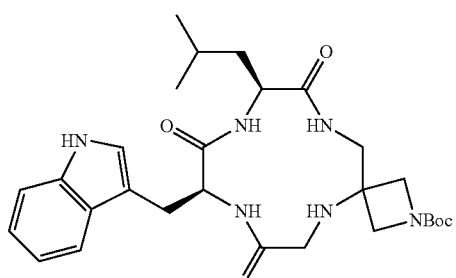

80%

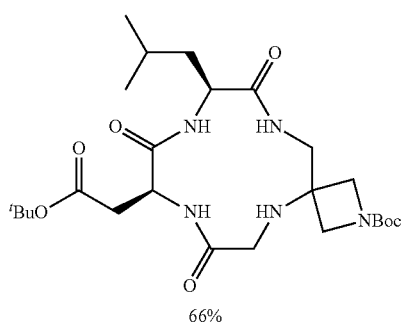

66%

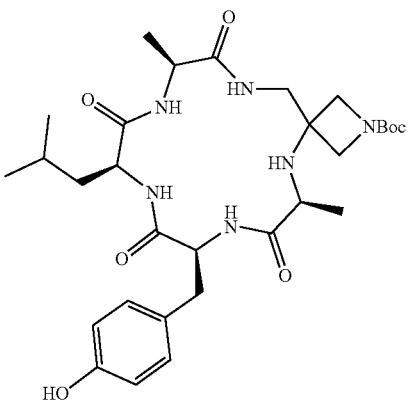

75%

Example 14—Solid Phase Synthesis of Other Azetidine-Containing Macrocycles

The following cyclic peptides were prepared by SPPS using methods analogous to that in Example 12:

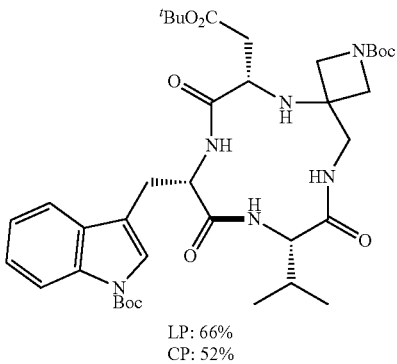

LP: 66%
CP: 52%

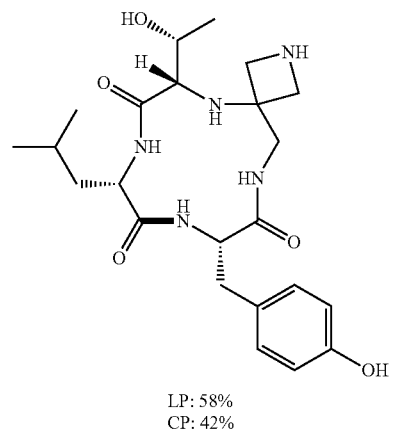

LP: 58%
CP: 42%

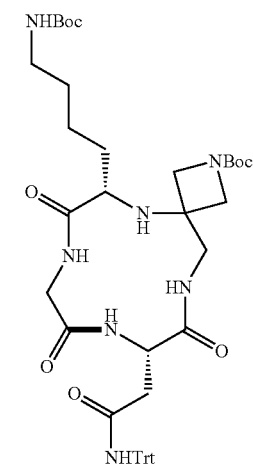

LP: 72%
CP: 54%

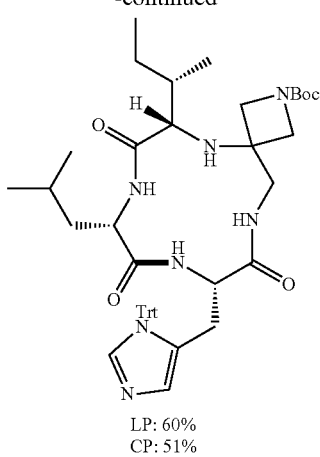

LP: 60%
CP: 51%

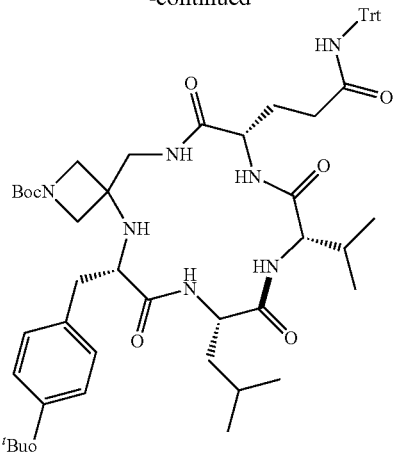

LP: 73%
CP: 49%

LP=yield of linear precursor from resin
CP=yield of cyclic peptide after cyclisation Example 15—Relative Stability of Cyclic Peptides Including the Oxetane and Azetidine Turn-Inducing Elements An experiment was conducted to determine the relative stability of the following oxetane and azetidine-containing compounds in acid (TFA):

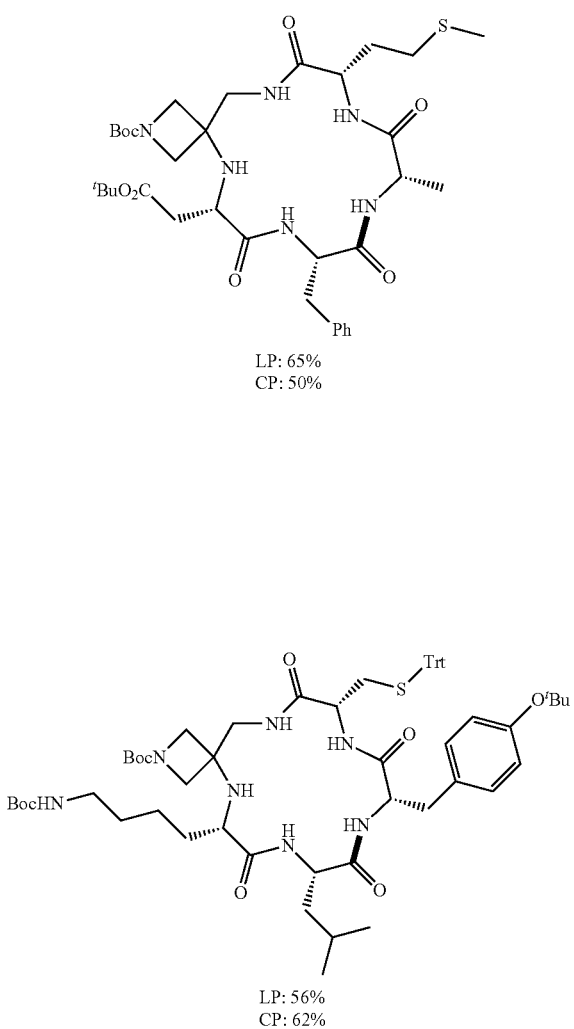

Each compound was added to 70% TFA with stirring. After 24 hours the resulting products were analysed by $^1$H NMR and LC-MS.

The LC-MS traces are provided in FIG. 10. The ring-opened azetidine product is visible by LC-MS, but is not present in a high quantity and was not observed in $^1$H NMR. This is in contrast with the ring-opened oxetane which was visible by LC-MS and clearly present in a higher concentration. It was also observed in $^1$H NMR.

This demonstrates that the macrocycle containing the azetidine ring is more stable than that containing the oxetane ring under the forcing conditions used.

Example 16—Comparison of Yield of Macrocyclisation for Oxetane and Azetidine-Containing Peptides

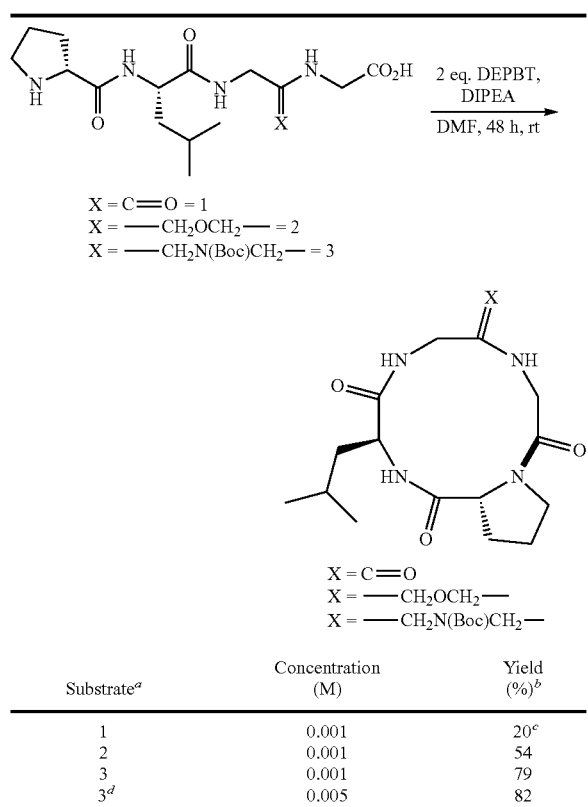

| Substrate[a] | Concentration (M) | Yield (%)[b] |
|---|---|---|
| 1 | 0.001 | 20[c] |
| 2 | 0.001 | 54 |
| 3 | 0.001 | 79 |
| 3[d] | 0.005 | 82 |

[a]Reactions were run at 0.1 mmol scale
[b]Isolated yield of macrocycle after column chromatography
[c]Product isolated as the dimeric octapeptide
[d]Reaction carried out on 0.44 mmol scale The macrocyclisation yield is lowest for the non-modified compound 1. Higher yields are obtained for both the oxetane and azetidine-containing compounds 2 and 3. In this example, the highest yield of the macrocycle is obtained for the peptide containing the azetidine turn-inducing element.

SUMMARY

We have established that the introduction of a carbonyl bioisosteric turn-inducing residue into the peptide backbone offers a new way to improve difficult peptide macrocyclizations. The substrates are easily made and the cyclization works across a range of ring sizes. It is beneficial for head-to-tail, head-to-side-chain, side-chain-to-tail, and side-chain-to-side-chain cyclizations, and tolerates variation in location of the turn-inducing element with respect to the bond being formed. The products are compatible with the harsh acidic conditions needed to deprotect amino acid side chains, and CBMCPs have clear potential as bioisosteres for conventional cyclic peptides.

REFERENCES

1. Zorzi, A.; Deyle, K.; Heinis, C. Curr. Opin. Chem. Biol. 2017, 38, 24-29.
2. (a) Nielsen, D. S.; Shepherd, N. E.; Xu, W.; Lucke, A. J.; Stoermer, M. J.; Fairlie, D. P. Chem. Rev. 2017, 117, 8094-8128. (b) Bockus, A. T.; McEwen, C. M.; Lokey, R. S. Curr. Top. Med. Chem. 2013, 13, 821-836.
3. (a) Dougherty, P. G.; Qian, Z.; Pei, D. Biochem. J. 2017, 474, 1109-1125. (b) Cardote, T. A. F.; Ciulli, A. ChemMedChem 2016, 11, 787-794.
4. For reviews, see: (a) Passioura, T.; Suga, H. Chem. Commun. 2017, 53, 1931. (b) De Leon Rodriguez, L. M.; Weidkamp, A. J.; Brimble, M. A. Org. Biomol. Chem. 2015, 13, 6906-6921. (c) Mar-tí-Centelles, V.; Pandey, M. D.; Burguete, M. I.; Luis, S. V. Chem. Rev. 2015, 115, 8736-8834. (d) Yudin, A. K. Chem. Sci. 2015, 6, 30-49. (e) White, C. J.; Yudin, A. K. Nature Chem. 2011, 3, 509-524.
5. (a) Hubert, J. G.; Stepek, I. A.; Noda, H.; Bode, J. W. Chem. Sci. 2018, 9, 2159-2167. (b) Malins, L. R.; deGruyter, J. N.; Rob-bins, K. J.; Scola, P. M.; Eastgate, M. D.; Ghadiri, M. R.; Baran, P. S. J. Am. Chem. Soc. 2017, 139, 5233-5241. (c) Johnson, A. M.; An-slyn, E. V. Org. Lett. 2017, 19, 1654-1657. (d) Le, D. N.; Riedel, J.; Kozlyuk, N.; Martin, R. W.; Dong, V. M. Org. Lett. 2017, 19, 114-117. (e) McCarver, S. J.; Qiao, J. X.; Carpenter, J.; Borzilleri, R. M.; Poss, M. A.; Eastgate, M. D.; Miller, M. M.; MacMillan, D. W. C. Angew. Chem. Int. Ed. 2017, 56, 728-732. (f) Puentes, A. R.; More-jón, M. C.; Rivera, D. G.; Wessjohann, L. A. Org. Lett. 2017, 19, 4022-4025. (g) Tang, J.; He, Y.; Chen, H.; Sheng, W.; Wang, H. Chem. Sci. 2017, 8, 4565-4570. (h) Rojas, A. J.; Zhang, C.; Vinogradova, E. V.; Buchwald, N. H.; Reilly, J.; Pentelute, B. L.; Buchwald, S. L. Chem. Sci. 2017, 8, 4257-4563. (i) Stephens, T. C.; Lodi, M.; Steer, A. M.; Lin, Y.; Gill, M. T.; Unsworth, W. P. Chem. Eur. J. 2017, 23, 13314-13318. (j) Frost, J. R.; Scully, C. C. G.; Yudin, A. K. Nature Chem. 2016, 8, 1105-1111.
6. (a) Skropeta, D.; Jolliffe, K. A.; Turner, P. J. Org. Chem. 2004, 69, 8804-8809. (b) Fairweather, K. A.; Sayyadi, N.; Luck, I. J.; Clegg, J. K.; Jolliffe, K. A. Org. Lett. 2010, 12, 3136-3139.
7. Powell, N. H.; Clarkson, G. J.; Notman, R.; Raubo, P.; Martin, N. G.; Shipman, M. Chem. Commun. 2014, 50, 8797-8800.
8. (a) Bull, J. A.; Croft, R. A.; Davis, O. A.; Doran, R.; Morgan, K. F. Chem. Rev. 2016, 116, 12150-12233. (b) Wuitschik, G.; Car-reira, E. M.; Wagner, B.; Fischer, H.; Parrilla, I.; Schuler, F.; Roger-Evans, M.; Müller, K. J. Med. Chem. 2010, 53, 3227-3246.
9. (a) Boutureira, O.; Martínez-Sáez, N.; Brindle, K. M.; Neves, A. A.; Corzana, F.; Bernardes, G. J. L. Chem. Eur. J. 2017, 23, 6483-6489. (b) Martínez-Sáez, N.; Sun, S.; Oldrini, D.; Sormanni, P.; Boutureira, O.; Carboni, F.; Compañón, I.; Deery, M. J.; Vendruscolo, M.; Corzana, F.; Adamo, R.; Bernardes, G. J. L. An-gew. Chem. Int. Ed. 2017, 56, 14963-14967.
10. Möller, G. P.; Müller, S.; Wolfstädter, B. T.; Wolfrum, S.; Schepmann, D.; Wünsch, B.; Carreira, E. M. Org. Lett. 2017, 19, 2510-2513.
11. (a) Beadle, J. D.; Knuhtsen, A.; Hoose, A.; Raubo, P.; Jamieson, A. G.; Shipman, M. Org. Lett. 2017, 19, 3303-3306. (b) McLaughlin, M.; Yazaki, R.; Fessard, T. C.; Carreira, E. M. Org. Lett. 2014, 16, 4070-4073.

12. Tang, Y.; Xie, H.; Tian, G.; Ye, Y. J. Peptide Res. 2002, 60, 95-103.

13. Wong, M. S. Y.; Taleski, D.; Jolliffe, K. A. Aust. J. Chem. 2015, 68, 627-634.

14. Arap, W.; Pasqualini, R.; Ruoslahti, E. Science 1998, 279, 377-380.

15. Graziadio, A.; Zanda, M.; Frau, S.; Fleming, I. N.; Musolino, M.; Dall'Angelo, S.; Baldassarre, M.; Piras, M. Bioconjugate Chem. 2016, 27, 1332-1340.

---

The invention claimed is:

1. A method of synthesizing a peptidomimetic macrocycle which is a continuous loop of 11 atoms or more and which comprises a carbonyl bioisosteric turn-inducing element comprising the steps:
   (a) synthesizing a linear peptidomimetic comprising the carbonyl bioisosteric turn-inducing element and
   (b) performing a cyclisation reaction of the linear peptidomimetic;
   wherein the turn-inducing element is:

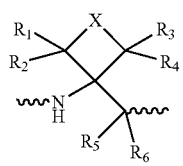

wherein X is a secondary or tertiary amine; and
wherein $R_1$ to $R_6$ are each independently selected from the group consisting of alkyl, aryl, heteroaryl and H.

2. The method according to claim 1, wherein the cyclisation reaction is selected from the group consisting of: a head-to-tail reaction; a sidechain-to-sidechain reaction; a head-to-sidechain reaction; and a sidechain-to-tail reaction.

3. The method according to claim 2, wherein the cyclization reaction is a sidechain-to-sidechain reaction and is achieved by an amide, ester, thioester, or disulfide bond formation.

4. The method according to claim 1, which comprises solution-phase or solid-phase peptide synthesis.

5. The method according to claim 1, wherein a compound of formula (III) is employed in synthesizing the linear peptidomimetic comprising the carbonyl bioisosteric turn-inducing element:

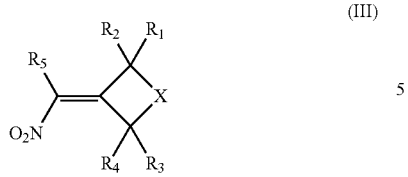 (III)

wherein X is a secondary or tertiary amine; and
wherein $R_1$ to $R_5$ are each independently selected from the group consisting of alkyl, aryl, heteroaryl and H.

6. The method according to claim 5, wherein X is NH.

7. The method according to claim 5, wherein the compound of formula (III) is:

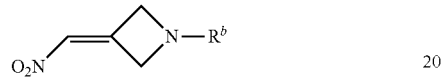

wherein $R^b$ is H, alkyl, aryl, heteroaryl, or a removable protecting group.

8. The method according to claim 7, wherein the removable protecting group is tert-butyloxycarbonyl (Boc), 9-fluorenylmethyloxycarbonyl (Fmoc), or carboxybenzyl (Cbz).

* * * * *